(12) United States Patent
Zhang et al.

(10) Patent No.: US 11,396,501 B2
(45) Date of Patent: Jul. 26, 2022

(54) HETEROARYL COMPOUNDS AS CXCR4 INHIBITORS, COMPOSITION AND METHOD USING THE SAME

(71) Applicant: CGENETECH (SUZHOU, CHINA) CO., LTD., Suzhou (CN)

(72) Inventors: Xiaohu Zhang, Suzhou (CN); Jiyue Zheng, Suzhou (CN); Haikuo Ma, Suzhou (CN)

(73) Assignee: CGENETECH (SUZHOU, CHINA) CO., LTD., Suzhou (CN)

( * ) Notice: Subject to any disclaimer, the term of this patent is extended or adjusted under 35 U.S.C. 154(b) by 0 days.

(21) Appl. No.: 16/649,983

(22) PCT Filed: Sep. 24, 2018

(86) PCT No.: PCT/US2018/052503
§ 371 (c)(1),
(2) Date: Mar. 24, 2020

(87) PCT Pub. No.: WO2019/060860
PCT Pub. Date: Mar. 28, 2019

(65) Prior Publication Data
US 2020/0239439 A1    Jul. 30, 2020

(30) Foreign Application Priority Data

Sep. 25, 2017 (CN) .......................... 201710875041.9
Mar. 28, 2018 (CN) .......................... 201810265417.9
Jul. 2, 2018 (CN) .......................... 201810710340.1
Sep. 5, 2018 (CN) .......................... 201811034891.7

(51) Int. Cl.
C07D 401/14 (2006.01)
C07D 413/14 (2006.01)
C07D 405/14 (2006.01)
C07D 401/12 (2006.01)
C07D 491/052 (2006.01)
C07D 519/00 (2006.01)
C07D 487/04 (2006.01)

(52) U.S. Cl.
CPC ......... *C07D 401/14* (2013.01); *C07D 401/12* (2013.01); *C07D 405/14* (2013.01); *C07D 413/14* (2013.01); *C07D 487/04* (2013.01); *C07D 491/052* (2013.01); *C07D 519/00* (2013.01)

(58) Field of Classification Search
None
See application file for complete search history.

(56) References Cited

U.S. PATENT DOCUMENTS

| | | |
|---|---|---|
| 2008/0051387 A1 | 2/2008 | Xu et al. |
| 2011/0172217 A1 | 7/2011 | Fujioka et al. |
| 2011/0245265 A1 | 10/2011 | Zuk et al. |
| 2013/0172330 A1 | 7/2013 | Clark et al. |
| 2016/0256458 A1 | 9/2016 | Bair et al. |

FOREIGN PATENT DOCUMENTS

WO    2017011517 A1    1/2017

OTHER PUBLICATIONS

Database Registry Chemical Abstracts Service, Columbus, Ohio, Accession No. RN 1170071-62-1, Entered STN: Jul. 29, 2009.*
PUBCHEM-CID: 9897616 create date: Oct. 25, 2006; pp. 1-15; p. 4; Fig.

* cited by examiner

*Primary Examiner* — Samantha L Shterengarts
(74) *Attorney, Agent, or Firm* — Feng Tian

(57) ABSTRACT

The present disclosure provides heteroaryl compounds of Formula (I), processes for their preparation, pharmaceutical compositions containing them, and their use in the treatment of diseases and disorders, arising from or related to the CXCR4 pathway.

(I)

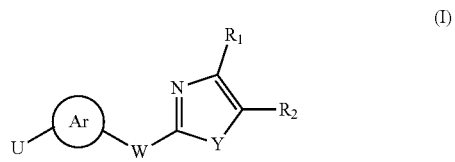

6 Claims, 2 Drawing Sheets

HETEROARYL COMPOUNDS AS CXCR4 INHIBITORS, COMPOSITION AND METHOD USING THE SAME

CROSS REFERENCE TO RELATED APPLICATIONS

This application claims the benefit of Chinese Patent Applications 201710875041.9, filed on Sep. 25, 2017; 201810265417.9, filed on Mar. 28, 2018; 201810710340.1, filed on Jul. 2, 2018; and 201811034891.7, filed on Sep. 5, 2018, 2018; all of which are hereby incorporated by reference.

FIELD OF INVENTION

The present invention generally relates to heteroaryl compounds and, more particularly, relates to novel heteroaryl compounds that are useful in the therapies targeting C—X—C chemokine receptor type 4 (CXCR4) inhibitors, and use of the CXCR4 inhibitors for therapeutic intervention in infectious diseases, inflammatory diseases, tumors, and cancers.

BACKGROUND OF THE INVENTION

C—X—C chemokine receptor type 4 (CXCR4) is a transmembrane protein that belongs to the G-protein-coupled receptors and it is involved in physiological processes in the hematopoietic and immune systems. Studies show that CXCR4 is expressed in tissues including lymphatic tissues, thymus, brain, spleen, stomach and small intestine. CXCR4/transmits signals from its natural chemokine ligand, stromal cell-derived factor (SDF)-1α, to intracellular biological pathways via G-proteins. The interaction between CXCR4 and SDF-1α has been targeted in various therapeutic treatments for a number of diseases, including, for example, human immunodeficiency virus (HIV) infection, cancers, tumors, and inflammation and autoimmune disease such as rheumatoid arthritis and allergic asthma. The CXCR4 antagonist, Plerixafor, was approved by the FDA in 2008 for the mobilization of hematopoietic stem cells. See Cho W. T., et al., *J. Med. Chem.* 2011; 55: 977-94; Debnath B. et al., *Theranostics* 2013, 3 (1): 47-75.

SUMMARY OF THE INVENTION

The present disclosure provides heteroaryl compounds as CXCR4 inhibitors, and compositions and applications thereof. These disclosed heteroaryl compounds, and compositions and applications thereof, may effectively inhibit necrosis, thereby finding application in treatments of necrotic pathway-related diseases and disorders, including, for example, inflammation, tumors, metabolic diseases and neurodegenerative diseases such as cerebral ischemia and stroke.

An aspect of the present disclosure provides a compound of formula I:

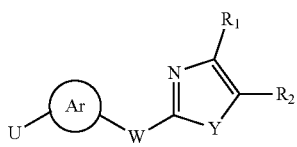

I or a pharmaceutically acceptable salt, hydrate, solvate, stereoisomer or tautomer thereof, wherein Ar is 5-10 membered heteroaryl comprising one N and 1-3 additional heteroatoms independently selected from the group consisting of N, O, and S, and Ar is unsubstituted or substituted with 1-4 $R_{31}$;

W is

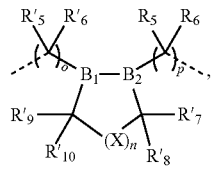

each X is independently a bond, $CR_{32}R_{33}$, O, $NR_{34}$, S, $S(=O)$ or $S(=O)_2$; n is 0, 1, 2 or 3; o and p are different integers with values of o or 1; wherein when o is 0, p is 1, $B_1$ is $CR_{11}$, $B_2$ is N, and $B_1$ is bonded with Ar; wherein when o is 1, p is 0, $B_1$ is N, $B_2$ is $CR_{11}$, and the carbon bearing $R'_5$ and $R'_6$ is bonded with Ar;

or W is

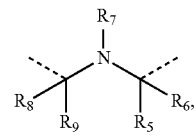

wherein the carbon bonded with $R_5$ and $R_6$ is connected the ring carbon bonded with Y;

Y is

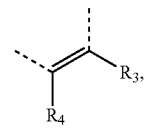

wherein the carbon bonded with $R_3$ is bonded with the carbon bonded with $R_2$;

or Y is

U is

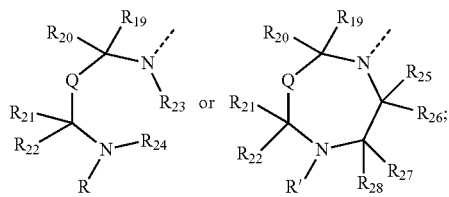

Q is a bond or $CR_{29}R_{30}$;

each of $R_1$, $R_2$, $R_3$, and $R_4$ is independently selected from the group consisting of H, deuterium, —CN, halide, —OH, amino, —NH($C_{1-6}$ alkyl), —N($C_{1-6}$ alkyl)$_2$, —NHC(=O)(C$_{1-6}$ alkyl), —NHC(=O)O(C$_{1-6}$ alkyl), —NHS(=O)$_2$(C$_{1-6}$ alkyl), —S(=O)$_2$(C$_{1-6}$ alkyl), C$_{1-6}$ alkyl, C$_{3-6}$ cycloalkyl, C$_{1-8}$ alkoxy, C$_{2-6}$ alkenyl, and C$_{2-6}$ alkynyl, wherein each of C$_{1-6}$ alkyl, C$_{3-6}$ cycloalkyl, C$_{1-8}$ alkoxy, C$_{2-6}$ alkenyl, and C$_{2-6}$ alkynyl is unsubstituted or substituted with 1-3 groups independently selected from the group consisting of halide, —OH, methanesulfonyl, and deuterium;

or R$_4$ together with the atoms it attached to forms a carbocyclic, aryl, heterocyclic, or heteroaryl ring;

each of R$_5$ and R$_6$ is independently selected from the group consisting of H, deuterium, —CN, C$_{1-6}$ alkyl, and C$_{3-6}$ cycloalkyl, wherein each of C$_{1-6}$ alkyl and C$_{3-6}$ cycloalkyl is unsubstituted or substituted with 1-3 groups independently selected from the group consisting of halide, deuterium, —OH, amino, —NH(C$_{1-6}$ alkyl), —N(C$_{1-6}$ alkyl)$_2$, —NHC(=O)(C$_{1-6}$ alkyl), —NHC(=O)O(C$_{1-6}$ alkyl), and C$_{1-3}$ alkoxy;

or R$_5$ and R$_6$ together forms

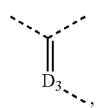

and D$_3$ bonded with R$_4$ to form:

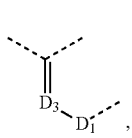 1)

wherein D$_3$ is N or CR'$_4$, and D$_1$ is NR'$_4$, O, S or C(R'$_4$)$_2$,

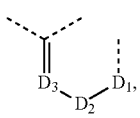 2)

wherein D$_3$ is N or CR'$_4$, D$_1$ is NR'$_4$, O, S or C(R'$_4$)$_2$, D$_2$ is NR'$_4$, or C(R'$_4$)$_2$, or

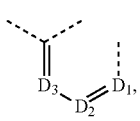 3)

wherein D$_3$ is N or CR'$_4$, D$_1$ is N or CR'$_4$, and D$_2$ is N or CR'$_4$, wherein each R'$_4$ is independently selected from the group consisting of H, deuterium, —CN, halide, —OH, amino, C$_{1-6}$ alkyl, —NH(C$_{1-6}$ alkyl), —N(C$_{1-6}$ alkyl)$_2$, —S(=O)$_2$(C$_{1-6}$ alkyl), C$_{3-6}$ cycloalkyl, C$_{1-8}$ alkoxy, C$_{2-6}$ alkenyl, and C$_{2-6}$ alkynyl, wherein each of —NH(C$_{1-6}$ alkyl), —N(C$_{1-6}$ alkyl)$_2$, —S(=O)$_2$(C$_{1-6}$ alkyl), C$_{1-6}$ alkyl, C$_{3-6}$ cycloalkyl, C$_{1-8}$ alkoxy, C$_{2-6}$ alkenyl, and C$_{2-6}$ alkynyl is unsubstituted or substituted with 1-3 groups independently selected from the group consisting of halide, —OH, methanesulfonyl, and deuterium;

R$_7$ is selected from the group consisting of H, deuterium, C$_{1-6}$ alkyl, C$_{3-6}$ cycloalkyl, and C$_{3-6}$ heterocycloalkyl, wherein each of C$_{1-6}$ alkyl, C$_{3-6}$ cycloalkyl, and C$_{3-6}$ heterocycloalkyl is unsubstituted or substituted with 1-3 groups independently selected from the group consisting of halide, deuterium, amino, —OH, acyl, —CN, C$_{1-6}$ alkoxy, —NH(C$_{1-6}$ alkyl), —N(C$_{1-6}$ alkyl)$_2$, —C(=O)O(C$_{1-6}$ alkyl), —C(=O)NH$_2$, —C(=O)NH(C$_{1-6}$ alkyl), —C(=O)N(C$_{1-6}$ alkyl)$_2$, —NHC(=O)O(C$_{1-6}$ alkyl), —S(=O)$_2$(C$_{1-6}$ alkyl), and C$_{3-6}$ cycloalkyl;

each of R$_8$ and R$_9$ is independently selected from the group consisting of H, deuterium, —CN, C$_{1-6}$ alkyl, and C$_{3-6}$ cycloalkyl, wherein each of C$_{1-6}$ alkyl and C$_{3-6}$ cycloalkyl is unsubstituted or substituted with 1-3 groups independently selected from the group consisting of halide, deuterium, —OH, and C$_{1-3}$ alkoxy; or R$_7$ and R$_8$, and atoms attached thereto, form a ring;

or R$_8$ and R$_9$, together with atoms they attached to, form a ring;

each of R'$_5$, R'$_6$, R'$_7$, R'$_8$, R'$_9$, R'$_{10}$, R$_{11}$, R$_{32}$, and R$_{33}$ is independently selected from the group consisting of H, deuterium, —CN, halide, C$_{1-6}$ alkyl, —C(=O)O(C$_{1-6}$ alkyl), C$_{3-6}$ cycloalkyl, C$_{1-6}$ alkoxy, and —OSi(C$_{1-6}$ alkyl)$_3$, wherein each of C$_{1-6}$ alkyl, C$_{3-6}$ cycloalkyl, and C$_{1-6}$ alkoxy is unsubstituted or substituted with 1-3 groups independently selected from the group consisting of halide, deuterium, —OH, amino, C$_{3-6}$ cycloalkyl, C$_{1-6}$ alkyl, —NHC(=O)(C$_{1-6}$ alkyl), —NHC(=O)O(C$_{1-6}$ alkyl), —NHC(=O)NH(C$_{1-6}$ alkyl), —NHC(=O)N(C$_{1-6}$ alkyl)$_2$, —NHS(=O)$_2$(C$_{1-6}$ alkyl), and C$_{1-6}$ alkoxy;

each of R$_{19}$, R$_{20}$, R$_{21}$, R$_{22}$, R$_{25}$, R$_{26}$, R$_{27}$, R$_{28}$, R$_{29}$, and R$_{30}$ is independently selected from the group consisting of H, deuterium, —CN, —OH, C$_{1-6}$ alkyl, C$_{3-6}$ cycloalkyl, and C$_{1-3}$ alkoxy, wherein each of C$_{1-6}$ alkyl, C$_{3-6}$ cycloalkyl, and C$_{1-3}$ alkoxy is unsubstituted or substituted with 1-3 groups independently selected from the group consisting of halide, deuterium, —OH, amino, —NH(C$_{1-6}$ alkyl), —N(C$_{1-6}$ alkyl)$_2$, —NHC(=O)(C$_{1-6}$ alkyl), —NHC(=O)O(C$_{1-6}$ alkyl), C$_{1-6}$ alkyl, and C$_{1-3}$ alkoxy; or R$_{21}$ and R$_{23}$, together with atoms they attached to, form a ring; or R$_{19}$ and R$_{27}$, together with atoms they attached to, form a ring; or R$_{21}$ and R$_{27}$, together with atoms they attached to, form a ring; or R$_{19}$ and R$_{26}$, together with atoms they attached to, form a ring; or R$_{21}$ and R$_{26}$, together with atoms they attached to, form a ring;

R$_{23}$ is selected from the group consisting of H, C$_{1-6}$ alkyl, and C$_{3-6}$ cycloalkyl, wherein each of C$_{1-6}$ alkyl and C$_{3-6}$ cycloalkyl is unsubstituted or substituted with 1-3 groups independently selected from the group consisting of halide, deuterium, —OH, amino, C$_{1-6}$ alkyl, —NH(C$_{1-6}$ alkyl), —N(C$_{1-6}$ alkyl)$_2$, —NHC(=O)(C$_{1-6}$ alkyl), —NHC(=O)O(C$_{1-6}$ alkyl), and C$_{1-3}$ alkoxy; or R$_{22}$ and R$_{23}$, together with atoms they attached to, form a 5-7 membered heterocycle;

R$_{24}$ is selected from the group consisting of H, C$_{1-6}$ alkyl, C$_{3-6}$ cycloalkyl, C$_{3-6}$ heterocycloalkyl comprising N or O, —C(=O)(C$_{1-6}$ alkyl), —C(=O)O(C$_{1-6}$ alkyl), and —C(=O)NH(C$_{1-6}$ alkyl), wherein each of C$_{1-6}$ alkyl and C$_{3-6}$ cycloalkyl is unsubstituted or substituted with 1-3 groups independently selected from the group consisting of halide, deuterium, —OH, —CN, amino, C$_{1-6}$ alkyl, C$_{3-6}$ cycloalkyl, C$_{3-6}$ heterocycloalkyl comprising N or O, —NH(C$_{1-6}$ alkyl), —N(C$_{1-6}$ alkyl)$_2$, —NHC(=O)(C$_{1-6}$ alkyl), —NHC(=O)O(C$_{1-6}$ alkyl), and $C_{1-3}$ alkoxy; or R and $R_{24}$, together with atoms they attached to, form a 5-7 membered heterocycle;

$R_{31}$ is selected from the group consisting of deuterium, halide, —CN, —OH, amino, $C_{1-6}$ alkyl, $C_{3-6}$ cycloalkyl, $C_{1-8}$ alkoxy, $C_{2-6}$ alkynyl, $C_{2-6}$ alkenyl, —S($C_{1-6}$ alkyl), —NH($C_{1-6}$ alkyl), —N($C_{1-6}$ alkyl)$_2$, aryl, 5-7 membered heteroaryl comprising 1-3 heteroatoms independently selected from the group consisting of O, N and S, and 5-7 membered heterocycle comprising 1-3 heteroatoms independently selected from the group consisting of O, N and S, wherein each of $C_{1-6}$ alkyl, $C_{3-6}$ cycloalkyl, $C_{1-6}$ alkoxy, aryl, heteroaryl, and heterocycle is unsubstituted or substituted with 1-3 groups independently selected from the group consisting of deuterium, halide, —CN, —OH, amino, $C_{1-6}$ alkyl, $C_{3-6}$ cycloalkyl, and $C_{1-6}$ alkoxy;

$R_{34}$ is selected from the group consisting of H, $C_{1-6}$ alkyl, $C_{3-6}$ cycloalkyl, —C(=O)($C_{1-8}$ alkyl), —S(=O)$_2$($C_{1-8}$ alkyl), —C(=O)O($C_{1-6}$ alkyl), and —C(=O)NH($C_{1-6}$ alkyl), wherein each of $C_{1-6}$ alkyl, $C_{1-8}$ alkyl, and $C_{3-6}$ cycloalkyl is unsubstituted or substituted with 1-3 groups independently selected from the group consisting of halide, deuterium, —OH, amino, $C_{1-6}$ alkyl, —NH($C_{1-6}$ alkyl), —NH($C_{1-6}$ alkyl), —N($C_{1-6}$ alkyl)$_2$, —NHC(=O)($C_{1-6}$ alkyl), —NHC(=O)O($C_{1-6}$ alkyl), and $C_{1-3}$ alkoxy;

R is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R and $R_{24}$, together with N atom they attached to, form a 5-7 membered heterocycle; or R and $R_{21}$, together with N atom they attached to, form a 5-7 membered heterocycle; and R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R' and $R_{21}$, together with atoms they attached to, form a 5-7 membered heterocycle.

In some embodiments of the present disclosure, the disclosed compound is according to Formula Ia

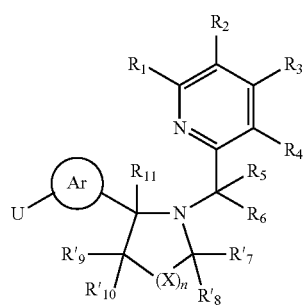

Ia or a pharmaceutically acceptable salt, hydrate, solvate, stereoisomer or tautomer thereof, wherein Ar is unsubstituted or substituted with 1-4 groups of $R_{31}$, and Ar is selected from the group consisting of:

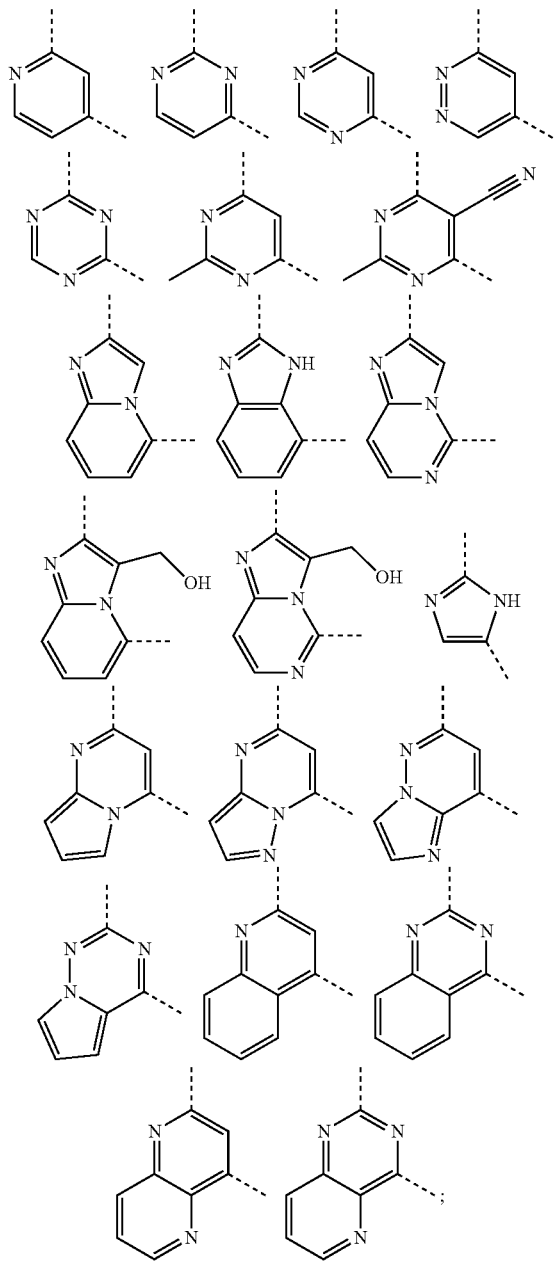

each X is independently a bond, $CR_{32}R_{33}$, O, or $NR_{34}$;

each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, amino, $C_{1-6}$ alkyl, and $C_{1-3}$ alkoxy; or $R_{19}$ and $R_{27}$, together with atoms they attached to, form a ring; or $R_{21}$ and $R_{27}$, together with atoms they attached to, form a ring;

each of $R_{23}$ and $R_{24}$ is independently selected from the group consisting of H, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, $C_{1-6}$ alkyl, and $C_{1-3}$ alkoxy; or $R_{22}$ and $R_{23}$, together with atoms they attached to, form a 5-7 membered heterocycle;

$R_{31}$ is selected from the group consisting of deuterium, halide, —CN, —OH, amino, $C_{1-6}$ alkyl, $C_{3-6}$ cycloalkyl, $C_{1-6}$ alkoxy, $C_{2-6}$ alkynyl, $C_{2-6}$ alkenyl, —S($C_{1-6}$ alkyl), —NH($C_{1-6}$ alkyl), —N($C_{1-6}$ alkyl)$_2$, aryl, 5-7 membered heteroaryl comprising 1-3 heteroatoms independently selected from the group consisting of O, N and S, and 5-7 membered heterocycle comprising 1-3 heteroatoms independently selected from the group consisting of O, N and S, wherein each of $C_{1-6}$ alkyl, $C_{3-6}$ cycloalkyl, $C_{1-6}$ alkoxy, aryl, heteroaryl, and heterocycle is unsubstituted or substituted with 1-3 groups independently selected from the group consisting of deuterium, halide, —CN, —OH, amino, $C_{1-6}$ alkyl, $C_{3-6}$ cycloalkyl, and $C_{1-6}$ alkoxy;

R is selected from the group consisting of H, $C_{1-6}$ alkyl, $C_{3-6}$ cycloalkyl, $C_{3-8}$ heterocycloalkyl comprising N or O, —C(=O)($C_{1-6}$ alkyl), —C(=O)O($C_{1-6}$ alkyl), and —C(=O)NH($C_{1-6}$ alkyl) wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R and $R_{24}$, together with N atom they attached to, form a 5-7 membered heterocycle; and R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R' and $R_{21}$, together with N atom they attached to, form a 5-7 membered heterocycle.

In some embodiments of the present disclosure, the disclosed compound is according to Formula Ib:

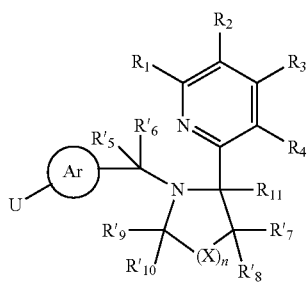

Ib or a pharmaceutically acceptable salt, hydrate, solvate, stereoisomer or tautomer thereof, wherein Ar is unsubstituted or substituted with 1-4 groups of $R_{31}$, and Ar is selected from the group consisting of:

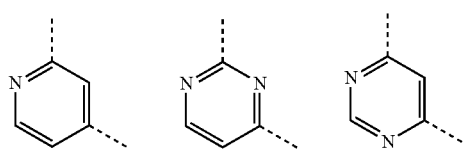

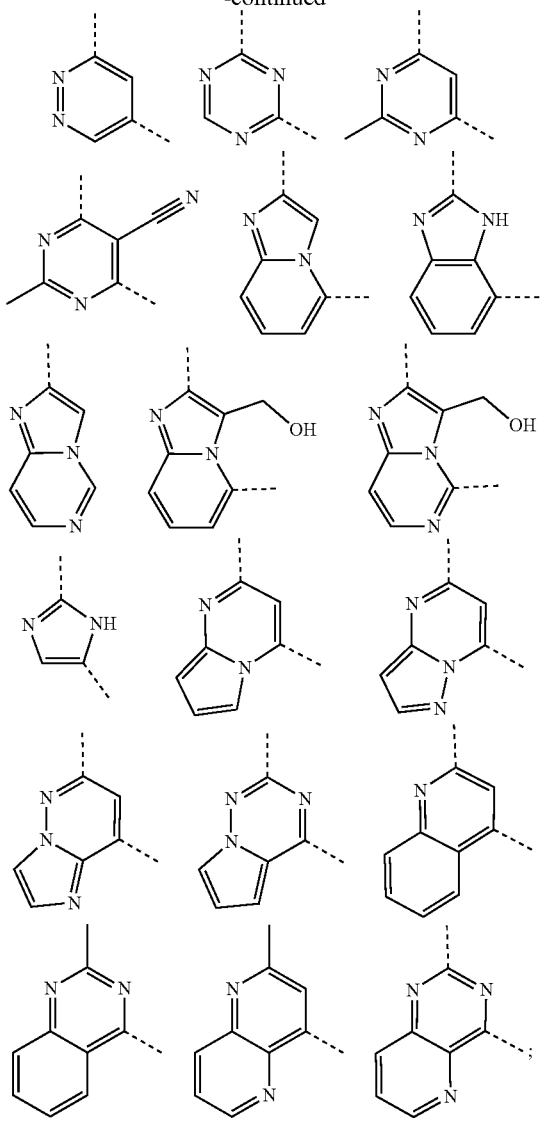

each X is independently a bond, $CR_{32}R_{33}$, O, or $NR_{34}$;
each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, amino, $C_{1-6}$ alkyl, and $C_{1-3}$ alkoxy; or $R_{19}$ and $R_{27}$, together with atoms they attached to, form a ring; or $R_{21}$ and $R_{27}$, together with atoms they attached to, form a ring;

each of $R_{23}$ and $R_{24}$ is independently selected from the group consisting of H, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, $C_{1-6}$ alkyl, and $C_{1-3}$ alkoxy; or $R_{22}$ and $R_{23}$, together with atoms they attached to, form a 5-7 membered heterocycle;

$R_{31}$ is selected from the group consisting of deuterium, halide, —CN, —OH, amino, $C_{1-6}$ alkyl, $C_{3-6}$ cycloalkyl, $C_{1-6}$ alkoxy, $C_{2-6}$ alkynyl, $C_{2-6}$ alkenyl, —S($C_{1-6}$ alkyl), —NH($C_{1-6}$ alkyl), —N($C_{1-6}$ alkyl)$_2$, aryl, 5-7 membered heteroaryl comprising 1-3 heteroatoms independently selected from the group consisting of O, N and S, and 5-7 membered heterocycle comprising 1-3 heteroatoms independently selected from the group consisting of O, N and S, wherein each of $C_{1-6}$ alkyl, $C_{3-6}$ cycloalkyl, $C_{1-6}$ alkoxy, aryl, heteroaryl, and heterocycle is unsubstituted or substituted with 1-3 groups independently selected from the group consisting of deuterium, halide, —CN, —OH, amino, $C_{1-6}$ alkyl, $C_{3-6}$ cycloalkyl, and $C_{1-6}$ alkoxy;

R is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R and $R_{24}$, together with N atom they attached to, form a 5-7 membered heterocycle; and R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R' and $R_{21}$, together with N atom they attached to, form a 5-7 membered heterocycle.

In some embodiments of the present disclosure, the disclosed compound is according to Formula Ic:

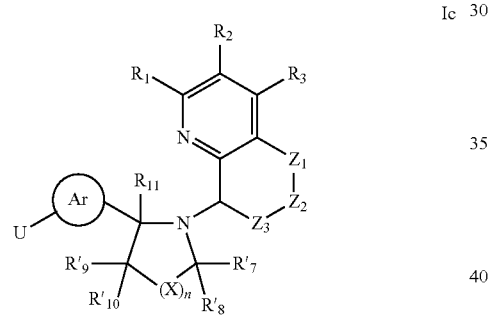

Ic or a pharmaceutically acceptable salt, hydrate, solvate, stereoisomer or tautomer thereof, wherein
each of Z1, Z2 and Z3 is independently selected from the group consisting of O and $CR_{41}R_{42}$; and
each of $R_{41}$ and $R_{42}$ is independently selected from the group consisting of H, deuterium, halide and $C_{1-3}$ alkyl.

In some embodiments of the present disclosure, for the disclosed compound:
each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, $C_{1-6}$ alkyl, and $C_{1-3}$ alkoxy;
each of $R_{23}$ and $R_{24}$ is independently selected from the group consisting of H, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, $C_{1-6}$ alkyl, and $C_{1-3}$ alkoxy; or $R_{22}$ and $R_{23}$, together with atoms they attached to, form a 5-7 membered heterocycle; and
each of R and R' is independently selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O.

In some embodiments of the present disclosure, the disclosed compound is selected from the group consisting of:

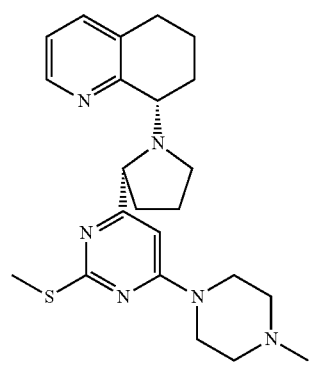

C1

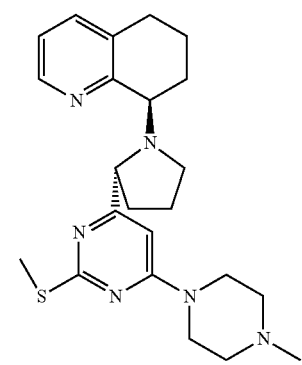

C2

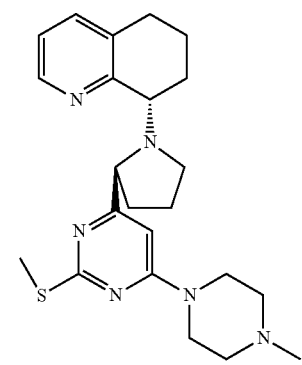

C3

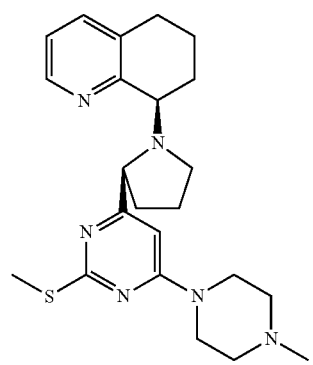

C4

C5 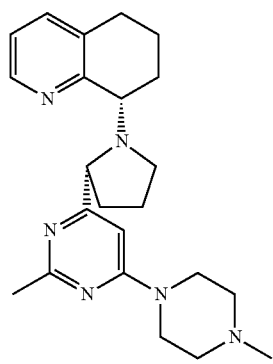
C6 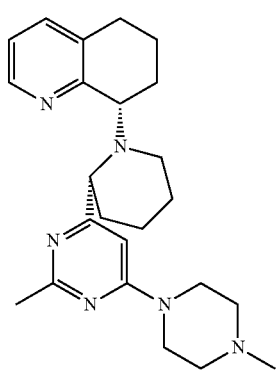
C7 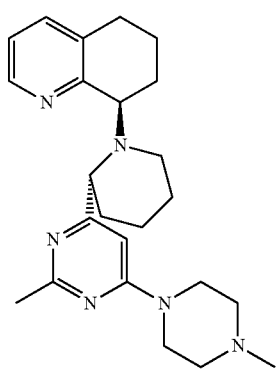
C8 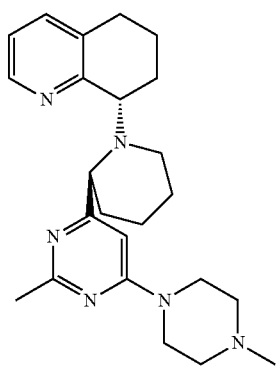
C9 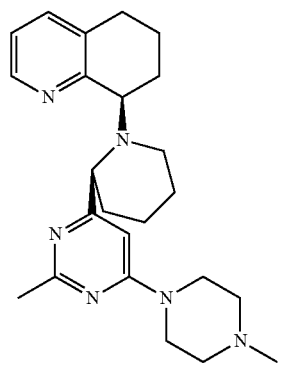
C10 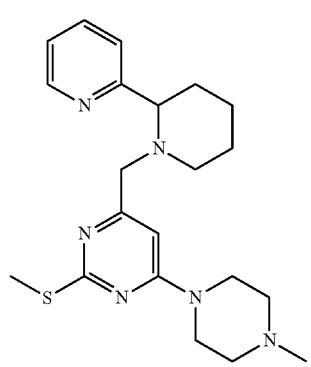
C11 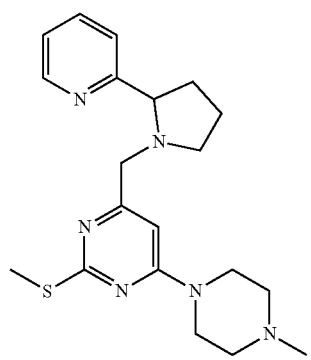
C12 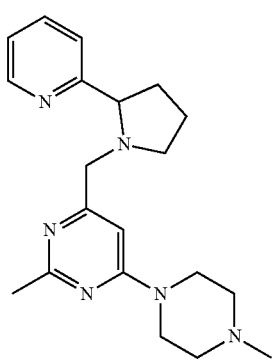

-continued
C13
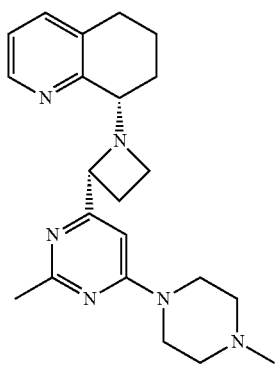
C14
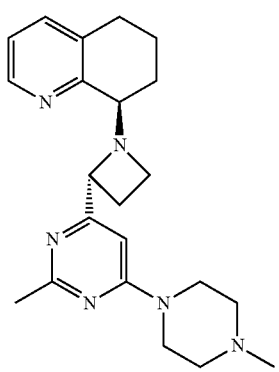
C15
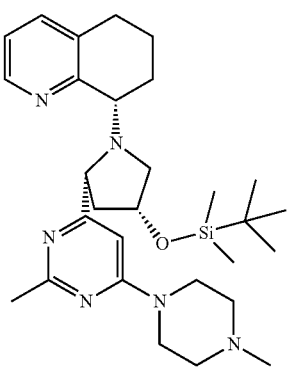
C16
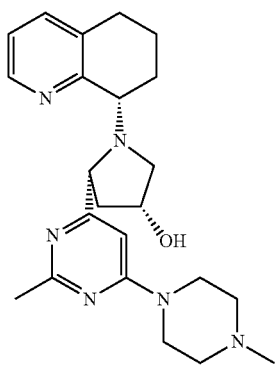
-continued
C17
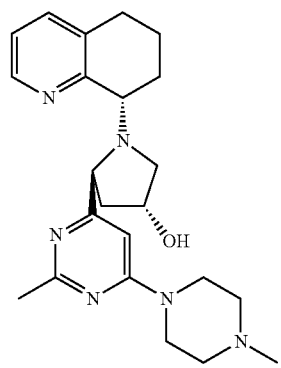
C18
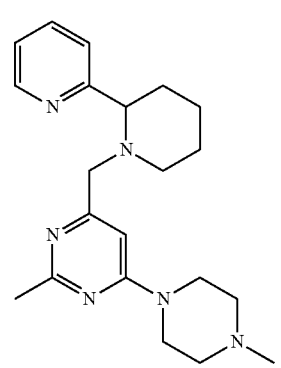
C19
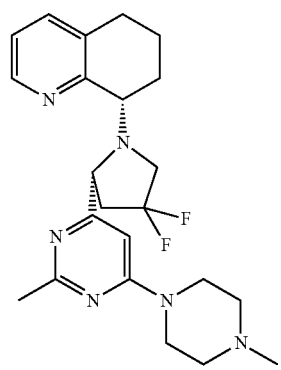
C20
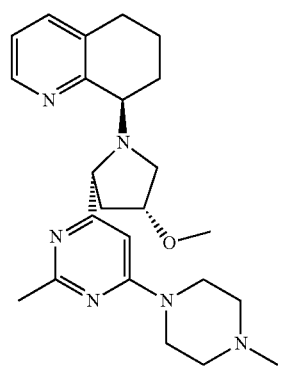

-continued
C21
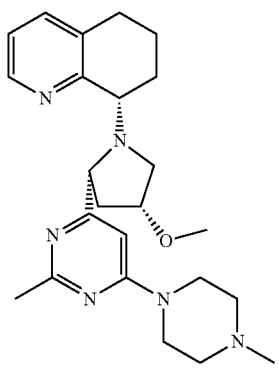
C22
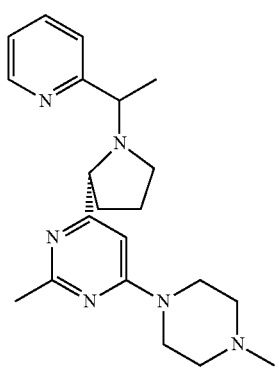
C23
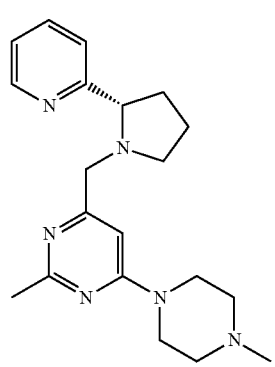
C24
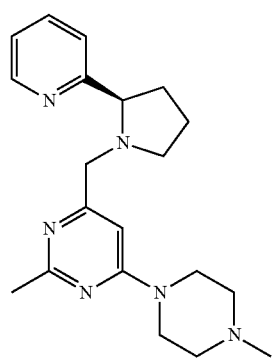
-continued
C25
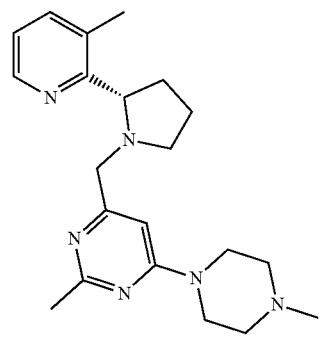
C26
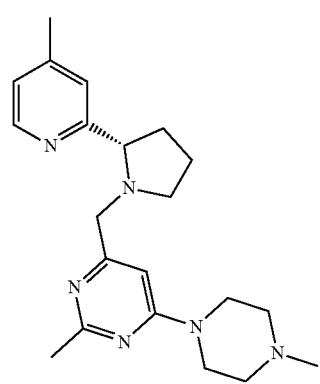
C27
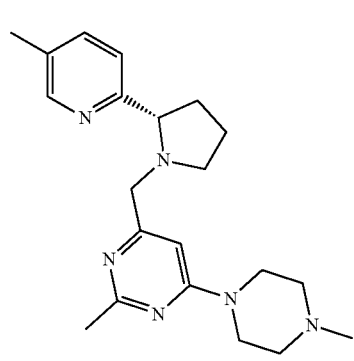
C28
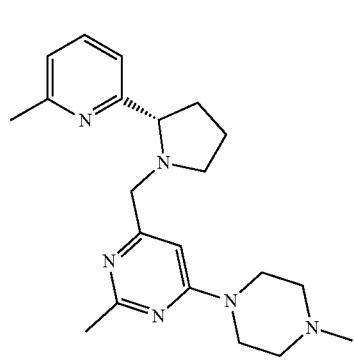

-continued
C29
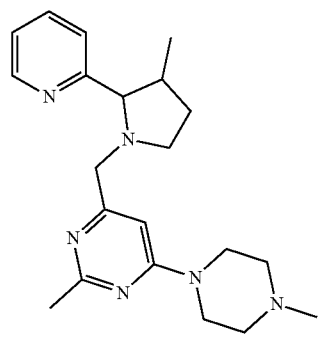
C30
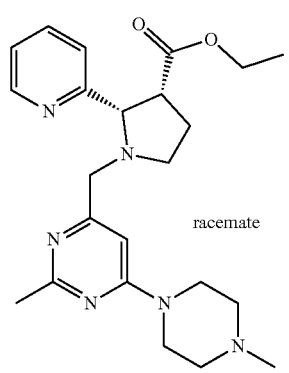
racemate
C31
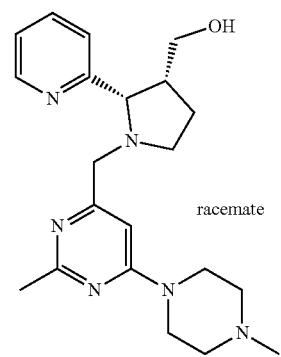
racemate
C32
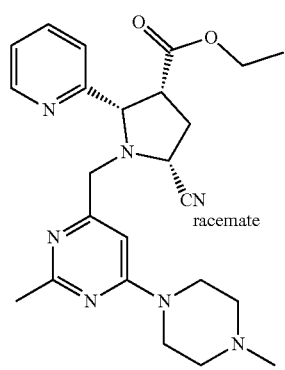
racemate
-continued
C33
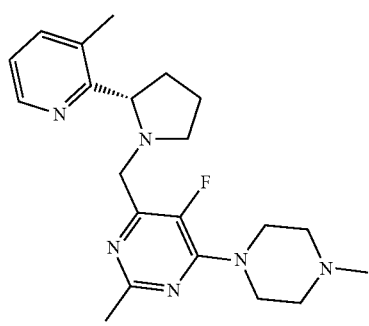
C34
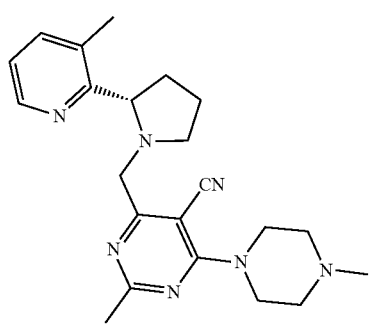
C35
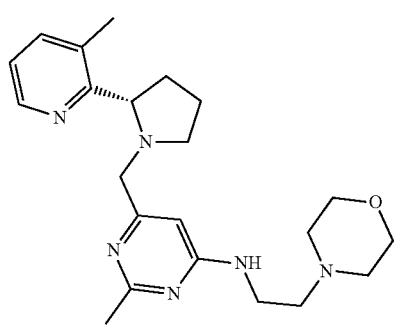
C36
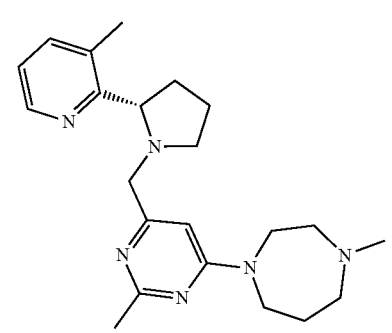
C37
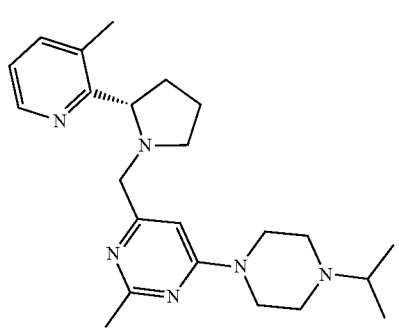

-continued

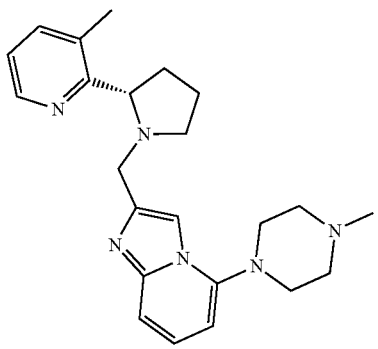

C38

C39

In some embodiments of the present disclosure, the disclosed compound is according to Formula II:

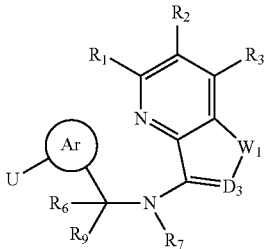

II wherein
  $W_1$ is $D_1$, $D_1$-$D_2$, or $D_1$=$D_2$, and $D_1$ is bonded with the pyridine ring;
  each of $R_1$, $R_2$, and $R_3$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, —S(=O)$_2$($C_{1-6}$ alkyl), $C_{3-6}$ cycloalkyl, $C_{1-8}$ alkoxy, $C_{2-6}$ alkenyl, and $C_{2-6}$ alkynyl, wherein each of $C_{1-6}$ alkyl, $C_{3-6}$ cycloalkyl, $C_{1-8}$ alkoxy, $C_{2-6}$ alkenyl, and $C_{2-6}$ alkynyl is unsubstituted or substituted with 1-3 groups independently selected from the group consisting of halide, —OH, methanesulfonyl, and deuterium;
  $R_7$ is selected from the group consisting of H, deuterium, $C_{1-6}$ alkyl, and $C_{3-6}$ cycloalkyl, wherein each of $C_{1-6}$ alkyl, and $C_{3-6}$ cycloalkyl is unsubstituted or substituted with 1-3 groups independently selected from the group consisting of halide, deuterium, amino, —OH, acyl, —CN, $C_{1-6}$ alkoxy, —NH($C_{1-6}$ alkyl), —N($C_{1-6}$ alkyl)$_2$, —C(=O)O($C_{1-6}$ alkyl), —C(=O)NH$_2$, —C(=O)NH($C_{1-6}$ alkyl), —C(=O)N($C_{1-6}$ alkyl)$_2$, —NHC(=O)O($C_{1-6}$ alkyl), —S(=O)$_2$($C_{1-6}$ alkyl), and $C_{3-6}$ cycloalkyl;

$R_{23}$ is selected from the group consisting of H, $C_{1-6}$ alkyl and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, —NH($C_{1-6}$ alkyl), —N($C_{1-6}$ alkyl)$_2$, and $C_{1-3}$ alkoxy;
  each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), and $C_{1-3}$ alkoxy; or $R_{22}$ and $R_{23}$, together with atoms they attached to, form a ring; or $R_{19}$ and $R_{26}$, together with atoms they attached to, form a ring; or $R_{21}$ and $R_{26}$, together with atoms they attached to, form a ring;
  each of R and $R_{24}$ is independently selected from the group consisting of H, $C_{1-6}$ alkyl, $C_{3-6}$ cycloalkyl, $C_{3-6}$ heterocycloalkyl comprising N or O, —C(=O)($C_{1-6}$ alkyl), —C(=O)O($C_{1-6}$ alkyl), and —C(=O)NH($C_{1-6}$ alkyl), wherein each of $C_{1-6}$ alkyl, $C_{3-6}$ cycloalkyl, and $C_{3-6}$ heterocycloalkyl is unsubstituted or substituted with 1-3 groups independently selected from the group consisting of halide, deuterium, —OH, —CN, $C_{3-6}$ cycloalkyl, $C_{1-3}$ alkoxy, and $C_{3-6}$ heterocycloalkyl comprising N or O; or R and $R_{24}$, together with N atom they attached to, form a 5-7 membered heterocycle; and
  R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or
  R' and $R_{21}$, together with N atom they attached to, form a 5-7 membered heterocycle.

In some embodiments of the present disclosure, the disclosed compound is according to Formula IIa:

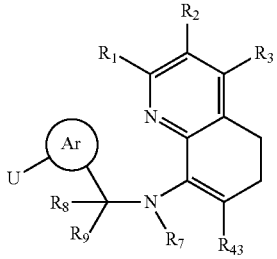

IIa or a pharmaceutically acceptable salt, hydrate, solvate, stereoisomer or tautomer thereof, wherein
  Ar is unsubstituted or substituted with 1-4 groups of $R_{31}$, and Ar is selected from the group consisting of:

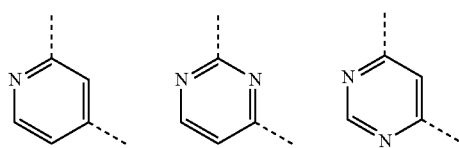

-continued

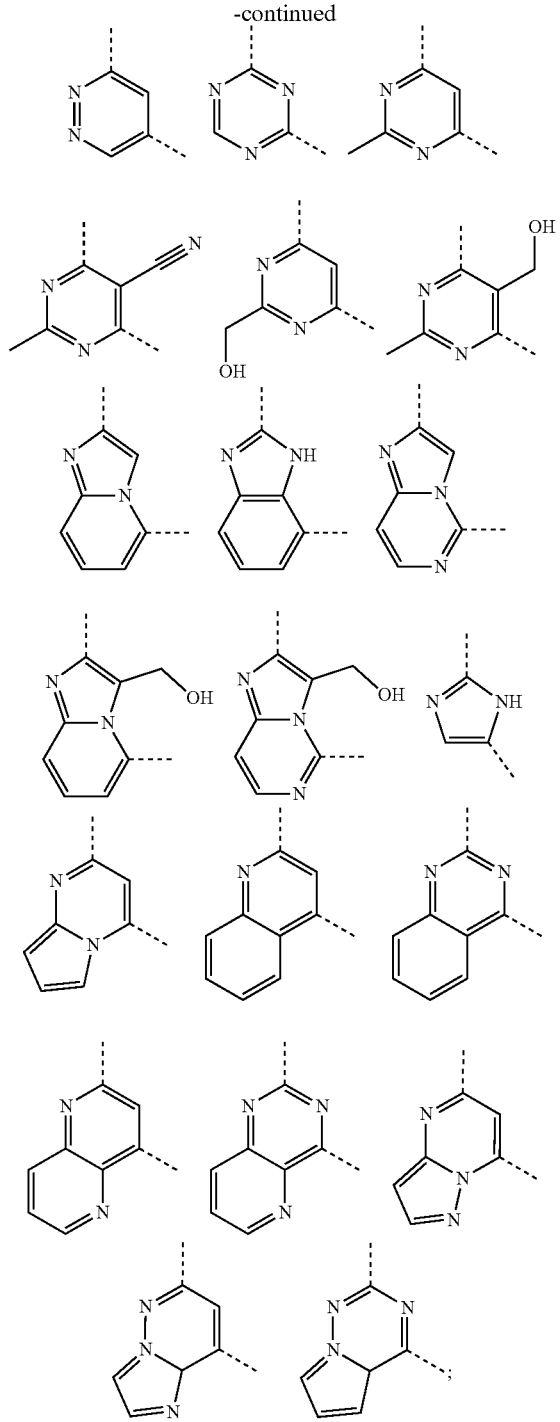

each of $R_1$, $R_2$, $R_3$, and $R_{43}$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, —S(=O)$_2$($C_{1-6}$ alkyl), $C_{3-6}$ cycloalkyl, $C_{1-8}$ alkoxy, $C_{2-6}$ alkenyl, and $C_{2-6}$ alkynyl, wherein each of $C_{1-6}$ alkyl, $C_{3-6}$ cycloalkyl, $C_{1-8}$ alkoxy, $C_{2-6}$ alkenyl, and $C_{2-6}$ alkynyl is unsubstituted or substituted with 1-3 groups independently selected from the group consisting of halide, —OH, methanesulfonyl, and deuterium.

In some embodiments of the present disclosure, the disclosed compound is according to Formula IIb:

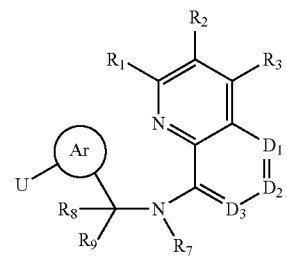

IIb or a pharmaceutically acceptable salt, hydrate, solvate, stereoisomer or tautomer thereof, wherein each of $D_1$, $D_2$ and $D_3$ is independently selected from the group consisting of N and $CR'_4$;

Ar is unsubstituted or substituted with 1-4 groups of $R_{31}$, and Ar is selected from the group consisting of:

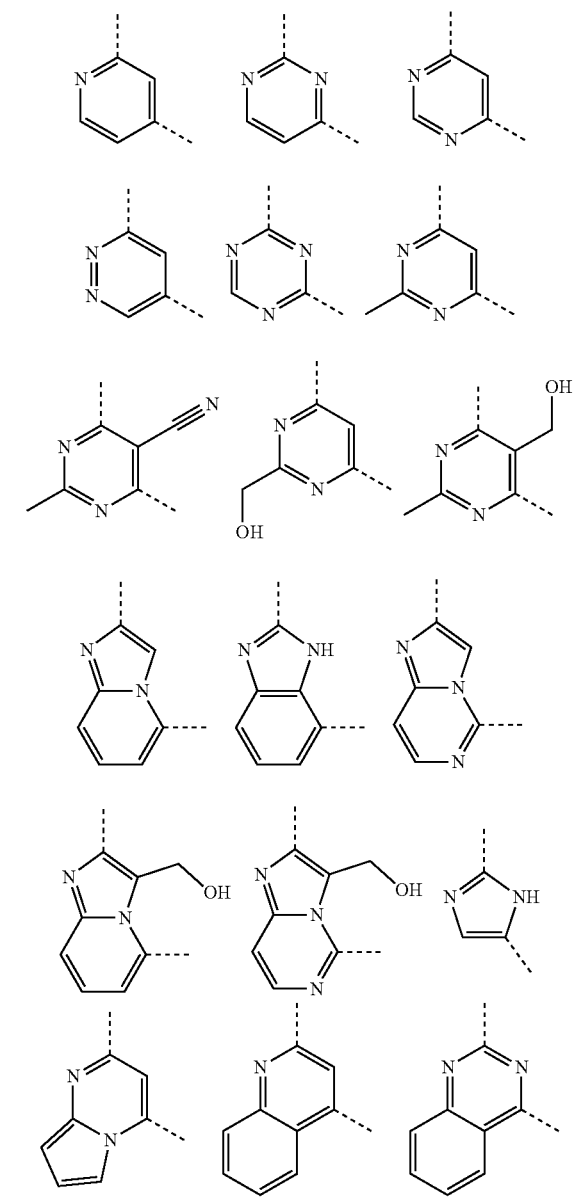

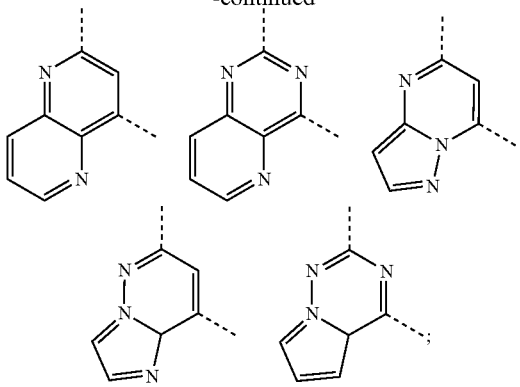

each of $R_1$, $R_2$, $R_3$, and $R'_4$ is independently selected from the group consisting of H, deuterium, —CN, halide, —OH, amino, $C_{1-6}$ alkyl, —NH($C_{1-6}$ alkyl), —N($C_{1-6}$ alkyl)$_2$, —S(=O)$_2$($C_{1-6}$ alkyl), $C_{3-6}$ cycloalkyl, $C_{1-8}$ alkoxy, $C_{2-6}$ alkenyl, and $C_{2-6}$ alkynyl, wherein each of $C_{1-6}$ alkyl, $C_{3-6}$ cycloalkyl, $C_{1-8}$ alkoxy, $C_{2-6}$ alkenyl, and $C_{2-6}$ alkynyl is unsubstituted or substituted with 1-3 groups independently selected from the group consisting of halide, —OH, methanesulfonyl, and deuterium.

In some embodiments of the present disclosure, for the disclosed compound:

$R_{23}$ is selected from the group consisting of H, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, —NH($C_{1-6}$ alkyl), —N($C_{1-6}$ alkyl)$_2$, and $C_{1-3}$ alkoxy;

each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), and $C_{1-3}$ alkoxy; or $R_{21}$ and $R_{23}$, together with atoms they attached to, form a ring;

each of R and $R_{24}$ is independently selected from the group consisting of H, $C_{1-6}$ alkyl, $C_{3-6}$ cycloalkyl, $C_{3-6}$ heterocycloalkyl comprising N or O, —C(=O)($C_{1-6}$ alkyl), —C(=O)O($C_{1-6}$ alkyl), and —C(=O)NH($C_{1-6}$ alkyl), wherein each of $C_{1-6}$ alkyl and $C_{3-6}$ cycloalkyl is unsubstituted or substituted with 1-3 groups independently selected from the group consisting of halide, deuterium, —OH, —CN, $C_{3-6}$ cycloalkyl, $C_{1-3}$ alkoxy, and $C_{3-6}$ heterocycloalkyl comprising N or O; or R and $R_{24}$, together with atoms they attached to, form a 5-7 membered heterocycle;

R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{1-6}$ alkyl, $C_{3-6}$ cycloalkyl, $C_{1-3}$ alkoxy; or R' and $R_{21}$, together with atoms they attached to, form a 5-7 membered heterocycle.

In some embodiments of the present disclosure, for the disclosed compound selected from the group consisting of:

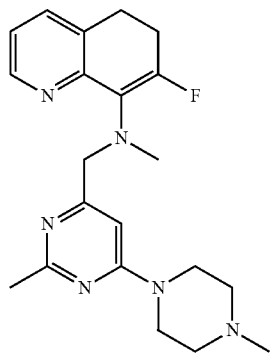

D1

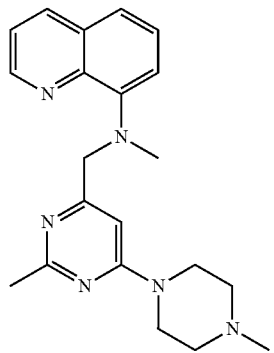

D2

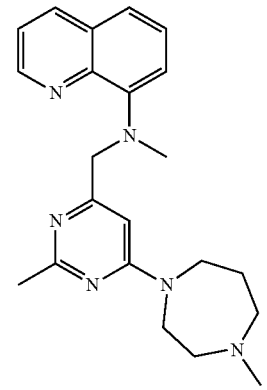

D3

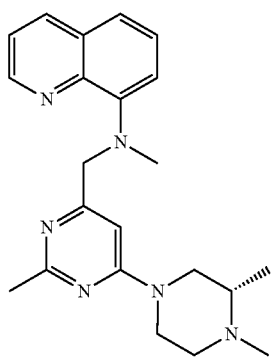

D4

D5
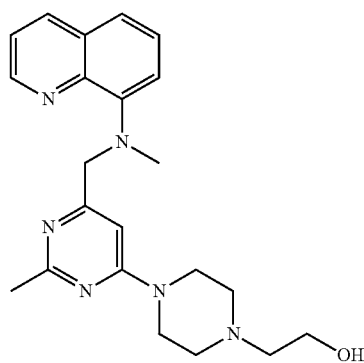
D6
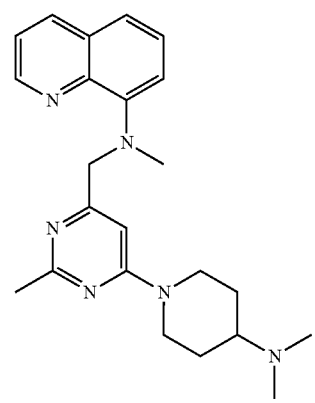
D7
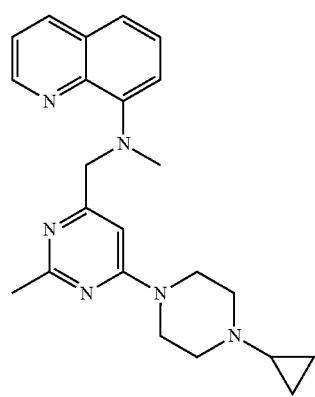
D8
D9
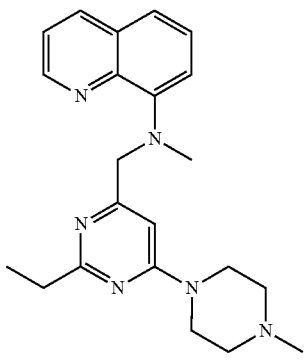
D10
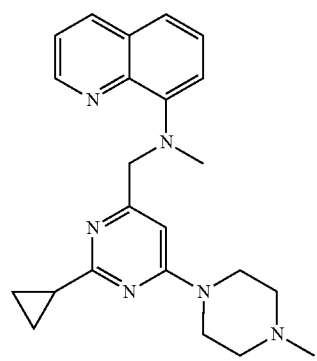
D11
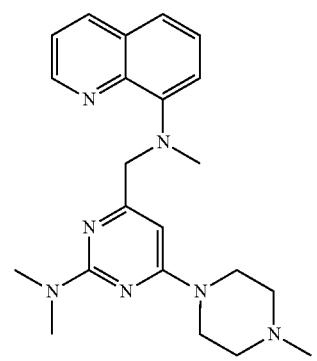
D12
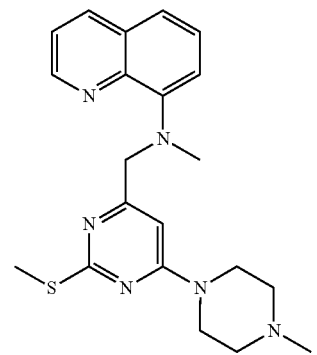

D13
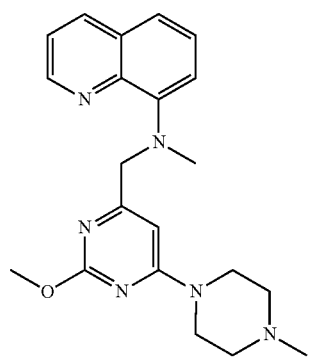
D14
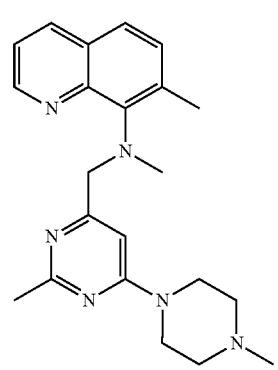
D15
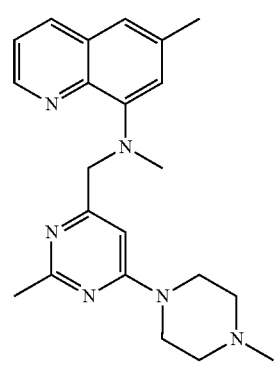
D16
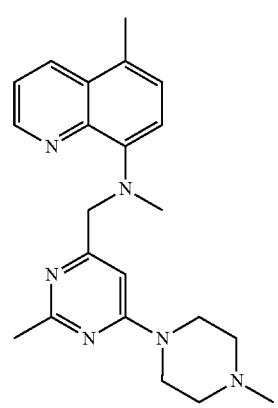
D17
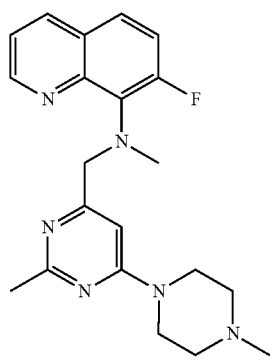
D18
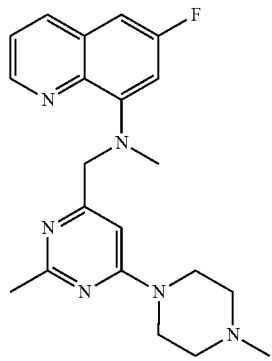
D19
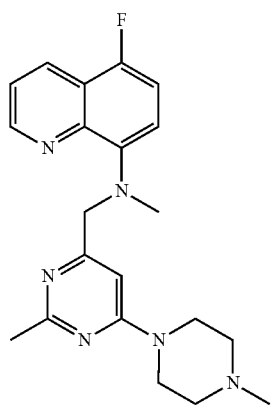
D20
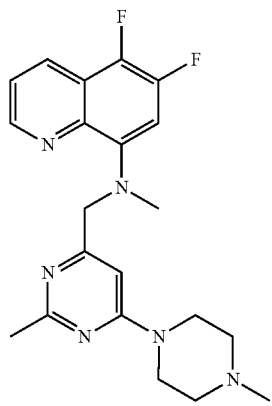

-continued
D21
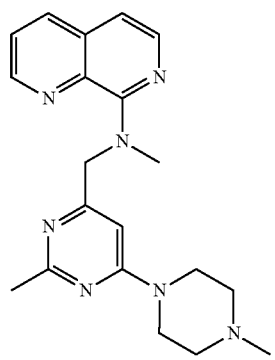
D22
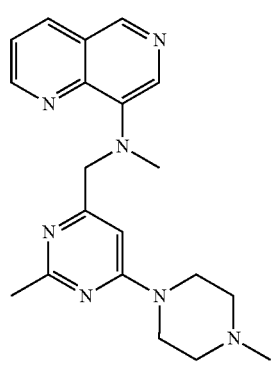
D23
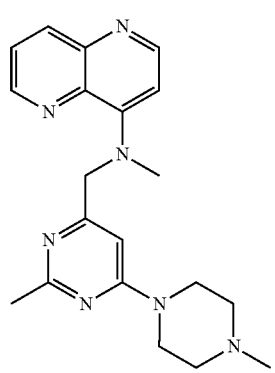
D24
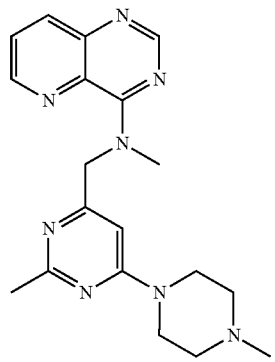
-continued
D25
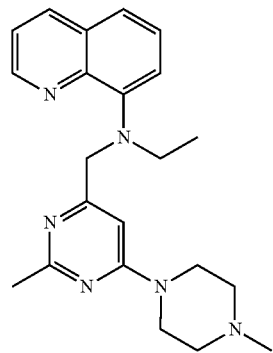
D26
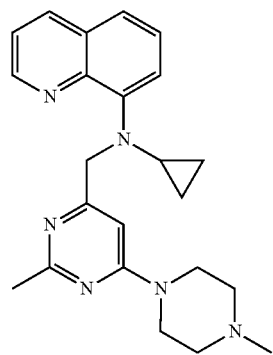
D27
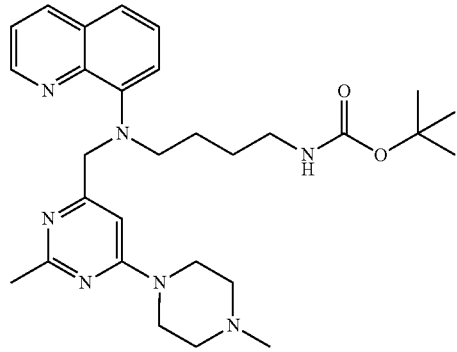
D28
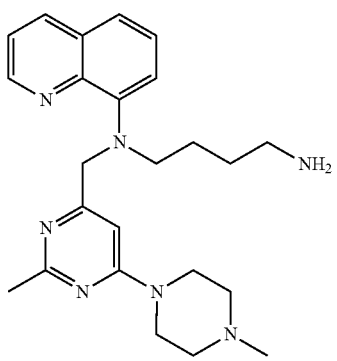

-continued
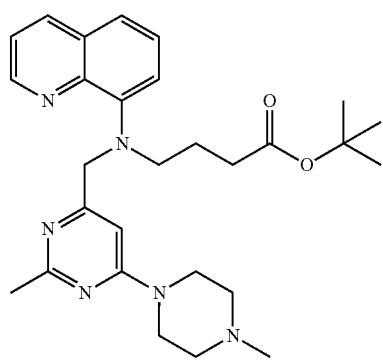
D29
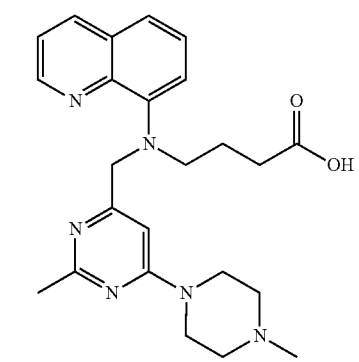
D30
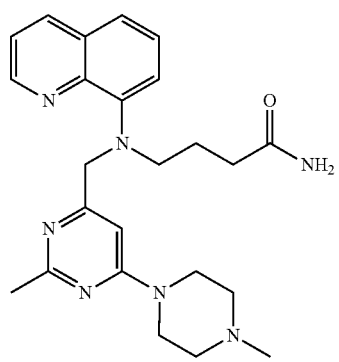
D31
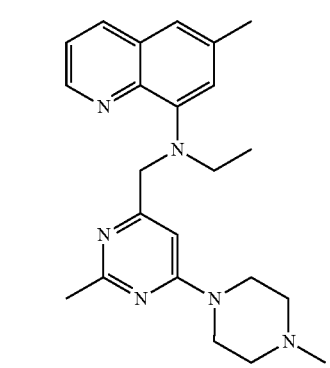
D32
-continued
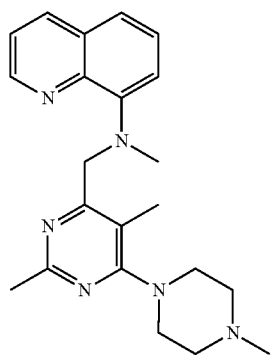
D33
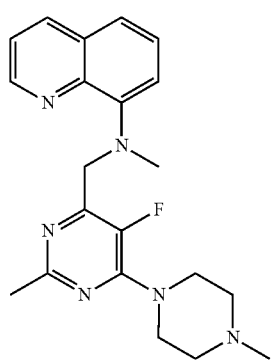
D34
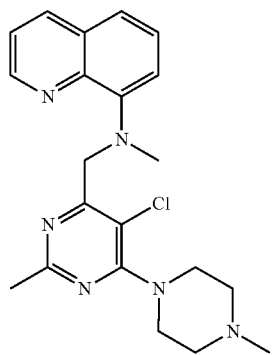
D35
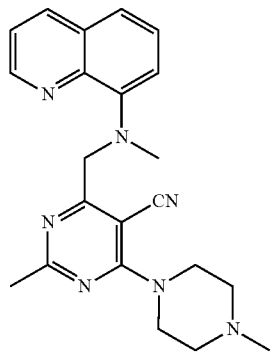
D36

D37 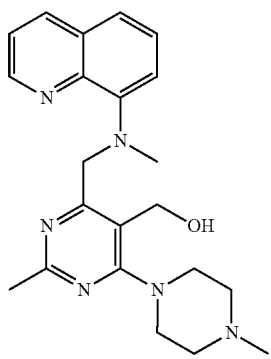
D38 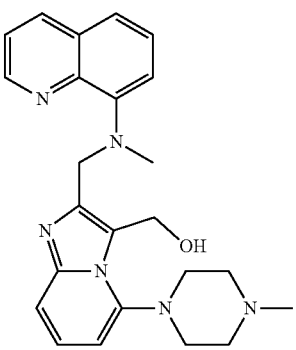
D39 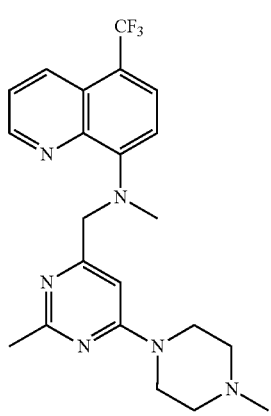
D40
D41 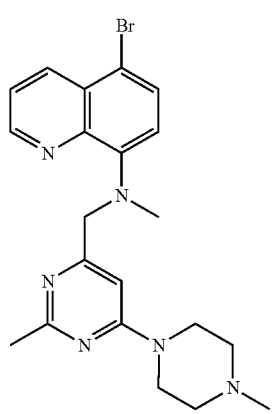
D42 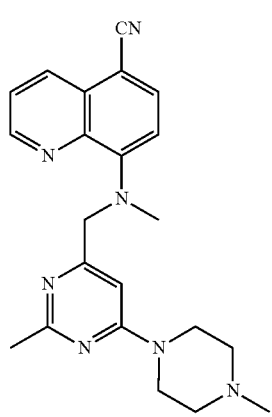
D43 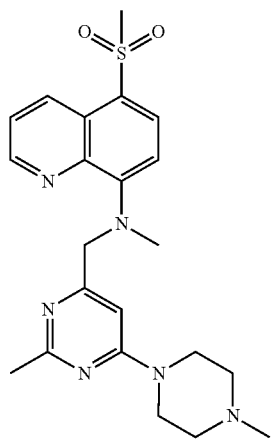
D44 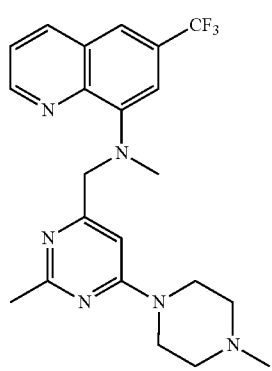

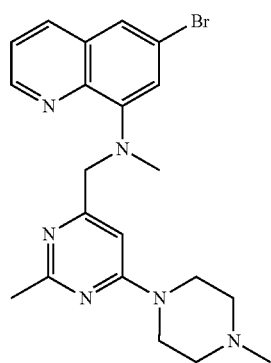
D45
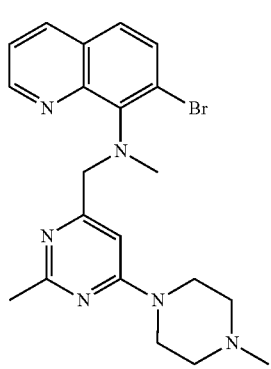
D49
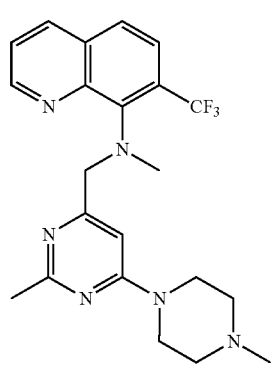
D46
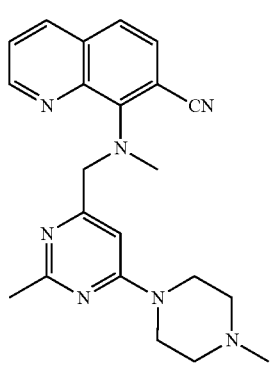
D50
D47
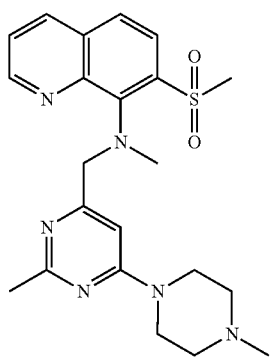
D51
D48
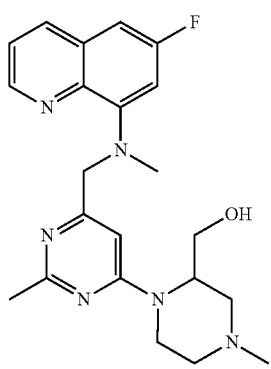
D52

-continued
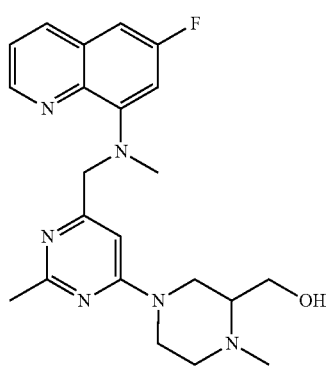
D53
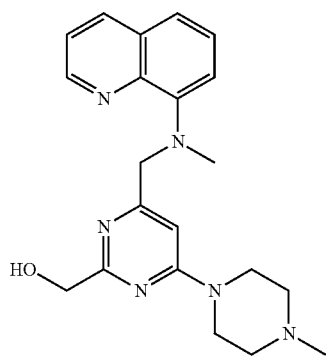
D54
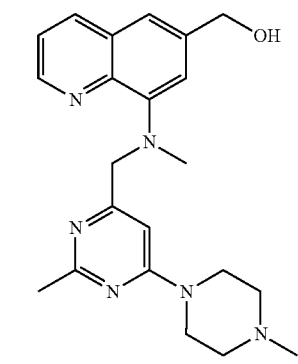
D55
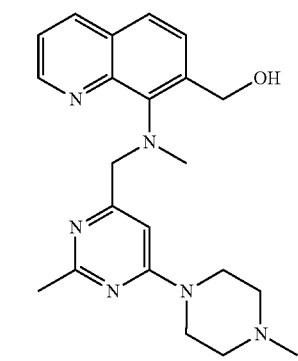
D56
-continued
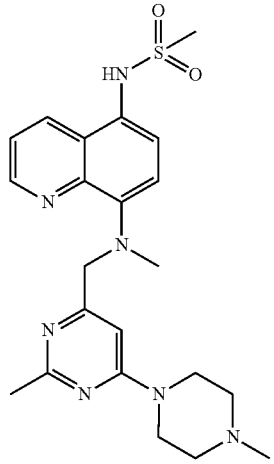
D57
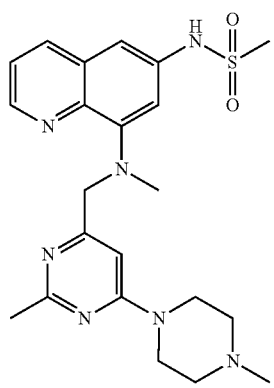
D58
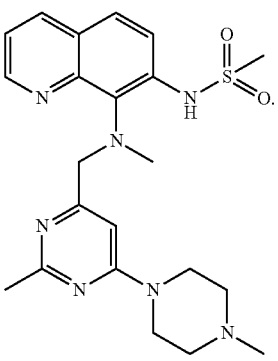
D59
In some embodiments of the present disclosure, the disclosed compound is according to Formula III:
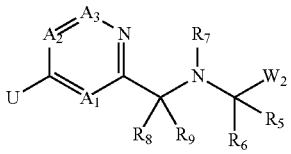
III
wherein
each of $A_1$, $A_2$, and $A_3$ is independently selected from the group consisting of N and $CR_{44}$, wherein at least one of $A_1$, $A_2$, and $A_3$ is N;

$W_2$ is

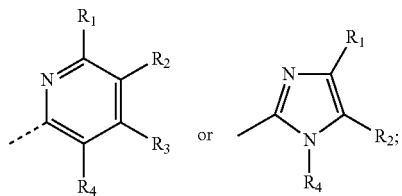

each of $R_1$, $R_2$, $R_3$, and $R_4$ is independently selected from the group consisting of H, deuterium, —CN, halide, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), —NHS(=O)$_2$($C_{1-6}$ alkyl), $C_{1-6}$ alkyl, $C_{3-6}$ cycloalkyl, $C_{1-8}$ alkoxy, $C_{2-6}$ alkenyl, and $C_{2-6}$ alkynyl, wherein each of $C_{1-6}$ alkyl, $C_{3-6}$ cycloalkyl, and $C_{1-8}$ alkoxy is unsubstituted or substituted with 1-3 groups independently selected from the group consisting of halide and deuterium;

each of $R_5$ and $R_6$ is independently selected from the group consisting of H, deuterium, —CN, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), and $C_{1-3}$ alkoxy; or $R_5$ is O or $CR_{45}R_{46}$, and $R_4$ and $R_5$, together with atoms they attached to, form a ring;

$R_7$ is selected from the group consisting of H, $C_{1-6}$ alkyl, $C_{3-6}$ cycloalkyl, and $C_{3-6}$ heterocycloalkyl comprising an O, wherein each of $C_{1-6}$ alkyl, $C_{3-6}$ cycloalkyl, and $C_{3-6}$ heterocycloalkyl is unsubstituted or substituted with 1-3 groups independently selected from the group consisting of halide, deuterium, $C_{3-6}$ cycloalkyl, and $C_{3-6}$ heterocycloalkyl comprising an O;

each of $R_8$ and $R_9$ is independently selected from the group consisting of H, deuterium, —CN, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, and $C_{1-3}$ alkoxy; or $R_7$ and $R_8$, and atoms attached thereto, form a ring;

or $R_8$ and $R_9$, together with atoms they attached to, form a ring;

$R_{44}$ is H, deuterium, halide, —CN, —OH, amino, $C_{1-6}$ alkyl, $C_{3-6}$ cycloalkyl, $C_{1-8}$ alkoxy, —NH($C_{1-6}$ alkyl), —N($C_{1-6}$ alkyl)$_2$, —C(=O)NH($C_{1-6}$ alkyl), —C(=O)N($C_{1-6}$ alkyl)$_2$, —S($C_{1-6}$ alkyl), $C_{2-6}$ alkenyl, $C_{2-6}$ alkynyl, 4-7 membered heterocycle comprising 1-3 heteroatoms independently selected from the groups consisting of O, N and S, aryl, and 5-6 membered heteroaryl, wherein each of $C_{1-6}$ alkyl, $C_{3-6}$ cycloalkyl, $C_{1-8}$ alkoxy, heterocycle, aryl and heteroaryl is unsubstituted or substituted with 1-3 groups independently selected from the group consisting of halide, deuterium, —OH and $C_{1-3}$ alkoxy;

$R_{23}$ is selected from the group consisting of H, $C_{1-6}$ alkyl and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, —NH($C_{1-6}$ alkyl), —N($C_{1-6}$ alkyl)$_2$, and $C_{1-3}$ alkoxy;

each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, amino, —NH($C_{1-6}$ alkyl), —N($C_{1-6}$ alkyl)$_2$, —NHC(=O) ($C_{1-6}$ alkyl), —NHC(=O)O($C_{1-6}$ alkyl), and $C_{1-3}$ alkoxy; or $R_{22}$ and $R_{23}$, together with atoms they attached to, form a ring; or $R_{19}$ and $R_{26}$, together with atoms they attached to, form a ring; or $R_{21}$ and $R_{26}$, together with atoms they attached to, form a ring;

each of R and $R_{24}$ is independently selected from the group consisting of H, $C_{1-6}$ alkyl, $C_{3-6}$ cycloalkyl, $C_{3-6}$ heterocycloalkyl comprising N or O, —C(=O)($C_{1-6}$ alkyl), —C(=O)O($C_{1-6}$ alkyl), and —C(=O)NH($C_{1-6}$ alkyl), wherein each of $C_{1-6}$ alkyl, $C_{3-6}$ cycloalkyl, and $C_{3-6}$ heterocycloalkyl is unsubstituted or substituted with 1-3 groups independently selected from the group consisting of halide, deuterium, —OH, —CN, $C_{3-6}$ cycloalkyl, $C_{1-3}$ alkoxy, and $C_{3-6}$ heterocycloalkyl comprising N or O; or R and $R_{24}$, together with N atom they attached to, form a 5-7 membered heterocycle; or R and $R_{21}$, together with N atom they attached to, form a 5-7 membered heterocycle;

R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R' and $R_{21}$, together with N atom they attached to, form a 5-7 membered heterocycle; and each of $R_{45}$ and $R_{46}$ is independently selected from the group consisting of H, deuterium, halide, $C_{1-3}$ alkyl; or $R_{45}$ and $R_{46}$, together with the atoms they attached to, form a ring.

In some embodiments of the present disclosure, the disclosed compound is according to Formula IIIa or IIIb:

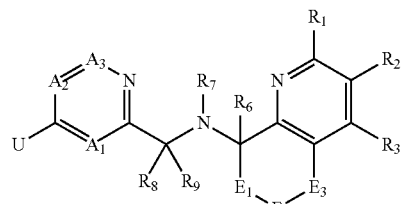

IIIa

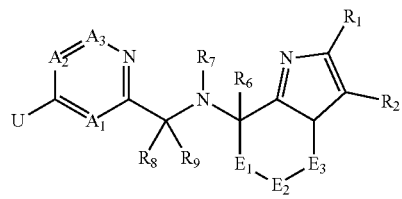

IIIb wherein each of $E_1$, $E_2$, and $E_3$ is independently selected from the group consisting of O and $CR_{45}R_{46}$; and each of $R_{45}$ and $R_{46}$ is independently selected from the group consisting of H, deuterium, halide, $C_{1-3}$ alkyl; or $R_{45}$ and $R_{46}$, together with the atoms they attached to, form a ring.

In some embodiments of the present disclosure, the disclosed compound is according to formula IIIa and IIIb, and each of $E_1$, $E_2$, and $E_3$ is independently selected from the group consisting of $CH_2$, O and

and at least one of $E_1$, $E_2$, and $E_3$ is

In some embodiments of the present disclosure, the disclosed compound is according to formula IIIa and IIIb, and $A_3$ is $CR_{44}$;

each of $A_1$ and $A_2$ is independently selected from the group consisting of N and $CR_{44}$, wherein at least one of $A_1$ and $A_2$ is N;

$W_2$ is

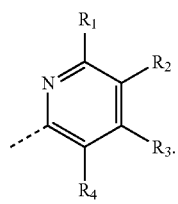

In some embodiments of the present disclosure, $-C(R_5R_6)W_2$ is selected from the group consisting of:

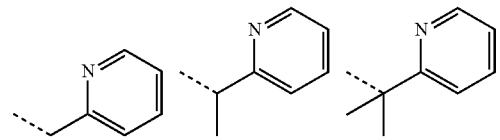

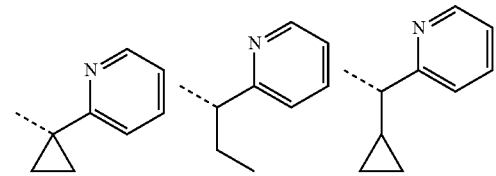

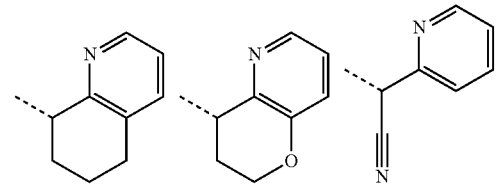

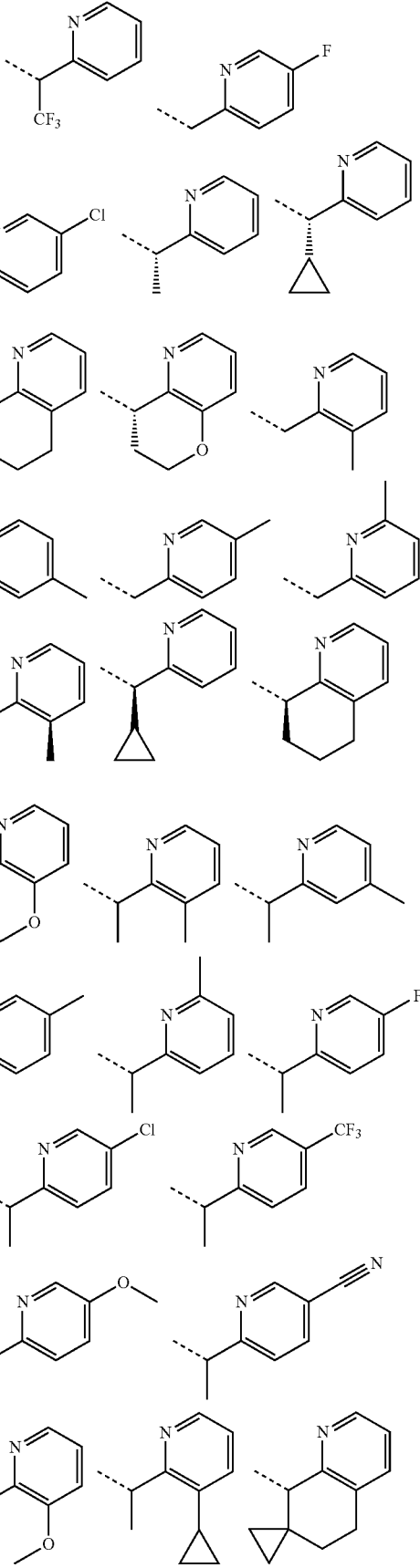

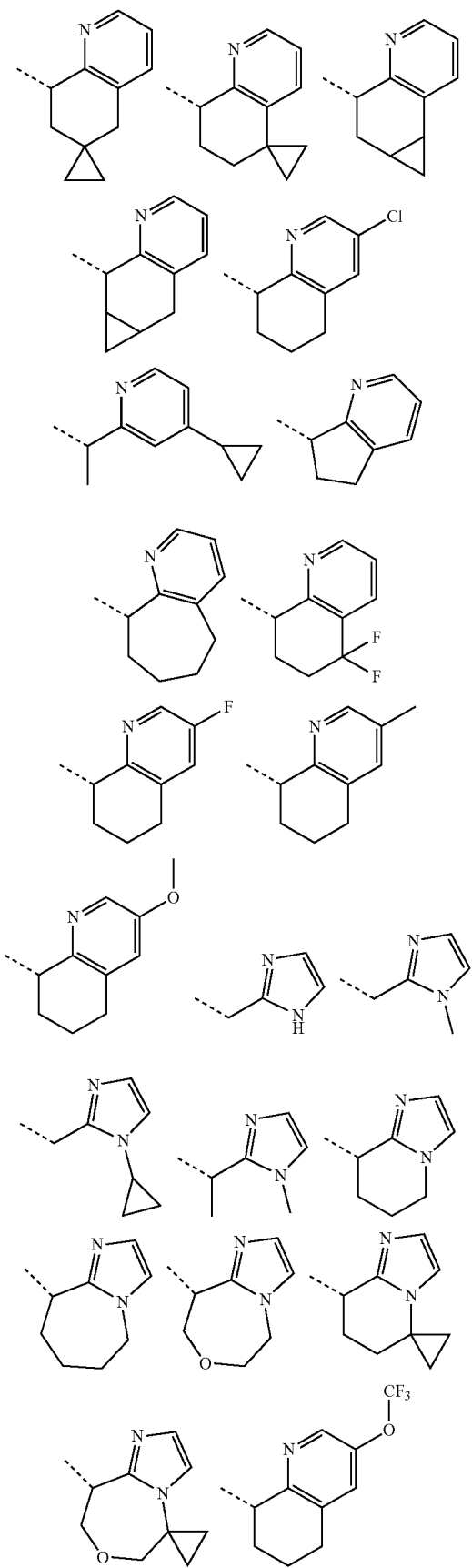
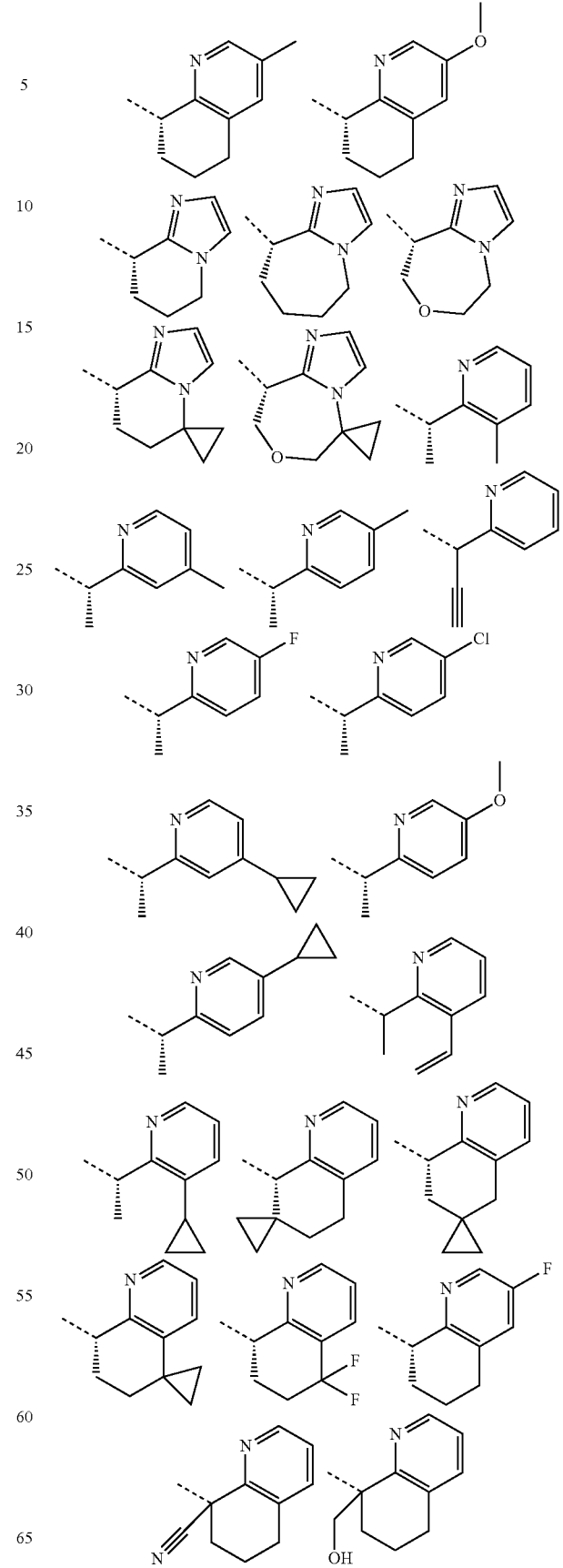

-continued
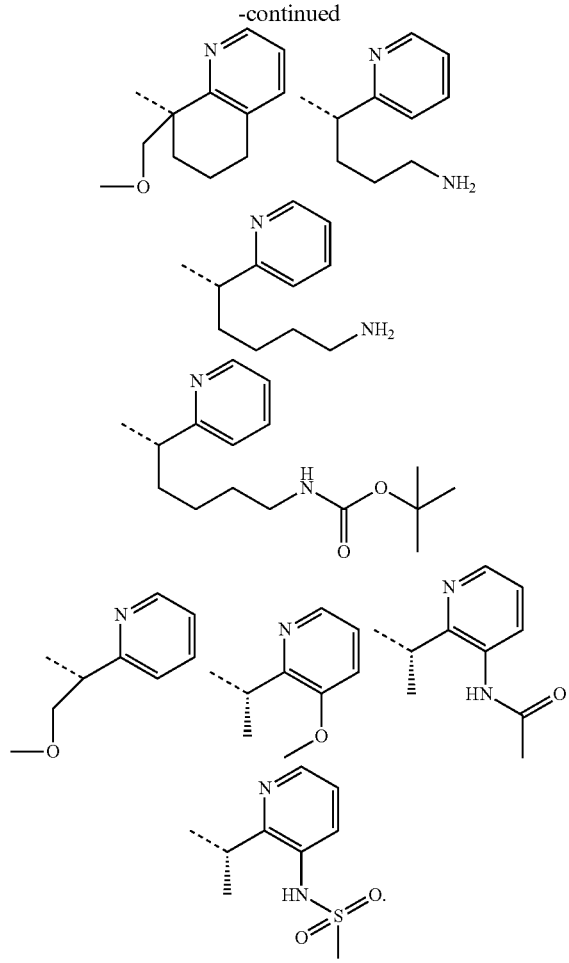
In some embodiments of the present disclosure, for the disclosed compound is selected from the group consisting of:
-continued
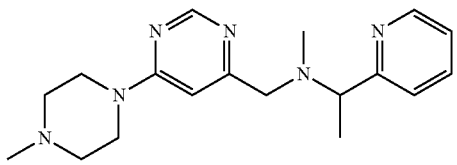
A4
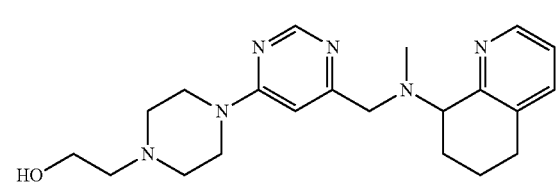
A5
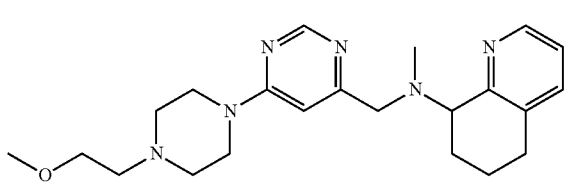
A6
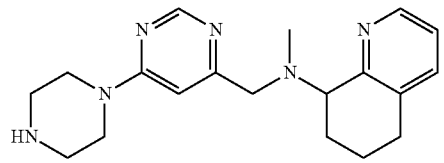
A7
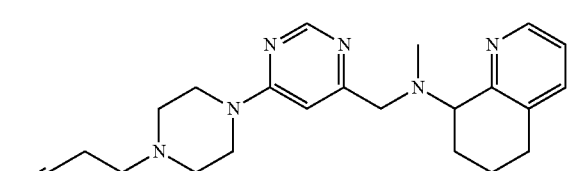
A8
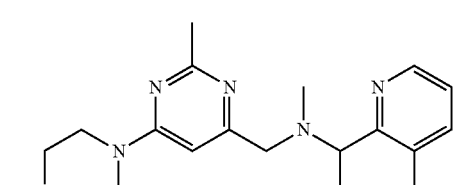
A9
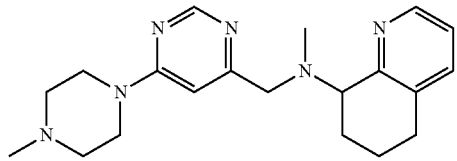
A1
A10
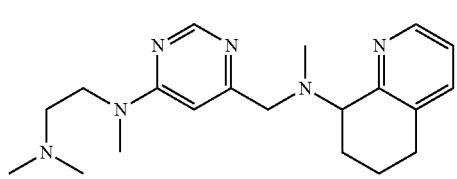
A2
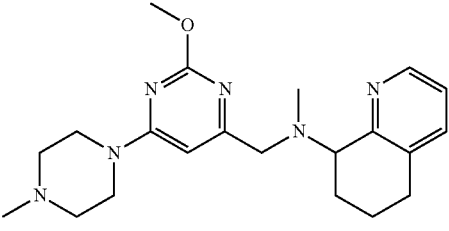
A10
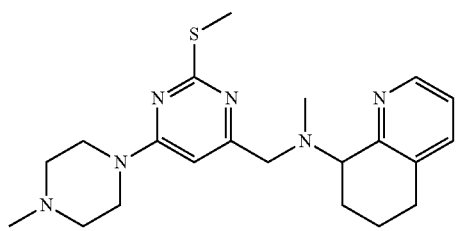
A3
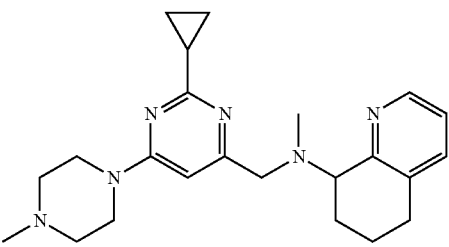
A11

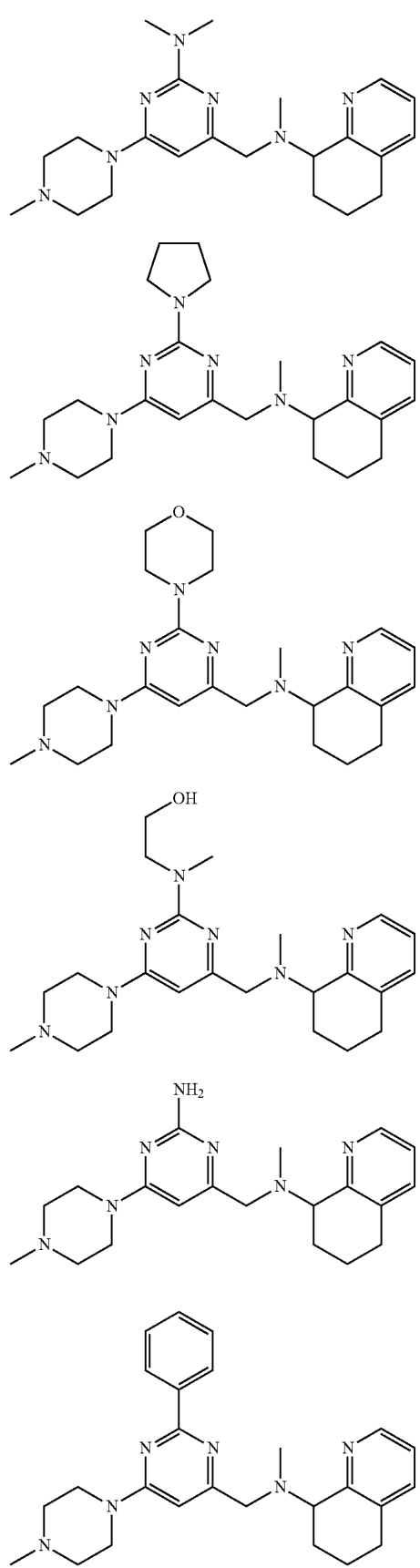
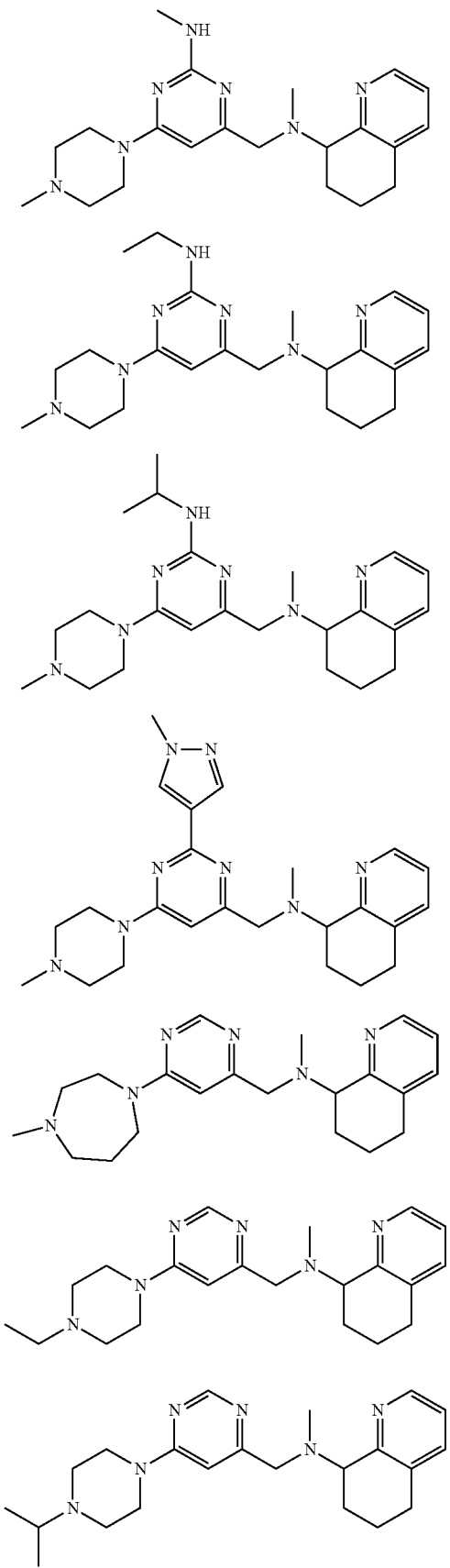

A25 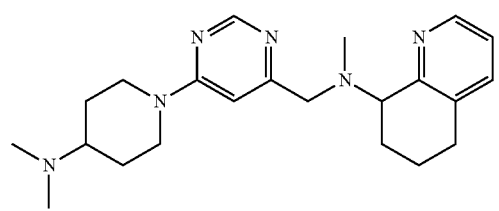
A26 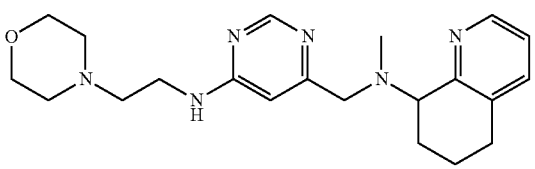
A27 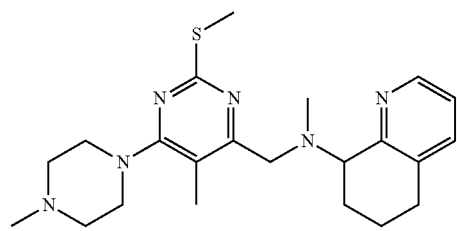
A28 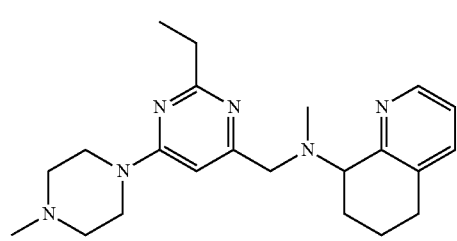
A29 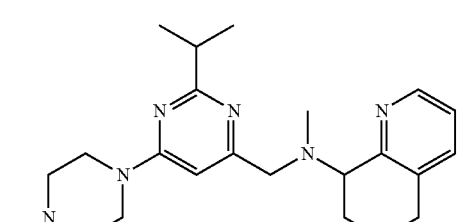
A30 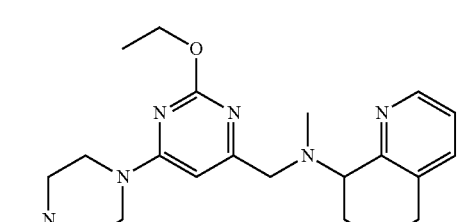
A31
A32 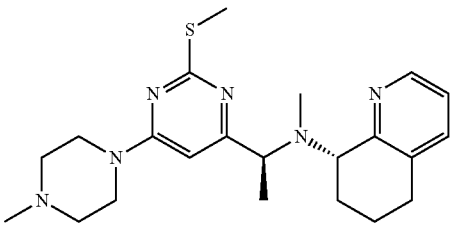
A33 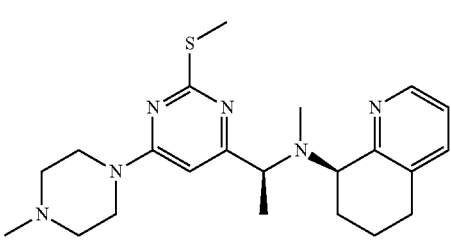
A34 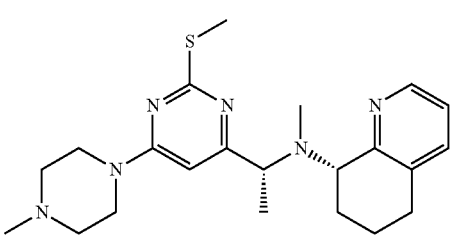
A35 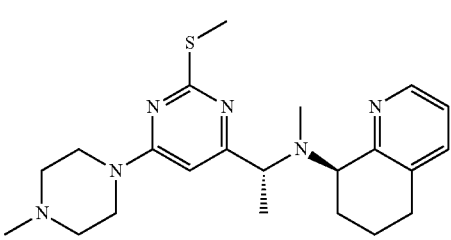
A36 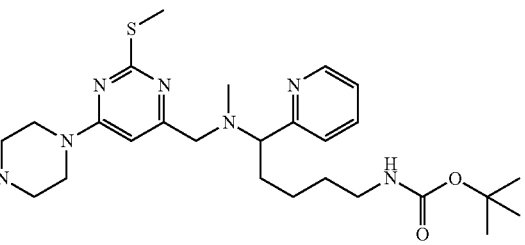
A37 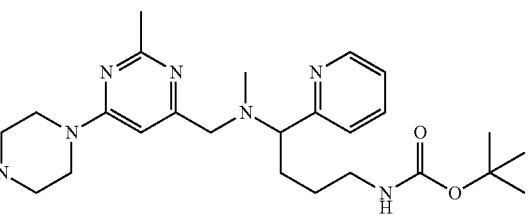

-continued
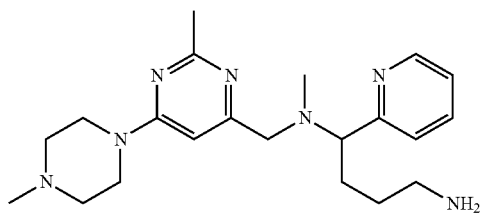
A38
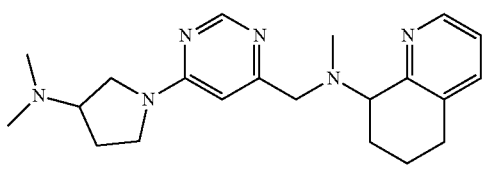
A39
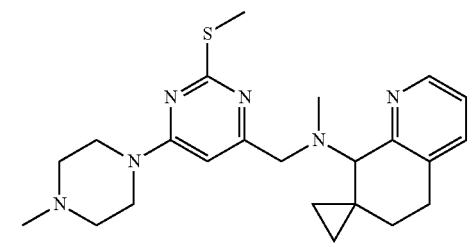
A40
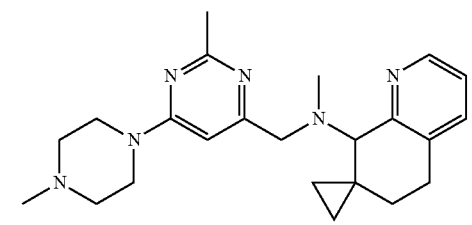
A41
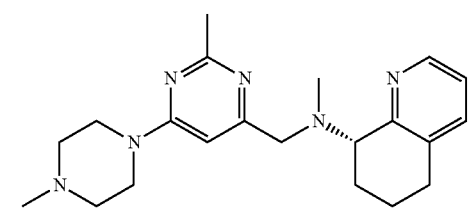
A42
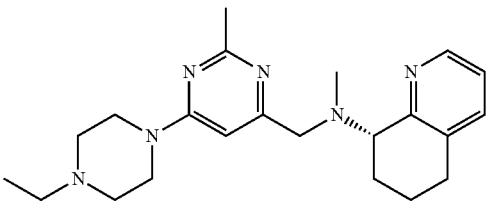
A43
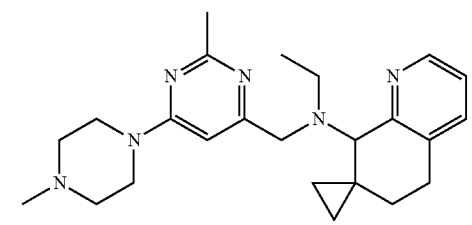
A44
-continued
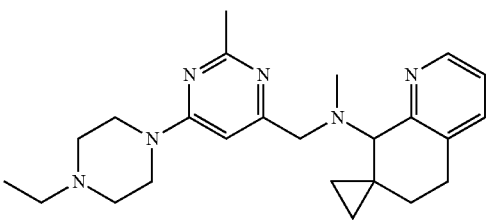
A45
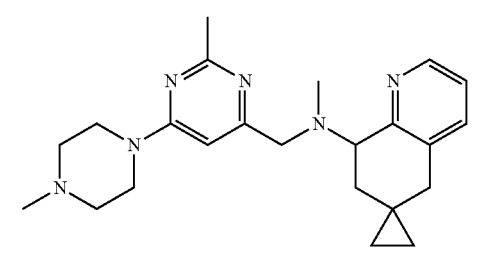
A46
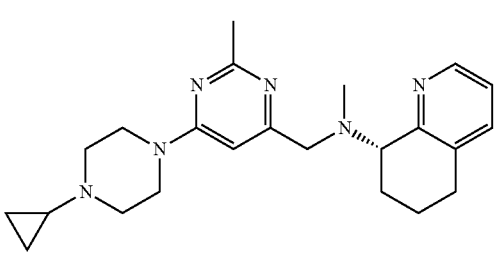
A47
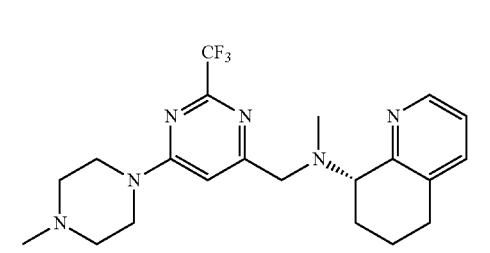
A48
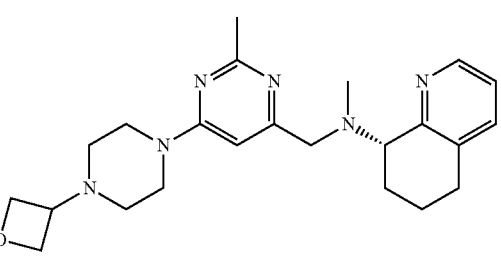
A49
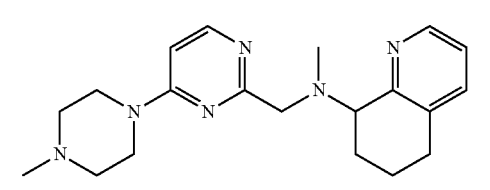
A50
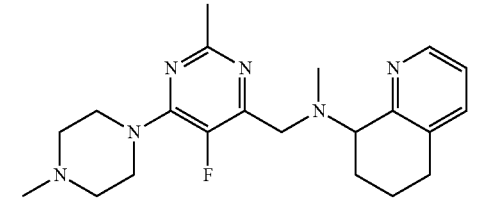
A51

A52 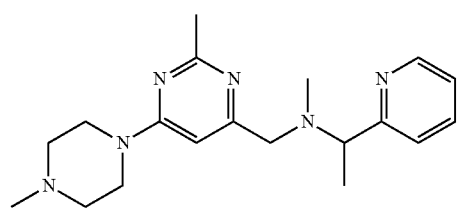
A53 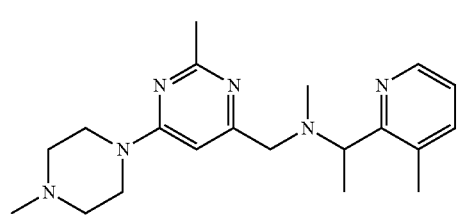
A54 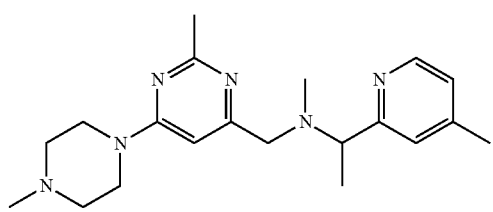
A55 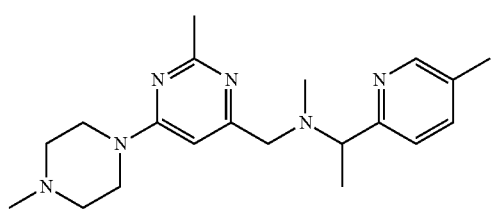
A56 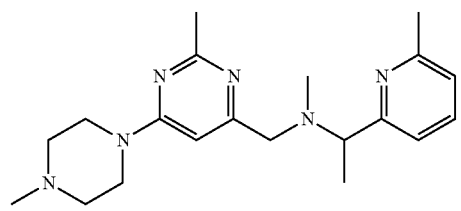
A57 
A58 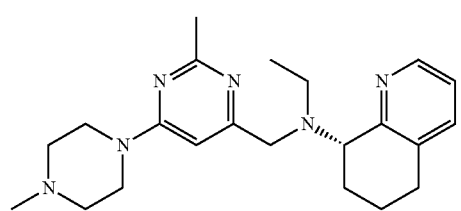
A59 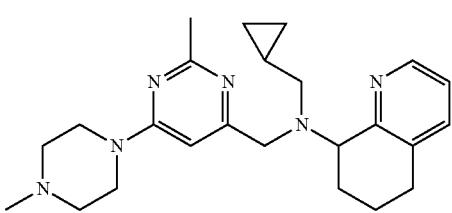
A60 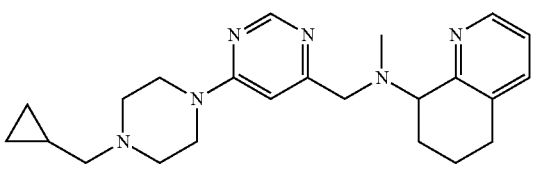
A61 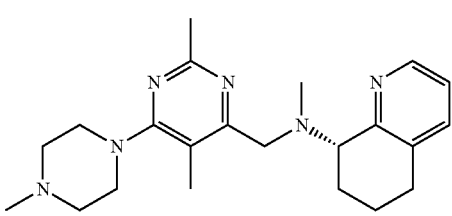
A62 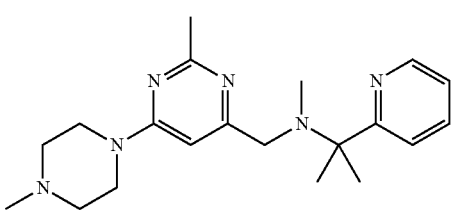
A63 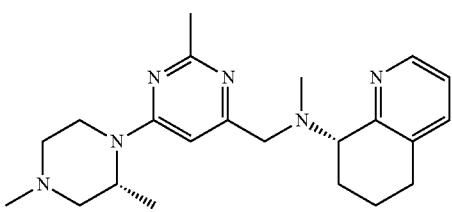
A64 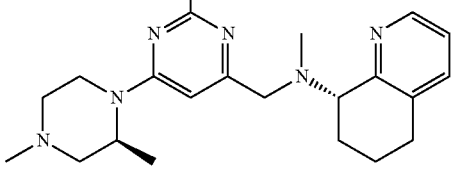
A65 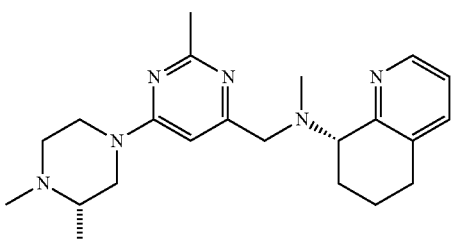

A66
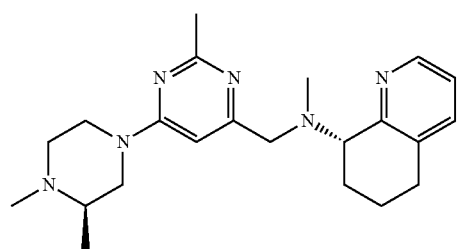
A67
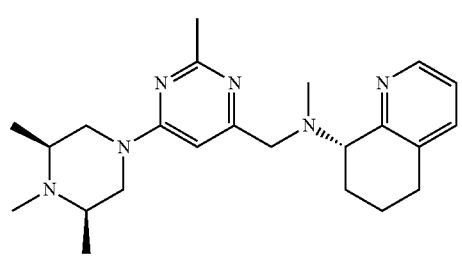
A68
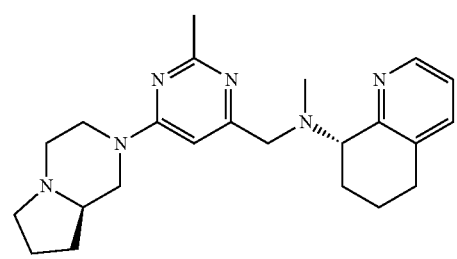
A69
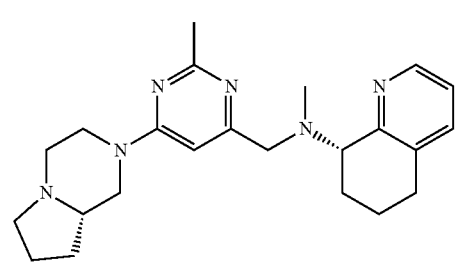
A70
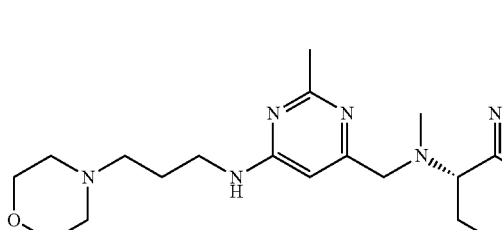
A71
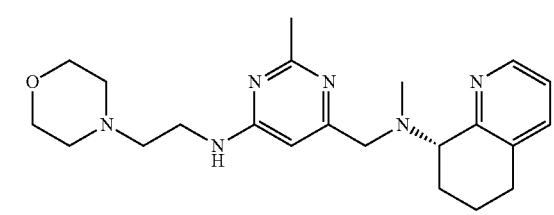
A72
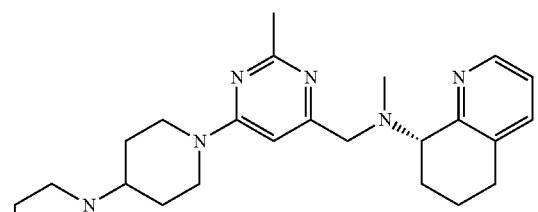
A73
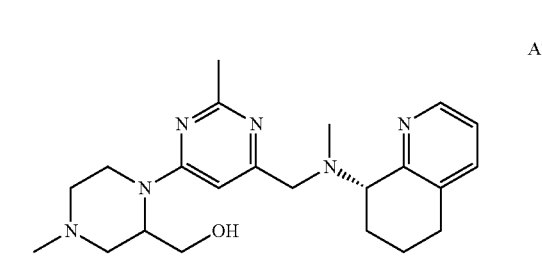
A74
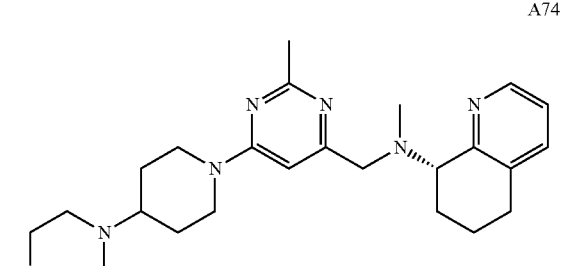
A75
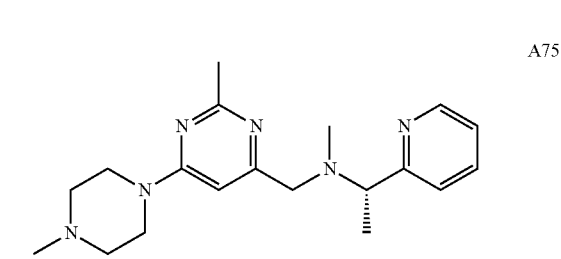
A76
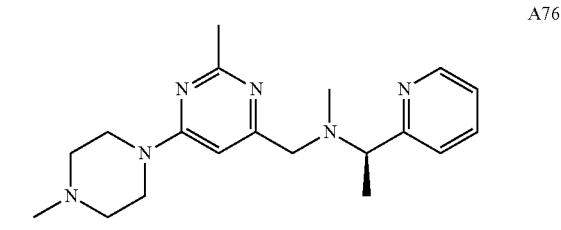
A77
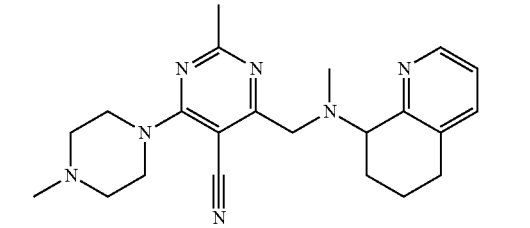

-continued
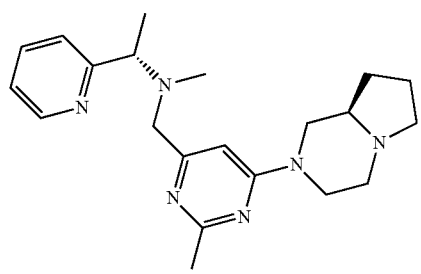
A78
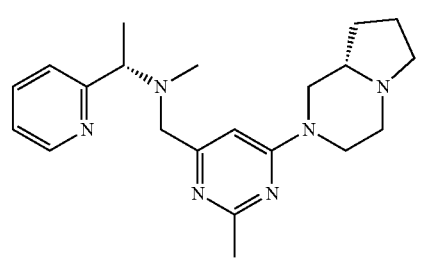
A79
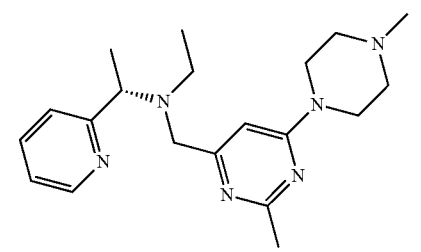
A80
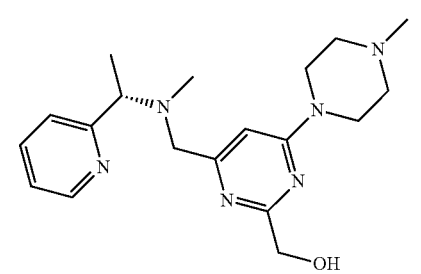
A81
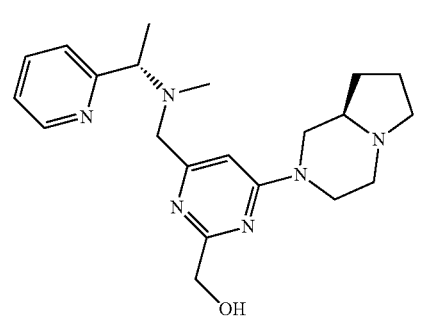
A82
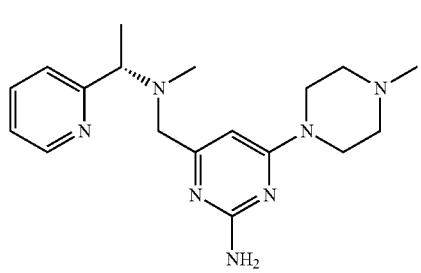
A83
-continued
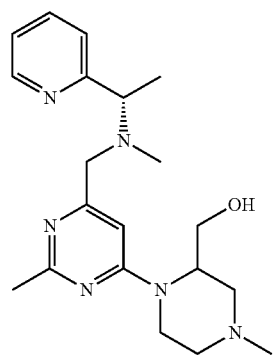
A84
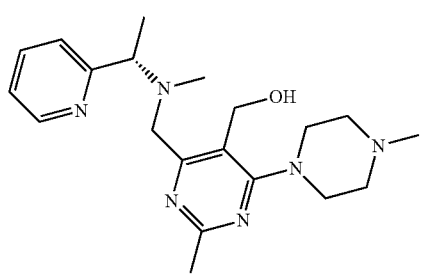
A85
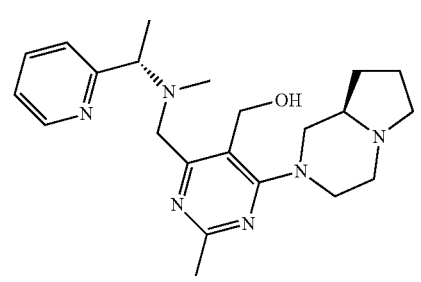
A86
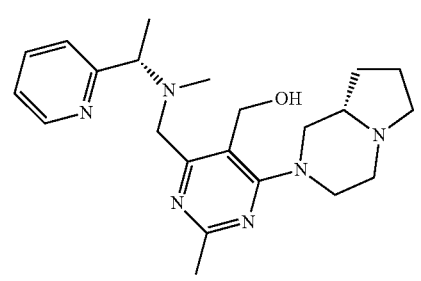
A87
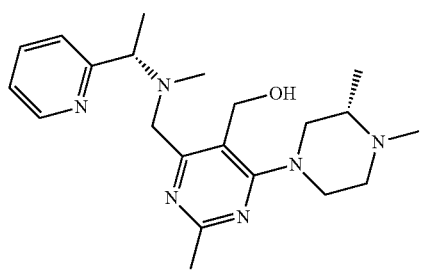
A88

-continued
A89
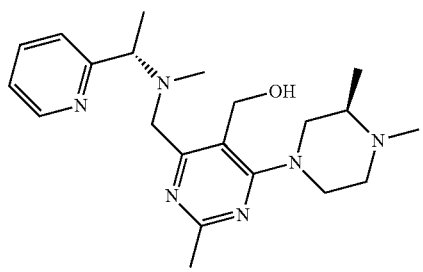
A90
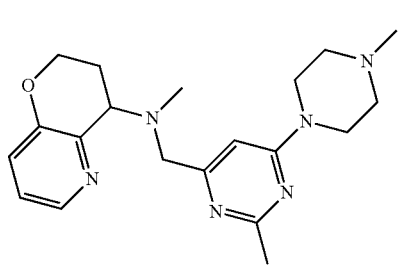
A91
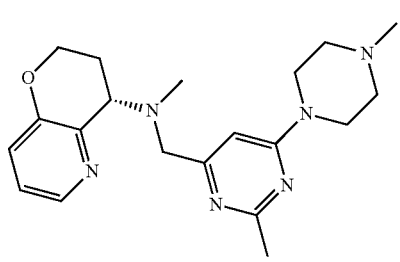
A92
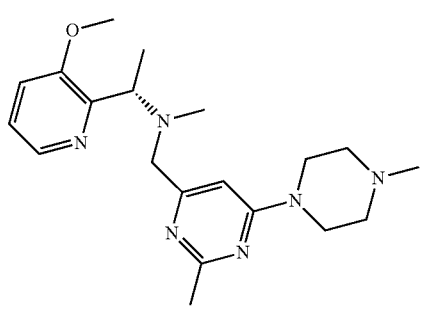
A93
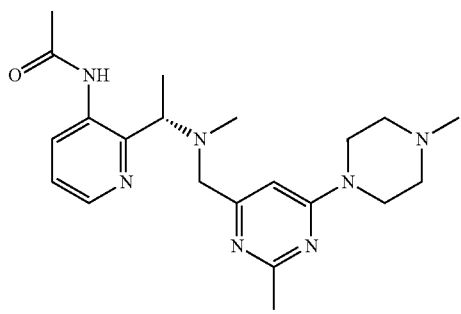
-continued
A94
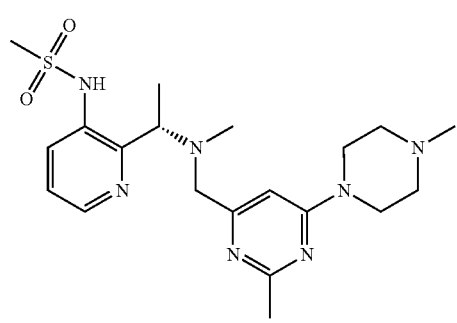
A95
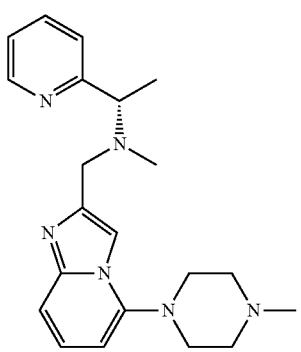
A96
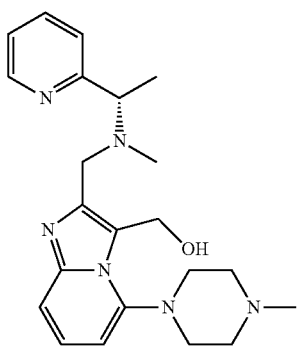
A97
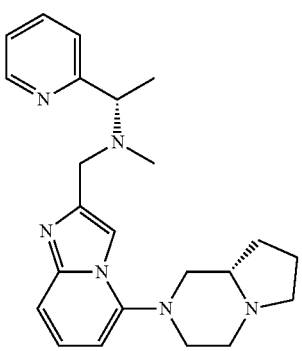

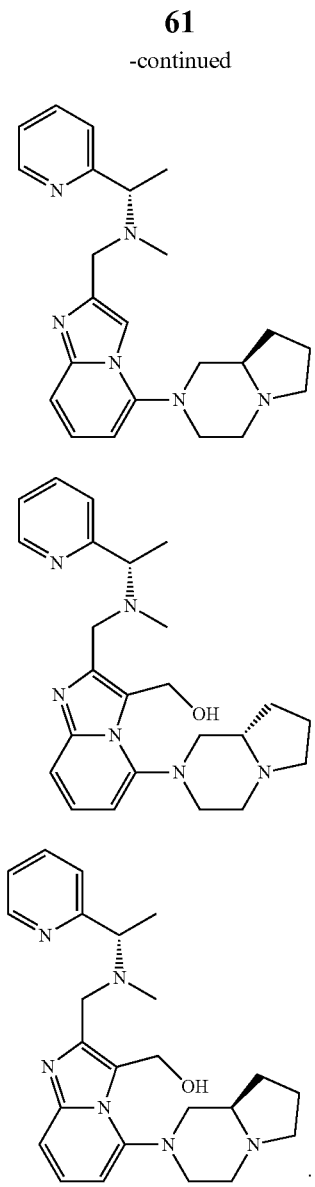
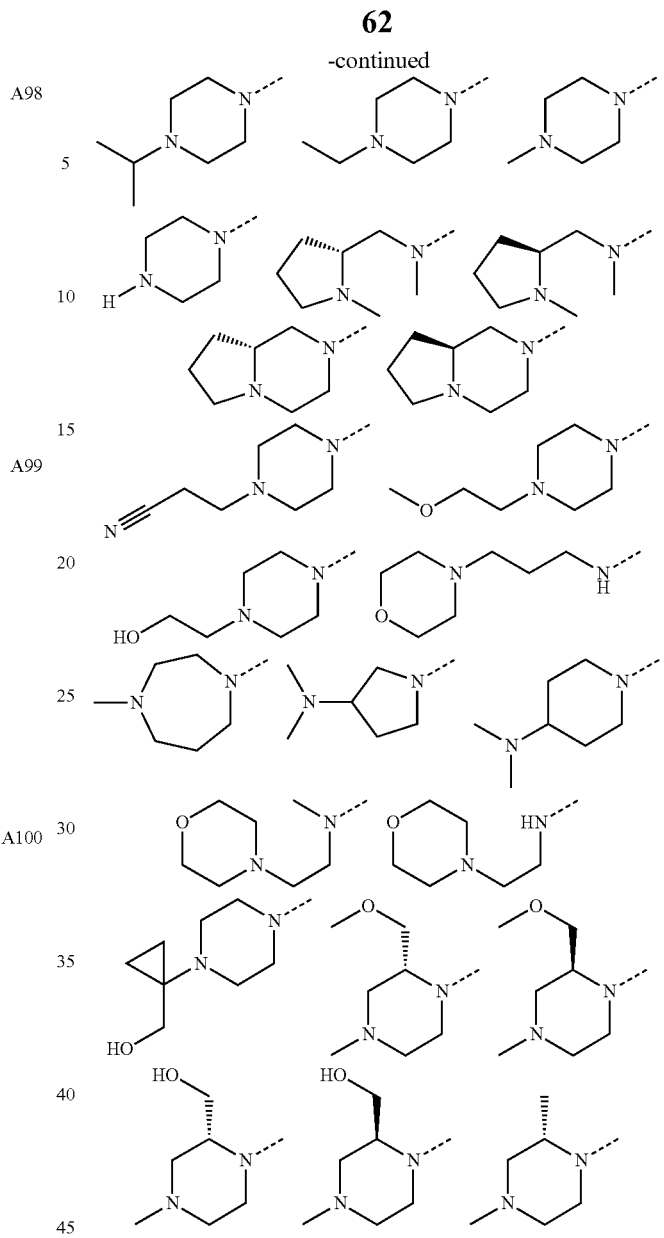
In some embodiments of the present disclosure, of formulas I, Ia, Ib, Ic, II, IIa, IIb, III, IIIa, and IIIb or other compounds disclosed herein, U is unsubstituted or substituted with is unsubstituted or substituted with 1-3 groups selected from the group consisting of deuterium, halide, —OH, $C_{1-3}$ alkyl, and $C_{1-3}$ alkoxy, and U is selected from the group consisting of:
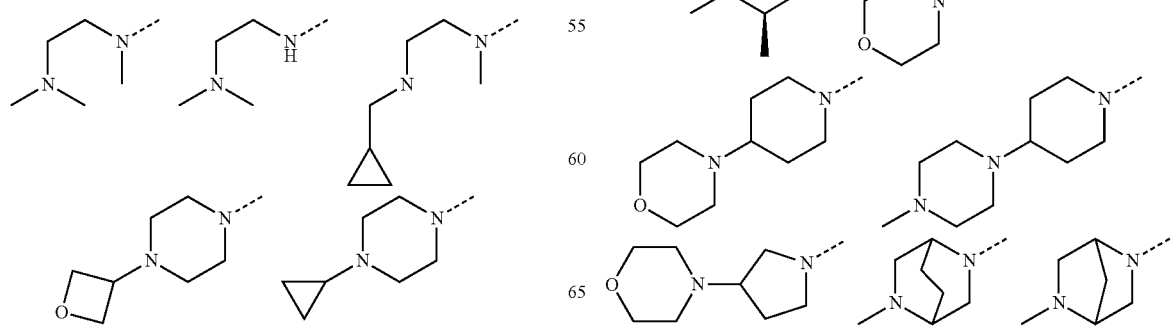

-continued

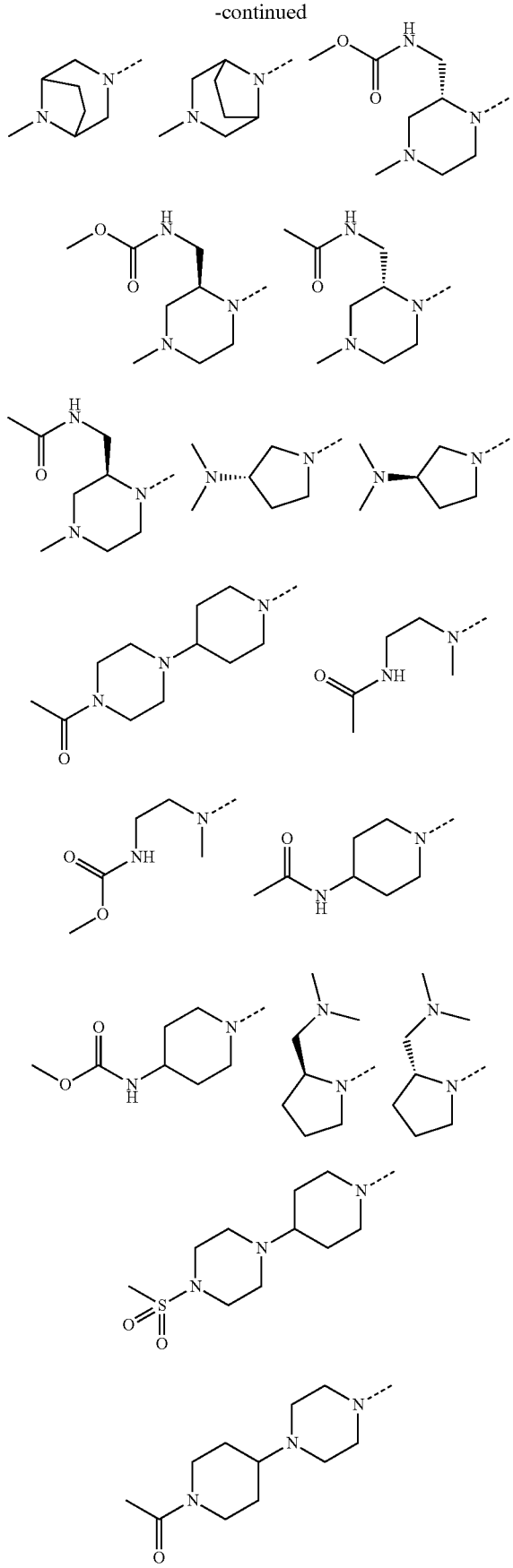

Another aspect of the present disclosure provides a pharmaceutical composition comprising a therapeutically effective amount of a compound of formulas I, Ia, Ib, Ic, II, IIa, IIb, III, IIIa, and IIIb or other compounds disclosed herein, or a pharmaceutically acceptable salt, hydrate, solvate, stereoisomer or tautomer thereof, and a pharmaceutically acceptable carrier, diluent, adjuvant or excipient.

Another aspect of the present disclosure provides a combination composition comprising:
(a) a compound of formulas I, Ia, Ib, Ic, II, IIa, IIb, III, IIIa, and IIIb or other compounds disclosed herein, or a pharmaceutically acceptable salt, hydrate, solvate, stereoisomer or tautomer thereof; and
(b) one or more additional compounds selected from the group consisting of antitumor agents, anti-cancer agents, antibacterial agents, antiviral agents, central nervous system agents, and anti-diabetes agents.

Another aspect of the present disclosure provides a compound of formulas I, Ia, Ib, Ic, II, IIa, IIb, III, IIIa, and IIIb or other compounds disclosed herein, or a pharmaceutically acceptable salt, hydrate, solvate, stereoisomer or tautomer thereof, for treating diseases, mobilizing stem cells, and treating wounded or burned skin by antagonizing the CXCR4 pathway, wherein the diseases is selected from the group consisting of HIV infection, myocardial infarction, diseases associated with hematopoiesis, inflammation, allergic diseases, asthma, allergic pneumonia, interstitial lung disease, lupus erythematosus, ankylosing spondylitis, multiple sclerosis, systemic sclerosis, polymyositis, rheumatoid arthritis, myasthenia gravis, juvenile diabetes, glomerulonephritis, autoimmune thyroiditis, graft rejection, inflammatory bowel disease, Crohn's disease, ulcerative colitis, scleroderma, psoriasis, dermatitis, retinitis pigmentosa, proliferative vitreoretinopathy, Best's vitelliform macular degeneration, eczema, urticaria, vasculitis, eosinophilic fasciitis, wet and dry age-related macular degeneration (ARMD), diabetic retinopathy, retinopathy of prematurity (ROP), diabetic macular edema, uveitis, retinal vein occlusion, cystic macular edema, glaucoma, vein branch occlusion, breast cancer, lung cancer, bladder cancer, pancreatic cancer, liver cancer, head and neck squamous cell carcinoma, thyroid cancer, sarcoma, osteosarcoma, desmofibroma, melanoma, prostate cancer, colorectal cancer, ovarian cancer, cervical cancer, esophageal cancer, gastric cancer, myeloma, lymphoma, mantle cell lymphoma, cutaneous T cell lymphoma, chronic and non-progressive anemia, spontaneous or primary thrombocytosis, idiopathic myelofibrosis, pulmonary fibrosis, renal fibrosis, liver fibrosis, cirrhosis, diabetic retinopathy, macroglobulinemia, leukemia, acute leukemia, chronic leukemia, lymphoblastic leukemia, myeloid leukemia, myelodysplastic syndrome, myeloproliferative disorders, encephaloma, astrocytoma, medulloblastoma, schwannoma, primary neuroectodermal tumor, and pituitary adenoma.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
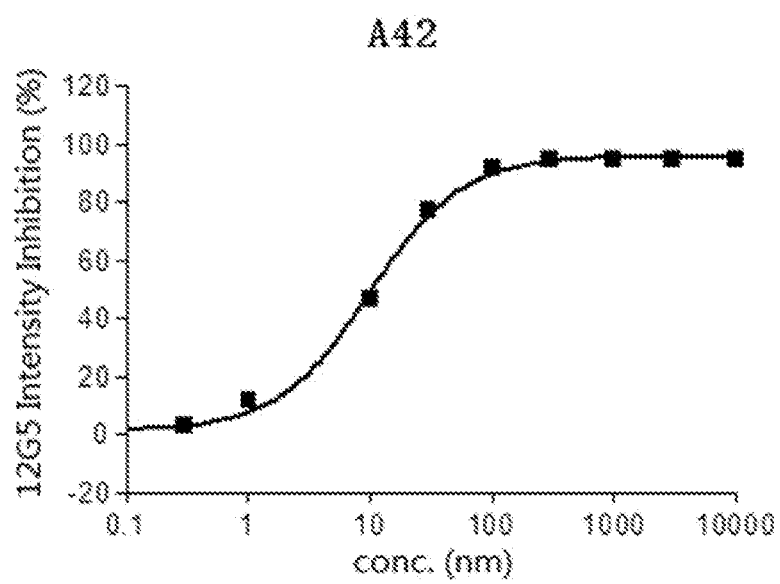
FIG. 1 depicts the 12G5 assay by compound A42.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E- forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E- forms, with all isomeric forms of the compounds being included in the present invention unless otherwise specified. Where a compound exists in various tautomeric forms, a recited compound is not limited to any one specific tautomer, but rather is intended to encompass all tautomeric forms.

The term "alkyl" as used herein generally refers to a straight or branched chain saturated aliphatic hydrocarbon. Alkyl groups include groups having from 1 to 8 carbon atoms ($C_1$-$C_8$ alkyl), from 1 to 6 carbon atoms ($C_1$-$C_6$ alkyl) and from 1 to 4 carbon atoms ($C_1$-$C_4$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

The term "alkenyl" as used herein generally refers to straight or branched chain alkene groups, which comprise at least one unsaturated carbon-carbon double bond. Alkenyl groups include $C_2$-$C_8$ alkenyl, $C_2$-$C_6$ alkenyl and $C_2$-$C_4$ alkenyl groups, which have from 2 to 8, 2 to 6 or 2 to 4 carbon atoms, respectively, including, for example, ethenyl, allyl or isopropenyl. The term "alkynyl" as used herein generally refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively.

The term "cycloalkyl" as used herein generally refers to a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. For example, certain cycloalkyl groups are $C_3$-$C_7$ cycloalkyl, in which the cycloalkyl group contains a single ring having from 3 to 7 ring members, all of which are carbon. The term "cycloalkenyl" as used herein generally refers to a group that comprises one or more unsaturated rings in which all ring members are carbon.

The term "alkoxy" as used herein generally refers to an alkyl group as described above attached via an oxygen bridge. Alkoxy groups include $C_1$-$C_6$ alkoxy and $C_1$-$C_4$ alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term "alkylamino" as used herein generally refers to a secondary or tertiary amine that has the general structure —NH—R1 or —N(R1)(R2), wherein R1 and R2 are selected independently from alkyl, cycloalkyl and (cycloalkyl)alkyl groups. Such groups include, but are not limited to, for example, mono- and di-($C_1$-$C_6$ alkyl)amino groups, in which each $C_1$-$C_6$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

The term "alkylthio" as used herein generally refers to an alkyl-substituted thio group, wherein the term alkyl is as defined above.

The term "halogen" or "halide" as used herein generally refers to fluorine, chlorine, bromine, and iodine. The term "haloalkyl" as used herein generally refers to an alkyl group that is substituted with one or more independently chosen halogens (e.g., "$C_1$-$C_6$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

The term "heteroaryl" as used herein generally refers to an aromatic group in which at least one aromatic ring comprises at least one heteroatom selected from N, O and S. Heteroaryls include, for example, 5-12 membered heteroaryls. Examples include, but are not limited to, imidazole, furan, furazan, isothiazole, isoxazole, oxadiazole, oxazole, pyrazine, pyrazole, pyridazine, pyridine, pyrimidine, tetrazole, thiazole and thiophene.

The term "heterocycloalkyl" as used herein generally refers to a ring structure containing 3-12 ring atoms, in which in which at least one ring atom is carbon and at least one ring atom is heteroatom selected from N, O, and S. Examples include, but are not limited to, aziridine, oxiran, thiirane, azetidine, oxetane, thietane, pyrrolidine, tetrahydrofuran, and tetrahydrothiophene.

The term "heterocyclic" or "heterocycle" as used herein generally refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

The terms "substituent" and "substituted," as used herein, generally denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. A straight chain substituent may be a moiety such as a halogen, alkyl group, haloalkyl group or other group that is covalently bonded to an atom (preferably a carbon or nitrogen atom) that is a member of a straight chain.

The term "pharmaceutically acceptable" as used herein generally refers to a form of the compound that is safe for administration to a subject. For example, a free base, a salt form, a solvate, a hydrate, a prodrug or derivative form of a compound of formula I, which has been approved for mammalian use, via oral ingestion or any other route of administration, by a governing authority or regulatory agency, such as the Food and Drug Administration (FDA) of the United States, is pharmaceutically acceptable.

Included in the compounds of formulas I, Ia, Ib, Ic, II, IIa, IIb, III, IIIa, and IIIb are the pharmaceutically acceptable salt forms of the free-base compounds. The term "pharmaceutically-acceptable salts" as used herein generally refers to salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of formulas I, Ia, Ib, Ic, II, IIa, IIb, III, IIIa, and IIIb is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient" as used herein generally refers to any pharmaceutically acceptable additive, carrier, adjuvant, or other suitable ingredient, other than the active pharmaceutical ingredient (API), which is typically included for formulation and/or administration purposes.

The term "diluent" as used herein generally refers to an agent used as filler in order to achieve the desired composition volume or weight. The diluent may be present in the pharmaceutical composition within granules in the form of a single compound or in the form of a mixture of compounds. Non-limiting examples of diluent include lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

The term "adjuvant," as used herein generally refers to any substance or mixture of substances that increases the efficacy or potency of a compound disclosed herein on a target where the adjuvant is used together with the compound disclosed herein. However, when the adjuvant is used alone, no pharmacological effect is observed on the same target.

The terms "treat", "treating," "treatment," and "therapy" as used herein generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" as used herein generally refers to quantifying the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of formula I, or a stereoisomer, tautomer, hydrate, solvate or pharmaceutically acceptable salt thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention may include the use of at least one compound of Formulas I, Ia, Ib, Ic, II, IIa, IIb, III, IIIa, and IIIb, which inhibits necrosis in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of necrosis may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

All reagents and solvents were obtained commercially unless stated otherwise. All commercial reagents and solvent were used without purification unless stated otherwise. When required, some reagents and solvents were purified by standard techniques. For example, tetrahydrofuran may be purified by distillation from sodium. All thin-layer chromatography (TLC, GF254) analyses and column purification (100-200 mesh) were performed on silica gel (Qingdao Haiyang Chemical Co. Ltd. or Yantai Chemical Co. Ltd.), using petroleum ether (b.p. 60-90° C.)/ethyl acetate (v/v) as eluent; and spots revealed by UV visualization at 254 nm and $I_2$ vapor or phosphomolybdic acid. All organic layers after extraction were dried over anhydrous $Na_2SO_4$ unless stated otherwise. All nuclear magnetic resonance spectra were recorded using a Bruck-400 spectrometer at 400 MHz using TMS as an internal standard. LC-MS was run using an Agilent 1100 system with LC-MSDTrap recorder, diode array detector (DAD) with detecting wavelength at 214 nm and 254 nm, and ESI source. The HPCL column is an Agela Durashell C18 3.5 μm 4.6×50 mm column. Gradients were run using 0.1 $NH_4HCO_3$ aqueous solution and acetonitrile with gradient 5/95 to 95/5 in the run time indicated (for example, 5 min), flow rate at 1.8 mL/min.

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent, such as anhydrous $Na_2SO_4$, to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

General Synthetic Routes

The methods and examples provided below illustrated and exemplified the compounds described herein and methods of preparing such compounds. In general, the compounds described herein may be prepared by processes known in the general chemical arts. The following methods are embodiments for some general synthetic routes leading to compounds of Formulas I, Ia, Ib, Ic, II, IIa, IIb, III, IIIa, and IIIb. Detailed reaction conditions for each Method can be found in the examples shown vide infra.

The compounds of the present invention can be prepared using various synthetic routes, including those described by methods A-N, BA-BS and AA-AT below, starting from commercially available materials. Starting materials of the invention, are either known, commercially available, or can be synthesized in analogy to or according to methods that are known in the art. Many starting materials may be prepared according to known processes and, in particular, can be prepared using processed described in the methods and examples. In synthesizing starting materials, functional groups in some cases are protected with suitable protecting groups when necessary. Functional groups may be removed according to known procedures in the art.

Method A:

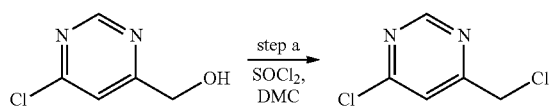 [SMILES: OCc1cc(Cl)ncn1 ; ClCc1cc(Cl)ncn1]

The (6-chloropyrimidin-4-yl)methanol could be converted to 4-chloro-6chloromethyl)pyrimidinetreated with SOCl$_2$ (step a).

Method B:

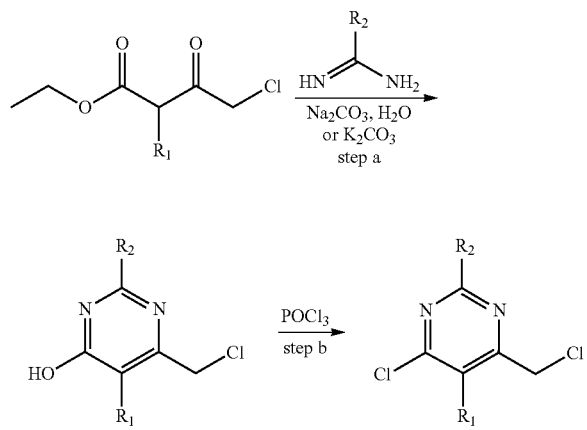

Substituted 4-chloro-3-oxobutanoate could be reacted with amidine and carbonate to give the pyrimidine intermediate (step a). Conversion of the hydroxypyrimidine to the chloropyrimidine may be achieved with POCl$_3$(step b).

Method C, D:

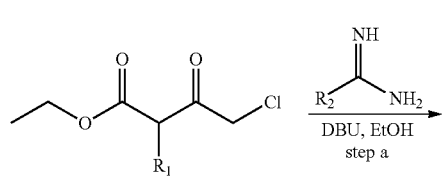

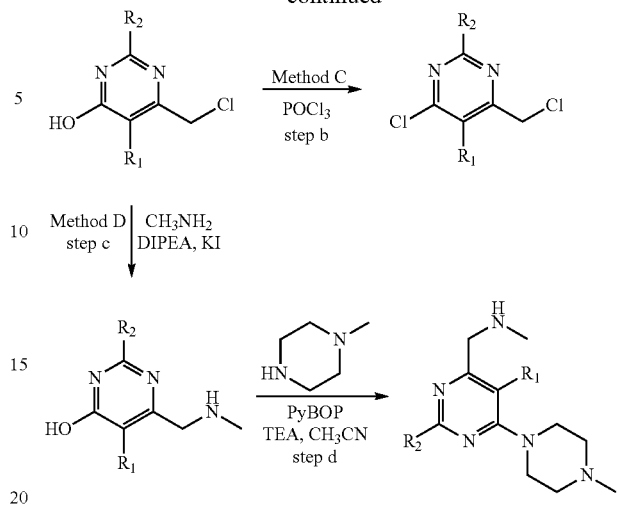

Substituted 4-chloro-3-oxobutanoate could also be reacted with amidine and DBU to give the pyrimidine intermediate (step a). Conversion of the hydroxypyrimidine to the chloropyrimidine may be achieved with POCl$_3$(step b) 4-aminopyrimidine core may be synthesized via methyl amine substitution (step c) followed by condensation of hydroxypyrimidine with 1-methylpiperazine (step d).

Method E

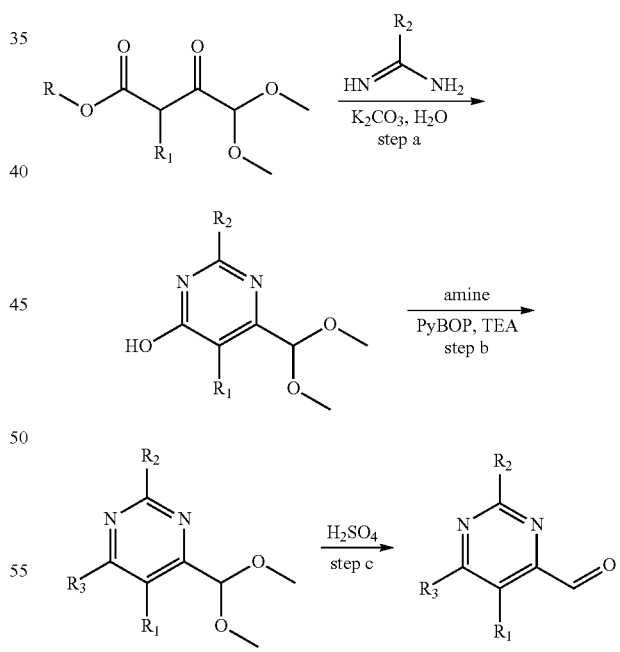

Pyrimidine-4-carbaldehyde core could be synthesized via cyclization to the pyrimidine core (step a) followed by condensation of hydroxypyrimidine with corresponded amine (step b), following hydrolysis (step c).

Method F, G, H

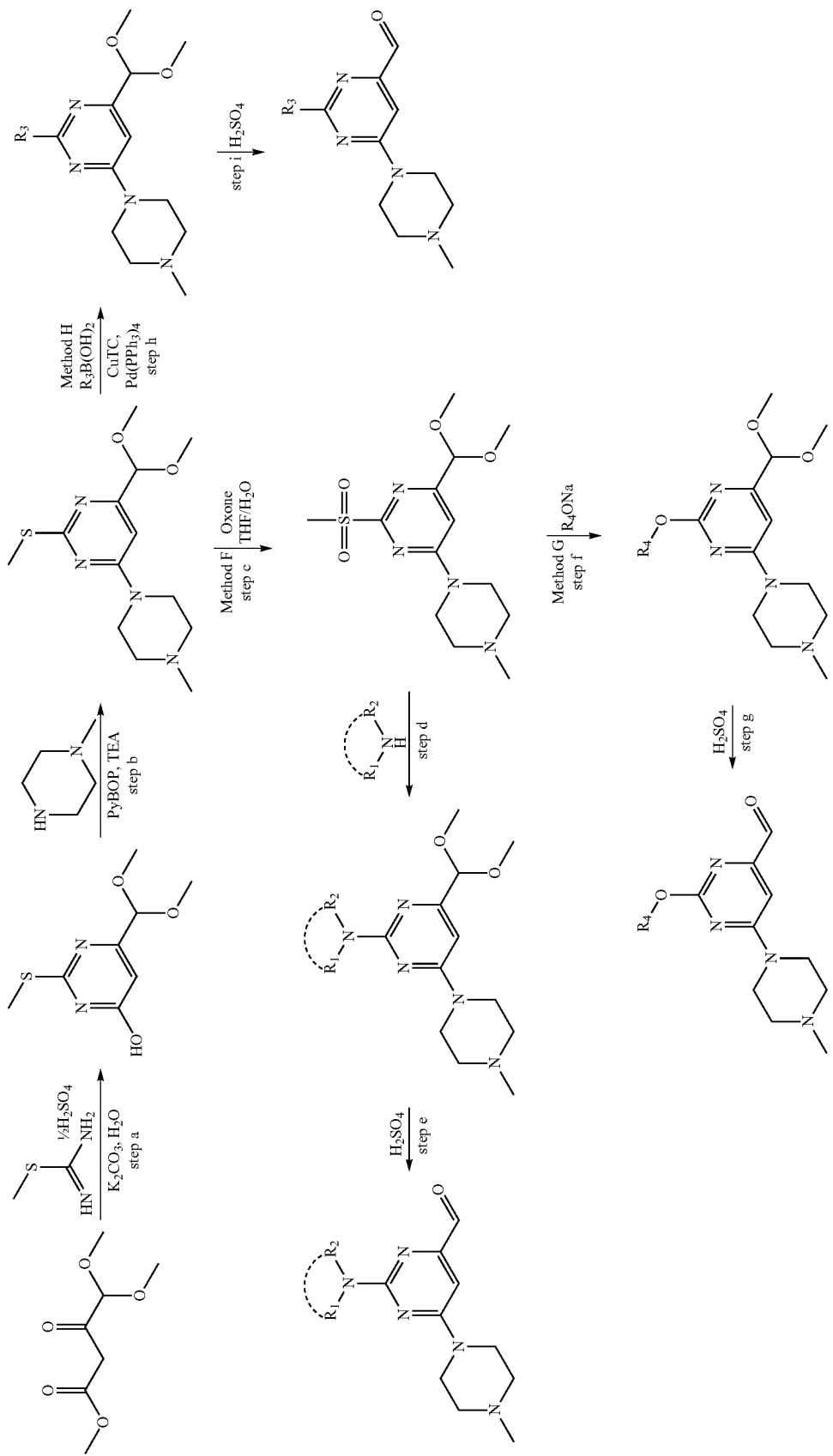

The key intermediate 4-(dimethoxymethyl)-6-(4-methylpiperazin-1-yl)-2-(methylthio)pyrimidine may be formed via cyclization followed condensation 6-(dimethoxymethyl)-2-(methylthio)pyrimidin-4-ol with 1-methylpiperazine (step b). Then 2-subsituted Pyrimidine-4-carbaldehyde core could be synthesized via oxidation of methyl sulfide to methylsulfonyl (step c), substitution with corresponding alcohol (step f) or amine (step d) followed by hydrolysis (step e, g) or can be formed by Suzuki coupling (step h) followed hydrolysis (step i).

Method I

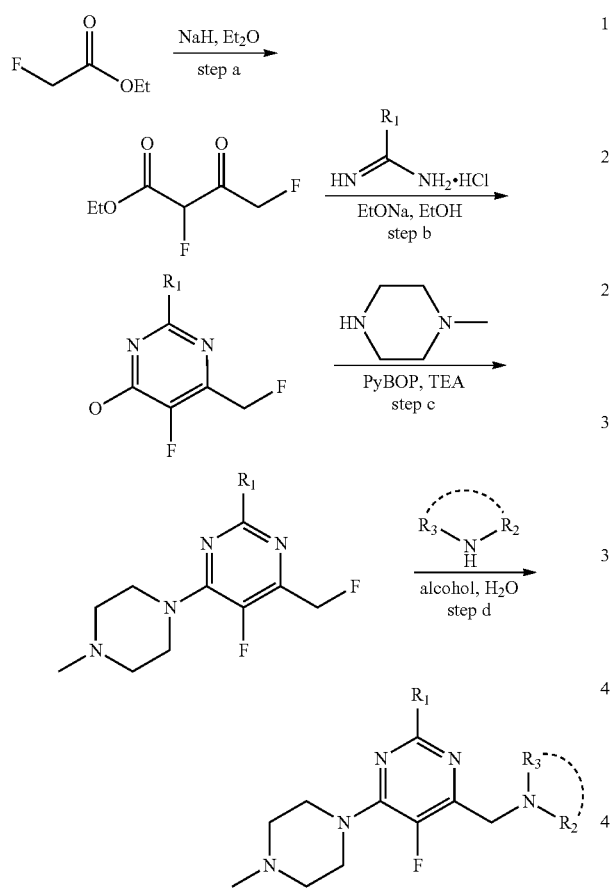

The targeted compounds may be formed via cyclization (step a) followed condensation hydroxypyrimidine with 1-methylpiperazine (step b), following substitution with corresponding amine (step c).

Method J

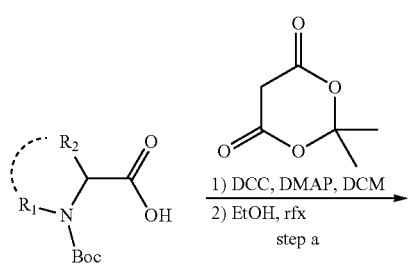

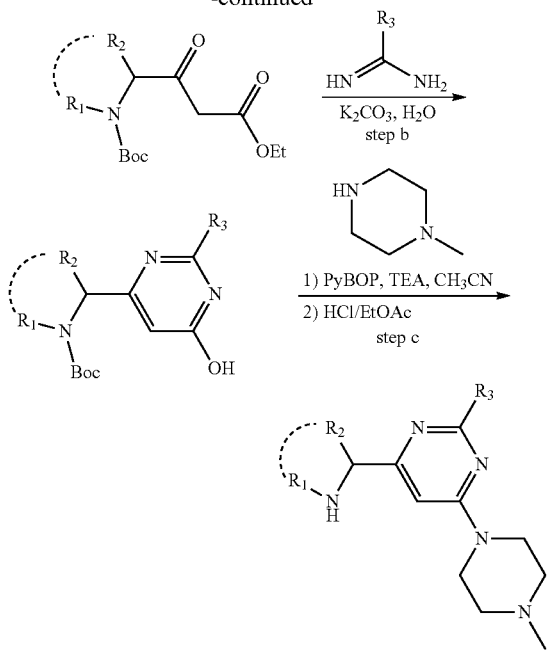

4-(4-methylpiperazin-1-yl)pyrimidine core can be achieved by condensation the amino acid with 2,2-dimethyl-1,3-dioxane-4,6-dione followed decarboxylation (step a); following cyclization (step b) followed condensation hydroxypyrimidine with 1-methylpiperazine (step c) and at last de-Boc protective group (step c).

Method K

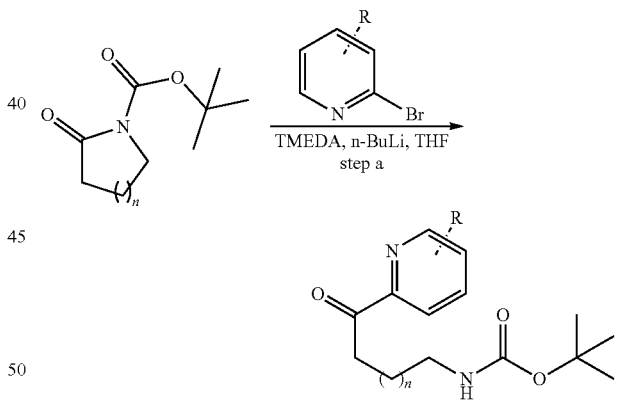

The pyridine-2-one core could be formed vis treatment pyridine lithium reagent with N-Boc lactam (n=0, 1, 2).

Method L

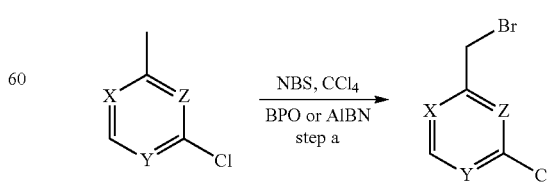

The heteroaromatic core could be substituted with bromine treated with NBS and free radical initiator.

Method M

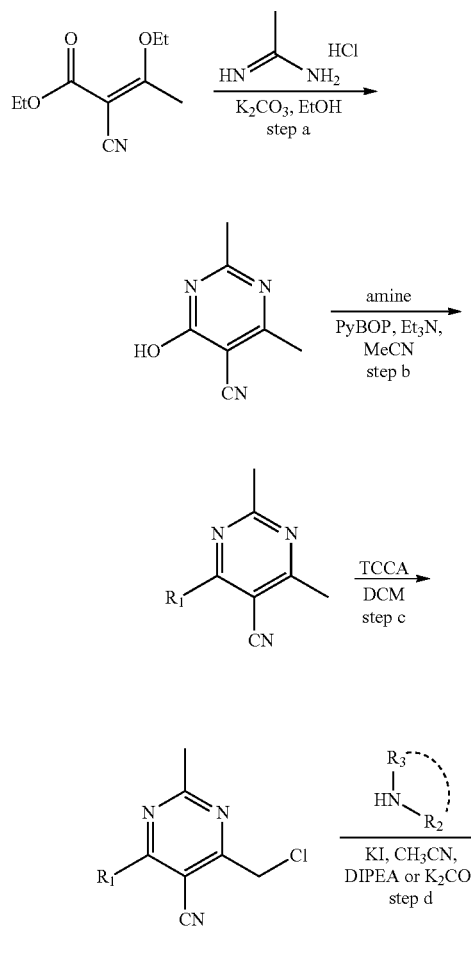

The 2-methyl-5-nynaopyrimidine core may be achieved by cyclization (step a) followed condensation hydroxypyrimidine with corresponding amine (step b), following chlorination (step c) and substitution with corresponding amine (step d).

Method N

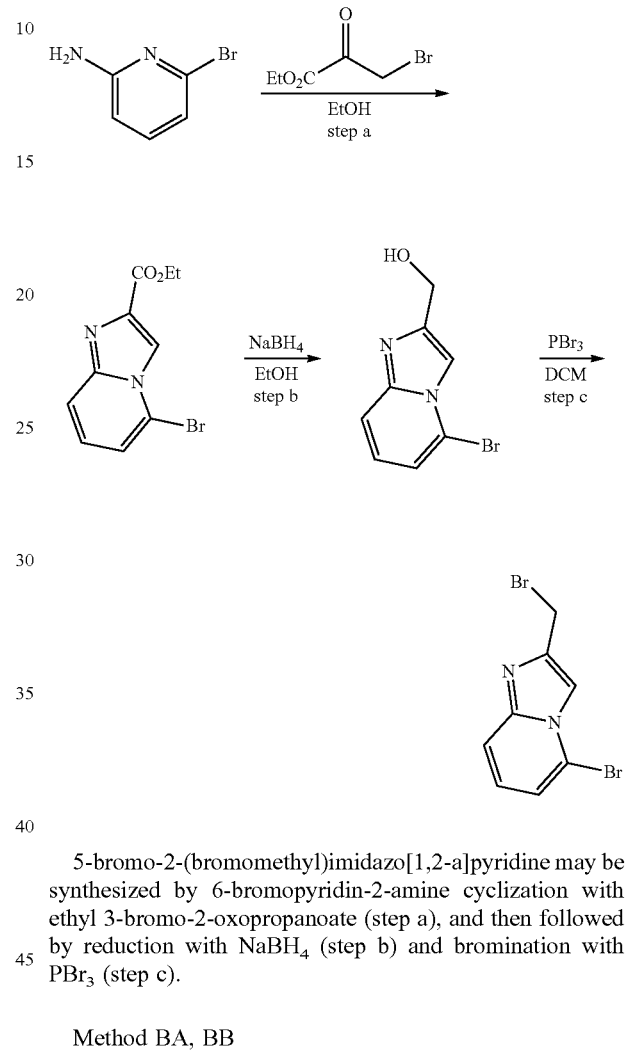

5-bromo-2-(bromomethyl)imidazo[1,2-a]pyridine may be synthesized by 6-bromopyridin-2-amine cyclization with ethyl 3-bromo-2-oxopropanoate (step a), and then followed by reduction with NaBH$_4$ (step b) and bromination with PBr$_3$ (step c).

Method BA, BB

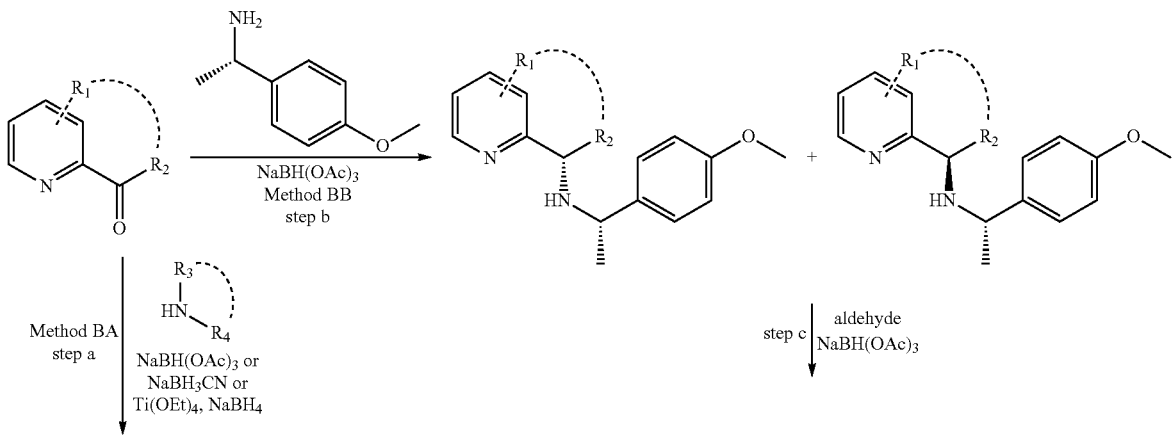

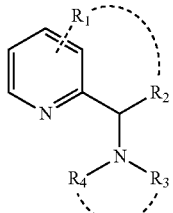

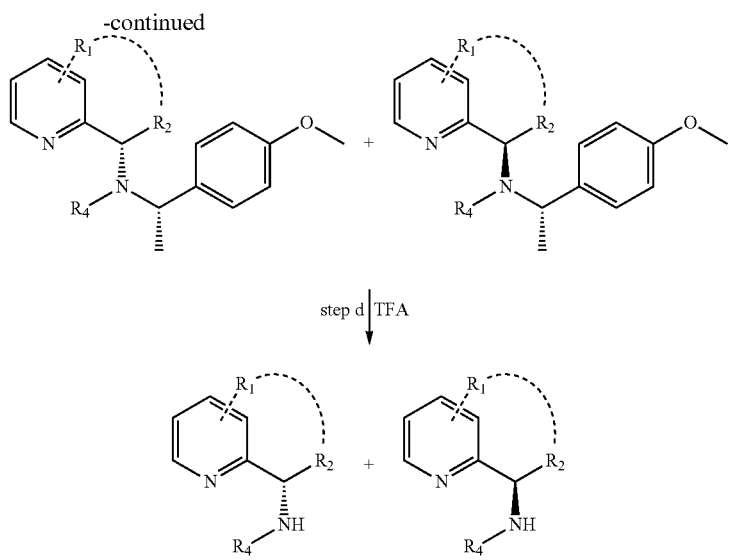

The targeted core can be synthesized via the reductive amination(step a, b) with the ketone, or followed the reductive amination(step c) again with the aldehyde, then de-protective group treated with TFA (step d).

Method BC

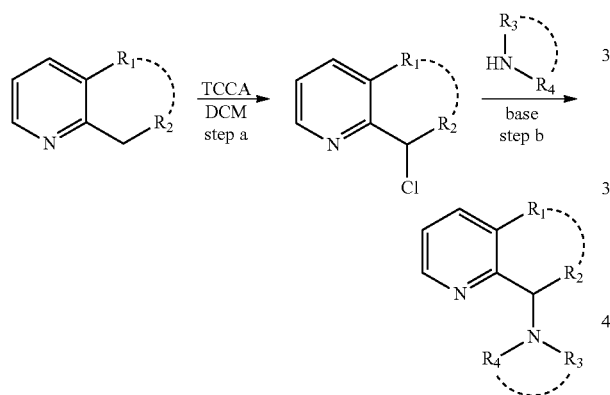

The targeted core may be achieved by chlorination (step a) with TCCA and substitution with corresponding amine (step b).

Method BD

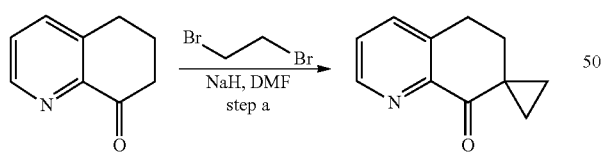

The 6,7-dihydroquinolin-8(5H)-one was treated with NaH and then added 1,2-dibromoethane to give 5',6'-dihydro-8'H-spiro[cyclopropane-1,7'-quinolin]-8'-one (step a).

Method BE

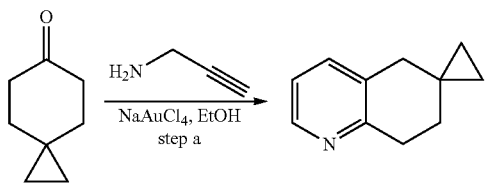

The spiro[2.5]octan-6-one was reacted with prop-2-yn-1-amineat presence of NaAuCl₄ to give 7',8'-dihydro-5'H-spiro[cyclopropane-1,6'-quinoline](step a).

Method BF, BG

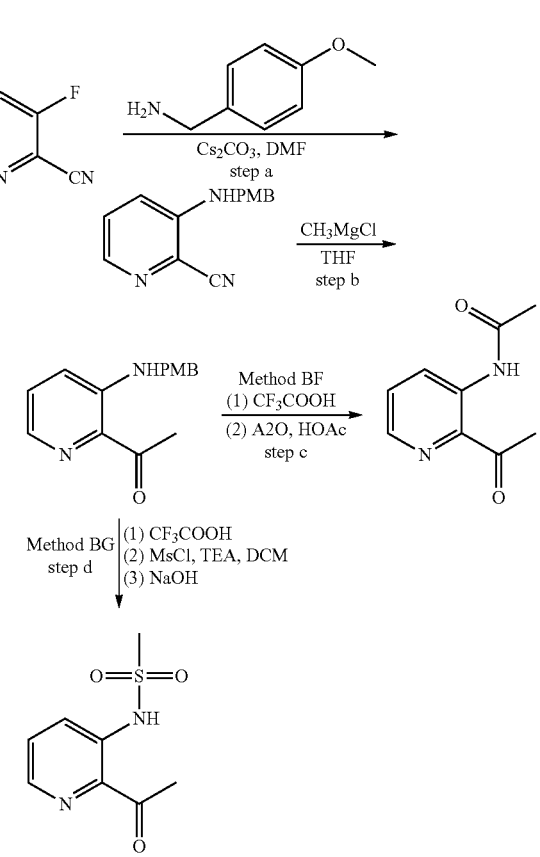

The intermediate 1-(3-aminopyridin-2-yl)ethan-1-one may be formed by substitution with (4-methoxyphenyl)methanamine (step a) followed Grignard reaction using CH₃MgCl (step b), then de-PMB group with TFA (step c). The targeted compounds can be obtained by acylation (step c) or mesylation (step d).

83

Method BH, BI

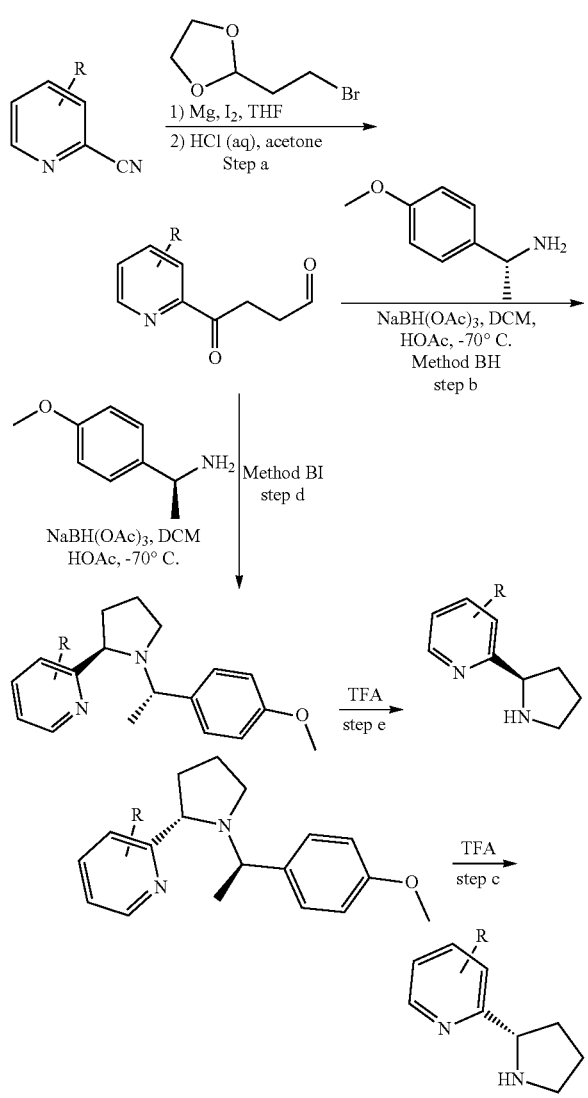

The 2-(pyrrolidin-2-yl)pyridine(S/R) can be formed by Grignard reaction with picolinonitrile and hydrolysis (step a), following the reductive amination with (4-methoxyphenyl)ethan-1-amine (R/S) (step b, d), then de-protective group treated with TFA (step c, e).

Method BJ

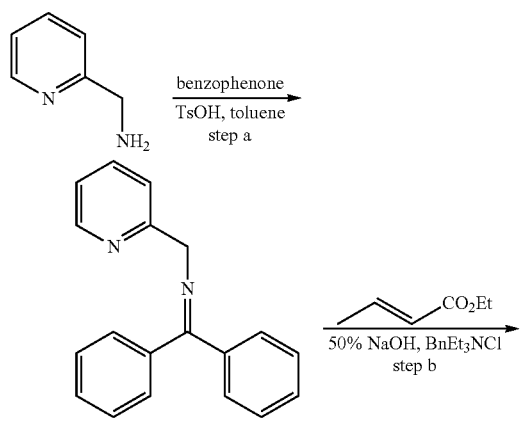

84

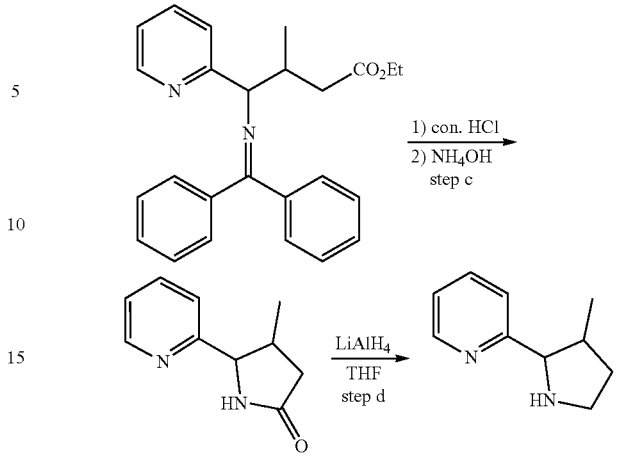

The racemic 2-(3-methylpyrrolidin-2-yl)pyridine may achieved by imidization catalysis by TsOH (step a) followed Michael addition reaction treatment with ethyl (E)-but-2-enoate (step b), following formation lactam with con. HCl (step c), then reduction using LiAlH₄ (step d).

Method BK

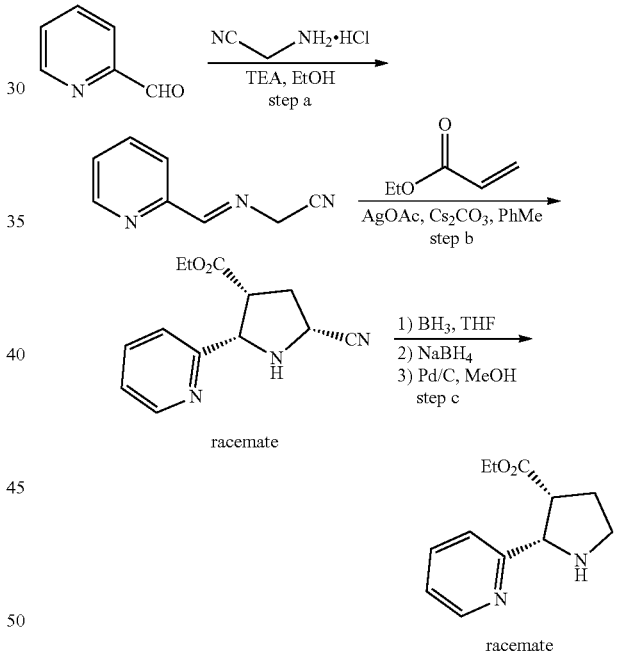

The Picolinaldehyde may be reacted with aminoacetonitrile to generate the Schiff base. Pyrrole ring could be made via a [3+2] cyclization. The cyano group could be knock out by a series of reductive reaction.

Method BL

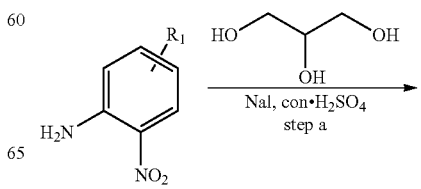

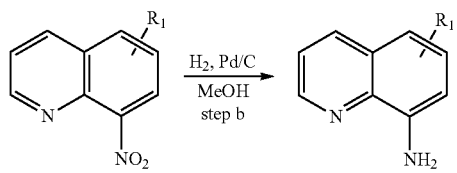

The substituted 8-nitroquinoline can be formed by cyclization treatment glycerin with 2-nitroaniline (step a), then substituted 8-nitroquinoline was reduced to the 8-aminoquinoline core with Pd/C(step b).

Method BM

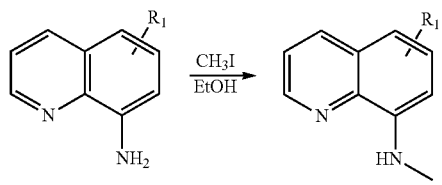

The 8-aminoquinolinecore could be methylated using methyl iodide.

Method BN

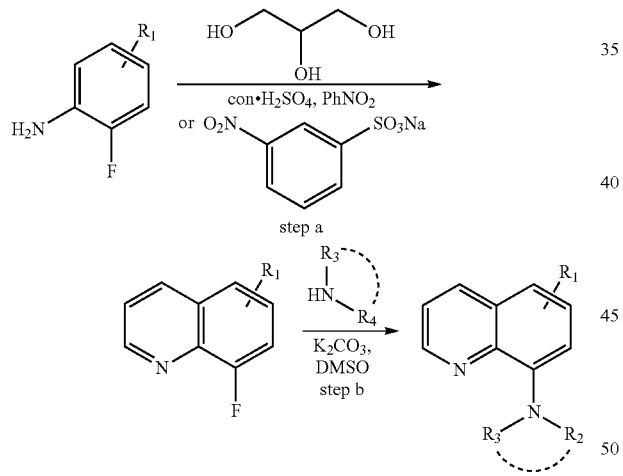

The quinoline containing core can be formed by cyclization treatment glycerin with 2-fluoroaniline (step a) and substitution with corresponding amine (step b).

Method BO

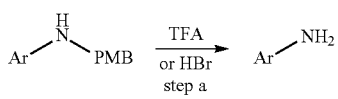

The PMB protective group could be removed under the acid condition.

Method BP

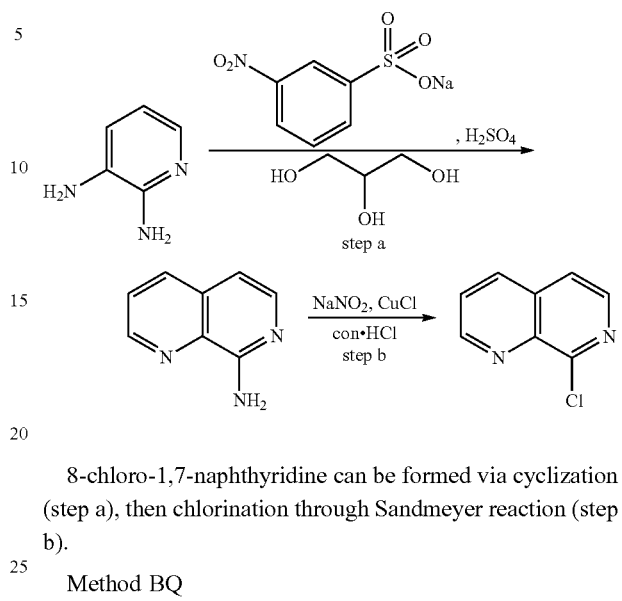

8-chloro-1,7-naphthyridine can be formed via cyclization (step a), then chlorination through Sandmeyer reaction (step b).

Method BQ

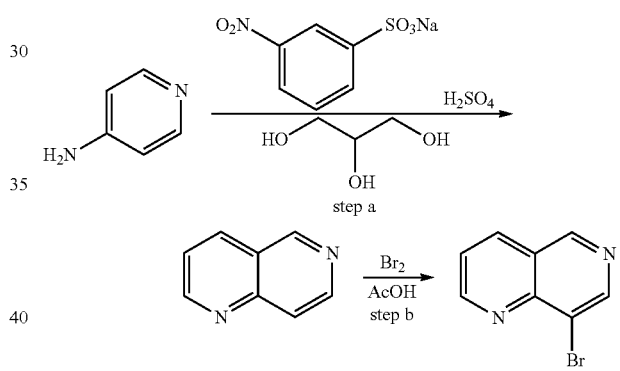

8-bromo-1,6-naphthyridine can be formed via cyclization (step a), then bromination with bromine.

Method BR

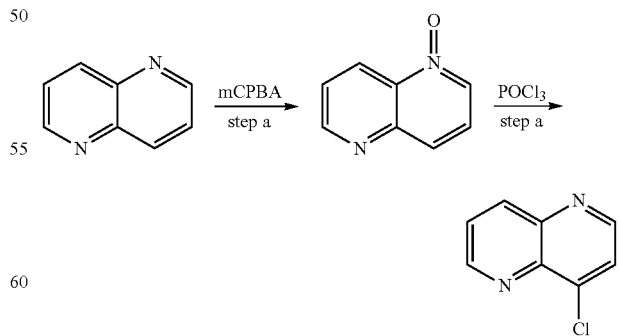

4-chloro-1,5-naphthyridine could be obtained via oxidation with mCPBA (step a) followed chlorination treatment with POCl$_3$ (step b).

Method BS

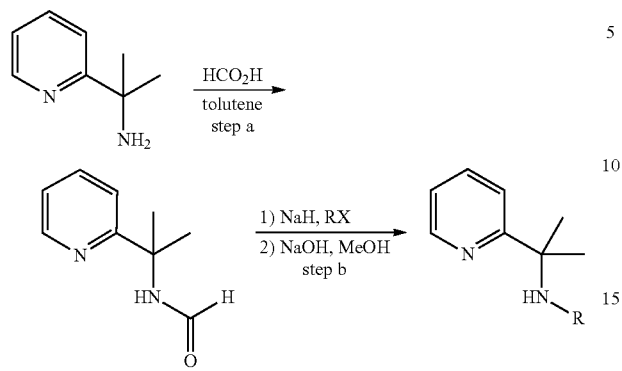

2-(pyridin-2-yl)propan-2-amine could be formylated (step a) followed by alkylation and hydrolyzation (step b) to give the desired target.

Method AA

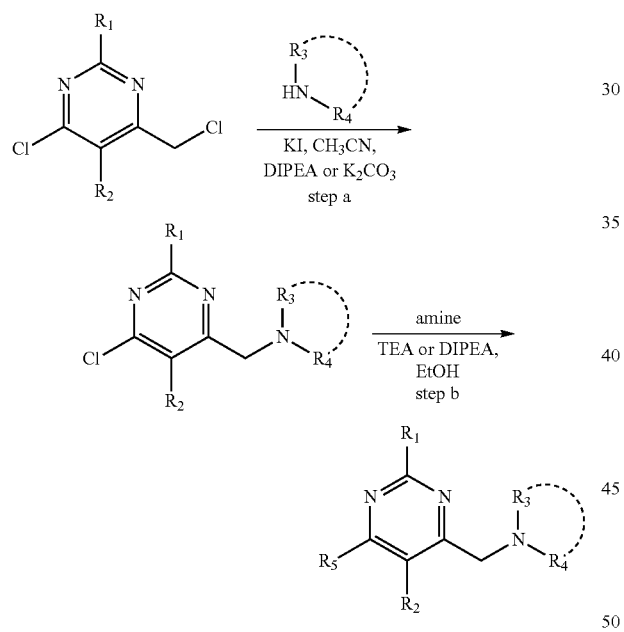

The finally targeted compounds can be obtained by substitution the chlorine of 4-chloro-6-(chloromethyl)pyrimidine with corresponding amines respectively (step a, b).

Method AB

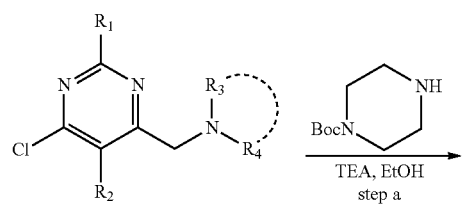

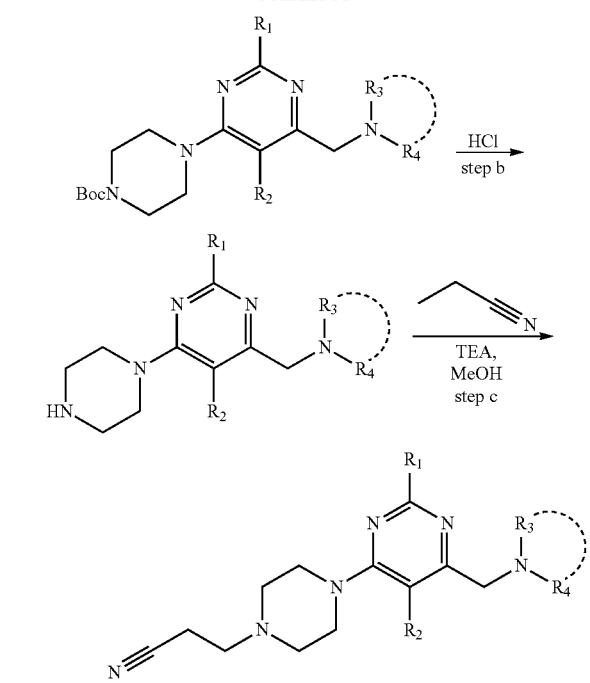

The finally targeted compounds can be obtained by substitution the chlorine of 4-chloropyrimide core with N-Boc-piperazine (step a) followed de-Boc group treatment with acid (step b), following Michael addition reaction treatment with acrylonitrile (step c).

Method AC

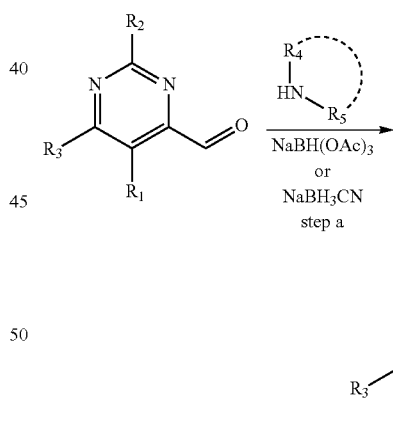

The finally targeted compounds may be formed by reduced amination using NaBH(OAc)$_3$ or NaBH$_3$CN (step a).

Method AD

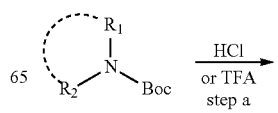

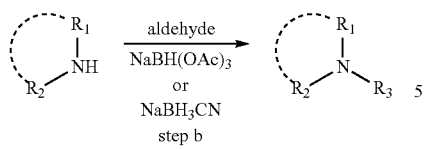

The finally targeted compounds may be formed by de-Boc group under acid condition (step a) followed reduced amination using NaBH(OAc)₃ or NaBH₃CN (step b).

Method AE

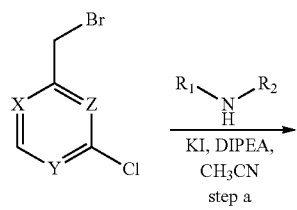

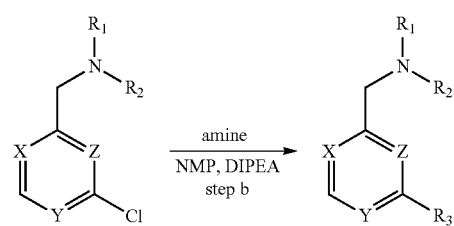

The finally targeted compounds can be obtained by substitution the bromine of 4-(bromomethyl)-6-chloropyrimidine with corresponding amines firstly (step a), then substitution the chlorine of 6-chloropyrimidine with corresponding amines (step b).

Method AF

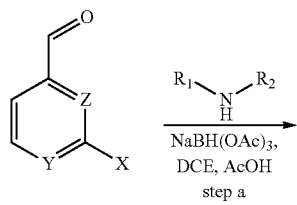

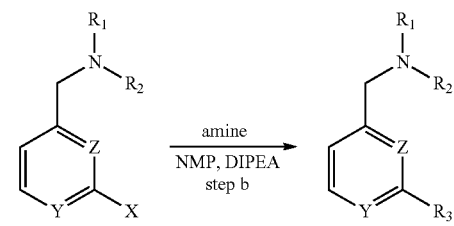

The heteroaromatic derivatives could be synthesized via the reductive amination (step a) followed by substitution with corresponding amine (step b).

Method AG

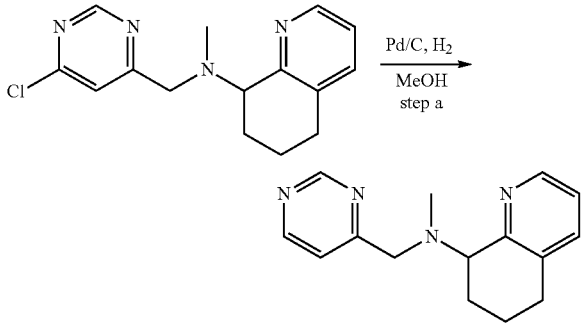

The chlorine of the pyrimidine core was removed under Pd/C condition to give N-methyl-N-(pyrimidin-4-ylmethyl)-5,6,7,8-tetrahydroquinolin-8-amine Method AH

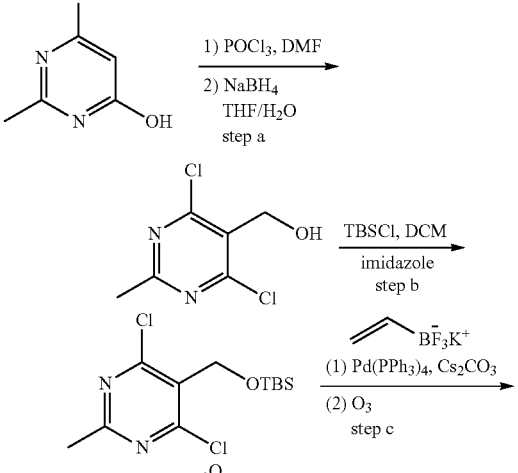

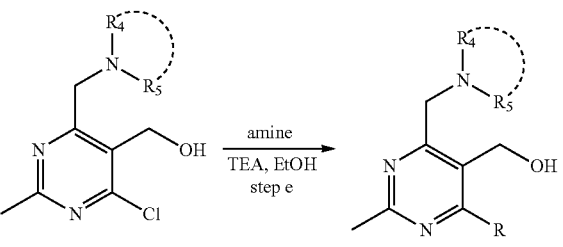

The (2-methylpyrimidin-5-yl)methanol containing targeted compounds could be synthesized from 2-methylpyrimidine-4,6-diol. The Vilsmeier-Haack reaction with DMF and POCl₃ (step a) followed by reduction aldehyde to alcohol with NaBH₄ (step a); protection of the alcohol group with TBSCl (step b), and then heck reaction with trifluoroborate (step c).

Oxidation of the double bind to aldehyde with ozone (step c); the reductive amination (step d) followed by displacement of the pyrimidine chlorine with corresponding amines (step e).

Method AI

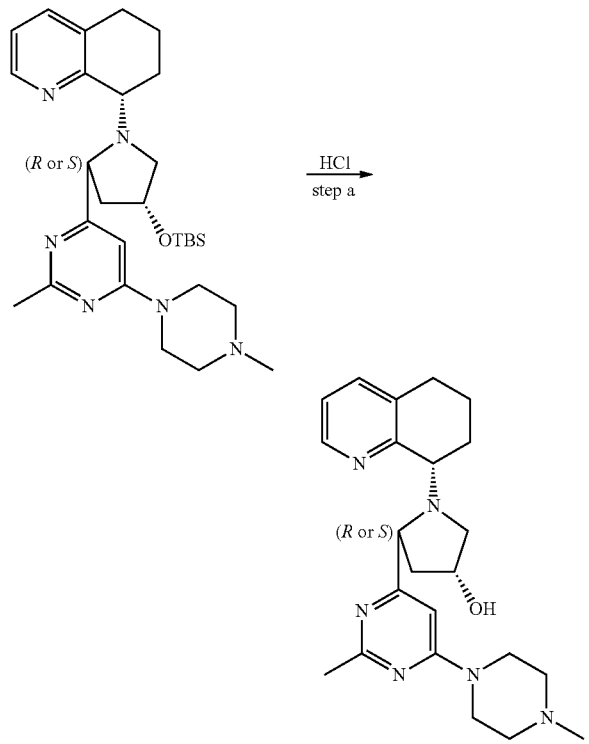

The TBS protective group could be removed under the acid condition.

Method AJ

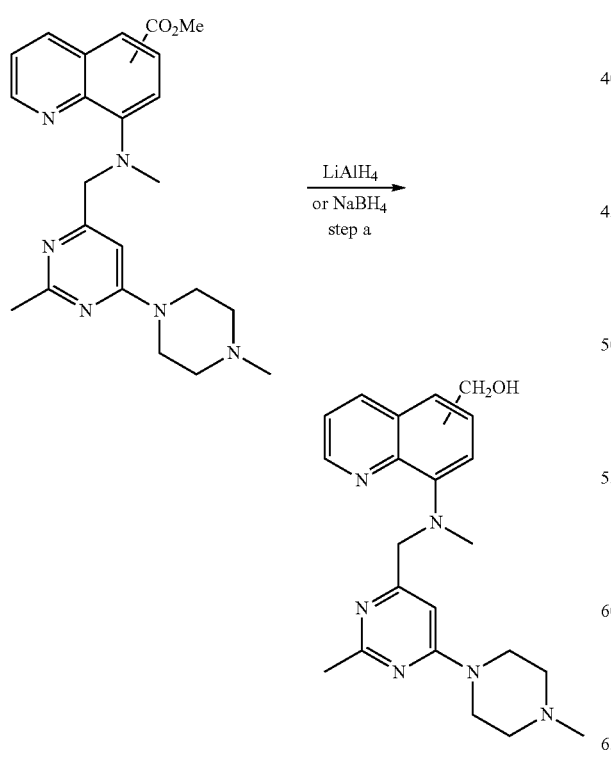

The methyl ester of quinoline core could be reduced to alcohol by NaBH₄ or LiAlH₄.

Method AK

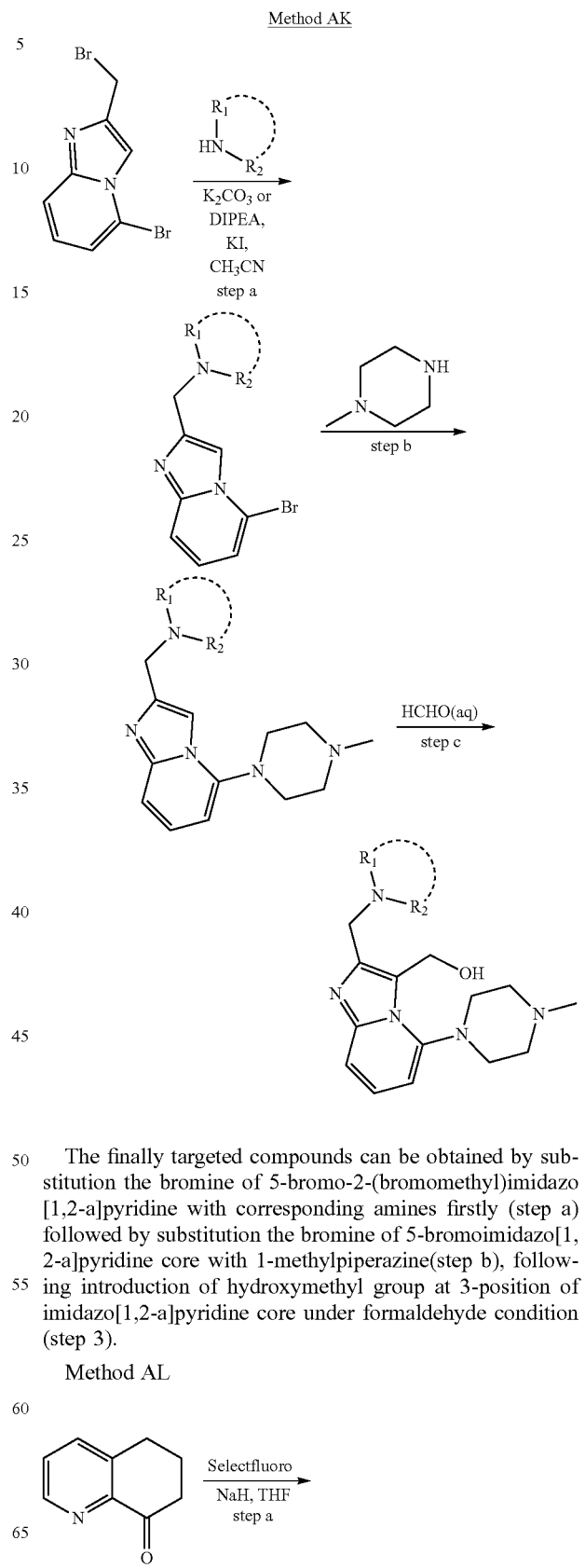

The finally targeted compounds can be obtained by substitution the bromine of 5-bromo-2-(bromomethyl)imidazo[1,2-a]pyridine with corresponding amines firstly (step a) followed by substitution the bromine of 5-bromoimidazo[1,2-a]pyridine core with 1-methylpiperazine(step b), following introduction of hydroxymethyl group at 3-position of imidazo[1,2-a]pyridine core under formaldehyde condition (step 3).

Method AL

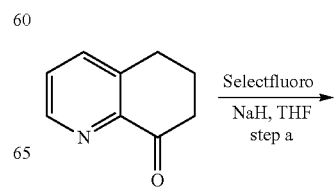

-continued

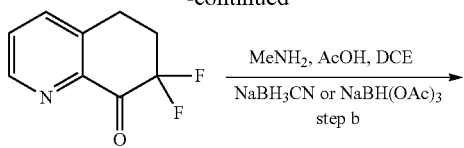

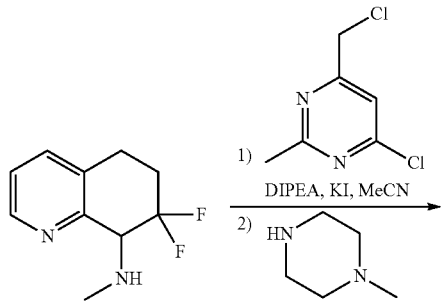

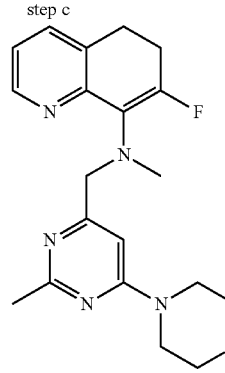

The finally targeted compound can be synthesized by fluorination of the commercially 6,7-dihydroquinolin-8 (5H)-one using selectfluoro (step a), then the reduced amination of ketone with methyl amine (step b), following by alkylation with 4-chloro-6-(chloromethyl)-2-methylpyrimidine (step c), and finally substitution with 1-methylpiperazine(step d).

Method AM

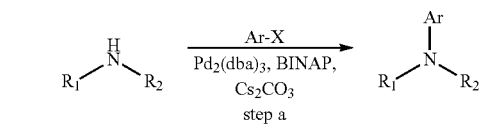

The finally targeted compounds may be formed by reduced amination with corresponding aldehydes using NaBH(OAc)$_3$ or NaBH$_3$CN (step a).

Method AN

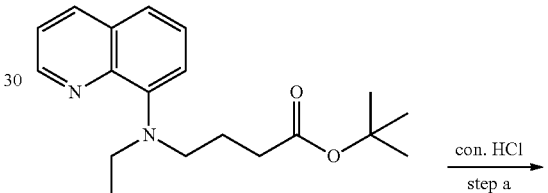

-continued

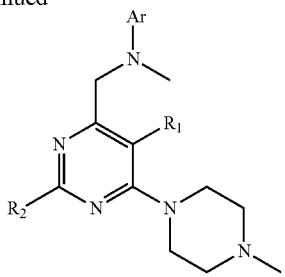

The finally targeted compounds may be formed by substitution with aryl halogen under base, high temperature condition (step a).

Method AO

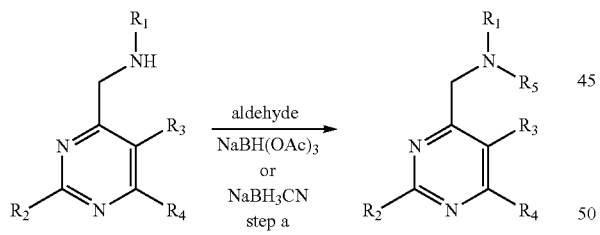

The finally targeted compounds may be formed by Buchwald coupling reaction with aryl halogen Pd$_2$(dba)$_3$, BINAP, Cs$_2$CO$_3$ condition (step a).

Method AP

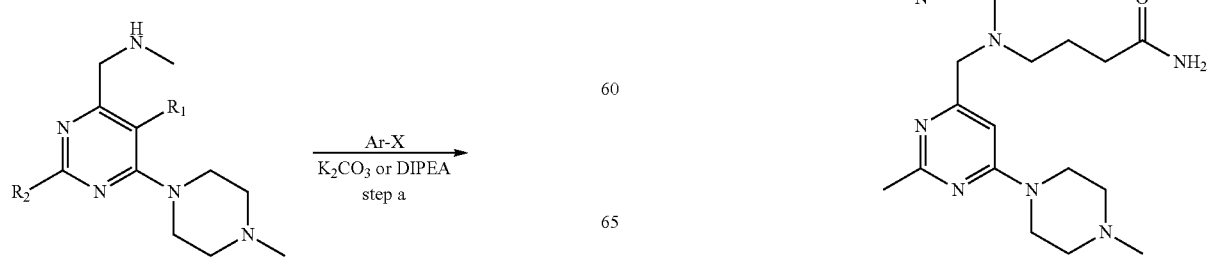

The finally targeted compound may be formed by de-Boc group under the acid condition (step a) followed condensation using HATU (step b).

Method AQ

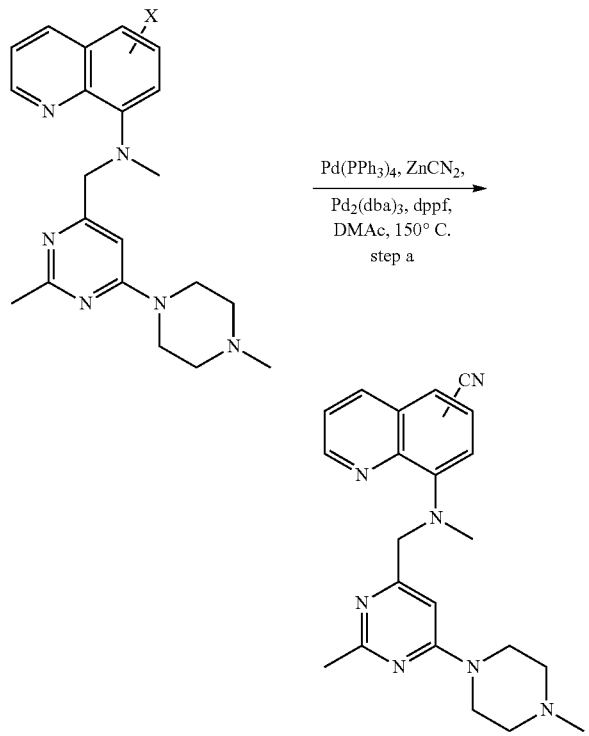

The halogen of quinoline core could be converted to cyano group under the condition of Pd(PPh3)4, dppf, and zinc cyanide or Pd2(dba)3, dppf, and zinc cyanide.

Method AR

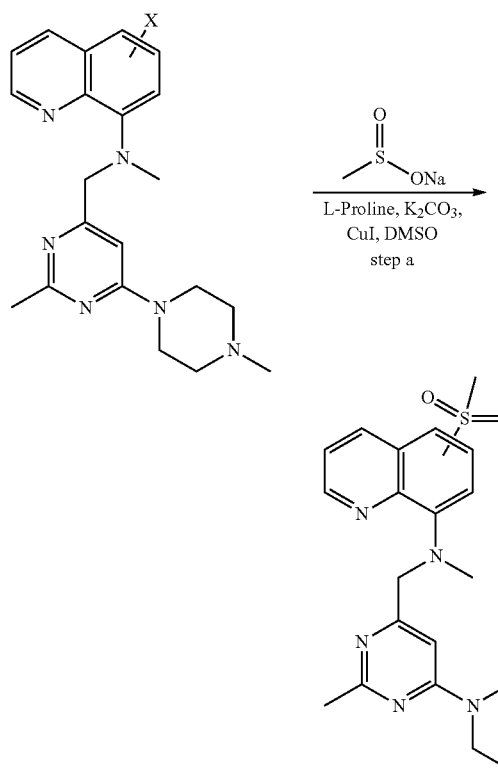

The halogen of quinoline core could be converted to methylsulfonyl group under the condition of sodium methanesulfinate, L-Proline and cuprous iodide.

Method AS

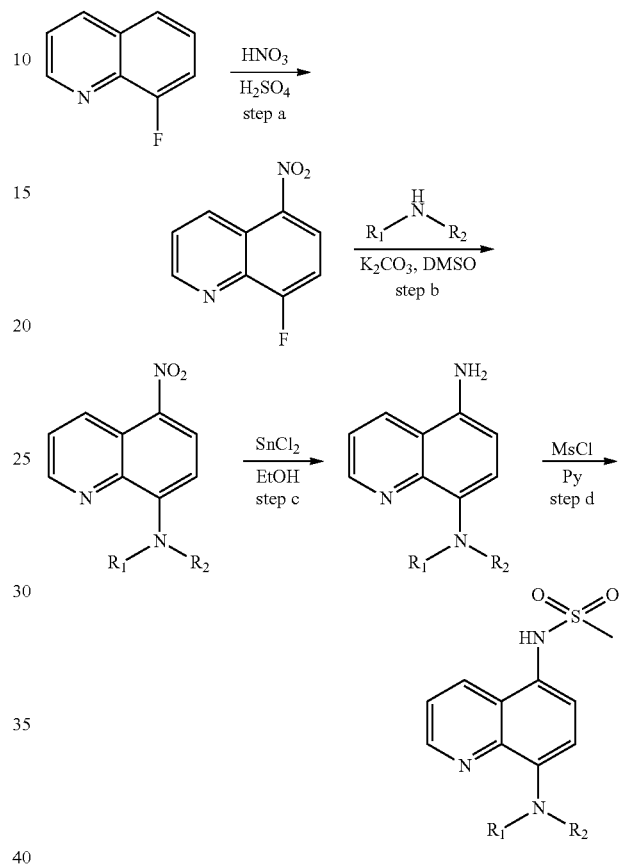

The finally targeted compounds could be synthesized from 8-fluoroquinoline. The nitrification with HNO3 (step a) followed by displacement of the aryl fluorine with corresponding amines (step b). The nitro group can be reduced to the amino group with SnCl2 (step c) and then mesylation with MsCl (step d).

Method AT

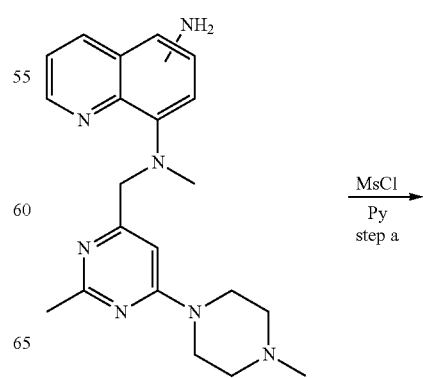

-continued

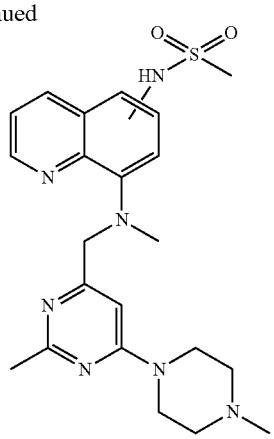

The finally targeted compounds could be synthesized under the MsCl and TEA condition.

EXAMPLES

General reaction progress was monitored by analytical thin layer chromatography performed on silica gel HSGF254 pre-coated plates. Organic solutions were dried over anhydrous $Na_2SO_4$, and the solvents were removed under reduced pressure. $^1H$ NMR were obtained on 400 MHz (Varian) spectrometers. Chemical shifts were given in ppm using tetramethylsilane as internal standard. Mass spectra were obtained using an Agilent 1100 LC/MSD Trap SL version Mass Spectrometer. Final compounds were purified with silica gel 100-200 mesh for column chromatography.

Method A

Preparation of 4-chloro-6-(chloromethyl)pyrimidine

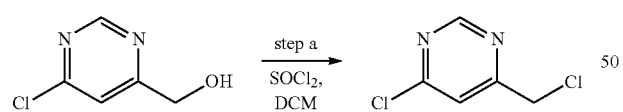

Step a. 4-chloro-6-(chloromethyl)pyrimidine: To a solution of (6-Chloropyrimidin-4-yl)methanol (280 mg, 1.9 mmol, see reference WO2016128529) in dichloromethane (10 mL) was added $SOCl_2$ (280 mg, 2.3 mmol). The reaction was stirred at room temperature overnight. The mixture was quenched with saturated $NaHCO_3$ aqueous solution (50 mL) and extracted with dichloromethane (20 mL×3). The combined organic layer was washed with brine, dried over $Na_2SO_4$ and concentrated to give the desired product (180 mg, 58%) as a yellow oil. $^1H$ NMR (400 MHz, $CDCl_3$) δ 8.95 (s, 1H), 7.62 (s, 1H), 4.62 (s, 2H).

Method B

Preparation of 4-chloro-6-(chloromethyl)-2-(methylthio)pyrimidine

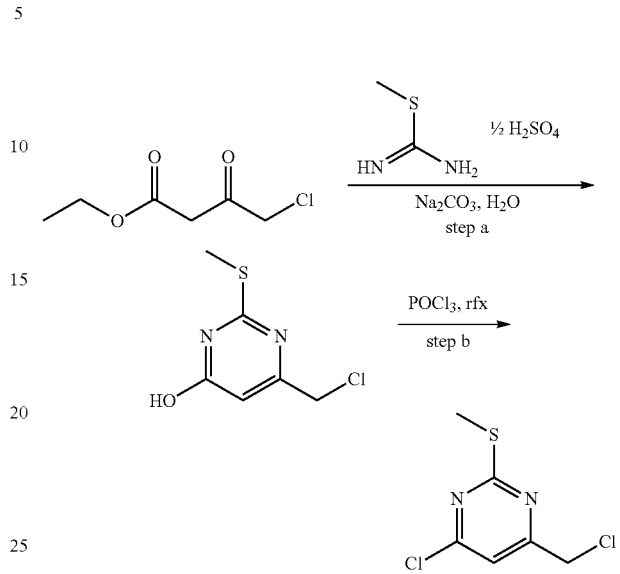

Step a. 6-(chloromethyl)-2-(methylthio)pyrimidin-4-ol: To a solution of ethyl 4-chloro-3-oxobutanoate (13 g, 79 mmol) and methyl carbamimidothioatesulphate (20 g, 72 mmol) in water (200 mL) was added sodium carbonate (11.5 g, 108 mmol). The reaction was stirred at room temperature overnight. The mixture was quenched with 6M HCl aqueous solution to pH acid and filtered. The filter cake was dried to give the desired product (11.1 g, 73%) as a white solid. $^1H$ NMR (400 MHz, $CDCl_3$) δ 12.91 (s, 1H), 6.42 (s, 1H), 4.36 (s, 2H), 2.59 (s, 3H).

Step b. 4-chloro-6-(chloromethyl)-2-(methylthio)pyrimidine: The solution of 6-(chloromethyl)-2-(methylthio)pyrimidin-4-ol (2.8 g, 14.7 mmol) in $POCl_3$ (10 mL) was heated to 100° C., and stirred for 1 h. The reaction mixture was concentrated and added saturated $NaHCO_3$ aqueous solution (100 mL) and extracted with ethyl acetate (100 mL). The organic layers was concentrated and the residue was purified by silica gel column chromatography (petroleum ether/ethyl acetate=100/3) to give the desired product (2.4 g, 80%) as a yellow oil. $^1H$ NMR (400 MHz, $CDCl_3$) δ 7.23 (s, 1H), 4.53 (s, 2H), 2.58 (s, 3H).

Method C

Preparation of 4-chloro-6-(chloromethyl)-2-methylpyrimidine

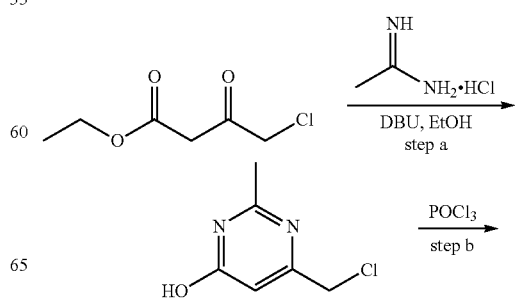

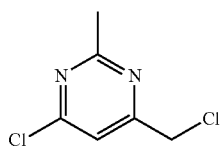

Step a. 6-(chloromethyl)-2-methylpyrimidin-4-ol: To a solution of ethyl 4-chloro-3-oxobutanoate (16.5 g, 100 mmol) and acetamidine hydrochloride (10 g, 106 mmol) in ethanol (150 mL) was slowly added DBU (30.4 g, 200 mmol) at 4° C. The reaction was stirred at room temperature overnight. The reaction mixture was concentrated and the residue was dissolved in dichloromethane (120 mL), then washed with brine (30 mL×3). The organic layer was dried over $Na_2SO_4$ and concentrated to give the desired product (7.93 g, 50%) as a yellow oil. $^1$H NMR (400 MHz, CDCl$_3$) δ 13.01 (s, 1H), 6.53 (s, 1H), 4.37 (s, 2H), 2.50 (s, 3H).

Step b. 4-chloro-6-(chloromethyl)-2-methylpyrimidine: The solution of 6-(chloromethyl)-2-methylpyrimidin-4-ol (7.93 g, 50 mmol) in POCl$_3$ (20 mL) was heated to 110° C., and stirred for 30 min. Then reaction mixture was concentrated and dissolved in ethyl acetate (20 mL), then added this solution into ice water (100 mL), extracted with ethyl acetate (30 mL×3). The combined organic layer was dried over $Na_2SO_4$ and concentrated. The residue was purified by silica gel column chromatography (petroleum ether/ethyl acetate=5/1) to give the desired product (4.0 g, 23%) as a yellow oil. $^1$H NMR (400 MHz, CDCl3) δ 7.41 (s, 1H), 4.55 (s, 2H), 2.71 (s, 3H).

Method D

Preparation of N-methyl-1-(2-methyl-6-(4-methylpiperazin-1-yl)pyrimidin-4-yl)methanamine

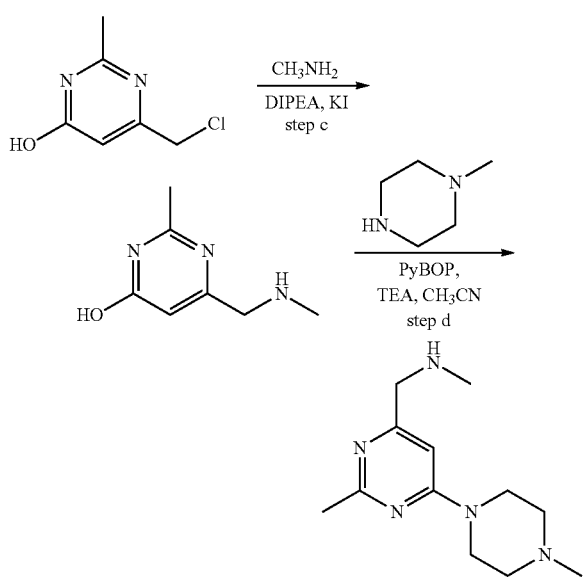

Step c. 2-methyl-6-((methylamino)methyl)pyrimidin-4-ol: The solution of 6-(chloromethyl)-2-methylpyrimidin-4-ol (1.7 g, 11 mmol), methylamine solution (30 wt percent in absolute ethanol, 3 g), KI (183 mg, 1.1 mmol) and DIPEA (7.1 g, 55 mmol) in CH$_3$CN (50 mL) was added into a sealed tube, and heated to 60° C. The reaction was stirred at this temperature overnight. The reaction mixture was concentrated and the residue was purified by silica gel column chromatography (dichloromethane/methanol=10/1) to give the desired product (600 mg, 35%) as a yellow solid. $^1$H NMR (400 MHz, DMSO-d$_6$) δ 6.36 (s, 1H), 3.80 (s, 2H), 2.66 (s, 1H), 2.55 (s, 3H), 2.43 (s, 2H).

Step d. N-methyl-1-(2-methyl-6-(4-methylpiperazin-1-yl)pyrimidin-4-yl)methanamine: To a solution of 2-methyl-6-((methylamino)methyl)pyrimidin-4-ol (300 mg, 1.96 mmol), TEA (1.9 g, 19.6 mmol) and N-methylpiperazine (980 mg, 9.8 mmol) in CH$_3$CN (20 mL) was added PyBOP (1.1 g, 2.15 mmol). The reaction mixture was stirred at reflux overnight. Then the reaction mixture was concentrated and the residue was purified by silica gel column chromatography (dichloromethane/methanol=20/1) to give the desired product (300 mg, 65%) as a yellow solid. $^1$H NMR (400 MHz, CDCl$_3$) δ 6.38 (s,1H), 3.67-3.63 (m, 6H), 2.47-2.45 (m, 10H), 2.32 (s, 3H).

Method E

Preparation of 2-methyl-6-(4-methylpiperazin-1-yl)pyrimidine-4-carbaldehyde

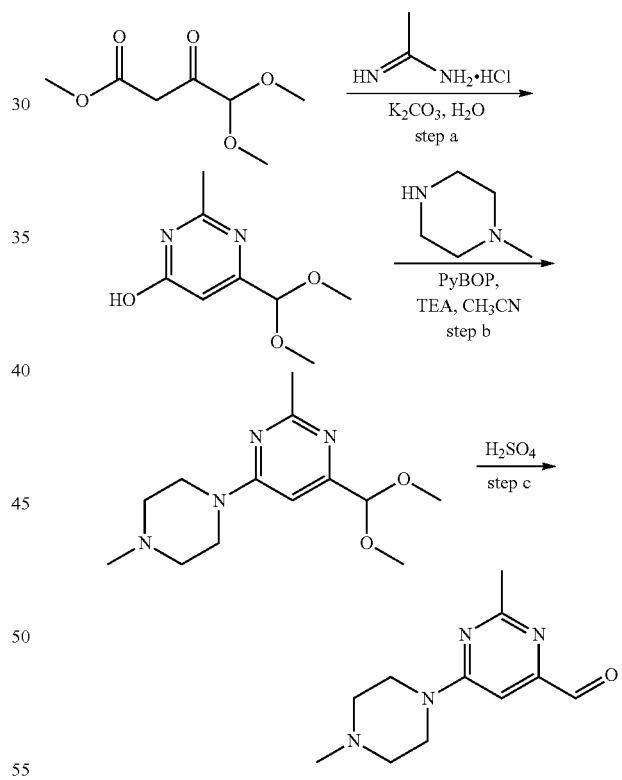

Step a. 6-(dimethoxymethyl)-2-methylpyrimidin-4-ol: To a solution of methyl 4,4-dimethoxy-3-oxobutanoate (300 mg, 1.7 mmol) and acetamidine hydrochloride (320 mg, 3.4 mmol) in water (10 mL) was added K$_2$CO$_3$ (940 mg, 6.8 mmol). The reaction was stirred at room temperature overnight. The mixture was quenched with AcOH to pH acid and extracted with dichloromethane (100 mL×3). The combined organic layer was dried over Na$_2$SO$_4$, filtered and evaporated. The residue was purified by silica gel column chromatography (dichloromethane/methanol=50/1) to give the desired product (110 mg, 35%) as a white solid.

Step b. 4-(dimethoxymethyl)-2-methyl-6-(4-methylpiperazin-1-yl)pyrimidine: To a solution of 6-(dimethoxymethyl)-2-methylpyrimidin-4-ol (110 mg, 0.6 mmol), TEA (600 mg, 6 mmol) and N-methylpiperazine (90 mg, 0.9 mmol) in CH₃CN (10 mL) was added PyBOP (340 mg, 0.7 mmol). The reaction mixture was stirred at reflux overnight. Then the reaction solution was evaporated to remove most of CH₃CN, added saturated NaHCO₃ aqueous solution (100 mL) and extracted with dichloromethane (100 mL). The organic layer was dried over Na₂SO₄, filtered and evaporated. The residue was purified by silica gel column chromatography (dichloromethane/methanol=100/3) to give the desired product (140 mg, 88%) as a yellow oil.

Step c. 2-methyl-6-(4-methylpiperazin-1-yl)pyrimidine-4-carbaldehyde: The mixture of 4-(dimethoxymethyl)-2-methyl-6-(4-methylpiperazin-1-yl)pyrimidine (140 mg, 0.5 mmol) and sulfuric acid (20 wt percent in water, 5 mL) was stirred at reflux overnight. Then the saturated NaHCO₃ aqueous solution was added to adjust pH to basic and extracted with dichloromethane (100 mL×3). The combined organic layer was dried over Na₂SO₄, filtered and evaporated to give the crude desired product (110 mg, 97%) as a yellow oil.

Method F

Preparation of 2-(dimethylamino)-6-(4-methylpiperazin-1-yl)pyrimidine-4-carbaldehyde

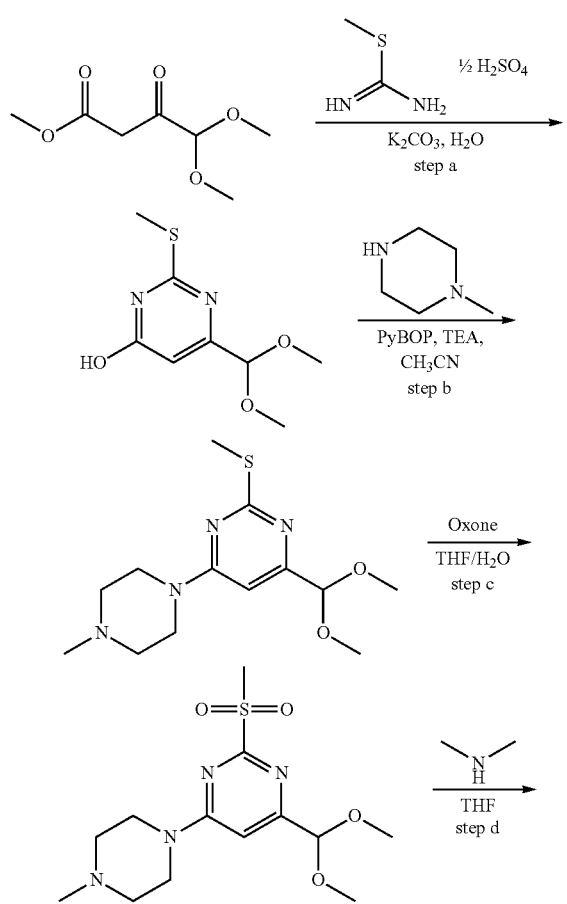

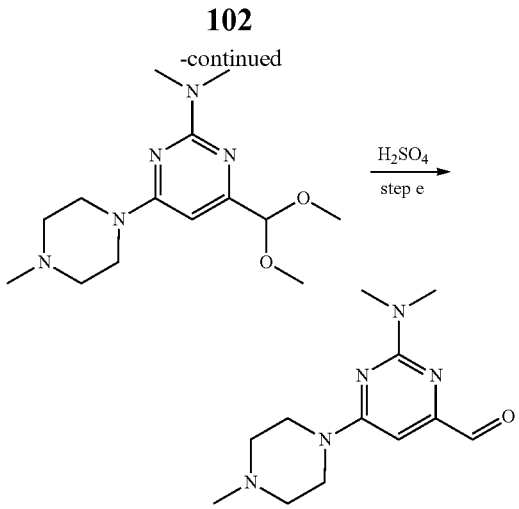

Step a. 6-(dimethoxymethyl)-2-(methylthio)pyrimidin-4-ol: To a solution of methyl 4,4-dimethoxy-3-oxobutanoate (3 g, 17 mmol) and methyl carbamimidothioatesulphate (9.5 g, 34 mmol) in water (100 mL) was added K₂CO₃ (17.6 g, 76.5 mmol). The reaction was stirred at room temperature overnight. The mixture was quenched with AcOH to adjust pH to acid and extracted with dichloromethane (100 mL×3). The combined organic layer was dried over Na₂SO₄, filtered and evaporated. The residue was purified by silica gel column chromatography (dichloromethane/methanol=100/1) to give the desired product (3.4 g, 92%) as a white solid. ¹H NMR (400 MHz, CDCl₃) δ 12.80 (s, 1H), 6.46 (s, 1H), 5.07 (s, 1H), 3.40 (s, 6H), 2.60 (s, 3H).

Step b. 4-(dimethoxymethyl)-6-(4-methylpiperazin-1-yl)-2-(methylthio)pyrimidine: To a solution of 6-(dimethoxymethyl)-2-(methylthio)pyrimidin-4-ol (3.4 g, 16 mmol), TEA (16 g, 160 mmol) and N-methylpiperazine (2.4 g, 40 mmol) in CH₃CN (100 mL) was added PyBOP (9 g, 17.6 mmol). The reaction mixture was stirred at reflux overnight. Then the reaction solution was evaporated to remove most of CH₃CN, added saturated NaHCO₃ aqueous solution (200 mL) and extracted with dichloromethane (200 mL). The organic layer was dried over Na₂SO₄, filtered and evaporated. The residue was purified by silica gel column chromatography (dichloromethane/methanol=100/3) to give the desired product (2.8 g, 59%) as a yellow oil. ¹H NMR (400 MHz, CDCl₃) δ 6.45 (s, 1H), 5.07 (s, 1H), 3.70 (s, 4H), 3.40 (s, 6H), 2.51 (s, 3H), 2.47 (t, J=5.0 Hz, 4H), 2.34 (s, 3H).

Step c. 4-(dimethoxymethyl)-6-(4-methylpiperazin-1-yl)-2-(methylsulfonyl)pyrimidine: To a solution of 4-(dimethoxymethyl)-6-(4-methylpiperazin-1-yl)-2-(methylthio)pyrimidine (2.8 g, 9.4 mmol) in THF (90 mL) and water (4.5 mL) was added Oxone (7 g, 11 mmol). The reaction was stirred at room temperature for 4 h. Then the reaction was added saturated NaHCO₃ aqueous solution (200 mL) and extracted with ethyl acetate (200 mL). The organic layer was dried over Na₂SO₄, filtered and evaporated to give the desired product (2.4 g, 78%) as a yellow oil.

Step d. 4-(dimethoxymethyl)-N,N-dimethyl-6-(4-methylpiperazin-1-yl)pyrimidin-2-amine: To a solution of 4-(dimethoxymethyl)-6-(4-methylpiperazin-1-yl)-2-(methylsulfonyl)pyrimidine (340 mg, 1 mmol) in THF (5 mL) in a sealed tube was added dimethylamine (5 mL). The reaction mixture was stirred at reflux overnight. Then the reaction solution was cooled to room temperature, added saturated NaHCO₃ aqueous solution (100 mL) and extracted with dichloromethane (100 mL). The organic layer was dried over Na$_2$SO$_4$, filtered and evaporated. The residue was purified by silica gel column chromatography (dichloromethane/methanol/ammonium hydroxide=100/1/1 to 100/3/1) to give the desired product (260 mg, 88%) as a yellow oil. $^1$H NMR (400 MHz, CDCl$_3$) δ 6.06 (s, 1H), 4.98 (s, 1H), 3.62 (s, 4H), 3.39 (s, 6H), 3.11 (s, 6H), 2.42 (s, 4H), 2.30 (s, 3H).

Step e. 2-(dimethylamino)-6-(4-methylpiperazin-1-yl)pyrimidine-4-carbaldehyde: The mixture of 4-(dimethoxymethyl)-N,N-dimethyl-6-(4-methylpiperazin-1-yl)pyrimidin-2-amine (260 mg, 1.3 mmol) and sulfuric acid(20 wt percent in water, 5 mL) was stirred at reflux overnight. Then the saturated NaHCO$_3$ aqueous solution was added to adjust pH to basic and extracted with dichloromethane (100 mL×3). The combined organic layer was dried over Na$_2$SO$_4$, filtered and evaporated to give the crude desired product (210 mg, 65%) as a yellow solid. $^1$H NMR (400 MHz, CDCl$_3$) δ 9.76 (s, 1H), 6.39 (s, 1H), 3.68 (s, 4H), 3.18 (s, 6H), 2.45 (s, 4H), 2.33 (s, 3H).

Method G

Preparation of 2-ethoxy-6-(4-methylpiperazin-1-yl)pyrimidine-4-carbaldehyde

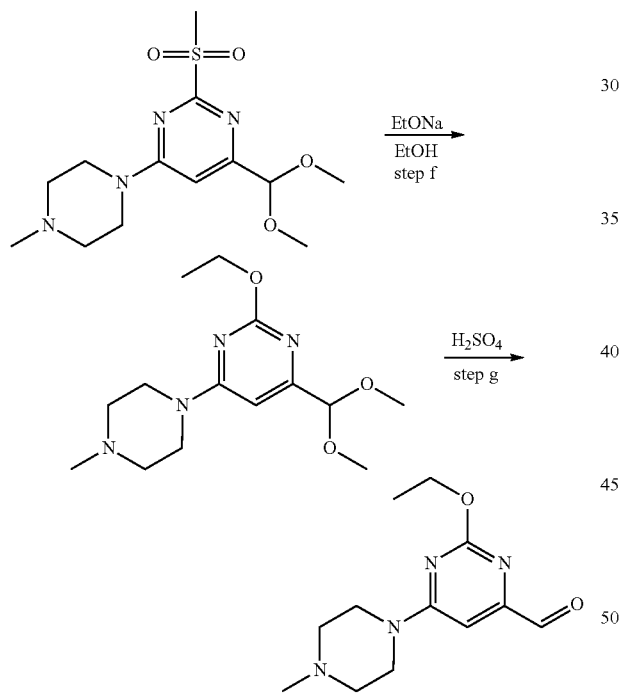

Step f. 4-(dimethoxymethyl)-2-ethoxy-6-(4-methylpiperazin-1-yl)pyrimidine: To a solution of 4-(dimethoxymethyl)-6-(4-methylpiperazin-1-yl)-2-(methylsulfonyl)pyrimidine (200 mg, 0.61 mmol) in ethanol (5 mL) was added sodium ethanolate (206 mg, 3 mmol). The reaction mixture was stirred at reflux overnight. Then the reaction solution was cooled to room temperature, added saturated NaHCO$_3$ aqueous solution (100 mL) and extracted with dichloromethane (100 mL). The organic layer was dried over Na$_2$SO$_4$, filtered and evaporated. The residue was purified by silica gel column chromatography (dichloromethane/methanol/ammonium hydroxide=100/1/1 to 100/3/1) to give the desired product (160 mg, 89%) as a yellow oil. $^1$H NMR (400 MHz, CDCl$_3$) δ 6.42 (s, 1H), 5.04 (s, 1H), 4.35 (q, J=7.2 Hz, 2H), 3.68 (s, 4H), 3.40 (s, 6H), 2.45 (t, J=5.0 Hz, 4H), 2.32 (s, 3H), 1.38 (t, J=7.0 Hz, 3H).

Step g. 2-ethoxy-6-(4-methylpiperazin-1-yl)pyrimidine-4-carbaldehyde: The mixture of 4-(dimethoxymethyl)-2-ethoxy-6-(4-methylpiperazin-1-yl)pyrimidine (160 mg, 0.5 mmol) and sulfuric acid (20 wt percent in water, 5 mL) was stirred at reflux overnight. Then the reaction solution was cooled to room temperature, and the saturated NaHCO$_3$ aqueous solution was added to adjust pH to basic and extracted with dichloromethane (100 mL×3). The combined organic layer was dried over Na$_2$SO$_4$, filtered and evaporated to give the crude desired product (100 mg, 80%) as a yellow solid.

Method H

Preparation of 6-(4-methylpiperazin-1-yl)-2-phenylpyrimidine-4-carbaldehyde

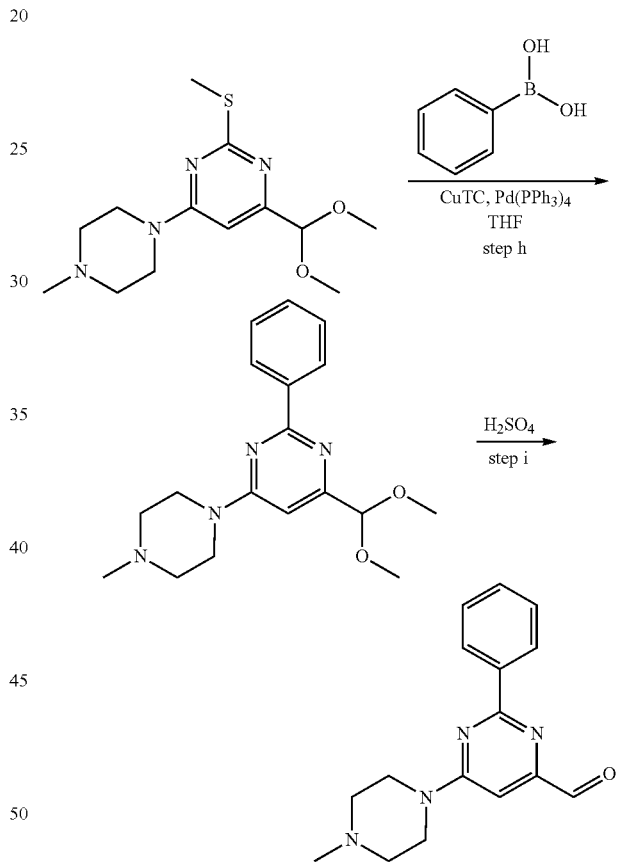

Step h. 4-(dimethoxymethyl)-6-(4-methylpiperazin-1-yl)-2-phenylpyrimidine: The mixture of 4-(dimethoxymethyl)-6-(4-methylpiperazin-1-yl)-2-(methylthio)pyrimidine (298 mg, 1 mmol), phenylboronic acid (244 mg, 2 mmol), copper (I) thiophene-2-carboxylate (497 mg, 2.6 mmol) and Pd(PPh$_3$)$_4$ (115 mg, 0.1 mmol) in THF (20 mL) was stirred at reflux overnight under N$_2$ atmosphere. Then the reaction solution was concentrated and the residue was purified by silica gel column chromatography (dichloromethane/methanol=100/1.5) to give the desired product (240 mg, 73%) as a colorless oil. $^1$H NMR (400 MHz, CDCl$_3$) δ 8.41 (d, J=3.6 Hz, 2H), 7.44-7.43 (m, 3H), 6.70 (s, 1H), 5.24 (s, 1H), 3.82-3.80 (m, 4H), 3.47 (s, 6H), 2.53-2.52 (m, 4H), 2.37 (s, 3H).

Step i. 6-(4-methylpiperazin-1-yl)-2-phenylpyrimidine-4-carbaldehyde: The mixture of 4-(dimethoxymethyl)-6-(4-methylpiperazin-1-yl)-2-phenylpyrimidine (240 mg, 0.73 mmol) and sulfuric acid (20 wt percent in water, 10 mL) was stirred at reflux overnight. Then the reaction solution was cooled to room temperature, and washed with diethyl ether (10 mL). The water phase was added 6M NaOH aqueous solution to adjust pH to 10 and extracted with dichloromethane (30 mL×3). The combined organic layer was dried over $Na_2SO_4$, filtered and evaporated. The residue was purified by silica gel column chromatography (dichloromethane/methanol=100/2) to give the desired product (170 mg, 82%) as a colorless oil. $^1$H NMR (400 MHz, CDCl$_3$) δ 10.02 (s, 1H), 8.50-8.45 (m, 2H), 7.50-7.49 (m, 3H), 6.99 (s, 1H), 3.95-3.80 (m, 4H), 2.63-2.47 (m, 4H), 2.37 (s, 3H).

Method I

Preparation of 1-(5-fluoro-2-methyl-6-(4-methylpiperazin-1-yl)pyrimidin-4-yl)-N-methylmethanamine

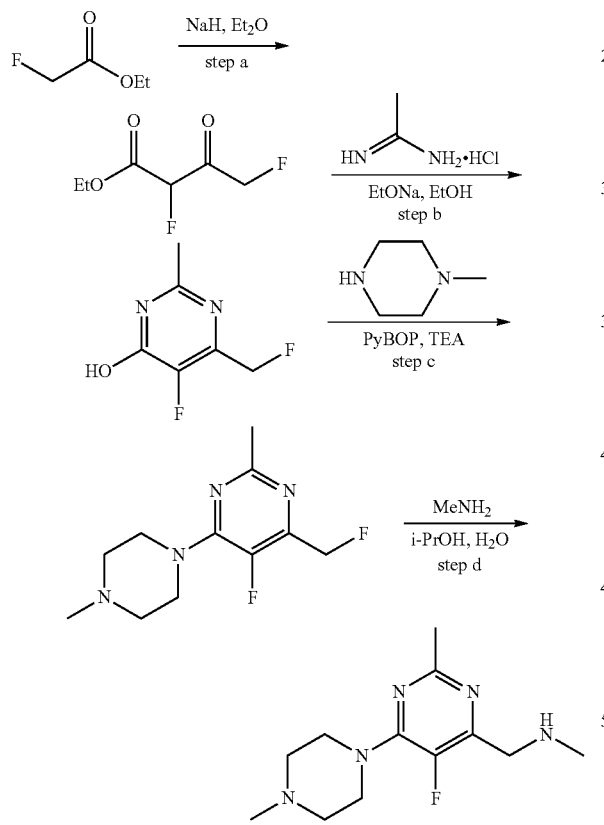

Step a. ethyl 2,4-difluoro-3-oxobutanoate: To a solution of NaH (60 wt percent moistened with oil, 936 mg, 23.4 mmol) in diethyl ether (50 mL) was added dropwise ethyl 2-fluoroacetate (5 g, 47.2 mmol) at room temperature. The reaction was stirred at 40° C. for 4 h. The reaction mixture was cooled to 0° C. and poured into 2M sulfuric acid aqueous solution (15 mL). The mixture was extracted with diethyl ether (50 mL×3). The combined organic layer was dried over $Na_2SO_4$, filtered and evaporated. The residue was purified by silica gel column chromatography (petroleum ether/ethyl acetate=10/1 to 2/1) to give the desired product (2 g, 25%) as a yellow oil.

Step b. 5-fluoro-6-(fluoromethyl)-2-methylpyrimidin-4-ol: To a solution of methyl 4,4-dimethoxy-3-oxobutanoate (1.9 g, 11.4 mmol) and acetamidine hydrochloride (2.2 g, 22.8 mmol) in ethanol (40 mL) was added EtONa (2.3 g, 34.2 mmol). The reaction was stirred at reflux overnight. The mixture was cooled to room temperature. 6M HCl aqueous solution (2 mL) was added and evaporated. The residue was purified by silica gel column chromatography (petroleum ether/ethyl acetate=3/1 to 1/1) to give the desired product (800 mg, 43%) as a yellow solid. $^1$H NMR (400 MHz, CDCl3) δ 13.07 (br s, 1H), 5.35 (d, J=46.8 Hz, 2H), 2.53 (s, 3H).

Step c. 5-fluoro-4-(fluoromethyl)-2-methyl-6-(4-methylpiperazin-1-yl)pyrimidine: To a solution of 5-fluoro-6-(fluoromethyl)-2-methylpyrimidin-4-ol (800 mg, 5 mmol), TEA (1.5 g, 15 mmol) and N-methylpiperazine (750 mg, 7.5 mmol) in CH$_3$CN (10 mL) was added PyBOP (2.9 g, 5.5 mmol). The reaction mixture was stirred at reflux overnight. Then the reaction solution was evaporated to remove most of CH$_3$CN, added dichloromethane (100 mL) to dilute, washed with saturated NaCl aqueous solution (50 mL×3). The organic layer was dried over $Na_2SO_4$, filtered and evaporated. The residue was purified by silica gel column chromatography (pure ethyl acetate) to give the desired product (1.0 g, 90%) as a yellow oil. $^1$H NMR (400 MHz, CDCl$_3$) δ 5.36 (d, J=47.2 Hz, 2H), 3.87-3.73 (m, 4H), 2.57-2.50 (m, 4H), 2.49 (s, 3H), 2.33 (s, 3H).

Step d. 1-(5-fluoro-2-methyl-6-(4-methylpiperazin-1-yl)pyrimidin-4-yl)-N-methylmethanamine: The mixture of 5-fluoro-4-(fluoromethyl)-2-methyl-6-(4-methylpiperazin-1-yl)pyrimidine (1.0 g, 4.1 mmol) and 2M methyl amine (in methanol, 6 mL) in water (15 mL) and i-propanol (15 mL) in a sealed tube was stirred at reflux overnight. The reaction solution was evaporated to remove most of i-propanol, and extracted with dichloromethane (30 mL×3). The combined organic layer was dried over $Na_2SO_4$, filtered and evaporated. The residue was purified by silica gel column chromatography (dichloromethane/methanol/ammonium hydroxide=400/10/1 to 200/10/1) to give the desired product (800 mg, 76%) as a yellow oil. $^1$H NMR (400 MHz, CDCl$_3$) δ 3.80-3.74 (m, 4H), 3.73 (s, 2H), 2.48-2.46 (m, 4H), 2.44 (s, 6H), 2.31 (s, 3H).

Method J

Preparation of (S)-4-(4-methylpiperazin-1-yl)-2-(methylthio)-6-(pyrrolidin-2-yl)pyrimidine

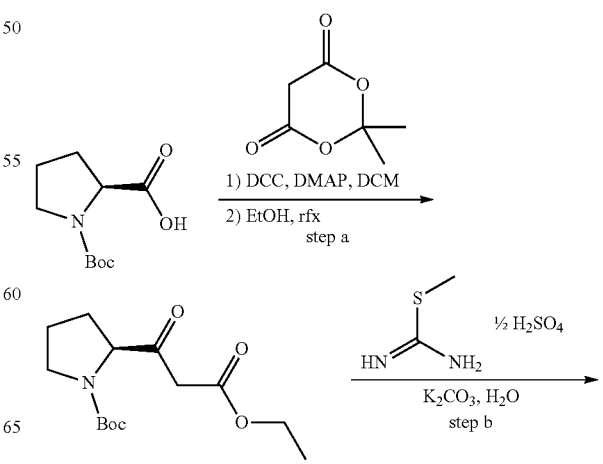

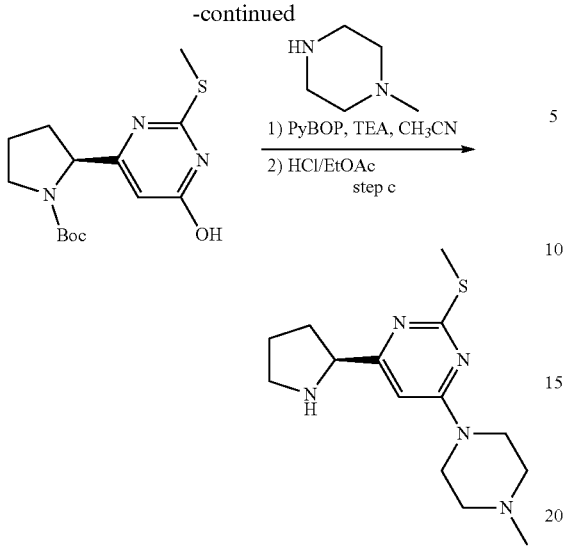

Step a. (S)-tert-butyl 2-(3-ethoxy-3-oxopropanoyl)pyrrolidine-1-carboxylate: To a mixture of Boc-L-Proline-OH (5 g, 23 mmol), 2,2-dimethyl-1,3-dioxane-4,6-dione (3.4 g, 23 mmol) and DMAP (5.7 g, 46 mmol) in dichloromethane (70 mL) was added DCC (4.8 g, 23 mmol) at 0° C. The mixture was stirred at room temperature for 48 h before the reaction mixture was filtered. The filtrate was added 1M HCl aqueous solution (100 mL) and the water phase was extracted with dichloromethane (200 mL). The combined organic layer was dried over Na$_2$SO$_4$, filtered and evaporated to give a yellow oil, about 7.5 g. This residue was diluted with EtOH (100 mL) and stirred at reflux for 2 h. The resulting solution was concentrated and purified by silica gel column chromatography (petroleum ether/ethyl acetate=4/1) to give the desired product (4.0 g, 60%) as a yellow oil. $^1$H NMR (400 MHz, CDCl$_3$) δ 4.41-4.23 (m, 1H), 4.23-4.13 (m, 2H), 3.59-3.39 (m, 4H), 2.25-2.05 (m, 2H), 1.91-1.83 (m, 2H), 1.46-1.40 (m, 9H), 1.31-1.23 (m, 3H).

Step b. (S)-tert-butyl 2-(6-hydroxy-2-(methylthio)pyrimidin-4-yl)pyrrolidine-1-carboxylate: To a solution of (S)-tert-butyl 2-(3-ethoxy-3-oxopropanoyl)pyrrolidine-1-carboxylate (500 mg, 1.8 mmol) and methyl carbamimidothioatesulphate (1.0 g, 3.6 mmol) in water (25 mL) was added K$_2$CO$_3$ (1.1 g, 8.1 mmol). The reaction was stirred at room temperature overnight. The reaction mixture was quenched with 1M HCl aqueous solution to adjust pH to acid and extracted with dichloromethane (50 mL×3). The combined organic layer was dried over Na$_2$SO$_4$, filtered and evaporated. The residue was purified by silica gel column chromatography (dichloromethane/methanol=20/1) to give the desired product (200 mg, 37%) as a colorless oil. $^1$H NMR (400 MHz, CDCl$_3$) δ 6.09-6.05 (m, 1H), 4.75-4.50 (m, 1H), 3.59-3.39 (m, 2H), 2.55 (s, 3H), 2.28-2.14 (m, 1H), 2.00-1.80 (m, 3H), 1.51-1.32 (m, 9H).

Step c. (S)-4-(4-methylpiperazin-1-yl)-2-(methylthio)-6-(pyrrolidin-2-yl)pyrimidine: To a solution of (S)-tert-butyl 2-(6-hydroxy-2-(methylthio)pyrimidin-4-yl)pyrrolidine-1-carboxylate (200 mg, 0.64 mmol), TEA (650 mg, 6.4 mmol) and N-methylpiperazine (100 mg, 0.96 mmol) in CH$_3$CN (5 mL) was added PyBOP (510 mg, 0.96 mmol). The reaction mixture was stirred at reflux overnight. Then the reaction solution was evaporated to remove most of CH$_3$CN, added dichloromethane (100 mL) to dilute, washed with saturated NaHCO$_3$ aqueous solution (100 mL). The organic layer was dried over Na$_2$SO$_4$, filtered and evaporated. The residue was purified by silica gel column chromatography (dichloromethane/methanol=100/1) to give the crude intermediate (150 mg) as a yellow oil. Then it was diluted with ethyl acetate (3 mL), added 3M HCl/ethyl acetate (4 mL). The mixture was stirred at room temperature overnight. Then the reaction solution was evaporated, added saturated NaHCO$_3$ aqueous solution (50 mL), and extracted with dichloromethane (50 mL). The organic layer was dried over Na$_2$SO$_4$, filtered and evaporated to give the desired product (100 mg, 53%) as a yellow oil. $^1$H NMR (400 MHz, CDCl$_3$) δ 6.29 (s, 1H), 3.98 (t, J=7.4 Hz, 1H), 3.74-3.58 (m, 4H), 3.19-3.09 (m, 1H), 3.02-2.92 (m, 1H), 2.49 (s, 3H), 2.45 (t, J=5.2 Hz, 4H), 2.33 (s, 3H), 2.23-2.10 (m, 1H), 1.82-1.76 (m, 2H), 1.76-1.63 (m, 1H).

Method K

Preparation of tert-butyl 5-oxo-5-(pyridin-2-yl)pentylcarbamate

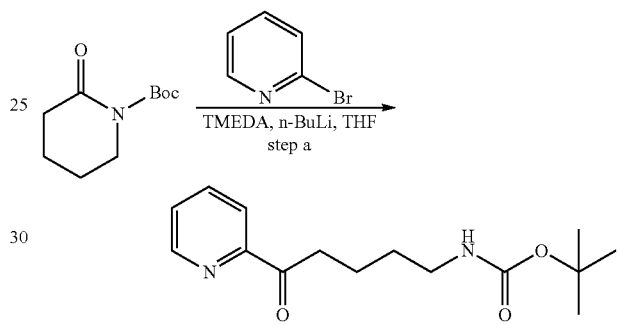

Step a. tert-butyl 5-oxo-5-(pyridin-2-yl)pentylcarbamate: To a THF solution (30 mL) containing commercially available 2-bromopyridine (1.4 g, 9 mmol) and N,N,N'-N'-tetramethyl ethylene diamine (960 mg, 6.5 mmol), a hexane solution (3 mL, 7.5 mmol) of 2.5M n-butyl lithium was added dropwise at −78° C., and the resulting solution was stirred at the same temperature for 2 h. To the reaction solution, tert-butyl 2-oxopiperidine-1-carboxylate (1 g, 5 mmol) was added at −78° C., and the resulting solution was stirred at the same temperature for 2 h. To the reaction solution, water (10 mL) was added, and the solution was extracted with ethyl acetate (100 mL). The organic layer was dried over Na$_2$SO$_4$, filtered and evaporated. The residue was purified by silica gel column chromatography (petroleum ether/ethyl acetate=5/1) to give the desired product (670 mg, 48%) as a yellow oil. $^1$H NMR (400 MHz, CDCl$_3$) δ 8.68 (d, J=4.8 Hz, 1H), 8.03 (d, J=8.0 Hz, 1H), 7.79-7.77 (m, 1H), 7.51-7.44 (m, 1H), 4.69 (s, 1H), 3.27-3.21 (m, 2H), 3.21-3.15 (m, 2H), 1.80-1.74 (m, 2H), 1.63-1.55 (m, 2H), 1.44 (s, 9H).

Method L

Preparation of 2-(bromomethyl)-4-chloropyrimidine

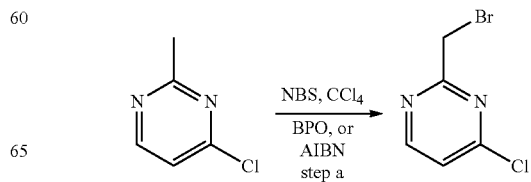

Step a. 2-(bromomethyl)-4-chloropyrimidine: To a solution 4-chloro-2-methylpyrimidine (370 mg, 2.9 mmol), NBS (566 mg, 3.2 mmol) and AIBN (50 mg, 0.3 mmol) in CCl$_4$ (10 mL) was stirred at reflux overnight. Then the reaction solution was cooled to room temperature, added saturated NaHCO$_3$ aqueous solution (50 mL) and extracted with dichloromethane (50 mL). The organic layer was dried over Na$_2$SO$_4$, filtered and evaporated. The residue was purified by silica gel column chromatography (petroleum ether/ethyl acetate=50/1) to give the desired product (130 mg, 22%) as a yellow oil. $^1$H NMR (400 MHz, CDCl$_3$) δ 8.62 (d, J=5.6 Hz, 1H), 7.27 (d, J=5.6 Hz, 1H), 4.54 (s, 2H).

Method M

Preparation of tert-butyl 4-(5-cyano-2-methyl-6-((methyl(1,2,3,4-tetrahydronaphthalen-1-yl)amino)methyl)pyrimidin-4-yl)piperazine-1-carboxylate

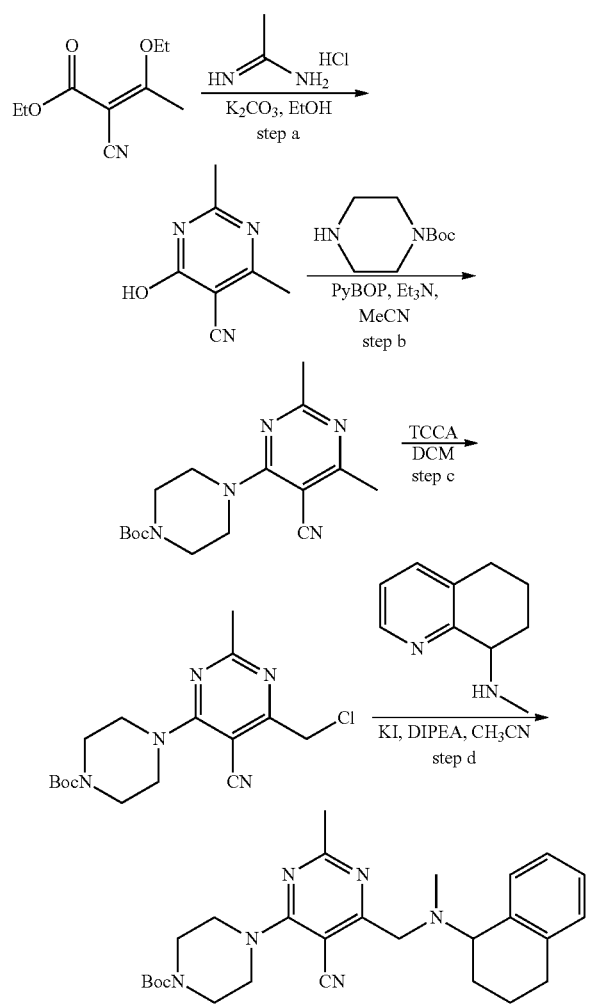

Step a. 4-hydroxy-2,6-dimethylpyrimidine-5-carbonitrile: To a solution of methyl (Z)-ethyl 2-cyano-3-ethoxybut-2-enoate (5.0 g, 27 mmol) and acetamidine hydrochloride (3.9 g, 41 mmol) in ethanol (80 mL) was added K$_2$CO$_3$ (11.3 g, 82 mmol). The mixture was stirred at room temperature overnight. The mixture was concentrated, added 3M HCl aqueous solution to adjust pH to 5 and extracted with n-butanol (50 mL×6). The combined organic layer was evaporated to give the desired product (3.5 g, 87%) as a yellow solid. $^1$H NMR (400 MHz, DMSO-d$_6$) δ 13.30 (s, 1H), 2.39 (s, 3H), 2.35 (s, 3H).

Step b. tert-butyl 4-(5-cyano-2,6-dimethylpyrimidin-4-yl)piperazine-1-carboxylate: To a solution of 4-hydroxy-2,6-dimethylpyrimidine-5-carbonitrile (2.5 g, 16.8 mmol), TEA (5.1 g, 50.4 mmol) and tert-butyl piperazine-1-carboxylate (4.7 g, 25.2 mmol) in CH$_3$CN (60 mL) was added PyBOP (9.6 g, 18.5 mmol). The reaction mixture was stirred at reflux overnight. Then the reaction solution was evaporated. The residue was purified by silica gel column chromatography (petroleum ether/ethyl acetate=5/1 to 3/1) to give the desired product (4.3 g, 81%) as a yellow solid. $^1$H NMR (400 MHz, CDCl$_3$) δ 3.94 (s, 4H), 3.55 (s, 4H), 2.57 (s, 3H), 2.50 (s, 3H), 1.47 (s, 9H)

Step c. tert-butyl 4-(6-(chloromethyl)-5-cyano-2-methylpyrimidin-4-yl)piperazine-1-carboxylate: A mixture of tert-butyl 4-(5-cyano-2,6-dimethylpyrimidin-4-yl)piperazine-1-carboxylate (10 g, 60 4.0 g, 12.6 mmol) in DCM (100 mL) was added TCCA (2.9 g, 12.6 mmol) at 0° C., and the resulting solution was stirred at the same temperature for 1 h, then stirred at room temperature for 6 h. The reaction was quenched with the saturated Na$_2$S$_2$O$_3$ aqueous solution. The reaction mixture was filtered and the filtrate was extracted with dichloromethane (50 mL×3). The combined organic layer was washed with brine and dried over Na$_2$SO$_4$, filtered and evaporated. The residue was purified by silica gel column chromatography (petroleum ether/ethyl acetate=10/1 to 5/1) to give the desired product (2.4 g, 54%) as a yellow solid. $^1$H NMR (400 MHz, CDCl$_3$) δ 3.94 (s, 4H), 3.55 (s, 4H), 2.57 (s, 3H), 2.50 (s, 3H), 1.47 (s, 9H)

Step d. tert-butyl 4-(5-cyano-2-methyl-6-((methyl(1,2,3,4-tetrahydronaphthalen-1-yl)amino)methyl)pyrimidin-4-yl)piperazine-1-carboxylate: A mixture of N-methyl-5,6,7,8-tetrahydroquinolin-8-amine (421 mg, 2.6 mmol, see reference WO2006026703), tert-butyl 4-(6-(chloromethyl)-5-cyano-2-methylpyrimidin-4-yl)piperazine-1-carboxylate (1.0 g, 2.8 mmol), KI (45 mg, 0.3 mmol) and DIPEA (671 mg, 5.2 mmol) in CH$_3$CN (10 mL) was stirred at room temperature overnight. The reaction solution was evaporated and the residue was purified by silica gel column chromatography (petroleum ether/ethyl acetate=1/1) to give the desired product (800 mg, 64%) as a yellow oil. $^1$H NMR (400 MHz, CDCl$_3$) δ 8.44 (d, J=3.6 Hz, 1H), 7.35 (d, J=7.2 Hz, 1H), 7.04 (dd, J=7.2, 4.8 Hz, 1H), 4.15-4.08 (m, 1H), 4.08-3.97 (m, 2H), 3.97-3.88 (m, 4H), 3.02-2.93 (m, 4H), 2.86-2.76 (m, 1H), 2.73-2.63 (m, 1H), 2.53 (s, 3H), 2.28 (s, 3H), 2.22-2.12 (m, 1H), 2.10-1.92 (m, 2H), 1.76 (s, 10H).

Method N

Preparation of 5-bromo-2-(bromomethyl)imidazo[1,2-a]pyridine

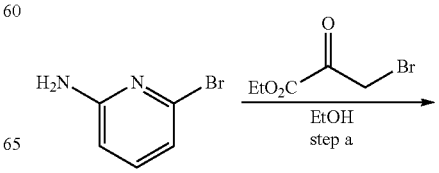

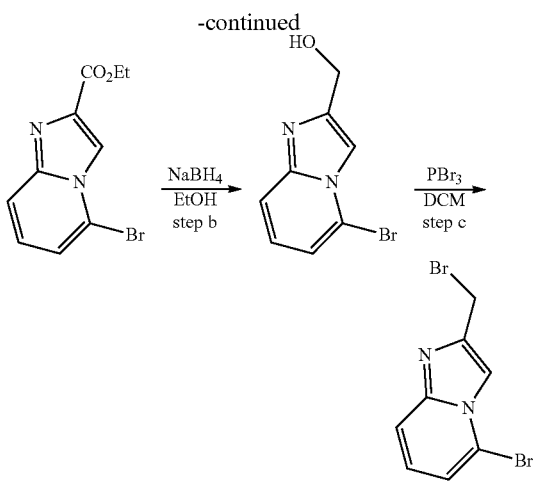

Step a. ethyl 5-bromoimidazo[1,2-a]pyridine-2-carboxylate: The solution of methyl 6-bromopyridin-2-amine (1.7 g, 10 mmol) and ethyl 3-bromo-2-oxopropanoate (2.3 g, 12 mmol) in ethanol (80 mL) was stirred at reflux overnight. The reaction mixture was cooled to room temperature and filtered. The filter cake was dried by oil pump to give the crude desired product (2.8 g) as a white solid. $^1$H NMR (400 MHz, DMSO-$d_6$) δ 8.49 (s, 1H), 7.76 (d, J=8.4 Hz, 1H), 7.53-7.50 (m, 1H), 7.47-7.43 (m, 1H), 4.36 (q, J=7.2 Hz, 2H), 1.34 (q, J=7.2 Hz, 3H).

Step b. (5-bromoimidazo[1,2-a]pyridin-2-yl)methanol: To the solution of ethyl 5-bromoimidazo[1,2-a]pyridine-2-carboxylate (1.5 g, 5.6 mmol) in ethanol (20 mL) was added NaBH$_4$ (1.0 g, 28 mmol), and stirred at reflux overnight. The reaction solution was evaporated. The residue was purified by silica gel column chromatography (dichloromethane/methanol=40/1) to give the desired product (500 mg, 39%) as a white solid. $^1$H NMR (400 MHz, DMSO-$d_6$) δ 7.84 (s, 1H), 7.59 (d, J=8.8 Hz, 1H), 7.31 (d, J=6.8 Hz, 1H), 7.27-7.23 (m, 1H), 5.27 (br s, 1H), 4.64 (s, 2H).

Step c. 5-bromo-2-(bromomethyl)imidazo[1,2-a]pyridine: The solution of (5-bromoimidazo[1,2-a]pyridin-2-yemethanol (400 mg, 1.76 mmol) in dichloromethane (50 mL) was added PBr$_3$ (475 mg, 1.73 mmol) at 0° C., and stirred at the same temperature for 4 h. The saturated NaHCO$_3$ aqueous solution (10 mL) was added to adjust pH to 8. The water phase was extracted with dichloromethane (100 mL). The combined organic layer was dried over Na$_2$SO$_4$, filtered and evaporated. The residue was purified by silica gel column chromatography (dichloromethane/methanol=40/1) to give the desired product (260 mg, 50%) as a white solid. $^1$H NMR (400 MHz, CDCl$_3$) δ 7.85 (s, 1H), 7.59 (s, 1H), 7.14(s, 1H), 7.07 (s, 1H), 4.67 (s, 2H).

Method BA

Preparation of
N-methyl-1-(3-methylpyridin-2-yl)ethanamine

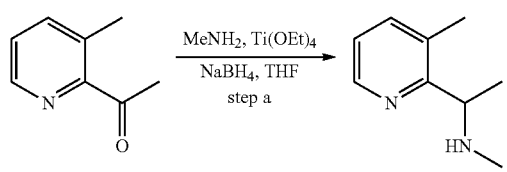

Step a. N-methyl-1-(3-methylpyridin-2-yl)ethanamine: To a solution of 1-(3-methylpyridin-2-yl)ethanone (500 mg, 3.7 mmol) in THF (10 mL) was added methylamine solution (30 wt percent in absolute ethanol, 14.8 mL) and Ti(OEt)$_4$ (1.7 g, 7.4 mmol). The reaction mixture was stirred for 10 min at room temperature, before NaBH$_4$ (563 mg, 14.8 mmol) was added, this reaction mixture was stirred for 2 h at room temperature. The saturated NaHCO$_3$ aqueous solution (100 mL) was added and extracted with dichloromethane (100 mL). The organic layer was dried over Na$_2$SO$_4$, filtered and evaporated. The residue was purified by silica gel column chromatography (dichloromethane/methanol/ammonium hydroxide=100/1/1) to give the desired product (300 mg, 54%) as a yellow oil. $^1$H NMR (400 MHz, CDCl$_3$) δ 8.44 (d, J=4.8 Hz, 1H), 7.41 (d, J=7.2 Hz, 1H), 7.09-7.02 (m, 1H), 3.95 (q, J=6.4 Hz, 1H), 2.34 (s, 3H), 2.25 (s, 3H), 1.31 (d, J=6.4 Hz, 3H).

Method BB

Preparation of
(S)-N-methyl-1-(pyridin-2-yl)ethanamine

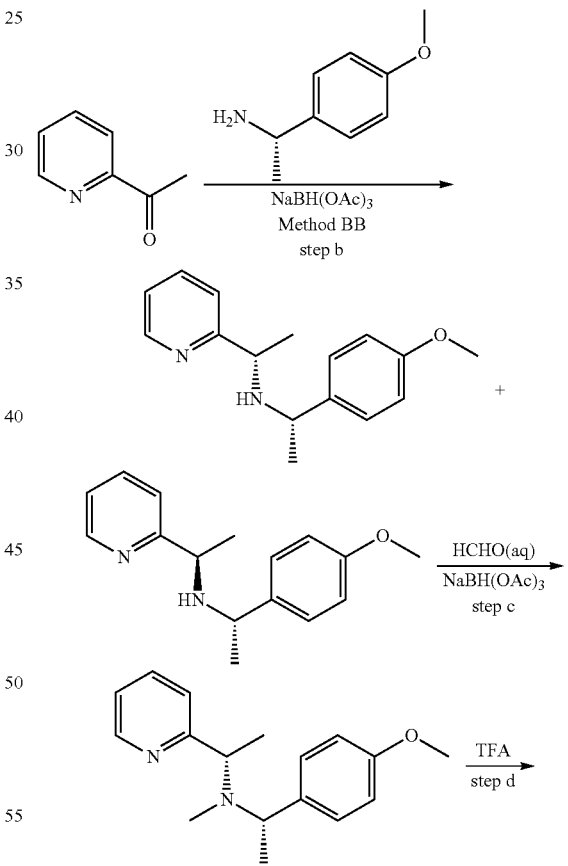

Step b. (S)-1-(4-methoxyphenyl)-N-((S)-1-(pyridin-2-yl)ethyl)ethanamine and (S)-1-(4-methoxyphenyl)-N-((R)-1-(pyridin-2-yl)ethyl)ethanamine: The solution of 1-(pyridin- 2-yl)ethanone (605 mg, 5 mmol) in dichloromethane (30 mL) was added NaBH(OAc)$_3$ (2.12 mg, 10 mmol) and (S)-1-(4-methoxyphenyl)ethanamine (755 mg, 5 mmol) at 0° C. The resulting suspension was stirred at room temperature overnight. The reaction mixture was added saturated NaHCO$_3$ aqueous solution (20 mL) and extracted with dichloromethane (50 mL). The organic layer was dried over Na$_2$SO$_4$, filtered and evaporated. The residue was purified by silica gel column chromatography (petroleum ether/acetone/ammonium hydroxide=200/5/2) to give the desired product (S)-1-(4-methoxyphenyl)-N-((S)-1-(pyridin-2-yl)ethyl)ethanamine (1.0 g, 78%) as a yellow oil. $^1$H NMR (400 MHz, CDCl$_3$) δ 8.60 (d, J=3.2 Hz, 1H), 7.66-7.54 (m, 1H), 7.20-7.12 (m, 3H), 7.06 (d, J=7.6 Hz, 1H), 6.86(d, J=8.0 Hz, 2H), 3.81 (s, 3H), 3.61-3.55 (m, 1H), 3.46-3.35 (m, 1H), 1.31-1.25 (m, 6H). And (S)-1-(4-methoxyphenyl)-N-((R)-1-(pyridin-2-yl)ethyl)ethanamine (70 mg, 6%) as a yellow oil. $^1$H NMR (400 MHz, CDCl$_3$) δ 8.54 (s, 1H), 7.61-7.50 (m, 1H), 7.26-7.11 (m, 4H), 6.81(d, J=7.2 Hz, 2H), 3.90-3.80 (m, 1H), 3.80-3.70 (m, 4H), 1.42-1.30 (m, 6H).

Step c. (S)-1-(4-methoxyphenyl)-N-methyl-N-((S)-1-(pyridin-2-yl)ethyl)ethanamine: The solution of (S)-1-(4-methoxyphenyl)-N-((S)-1-(pyridin-2-yl)ethyl)ethanamine (500 mg, 2 mmol) and formaldehyde (37 wt percent in water, 1 mL) in dichloromethane (20 mL) was added NaBH(OAc)$_3$ (636 mg, 3 mmol). The resulting suspension was stirred at room temperature overnight. The reaction mixture was added saturated NaHCO$_3$ aqueous solution (50 mL) and extracted with dichloromethane (100 mL). The organic layer was dried over Na$_2$SO$_4$, filtered and evaporated. The residue was purified by silica gel column chromatography (dichloromethane/methanol=100/1) to give the desired product (400 mg, 70%) as a yellow oil. $^1$H NMR (400 MHz, CDCl$_3$) δ 8.56 (d, J=3.6 Hz, 1H), 7.74-7.58 (m, 1H), 7.49 (d, J=7.6 Hz, 1H), 7.33-7.27 (m, 2H), 7.20-7.10 (m, 1H), 6.88 (d, J=8.0 Hz, 2H), 3.99-3.93 (m, 1H), 3.87-3.72 (m, 4H), 2.02 (s, 3H), 1.39-1.25 (m, 6H).

Step d. (S)-N-methyl-1-(pyridin-2-yl)ethanamine: To a solution of (S)-1-(4-methoxyphenyl)-N-methyl-N-((S)-1-(pyridin-2-yl)ethyl)ethanamine (400 mg, 1.48 mmol) in dichloromethane (10 mL) was added TFA (5 mL). The mixture was stirred at room temperature overnight. The reaction mixture was concentrated and 1M HCl aqueous (15 mL) was added. The water phase was wash with ethyl acetate (10 mL×3). Then 1M NaOH aqueous solution was added to adjust pH=9, and extracted with dichloromethane (10 mL×4). The combined organic layer was dried over Na$_2$SO$_4$, filtered and evaporated to give the desired product (90 mg, 45%) as a colorless oil. $^1$H NMR (400 MHz, CDCl$_3$) δ 8.56 (d, J=4.0 Hz, 1H), 7.65 (t, J=7.2 Hz, 1H), 7.28 (d, J=8.0 Hz, 1H), 7.16 (t, J=6.0 Hz, 1H), 3.81-3.70 (m, 1H), 2.31(s, 3H), 1.38 (d, J=6.4 Hz, 3H).

Method BC

Preparation of N-ethyl-5,6,7,8-tetrahydroquinolin-8-amine

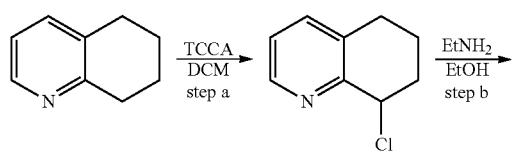

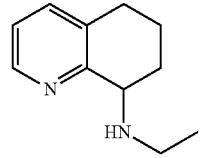

Step a. 8-chloro-5,6,7,8-tetrahydroquinoline: A mixture of 5,6,7,8-tetrahydroquinoline (10 g, 60 mmol) in DCM (200 mL) was added TCCA (21 g, 90 mmol) and stirred at reflux overnight. The reaction mixture was filtered and the filtrate was solution was added saturated NaHCO$_3$ aqueous solution (50 mL). The organic layer was dried over Na$_2$SO$_4$, filtered and evaporated. The residue was purified by silica gel column chromatography (petroleum ether/ethyl acetate=10/1 to 5/1) to give the desired product (8.6 g, 86%) as a yellow oil. $^1$H NMR (400 MHz, CDCl$_3$) δ 8.53 (d, J=4.6 Hz, 1H), 7.49 (d, J=7.8 Hz, 1H), 7.19 (dd, J=7.6, 4.8 Hz, 1H), 5.43 (d, J=3.4 Hz, 1H), 2.97-2.88 (m, 1H), 2.81-2.76 (m, 1H), 2.40-2.38 (m, 1H), 2.29-2.16 (m, 2H), 1.91-1.89 (m, 1H).

Step b. N-ethyl-5,6,7,8-tetrahydroquinolin-8-amine: The solution of 8-chloro-5,6,7,8-tetrahydroquinoline (500 mg, 3 mmol) in ethylamine/ethanol (10 mL) in a sealed tube was stirred at reflux overnight. Then the reaction solution was concentrated and added saturated NaHCO$_3$ aqueous solution (5 mL) and extracted with dichloromethane (10 mL×3). The organic layer was dried over Na$_2$SO$_4$, filtered and evaporated to give the crude desired product (960 mg) as a brown oil. $^1$H NMR (400 MHz, CDCl$_3$) δ 8.42-8.35 (m, 1H), 7.37 (d, J=7.6 Hz, 1H), 7.10-7.02 (m, 1H), 3.89-3.72 (m, 1H), 2.86-2.71 (m, 4H), 2.20-2.12 (m, 1H), 2.03-1.98 (m, 1H), 1.79-1.74 (m, 2H), 1.20 (t, J=7.0 Hz, 3H).

Method BD

Preparation of 5'H-spiro[cyclopropane-1,7'-quinolin]-8'(6'H)-one

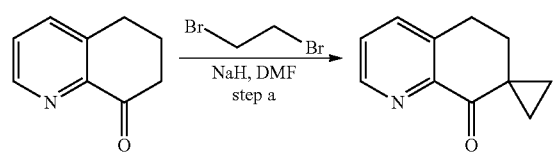

Step a. 5'H-spiro[cyclopropane-1,7'-quinolin]-8'(6'H)-one: To a solution of NaH (60 wt percent moistened with oil, 420 mg, 10.5 mmol) in DMF (50 mL) was added dropwise 6,7-dihydroquinolin-8(5H)-one (441 mg, 3.0 mmol) and 1,2-dibromoethane (1.95 g, 10.5 mmol) in DMF (5 mL) in sequence at 0° C. under N$_2$ atmosphere. The reaction was stirred at 0° C. for 1 h. The reaction mixture was diluted with dichloromethane (40 mL) and washed with saturated brine solution (40 mL). The organic layer was dried over Na$_2$SO$_4$, filtered and evaporated. The residue was purified by silica gel column chromatography (petroleum ether/ethyl acetate=10/3) to give the desired product (110 mg, 21%) as a white solid. $^1$H NMR (400 MHz, CDCl$_3$) δ 8.71 (s, 1H), 7.66 (s, 1H), 7.37 (s, 1H), 3.04 (d, J=4.4 Hz, 2H), 2.03 (d, J=4.8 Hz, 2H), 1.52 (s, 2H), 0.89 (s, 2H).

Method BE

Preparation of 7',8'-dihydro-5'H-spiro[cyclopropane-1,6'-quinoline]

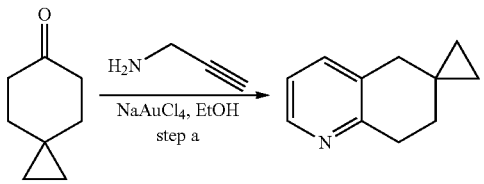

Step a. 7',8'-dihydro-5'H-spiro[cyclopropane-1,6'-quinoline]: To a solution of spiro[2.5]octan-6-one (667 mg, 6 mmol) in ethanol (25 mL) was added prop-2-yn-1-amine (1.3 g, 24 mmol) and NaAuCl₄ (60 mg, 0.15 mmol) in sequence. The reaction was stirred at 85° C. for 1 day. The reaction mixture was concentrated, diluted with ethyl acetate (30 mL) and washed with saturated NaHCO₃ aqueous solution (15 mL) and saturated brine solution (15 mL). The organic layer was dried over Na₂SO₄, filtered and evaporated. The residue was purified by silica gel column chromatography (petroleum ether/ethyl acetate=12/1) to give the desired product (118 mg, 12%) as a colorless oil. $^1$H NMR (400 MHz, CDCl₃) δ 8.37(s, 1H), 7.30(d, J=7.2 Hz, 1H), 7.07-6.98 (m, 1H), 3.00(t, J=6.4 Hz, 2H), 2.64(s, 2H), 1.69(t, J=6.0 Hz, 2H), 0.43(d, J=10.0 Hz, 4H).

Method BF

Preparation of N-(2-acetylpyridin-3-yl)acetamide

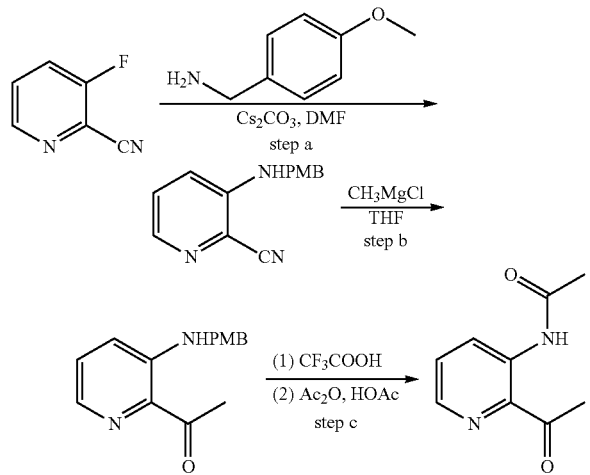

Step a. 3-(4-methoxybenzylamino)picolinonitrile: The solution of 3-fluoropicolinonitrile (10 g, 82 mmol), (4-methoxyphenyl)methanamine (16.8 g, 123 mmol) and Cs₂CO₃ (40 g, 123 mmol) in DMF (50 mL) was stirred at 70° C. overnight. The reaction mixture was concentrated, diluted with ethyl acetate (50 mL) and washed with saturated brine solution (20 mL×3). The organic layer was dried over Na₂SO₄, filtered and evaporated. The residue was purified by silica gel column chromatography (petroleum ether/ethyl acetate=20/1) to give the desired product (11 g, 56%) as a yellow solid. $^1$H NMR (400 MHz, CDCl₃) δ 7.98 (s, 1H), 7.28-7.18 (m, 3H), 7.00 (d, J=8.8 Hz, 1H), 6.90 (d, J=8.0 Hz, 2H), 5.05 (s, 1H), 4.36 (d, J=5.6 Hz, 2H), 3.81 (s, 3H).

Step b. 1-(3-(4-methoxybenzylamino)pyridin-2-yl)ethanone: To a solution of 3-(4-methoxybenzylamino)picolinonitrile (11 g, 46 mmol) in THF (200 mL) was added dropwise 3M CH₃MgCl/Et₂O solution (77 mL, 230 mmol) at 0° C. and stirred for 30 min. The reaction mixture was quenched with saturated brine (50 mL), and extracted with ethyl acetate (100 mL). The organic layer was dried over Na₂SO₄, filtered and evaporated. The residue was purified by silica gel column chromatography (petroleum ether/ethyl acetate=5/1) to give the desired product (4 g, 34%) as a yellow solid. $^1$H NMR (400 MHz, CDCl₃) δ 9.02 (s, 1H), 8.03-7.90 (m, 1H), 7.28-7.15 (m, 2H), 7.08-6.98 (m, 1H), 6.93-6.83 (m, 2H), 4.50-4.30 (m, 2H), 3.79 (s, 3H), 2.72 (s, 3H).

Step c. N-(2-acetylpyridin-3-yl)acetamide: The solution of 1-(3-(4-methoxybenzylamino)pyridin-2-yl)ethanone (1.5 g, 5.8 mmol) in TFA (5 mL) was stirred at room temperature overnight. The reaction mixture was concentrated and added saturated NaHCO₃ aqueous solution to adjust pH to 8, and extracted with dichloromethane (20 mL). The organic layer was dried over Na₂SO₄, filtered and evaporated. The residue was dissolved in acetate acid (10 mL), and added Ac₂O (20 mL), stirred at room temperature overnight. The reaction mixture was concentrated and added saturated NaHCO₃ to adjust pH to 8, and extracted with dichloromethane (20 mL). The organic layer was dried over Na₂SO₄, filtered and evaporated to give the desired product (1 g, 97%) as a white solid. $^1$H NMR (400 MHz, CDCl₃) δ 11.54 (s, 1H), 9.10 (d, J=8.8 Hz, 1H), 8.37 (d, J=4.4 Hz, 1H), 7.48 (dd, J=8.8 Hz, 4.4 Hz, 1H), 2.80 (s, 3H), 2.26 (s, 3H).

Method BG

Preparation of N-(2-acetylpyridin-3-yl)methanesulfonamide

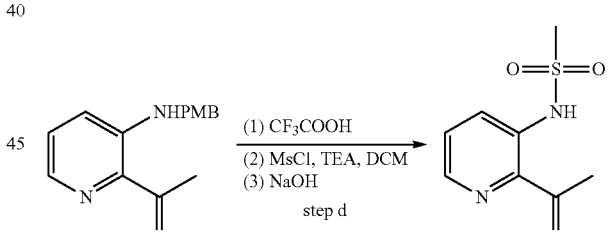

Step d. N-(2-acetylpyridin-3-yl)methanesulfonamide: The solution of 1-(3-(4-methoxybenzylamino)pyridin-2-yl)ethanone (1.3 g, 5.1 mmol) in TFA (7 mL) was stirred at room temperature overnight. The reaction mixture was concentrated and added saturated NaHCO₃ to adjust pH to 8, and extracted with dichloromethane (20 mL). The organic layer was dried over Na₂SO₄, filtered and evaporated. The residue was dissolved in dichloromethane (15 mL), and added TEA (1.5 g, 15.3 mmol) and MsCl (1.3 g, 11.2 mmol), stirred at room temperature for 1 h. The reaction mixture was concentrated and the residue was dissolved in THF (10 mL). 1M NaOH aqueous solution (5 mL) was added and stirred at room temperature overnight. 1M HCl aqueous solution was added to adjust pH to 8, and extracted with dichloromethane (20 mL). The organic layer was dried over Na₂SO₄, filtered and evaporated to give the desired product (800 mg, 73%) as a yellow solid. $^1$H NMR (400 MHz, CDCl₃) δ 11.13 (s, 1H), 8.45-8.32 (m, 1H), 8.15-8.03 (m, 1H), 7.51-7.45 (m, 1H), 3.09 (s, 3H), 2.79 (s, 3H).

Method BH

Preparation of (S)-2-(pyrrolidin-2-yl)pyridine

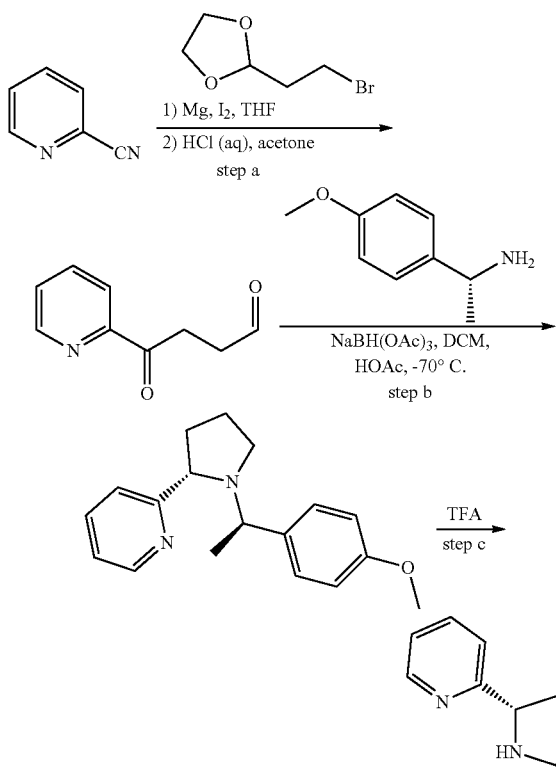

Step a. 4-oxo-4-(pyridin-2-yl)butanal: To a solution of Mg powder (1.06 g, 44 mmol) and I$_2$ (20 mg, 0.08 mmol) in THF (15 mL) was added dropwise the solution of 2-(2-bromoethyl)-1,3-dioxolane (7.16 g, 40 mmol) in THF (15 mL). The reaction mixture was stirred at room temperature for 1.5 h. Then this mixture was cooled to 0° C. and added dropwise to a THF (10 mL) containing picolinonitrile (2.08 g, 20 mmol) at 0° C. The reaction mixture was stirred at this temperature for 1.5 h. Water (10 mL) was added to quenched the reaction, and the mixture was filtered. The filtrate was diluted with ethyl acetate (50 mL), and washed with saturated brine solution (30 mL×2). The organic layer was dried over Na$_2$SO$_4$, filtered and evaporated to get the residue as a colorless oil (1.3 g). This residue was dissolved in acetone (15 mL), and added 3M HCl aqueous solution (10 mL), then stirred at room temperature overnight. The saturated NaHCO$_3$ solution was added to adjust pH to 9. The acetone was concentrated and the residue water phase was extracted with dichloromethane (10 mL×3). The combined organic layer was dried over Na$_2$SO$_4$, filtered and evaporated. The residue was purified by silica gel column chromatography (petroleum ether/ethyl acetate=10/1) to give the desired product (800 mg, 82%) as a slight green oil. $^1$H NMR (400 MHz, CDCl$_3$) δ 9.89 (s, 1H), 8.68 (d, J=4.0 Hz, 1H), 8.02 (d, J=8.0 Hz, 1H), 7.83 (t, J=7.6 Hz, 1H), 7.48 (t, J=5.6 Hz, 1H), 3.57 (t, J=8.0 Hz, 2H), 2.91 (t, J=8.0 Hz, 2H).

Step b. 2-((S)-1-((R)-1-(4-methoxyphenyl)ethyl)pyrrolidin-2-yl)pyridine: The solution of 4-oxo-4-(pyridin-2-yl)butanal (490 mg, 3 mmol) in dichloromethane (20 mL) was added NaBH(OAc)$_3$ (1.9 g, 9 mmol) and AcOH (20 mg, 0.33 mmol) at −70° C. The resulting suspension was stirred at the same temperature for 30 min. The reaction was warmed to 0° C. and added (R)-1-(4-methoxyphenyl)ethanamine (500 mg, 3.3 mmol). The resulting suspension was stirred at room temperature overnight. The reaction mixture was evaporated and the residue was purified by silica gel column chromatography (petroleum ether/ethyl acetate=1/10) to give the desired product (410 mg, 48%) as a red solid. $^1$H NMR (400 MHz, CDCl$_3$) δ 8.43 (s, 1H), 7.55 (s, 1H), 7.49 (d, J=4.0 Hz, 1H), 7.16 (d, J=8.0 Hz, 2H), 7.05 (s, 1H), 6.79 (d, J=8.0 Hz, 2H), 3.98 (s, 1H), 3.80-3.71 (m, 4H), 3.11 (s, 1H), 2.63 (s, 1H), 2.24 (s, 1H), 1.99-1.85 (m, 1H), 1.76 (s, 2H), 1.35 (d, J=4.8 Hz, 3H).

Step c. (S)-2-(pyrrolidin-2-yl)pyridine: The solution of 2-((S)-1-((R)-1-(4-methoxyphenyl)ethyl)pyrrolidin-2-yl)pyridine (400 mg, 1.48 mmol) in TFA (5 mL) was stirred at 50° C. for 12 h. The reaction mixture was concentrated and 1M HCl aqueous (15 mL) was added. This solution was wash with dichloromethane (5 mL×3). Then saturated NaHCO$_3$ solution was added to adjust pH to 9, and extracted with dichloromethane (10 mL×5). The combined organic layer was dried over Na$_2$SO$_4$, filtered and evaporated to give the desired product (110 mg, 50%) as a colorless oil.

Method BI

Preparation of (R)-2-(pyrrolidin-2-yl)pyridine

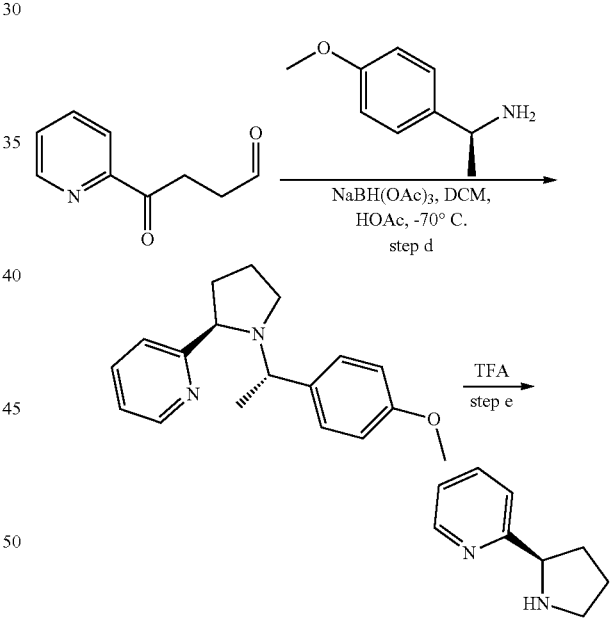

Step d. 2-((R)-1-((S)-1-(4-methoxyphenyl)ethyl)pyrrolidin-2-yl)pyridine: The solution of 4-oxo-4-(pyridin-2-yl)butanal (326 mg, 2 mmol) in dichloromethane (15 mL) was added NaBH(OAc)$_3$ (1.27 g, 6 mmol) and HOAc (20 mg, 0.33 mmol) at −70° C. The resulting suspension was stirred at the same temperature for 30 min. The reaction was warmed to 0° C. and added (S)-1-(4-methoxyphenyl)ethanamine (332 mg, 2.2 mmol). The resulting suspension was stirred at room temperature overnight. The reaction mixture was evaporated and the residue was purified by silica gel column chromatography (petroleum ether/ethyl acetate=1/10) to give the desired product (400 mg, 71%) as a red solid. $^1$H NMR (400 MHz, CDCl$_3$) δ 8.42 (s, 1H), 7.58-7.45 (m, 1H), 7.35 (d, J=7.2 Hz, 1H), 7.15 (d, J=7.6 Hz, 2H), 7.02 (s, 1H), 6.68 (d, J=8.0 Hz, 2H), 3.91 (s, 1H), 3.74-3.71 (m, 4H), 3.09 (s, 1H), 3.62 (d, J=7.2 Hz, 1H), 2.26-2.15 (m, 1H), 1.99-1.89 (m, 1H), 1.76 (s, 2H), 1.34 (d, J=4.8 Hz, 3H).

Step e. (R)-2-(pyrrolidin-2-yl)pyridine: The solution of 2-((R)-1-((S)-1-(4-methoxyphenyl)ethyl)pyrrolidin-2-yl)pyridine (400 mg, 1.48 mmol) in TFA (5 mL) was stirred at 50° C. for 12 h. The reaction mixture was concentrated and 1M HCl aqueous (15 mL) was added. This solution was wash with dichloromethane (5 mL×3). Then saturated NaHCO₃ solution was added to adjust pH to 9, and extracted with dichloromethane (10 mL×5). The combined organic layer was dried over Na₂SO₄, filtered and evaporated to give the desired product (100 mg, 45%) as a colorless oil.

Method BJ

Preparation of 2-(3-methylpyrrolidin-2-yl)pyridine

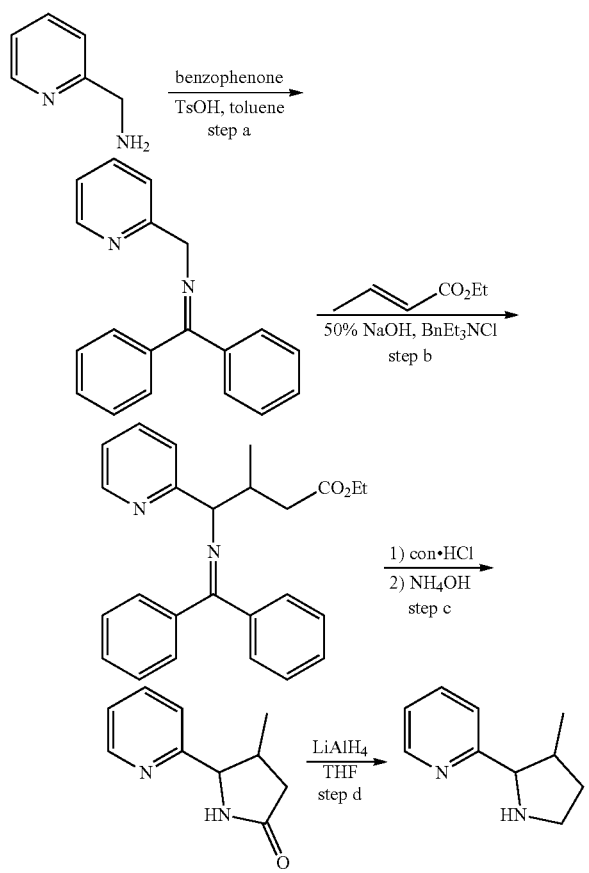

Step a. N-(diphenylmethylene)-1-(pyridin-2-yl)methanamine: To the solution of pyridin-2-ylmethanamine (3.97 g, 37 mmol) and benzophenone (6.69 g, 37 mmol) in toluene (50 mL) was added p-TsOH (10 mg, 0.058 mmol). The mixture was stirred at reflux overnight. The reaction solution was cooled to room temperature and washed with saturated NaHCO₃ solution (30 mL×2). The organic layer was dried over Na₂SO₄, filtered and evaporated to give the crude desired product (10 g) as a yellow oil.

Step b. ethyl 4-(diphenylmethyleneamino)-3-methyl-4-(pyridin-2-yl)butanoate: The solution of crude N-(diphenylmethylene)-1-(pyridin-2-yl)methanamine (1.5 g), NaOH solution (50 wt percent in water, 110 mg, 2.75 mmol) and BnEt₃NCl (60 mg, 0.3 mmol) in acetonitrile (50 mL) was stirred at room temperature for 30 min. Then (E)-ethyl but-2-enoate (630 mg, 5.5 mmol) was added. The mixture was stirred at room temperature overnight. The reaction solution was extracted with dichloromethane (10 mL×3). The combined organic layer was dried over Na₂SO₄, filtered and evaporated. The residue was purified by silica gel column chromatography (petroleum ether/ethyl acetate=1/10) to give the crude desired product (1.3 g,) as a yellow oil.

Step c. 4-methyl-5-(pyridin-2-yl)pyrrolidin-2-one: The solution of crude ethyl 4-(diphenylmethyleneamino)-3-methyl-4-(pyridin-2-yl)butanoate (1.3 g) in acetonitrile (15 mL) was added dropwise concentrated HCl aqueous (3 mL). The mixture was stirred at room temperature for 2 h. The reaction solution was washed with dichloromethane (10 mL×2). The water phase was diluted with acetonitrile (15 mL) and added dropwise ammonia water (5 mL). The mixture was stirred at room temperature for 5 h. Then the reaction solution was extracted with dichloromethane (10 mL×3). The combined organic layer was dried over Na₂SO₄, filtered and evaporated. The residue was purified by silica gel column chromatography (dichloromethane/methanol=100/1) to give the desired product (360 mg, 62%) as a yellow oil. ¹H NMR (400 MHz, CDCl₃) δ 8.58 (s, 1H), 7.73-7.70 (m, 1H), 7.34-7.32 (m, 1H), 7.25-7.22 (m, 1H), 6.57 (s, 1H), 4.40-4.39 (m, 1H), 2.66-2.60 (m, 1H), 2.51-2.46 (m, 1H), 2.14-2.08 (m, 1H), 1.27-1.26 (m, 3H).

Step d. 2-(3-methylpyrrolidin-2-yl)pyridine: The solution of 4-methyl-5-(pyridin-2-yl)pyrrolidin-2-one (200 mg, 1.1 mmol) in THF (5 mL) was added LiAlH₄ (174 mg, 4.5 mmol) in portions. The mixture was stirred at reflux overnight. Water (1 mL), NaOH solution (10 wt percent in water, 1 mL) and Water (1 mL) were added in sequence. The mixture was filtered and the filtrate was evaporated to give the desired product (89 mg, 50%) as a yellow oil. ¹H NMR (400 MHz, CDCl₃) δ 8.54 (s, 1H), 7.65-7.62 (m, 1H), 7.28 (m, 1H), 7.18-7.15 (m, 1H), 3.67-3.60 (m, 1H), 3.30-3.21 (m, 1H), 3.10-3.02 (m, 1H), 1.67 (s, 1H), 1.60-1.53 (m, 1H), 1.37-1.33 (m, 1H), 1.07 (d, J=6.0 Hz, 3H).

Method BK

Preparation of cis-ethyl 2-(pyridin-2-yl)pyrrolidine-3-carboxylate

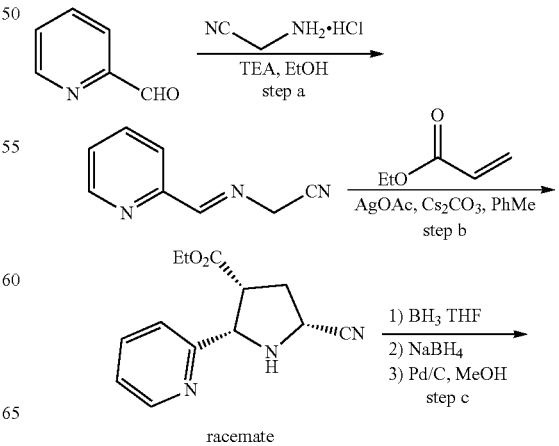

racemate

-continued

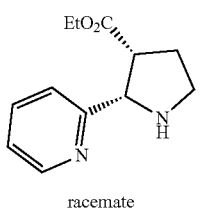

racemate

Step a. (E)-2-(pyridin-2-ylmethyleneamino)acetonitrile: The solution of 2-aminoacetonitrile hydrochloride (5.09 g, 55 mmol) and TEA (9.09 g, 90 mmol) in ethanol (250 mL) was added stirred at room temperature for 30 min. Then picolinaldehyde (5.36 g, 50 mmol) was added. The mixture was stirred at room temperature overnight. The reaction solution was concentrated and dissolved in $Et_2O$ (200 mL). The mixture was filtered and the filtrate was evaporated to give the crude desired product (4.8 g) as a yellow oil.

Step b. cis-ethyl 5-cyano-2-(pyridin-2-yl)pyrrolidine-3-carboxylate: To the solution of crude (E)-2-(pyridin-2-ylmethyleneamino)acetonitrile (4.8 g, 33 mmol) in toluene (120 mL) was added AgOAc (550 mg, 3.3 mmol) and $Cs_2CO_3$ (2.15 g, 66 mmol) at 0° C., and stirred for 5 min. Then ethyl acrylate (3.31 g, 66 mmol) was added. The mixture was stirred at room temperature overnight. The reaction solution was evaporated and the residue was purified by silica gel column chromatography (dichloromethane/methanol=50/1) to give the crude desired product (2.0 g, 25%) as a yellow oil.

Step c. cis-ethyl 2-(pyridin-2-yl)pyrrolidine-3-carboxylate: To the solution of crude cis-ethyl 5-cyano-2-(pyridin-2-yl)pyrrolidine-3-carboxylate (245 mg, 1 mmol) in THF (5 mL) was added 1M $BH_3$/THF solution (2 mL, 2 mmol), and stirred for 20 min. Then cooled to 0° C., $NaBH_4$ (76 mg, 2 mmol) was added. The mixture was stirred at the same temperature for 3 h before room temperature overnight. Water (1 mL) was added to quench the reaction, and extracted with ethyl acetate (20 mL×2). The combined organic layer was evaporated and the residue was dissolved in ethanol (20 mL). Pd/C (10 wt percent, 0.2 g) was added to this solution, and stirred at room temperature overnight. The mixture was filtered and the filtrate was evaporated. The residue was purified by silica gel column chromatography (dichloromethane/methanol=10/1) to give the desired product (88 mg, 40%) as a yellow oil.

Method BL

Preparation of 6-methylquinolin-8-amine

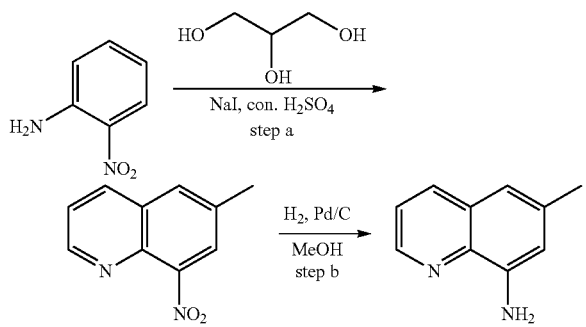

Step a. 6-methyl-8-nitroquinoline: The pure glycerol (5.0 g, 54 mmol) was heated to 150° C. for 30 min. Then it was cooled to 110° C., and added 4-methyl-2-nitroaniline (3.0 g, 20 mmol) and NaI (60 mg, 0.40 mmol). The mixture was heated to 150° C. again, and added concentrated sulfuric acid (4.51 g, 46 mmol). The resulting suspension was stirred at this temperature for 1 h. The reaction mixture was cooled to room temperature and added water (20 mL). This water phase was extracted with dichloromethane (20 mL×4). The combined organic layer was evaporated. The residue was purified by silica gel column chromatography (petroleum ether/ethyl acetate=5/1) to give the desired product (960 mg, 26%) as a yellow solid. $^1$H NMR (400 MHz, $CDCl_3$) δ 9.02-8.99 (m, 1H), 8.18-8.16 (m, 1H), 7.91-7.88 (m, 1H), 7.81-7.78 (m, 1H), 7.51 (s, 1H), 2.61 (s, 3H).

Step b. 6-methylquinolin-8-amine: To the solution of 6-methyl-8-nitroquinoline (350 mg, 1.86 mmol) in methanol (30 mL) was added Pd/C (10 wt percent, 0.2 g), and stirred at room temperature under $N_2$ atmosphere overnight. The mixture was filtered and the filtrate was evaporated to give the crude desired product (250 mg, 85%) as a yellow oil. $^1$H NMR (400 MHz, $CDCl_3$) δ 8.69 (s, 1H), 7.98 (s, 1H), 7.33 (s, 1H), 6.94 (s, 1H), 6.79 (s, 1H), 4.90 (s, 2H), 2.43 (s, 3H).

Method BM

Preparation of N,6-dimethylquinolin-8-amine hydroiodide

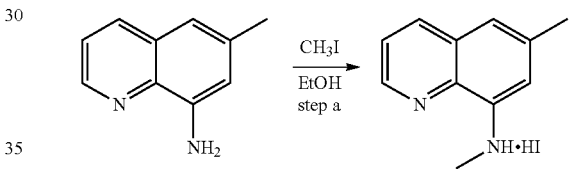

Step a. N,6-dimethylquinolin-8-amine hydroiodide: To the solution of 6-methylquinolin-8-amine (250 mg, 1.58 mmol) in ethanol (10 mL) in a sealed tube was added $CH_3I$ (337 mg, 2.37 mmol), and stirred at reflux overnight. The reaction mixture was cooled to room temperature and filtered. The filter cake was washed with diethyl ether (10 mL) and the filer cake obtained was dried by oil pump to give the crude desired product hydroiodide (200 mg, 42%) as a red solid. $^1$H NMR (400 MHz, $CDCl_3$) δ 8.79 (s, 1H), 8.58 (s, 1H), 7.75 (s, 1H), 7.08 (s, 1H), 6.82 (s, 1H), 3.08 (s, 3H), 2.57 (s, 3H).

Method BN

Preparation of 5,6-difluoro-N-methylquinolin-8-amine

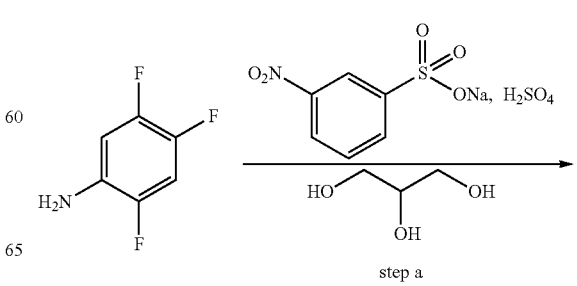

-continued

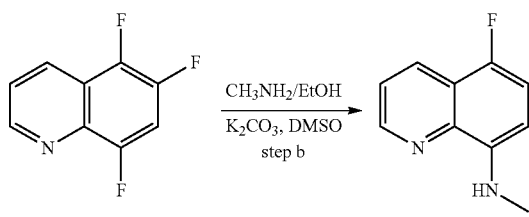

Step a. 5,6,8-trifluoroquinoline: To the solution of concentrated sulfuric acid (18 mL) diluted with water (6 mL), was added 2,4,5-trifluoroaniline (3.68 g, 25 mmol), glycerol (4.60 g, 50 mmol) and sodium 3-nitrobenzenesulfonate (6.75 g, 30 mmol) in sequence. The resulting suspension was stirred at 140° C. overnight. The reaction mixture was cooled to room temperature and added saturated $NaHCO_3$ aqueous solution to adjust pH to 7, extracted with dichloromethane (200 mL×2). The combined organic layer was evaporated. The residue was purified by silica gel column chromatography (petroleum ether/ethyl acetate=3/1) to give the desired product (3.5 g, 76%) as a yellow solid. $^1$H NMR (400 MHz, $CDCl_3$) δ 8.99 (s, 1H), 8.46-8.44 (m, 1H), 7.61-7.56 (m, 1H), 7.38-7.31 (m, 1H).

step b. 5,6-difluoro-N-methylquinolin-8-amine: To the solution of 5,6,8-trifluoroquinoline (436 mg, 2.38 mmol) and $K_2CO_3$ (657 mg, 4.76 mmol) in DMSO (3 mL) in a sealed tube, was added $MeNH_2$ solution (30 wt percent in ethanol, 3 mL). The resulting suspension was stirred at 120° C. for 2 days. The reaction mixture was cooled to room temperature and filtered. The filtrate was diluted with ethyl acetate (50 mL) was added, extracted with water (15 mL). The organic layer was evaporated. The residue was purified by silica gel column chromatography (petroleum ether/ethyl acetate=10/1) to give the desired product (200 mg, 43%) as a yellow solid. $^1$H NMR (400 MHz, $CDCl_3$) δ 8.88 (d, J=4.4 Hz, 1H), 8.31 (d, J=8.4 Hz, 1H), 7.47-7.44 (m, 1H), 6.40-6.35 (m, 1H), 6.08 (s, 1H), 3.00 (s, 3H).

Method BO

Preparation of 7-fluoroquinolin-8-amine

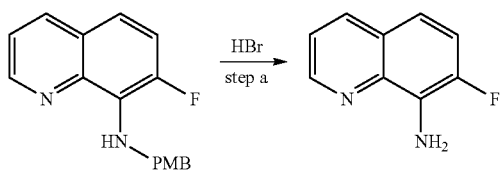

Step a. 7-fluoroquinolin-8-amine: The mixture of 7-fluoro-N-(4-methoxybenzyl)quinolin-8-amine (480 mg, 1.7 mmol) and HBr solution (48 wt percent in water, 15 mL) was stirred at 80° C. overnight. The reaction mixture was cooled to room temperature and added saturated $NaHCO_3$ aqueous solution to adjust pH to 8, extracted with dichloromethane (30 mL×2). The combined organic layer was evaporated. The residue was purified by silica gel column chromatography (petroleum ether/ethyl acetate=10/1) to give the desired product (232 mg, 84%) as a yellow oil. MS (ESI/APCI) m/z 163.0 $[M+H]^+$.

Method BP

Preparation of 8-chloro-1,7-naphthyridine

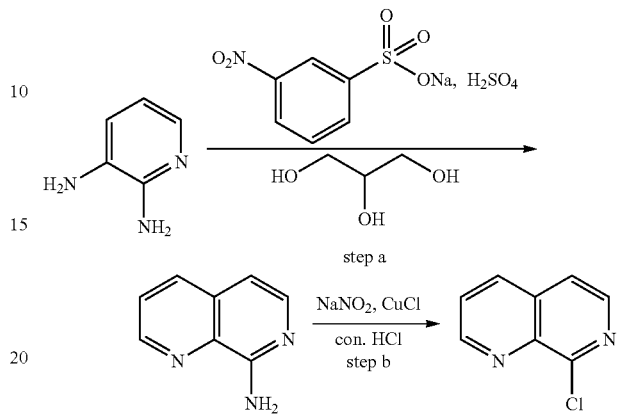

Step a. 1,7-naphthyridin-8-amine: To the solution of concentrated sulfuric acid (15 mL) diluted with water (15 mL), was added pyridine-2,3-diamine (1.09 g, 10 mmol), glycerol (4.1 g, 33.6 mmol) and sodium 3-nitrobenzenesulfonate (4.5 g, 20.1 mmol) in sequence. The resulting suspension was stirred at 125° C. overnight. The reaction mixture was cooled to room temperature and added saturated NaOH aqueous solution to adjust pH to 8, extracted with dichloromethane (100 mL×2). The combined organic layer was evaporated. The residue was purified by silica gel column chromatography (dichloromethane/methanol=50/1) to give the desired product (295 mg, 20%) as a white solid. $^1$H NMR (400 MHz, $CDCl_3$) δ 8.77 (s,1H), 8.00-7.96 (m, 2H), 7.54 (d, J=4.0 Hz, 1H), 6.93 (d, J=5.6 Hz, 1H), 5.92 (s, 2H).

step b. 8-chloro-1,7-naphthyridine: To the solution of 1,7-naphthyridin-8-amine (290 mg, 2.0 mmol) in concentrated HCl aqueous solution (5 mL), was added $NaNO_2$ (1.38 g, 20 mmol) and CuCl (238 mg, 33.6 mmol) in sequence. The resulting suspension was stirred at room temperature for 3 h. The reaction mixture was added saturated $NaHCO_3$ aqueous solution to adjust pH to 8, extracted with ethyl acetate (100 mL×3). The combined organic layer was evaporated. The residue was purified by silica gel column chromatography (petroleum ether/ethyl acetate=30/1) to give the desired product (85 mg, 26%) as a pale solid. $^1$H NMR (400 MHz, $CDCl_3$) δ 9.15 (d, J=2.4 Hz, 1H), 8.40 (d, J=5.2 Hz, 1H), 8.22 (d, J=8.4 Hz, 1H), 7.70 (dd, J=8.0, 4.0 Hz, 1H), 7.63 (d, J=5.2 Hz, 1H).

Method BQ

Preparation of 8-bromo-1,6-naphthyridine

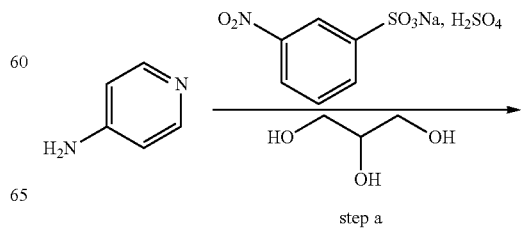

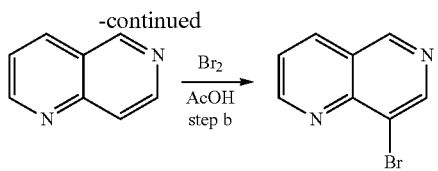

Step a. 1,6-naphthyridine: To the solution of concentrated sulfuric acid (30 mL) diluted with water (20 mL), was added pyridin-4-amine (3.76 g, 40.0 mmol), glycerol (12.52 g, 136 mmol) and sodium 3-nitrobenzenesulfonate (19.8 g, 88.0 mmol) in sequence. The resulting suspension was stirred at 130° C. overnight. The reaction mixture was cooled to room temperature and added saturated NaOH aqueous solution to adjust pH to 10, extracted with dichloromethane (200 mL×2). The combined organic layer was evaporated. The residue was purified by silica gel column chromatography (petroleum ether/ethyl acetate=1/1) to give the desired product (900 mg, 69%) as a white solid. $^1$H NMR (400 MHz, CDCl$_3$) δ 9.30 (s,1H), 9.12 (s,1H), 8.78 (d, J=5.2 Hz, 1H), 8.32 (d, J=8.0 Hz, 1H), 7.94 (d, J=5.2 Hz, 1H), 7.62-7.48 (m, 1H).

step b. 8-bromo-1,6-naphthyridine: To the solution of 1,6-naphthyridine (830 mg, 6.38 mmol) in HOAc (5 mL), was added dropwise dibromine (612 mg, 3.83 mmol). The resulting suspension was stirred at 80° C. overnight. The reaction mixture was cooled to room temperature and added saturated NaHCO$_3$ aqueous solution to adjust pH to 8, extracted with dichloromethane (100 mL×3). The combined organic layer was evaporated. The residue was purified by silica gel column chromatography (petroleum ether/ethyl acetate=1/1) to give the desired product (700 mg, 68%) as a pale solid. $^1$H NMR (400 MHz, CDCl$_3$) δ 9.24 (d, J=2.8 Hz, 1H), 9.21 (s, 1H), 9.02 (s, 1H), 8.34 (d, J=8.0 Hz, 1H), 7.64 (dd, J=8.0, 4.0 Hz, 1H).

Method BR

Preparation of 4-chloro-1,5-naphthyridine

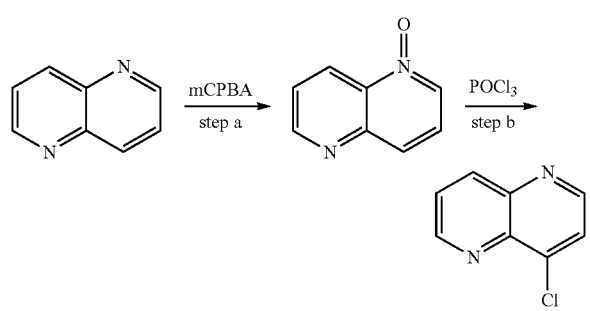

Step a. 1,5-naphthyridine 1-oxide: To the solution of 1,5-naphthyridine (3.0 g, 23.1 mmol), was added mCPBA (3.6 g, 20.9 mmol). The resulting suspension was stirred at room temperature overnight. The reaction mixture was evaporated. The residue was purified by silica gel column chromatography (dichloromethane/methanol=50/1) to give the desired product (3.0 g, 89%) as an off-white solid. $^1$H NMR (400 MHz, CDCl$_3$) δ 9.05 (d, J=4.0 Hz, 1H), 9.04 (s, 1H), 8.56 (d, J=6.0 Hz, 1H), 8.02 (d, J=8.8 Hz, 1H), 7.70-7.67 (m, 1H), 7.54 (dd, J=8.4, 6.0 Hz, 1H).

step b. 4-chloro-1,5-naphthyridine: The solution of 1,5-naphthyridine 1-oxide (3.0 g, 20.5 mmol) in POCl$_3$ (30 mL), was stirred at 100° C. for 6 h. The reaction mixture was concentrated and diluted with dichloromethane (100 mL). This solution was added saturated NaHCO$_3$ aqueous solution to adjust pH to 8. Filtered and the filtrate was partitioned. The water phase was extracted with ethyl acetate (100 mL). The combined organic layer was evaporated. The residue was purified by silica gel column chromatography (petroleum ether/ethyl acetate=5/1) to give the desired product (930 mg, 27%) as a pale solid. $^1$H NMR (400 MHz, CDCl$_3$) δ 9.11 (dd, J=4.4, 2.0 Hz, 1H), 8.87 (d, J=4.8 Hz, 1H), 8.46 (dd, J=8.4, 2.0 Hz, 1H), 7.78 (d, J=4.8 Hz, 1H), 7.74 (dd, J=8.4, 4.0 Hz, 1H). MS (ESI/APCI) m/z 164.9 [M+H]$^+$.

Method BS

Preparation of N-methyl-2-(pyridin-2-yl)propan-2-amine

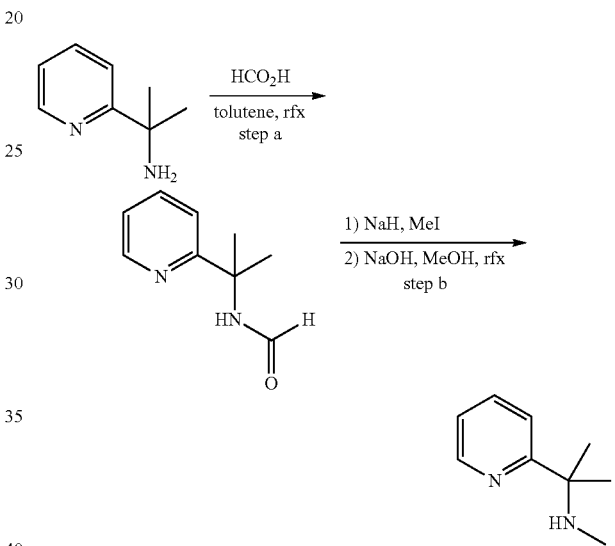

Step a. N-(2-(pyridin-2-yl)propan-2-yl)formamide: To the solution of 2-(pyridin-2-yl)propan-2-amine (350 mg, 2.6 mmol) in toluene(10 mL), was added formic acid (237 mg, 5.2 mmol). The resulting suspension was stirred at reflux for 6 h. The reaction mixture was cooled to room temperature and added saturated NaHCO$_3$ aqueous solution (50 mL), the water phase was extracted with dichloromethane (50 mL). The combined organic layer was evaporated. The residue was purified by silica gel column chromatography (dichloromethane/methanol/ammonium hydroxide=100/1/1 to 100/3/1) to give the desired product (300 mg, 70%) as a slight yellow oil. $^1$H NMR (400 MHz, CDCl$_3$) δ 8.56-8.49 (m, 1H), 8.40-8.25 (m, 1H), 7.90 (s, 1H), 7.78-7.65(m, 1H), 7.40 (d, J=7.8 Hz, 1H), 7.24-7.17 (m, 1H), 1.75 (d, J=28.0 Hz, 6H).

Step b. N-methyl-2-(pyridin-2-yl)propan-2-amine: To the solution of N-(2-(pyridin-2-yl)propan-2-yl)formamide (300 mg, 1.8 mmol) in THF (10 mL), was added NaH (60 wt percent moistened with oil, 222 mg, 5.4 mmol). The resulting suspension was stirred at room temperature for 15 min. Then CH$_3$I (390 mg, 2.7 mmol) was added, the reaction mixture was stirred at reflux for 2 h. The reaction mixture was cooled to room temperature and added the solution of NaOH (252 mg, 6.12 mmol) in methanol (5 mL) and water (1 mL). The reaction mixture was stirred at reflux overnight. The reaction mixture was cooled to room temperature and extracted with dichloromethane (100 mL×3). The combined organic layer was evaporated. The residue was purified by silica gel column chromatography (dichloromethane/methanol/ammonium hydroxide=100/1/1) to give the desired product (250 mg, 90%) as a yellow oil. $^1$H NMR (400 MHz, CDCl$_3$) δ 8.59 (d, J=4.4 Hz, 1H), 7.77-7.63 (m, 1H), 7.39 (d, J=8.0 Hz, 1H), 7.13 (dd, J=7.2, 4.8 Hz, 1H), 2.13 (s, 3H), 1.47 (s, 6H).

Example 1

Preparation of N-methyl-N-((6-(4-methylpiperazin-1-yl)pyrimidin-4-yl)methyl)-5,6,7,8-tetrahydroquinolin-8-amine (A1)

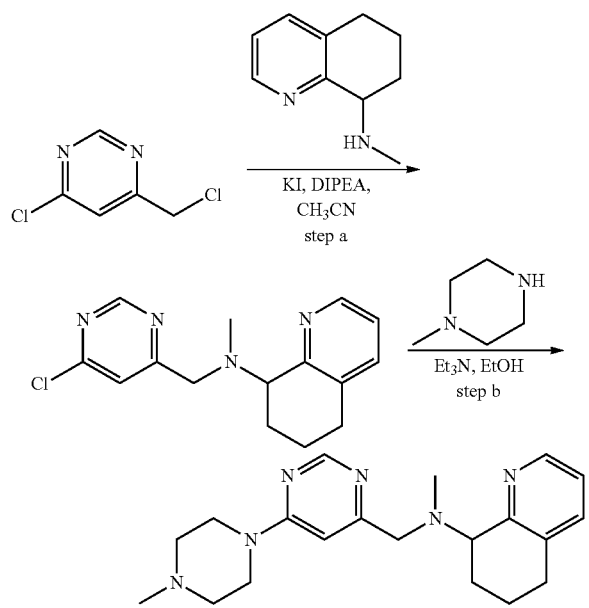

Method AA-Step a. N-((6-chloropyrimidin-4-yl)methyl)-N-methyl-5,6,7,8-tetrahydroquinolin-8-amine: A mixture of N-methyl-5,6,7,8-tetrahydroquinolin-8-amine (160 mg, 1 mmol, see reference WO2006026703), 4-chloro-6-(chloromethyl)pyrimidine (170 mg, 1.05 mmol), KI (16 mg, 0.1 mmol) and DIPEA (320 mg, 2.5 mmol) in CH$_3$CN (10 mL) was stirred at room temperature overnight. The reaction solution was evaporated to remove most of CH$_3$CN, diluted with water (50 mL) and extracted with dichloromethane (50 mL×3). The combined organic layer was dried over Na$_2$SO$_4$, filtered and evaporated. The residue was purified by silica gel column chromatography (dichloromethane/methanol=100/1 to 50/1) to give the desired product (200 mg, 69%) as a brown oil. $^1$H NMR (400 MHz, CDCl$_3$) δ 8.83 (s, 1H), 8.50 (d, J=8.0 Hz, 1H), 7.89 (s, 1H), 7.37 (d, J=8.0 Hz, 1H), 7.08 (dd, J=8.0, 4.0 Hz, 1H), 4.03-3.99 (m, 1H), 3.80 (s, 2H), 2.82-2.77 (m, 1H), 2.75-2.70 (m, 1H), 2.41 (s, 3H), 2.17-2.14 (m, 1H), 2.06-2.04 (m, 1H), 1.92-1.89 (m, 1H), 1.72-1.71 (m, 1H).

Method AA-Step b. N-methyl-N-46-(4-methylpiperazin-1-yl)pyrimidin-4-yl)methyl)-5,6,7,8-tetrahydroquinolin-8-amine: A mixture of N4(6-chloropyrimidin-4-yl)methyl)-N-methyl-5,6,7,8-tetrahydroquinolin-8-amine (100 mg, 0.35 mmol), TEA (350 mg, 3.5 mmol) and N-methylpiperazine (40 mg, 0.38 mmol) in ethanol (4 mL) was stirred at reflux overnight. The reaction mixture was concentrated and added saturated NaHCO$_3$ aqueous solution (50 mL) and extracted with dichloromethane (100 mL). The organic layer was dried over Na$_2$SO$_4$, filtered and evaporated. The residue was purified by silica gel column chromatography (dichloromethane/methanol=50/1) to give the desired product (98 mg, 80%) as a colorless oil. $^1$H NMR (400 MHz, CDCl$_3$) δ 8.45 (s, 2H), 7.33 (d, J=6.8 Hz, 1H), 7.20 (s, 1H), 7.03 (s, 4.8 Hz, 1H), 3.99 (s, 1H), 3.68 (s, 4H), 3.62 (s, 2H), 2.77 (s, 1H), 2.68-2.64 (m, 1H), 2.44 (s, 4H), 2.35 (s, 3H), 2.30 (s, 3H), 1.97 (s, 1H), 1.91-1.88 (m, 1H), 1.85 (s, 1H), 1.67 (s, 1H). HRMS (ESI): calcd for C$_{20}$H$_{29}$N$_6$ [M+H]$^+$353.2448, found 353.2451.

Example 2

Preparation of N-methyl-N-((6-(piperazin-1-yl)pyrimidin-4-yl)methyl)-5,6,7,8-tetrahydroquinolin-8-amine (A7) and 3-(4-(6-((methyl(5,6,7,8-tetrahydroquinolin-8-yl)amino)methyl)pyrimidin-4-yl)piperazin-1-yl)propanenitrile (A8)

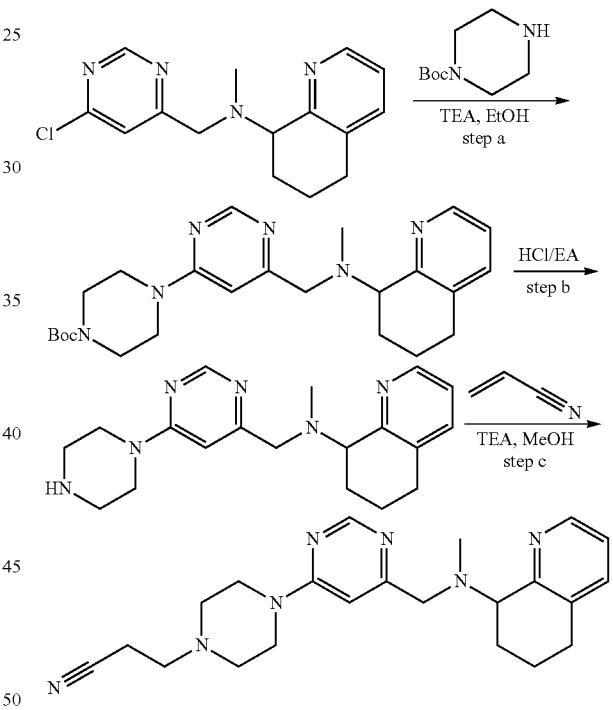

Method AB-Step a. tert-butyl-4-(6-((methyl(5,6,7,8-tetrahydroquinolin-8-yl)amino)methyl)pyrimidin-4-yl)piperazine-1-carboxylate: A mixture of N-((6-chloropyrimidin-4-yl)methyl)-N-methyl-5,6,7,8-tetrahydroquinolin-8-amine (200 mg, 0.7 mmol), TEA (700 mg, 7 mmol) and tert-butyl piperazine-1-carboxylate (140 mg, 0.77 mmol) in ethanol (10 mL) was stirred at reflux overnight. The reaction mixture was added saturated NaHCO$_3$ aqueous solution (50 mL) and extracted with dichloromethane (50 mL). The organic layer was dried over Na$_2$SO$_4$, filtered and evaporated. The residue was purified by silica gel column chromatography (dichloromethane/methanol=50/1 to 25/1) to give the desired product (290 mg, 94%) as a colorless oil. $^1$H NMR (400 MHz, CDCl$_3$) δ 8.50 (s, 2H), 7.37 (d, J=7.6 Hz, 1H), 7.29 (s, 1H), 7.08 (dd, J=7.6, 4.8 Hz, 1H), 4.02 (t, J=7.6 Hz, 1H), 3.71 (s, 4H), 3.67 (s, 2H), 3.50 (s, 4H), 2.88-2.76 (m, 1H), 2.76-2.66

(m, 1H), 2.39 (s, 3H), 2.17-2.08 (m, 1H), 2.01 (s, 1H), 1.94-1.89 (m, 1H), 1.74-1.68 (m, 1H), 1.49 (s, 9H). MS (ESI/APCI) m/z 438.8 [M+H]+.

Method AB-Step b. N-methyl-N-((6-(piperazin-1-yl)pyrimidin-4-yl)methyl)-5,6,7,8-tetrahydroquinolin-8-amine: To a solution of tert-butyl-4-(6-((methyl(5,6,7,8-tetrahydroquinolin-8-yl)amino)methyl)pyrimidin-4-yl)piperazine-1-carboxylate (270 mg, 0.6 mmol) in dichloromethane (5 mL) was added dropwise 3M HCl/ethyl acetate (5 mL). The mixture was stirred at room temperature for 12 h. Saturated aqueous NaHCO₃ solution was added to adjust pH=9, and the mixture was then extracted with dichloromethane (20 mL×3). The combined organic layer was dried over Na₂SO₄, filtered and evaporated. The residue was purified by silica gel column chromatography (dichloromethane/methanol=50/1 to 25/1) to give the desired product (180 mg, 90%) as a colorless oil. ¹H NMR (400 MHz, CDCl₃) δ 8.49-8.48 (m, 2H), 7.37 (d, J=7.6 Hz, 1H), 7.21 (s, 1H), 7.06 (dd, J=7.6, 4.8 Hz, 1H), 4.08-3.98 (m, 1H), 3.68-3.64 (m, 6H), 2.93 (t, J=4.8 Hz, 4H), 2.86-2.76 (m, 1H), 2.72 (s, 1H), 2.40 (s, 3H), 2.11 (s, 1H), 2.01-1.97 (m, 1H), 2.00-1.88 (m, 1H), 1.76-1.67 (m, 2H). MS (ESI/APCI) m/z 338.9 [M+H]+

Method AB-Step c. 3-(4-(6-((methyl(5,6,7,8-tetrahydroquinolin-8-yl)amino)methyl)pyrimidin-4-yl)piperazin-1-yl)propanenitrile: To a solution of N-methyl-N-((6-(piperazin-1-yl)pyrimidin-4-yl)methyl)-5,6,7,8-tetrahydroquinolin-8-amine (50 mg, 0.13 mmol) in methanol (2 mL) was added TEA (15 mg, 0.13 mmol) and acrylonitrile (20 mg, 0.26 mmol). The mixture was stirred at room temperature overnight. The reaction mixture was added saturated NaHCO₃ aqueous solution (50 mL) and extracted with dichloromethane (50 mL). The organic layer was dried over Na₂SO₄, filtered and evaporated. The residue was purified by silica gel column chromatography (dichloromethane/methanol=50/1 to 25/1) to give the desired product (40 mg, 78%) as a colorless oil. ¹H NMR (400 MHz, CDCl₃) δ 8.53-8.47 (m, 2H), 7.38 (d, J=7.6 Hz, 1H), 7.25 (s, 1H), 7.08 (dd, J=7.6, 4.8 Hz, 1H), 4.09-3.97 (m, 1H), 3.73 (s, 4H), 3.65 (s, 2H), 2.86-2.78 (m, 1H), 2.75-2.71 (m, 3H), 2.58-2.53 (m, 6H), 2.40 (s, 3H), 2.16-2.08 (s, 1H), 2.05-1.97 (m, 1H), 1.93-1.88 (m, 1H), 1.75-1.69 (m, 1H).

Example 3

Preparation of N-methyl-N-((2-methyl-6-(4-methylpiperazin-1-yl)pyrimidin-4-yl)methyl)-5,6,7,8-tetrahydroquinolin-8-amine (A9)

Method AC-Step a. N-methyl-N-((2-methyl-6-(4-methylpiperazin-1-yl)pyrimidin-4-yl)methyl)-5,6,7,8-tetrahydroquinolin-8-amine: A mixture of N-methyl-5,6,7,8-tetrahydroquinolin-8-amine (37 mg, 0.23 mmol, see reference WO2006026703), 2-methyl-6-(4-methylpiperazin-1-yl)pyrimidine-4-carbaldehyde (46 mg, 0.21 mmol) and AcOH (13 mg, 0.21 mmol) in 1,2-dichloroethane (5 mL) was stirred for 10 min NaBH(OAc)₃ (66 mg, 0.3 mmol) was then added to the reaction solution. The resulting suspension was stirred at room temperature overnight. The reaction mixture was added saturated NaHCO₃ aqueous solution (100 mL) and extracted with dichloromethane (100 mL). The organic layer was dried over Na₂SO₄, filtered and evaporated. The residue was purified by silica gel column chromatography (dichloromethane/methanol/ammonium hydroxide=100/1/1 to 50/1/1) to give the desired product (30 mg, 39%) as a colorless oil. ¹H NMR (400 MHz, CDCl₃) δ 8.49 (d, J=4.6 Hz, 1H), 7.35 (d, J=8.0 Hz, 1H), 7.07-7.03 (m, 2H), 4.04 (t, J=7.4 Hz, 1H), 3.71 (t, J=5.2 Hz, 4H), 3.60 (s, 2H), 2.86-2.75 (m, 1H), 2.73-2.65 (m, 1H), 2.46-2.43 (m, 7H), 2.39 (s, 3H), 2.33 (s, 3H), 2.15-2.07 (m, 1H), 2.04-1.96 (m, 1H), 1.95-1.87 (m, 1H), 1.74-1.71 (m, 1H).

Example 4

Preparation of (S)-N-((6-((R)-2,4-dimethylpiperazin-1-yl)-2-methylpyrimidin-4-yl)methyl)-N-methyl-5,6,7,8-tetrahydroquinolin-8-amine (A63)

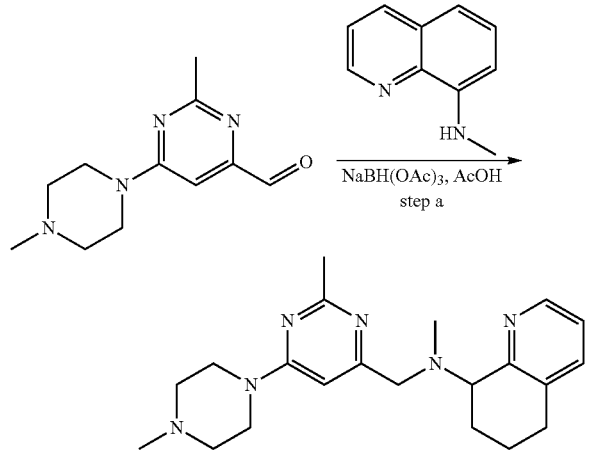

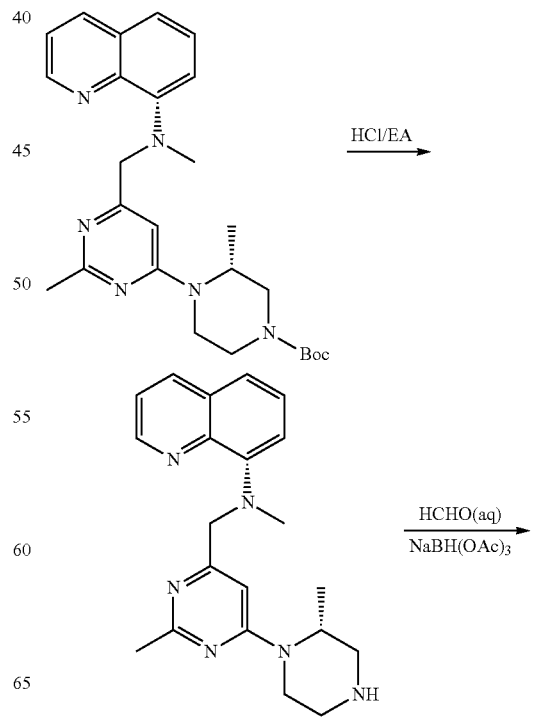

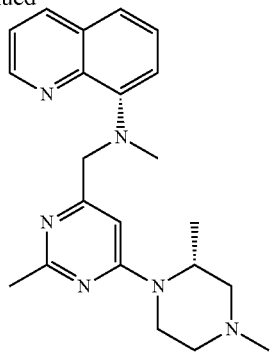

Method AD-Step a. (S)-N-methyl-N-((2-methyl-6-((R)-2-methylpiperazin-1-yl)pyrimidin-4-yl)methyl)-5,6,7,8-tetrahydroquinolin-8-amine: To a solution of (R)-tert-butyl 3-methyl-4-(2-methyl-6-((methyl((S)-5,6,7,8-tetrahydroquinolin-8-yl)amino)methyl)pyrimidin-4-yl)piperazine-1-carboxylate (50 mg, 0.11 mmol) in ethyl acetate (2 mL) was added 3M HCl/ethyl acetate (3 mL) and stirred at room temperature overnight. The reaction mixture was added saturated NaHCO₃ aqueous solution (50 mL) and extracted with dichloromethane (30 mL×3). The combined organic layer was dried over Na₂SO₄, filtered and evaporated to give the desired product (26 mg, 65%) as a colorless oil.

Method AD-Step b. (S)-N-((64(R)-2,4-dimethylpiperazin-1-yl)-2-methylpyrimidin-4-yl)methyl)-N-methyl-5,6,7,8-tetrahydroquinolin-8-amine: A mixture of (S)-N-methyl-N-((2-methyl-6-((R)-2-methylpiperazin-1-yl)pyrimidin-4-yl)methyl)-5,6,7,8-tetrahydroquinolin-8-amine (26 mg, 0.07 mmol) and formaldehyde (37 wt percent in water, 30 mg, 0.36 mmol) in 1,2-dichloroethane (4 mL) was added NaBH(OAc)₃ (30 mg, 0.14 mmol). The resulting suspension was stirred at room temperature overnight. The reaction mixture was added saturated NaHCO₃ aqueous solution (50 mL) and extracted with dichloromethane (30 mL×3). The combined organic layer was dried over Na₂SO₄, filtered and evaporated. The residue was purified by silica gel column chromatography (dichloromethane/methanol/ammonium hydroxide=100/1/1) to give the desired product (10 mg, 38%) as a colorless oil. ¹H NMR (400 MHz, CDCl₃) δ 8.48 (s, 1H), 7.35 (d, J=7.6 Hz, 1H), 7.09-6.92 (m, 2H), 4.62 (s, 1H), 4.35-4.28 (m, 1H), 4.09-3.98 (m, 1H), 3.74-3.49 (m, 2H), 3.23-3.08 (m, 1H), 2.91-2.83 (m, 1H), 2.82-2.75 (m, 1H), 2.74-2.65 (m, 2H), 2.46 (s, 3H), 2.42-2.36 (m, 3H), 2.28 (s, 3H), 2.22-2.17 (m, 1H), 2.14-2.07 (m, 1H), 2.05-1.91 (m, 3H), 1.74-1.63 (m, 1H), 1.29-1.23 (m, 3H).

Example 5

Preparation of N-methyl-N-((4-(4-methylpiperazin-1-yl)pyrimidin-2-yl)methyl)-5,6,7,8-tetrahydroquinolin-8-amine (A50)

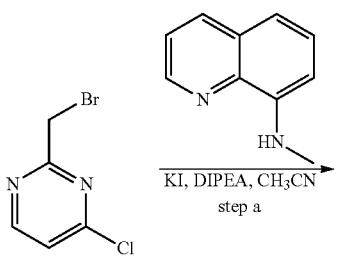

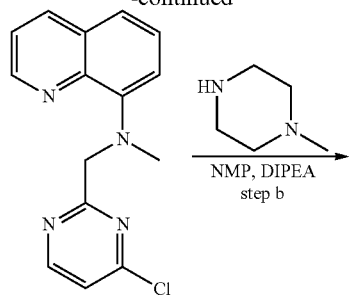

Method AE-Step a. N-((4-chloropyrimidin-2-yl)methyl)-N-methyl-5,6,7,8-tetrahydroquinolin-8-amine: The mixture of 2-(bromomethyl)-4-chloropyrimidine(94 mg, 0.58 mmol), N-methyl-5,6,7,8-tetrahydroquinolin-8-amine (130 mg, 0.6 mmol, see reference WO2006026703), KI (10 mg, 0.06 mmol) and DIPEA (740 mg, 5.8 mmol) in MeCN (10 mL) was stirred at room temperature for 4 h. The reaction solution was evaporated to remove most of MeCN, added saturated NaHCO₃ aqueous solution (50 mL) and extracted with dichloromethane (100 mL). The organic layer was dried over Na₂SO₄, filtered and evaporated. The residue was purified by silica gel column chromatography (dichloromethane/methanol/ammonium hydroxide=100/1/1) to give the desired product (140 mg, 84%) as a yellow oil. ¹H NMR (400 MHz, CDCl₃) δ 8.62 (d, J=4.8 Hz, 1H), 8.46 (d, J=2.8 Hz, 1H), 7.38 (d, J=7.6 Hz, 1H), 7.22 (d, J=4.8 Hz, 1H), 7.09-7.06 (m, 1H), 4.28-4.26 (m, 1H), 4.22 (s, 1H), 4.15-4.12 (m, 1H), 2.84-2.78 (m, 1H), 2.72-2.68 (m, 1H), 2.50 (s, 3H), 2.25-2.24 (m, 1H), 2.04-1.96 (m, 2H), 1.73-1.70 (m, 1H).

Method AE-Step b. N-methyl-N-((4-(4-methylpiperazin-1-yl)pyrimidin-2-yl)methyl)-5,6,7,8-tetrahydroquinolin-8-amine: The mixture of N-((4-chloropyrimidin-2-yl)methyl)-N-methyl-5,6,7,8-tetrahydroquinolin-8-amine (50 mg, 0.17 mmol), DIPEA (244 mg, 1.7 mmol) and 1-methylpiperazine (87 mg, 0.85 mmol) in NMP (2 mL) was stirred at 200° C. under microwave for 2 h. The reaction was diluted with ethyl acetate (50 mL) and washed with brine (50 mL). The organic layer was dried over Na₂SO₄, filtered and evaporated. The residue was purified by silica gel column chromatography (dichloromethane/methanol/ammonium hydroxide=100/1/1) to give the desired product (34 mg, 57%) as a yellow oil. ¹H NMR (400 MHz, CDCl₃) δ 8.46 (s, 1H), 8.18 (d, J=6.0 Hz, 1H), 7.34 (d, J=8.0 Hz, 1H), 7.05-7.02 (m, 1H), 6.32 (d, J=6.4 Hz, 1H), 4.15-4.12 (m, 1H), 3.81 (s, 2H), 3.65 (s, 4H), 2.87-2.77 (m, 1H), 2.72-2.69 (m, 1H), 2.65-2.44 (m, 7H), 2.32 (s, 3H), 2.11-1.98 (m, 3H), 1.73-1.64 (m, 1H). HRMS (ESI): calcd for C₂₀H₂₉N₆ [M+H]⁺353.2448, found 353.2448.

Example 6

Preparation of N-methyl-N-((6-(4-methylpiperazin-1-yl)pyridin-2-yl)methyl)-5,6,7,8-tetrahydroquinolin-8-amine (B6)

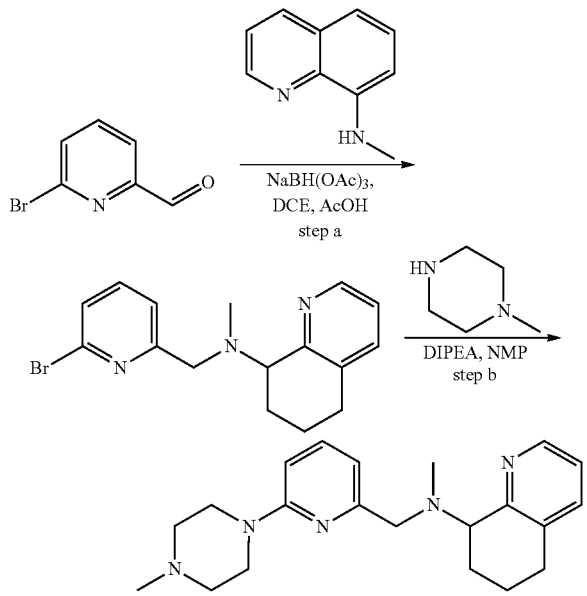

Method AF-Step a. N-((6-bromopyridin-2-yl)methyl)-N-methyl-5,6,7,8-tetrahydroquinolin-8-amine: The mixture of 6-bromopicolinaldehyde (162 mg, 0.68 mmol), N-methyl-5,6,7,8-tetrahydroquinolin-8-amine (100 mg, 0.62 mmol, see reference WO2006026703), AcOH (48 mg, 0.62 mmol) in 1,2-dichloroethane (10 mL) was stirred for 15 min. NaBH(OAc)$_3$ (252 mg, 0.93 mmol) was then added to the reaction solution. The resulting suspension was stirred at room temperature overnight. The reaction solution was added saturated NaHCO$_3$ aqueous solution (50 mL) and extracted with dichloromethane (100 mL). The combined organic layers was dried over Na$_2$SO$_4$, filtered and evaporated. The residue was purified by silica gel column chromatography (dichloromethane/methanol=100/1) to give the desired product (180 mg, 87%) as a yellow oil. $^1$H NMR (400 MHz, CDCl$_3$) δ 8.50 (s, 1H), 7.73 (d, J=7.6 Hz, 1H), 7.50 (t, J=7.6 Hz, 1H), 7.35 (d, J=7.2 Hz, 1H), 7.29 (d, J=7.6 Hz, 1H), 7.05 (t, J=5.8 Hz, 1H), 4.03 (t, J=7.0 Hz, 1H), 3.73 (s, 2H), 2.81-2.77 (m, 1H), 2.72-2.68 (m, 1H), 2.39 (s, 3H), 2.12 (s, 1H), 2.01(s, 1H), 1.95-1.87 (m, 1H), 1.71 (s, 1H).

Method AF-Step b. N-methyl-N-46-(4-methylpiperazin-1-yl)pyridin-2-yl)methyl)-5,6,7,8-tetrahydroquinolin-8-amine: The mixture of N-((6-bromopyridin-2-yl)methyl)-N-methyl-5,6,7,8-tetrahydroquinolin-8-amine (50 mg, 0.15 mmol), DIPEA (193 mg, 1.5 mmol) and 1-methylpiperazine (73 mg, 0.75 mmol) in NMP (2 mL) was stirred at 120° C. overnight. The reaction was diluted with ethyl acetate (50 mL) and washed with brine (30 mL×5). The organic layer was dried over Na$_2$SO$_4$, filtered and evaporated. The residue was purified by silica gel column chromatography (dichloromethane/methanol=100/1) to give the desired product (12 mg, 23%). $^1$H NMR (400 MHz, CDCl$_3$) δ 8.51 (d, J=4.4 Hz, 1H), 7.43 (t, J=7.8 Hz, 1H), 7.34 (d, J=7.6 Hz, 1H), 7.05 (d, J=4.8 Hz, 1H), 7.00 (d, J=7.2 Hz, 1H), 6.46 (d, J=8.4 Hz, 1H), 4.03 (s, 1H), 3.64 (q, J=15.0 Hz, 2H), 3.53 (s, 4H), 2.82-2.78 (m, 1H), 2.71-2.66 (m, 1H), 2.50 (t, J=4.4 Hz, 5H), 2.37 (s, 3H), 2.33 (s, 3H), 2.07 (s, 1H), 2.02-2.98 (m, 1H), 1.95-1.92 (m, 1H), 1.65 (s, 1H). HRMS (ESI): calcd for C$_{21}$H$_{30}$N$_5$ [M+H]$^+$352.2496, found 352.2514.

Example 7

Preparation of N-methyl-N-(pyrimidin-4-ylmethyl)-5,6,7,8-tetrahydroquinolin-8-amine (B2)

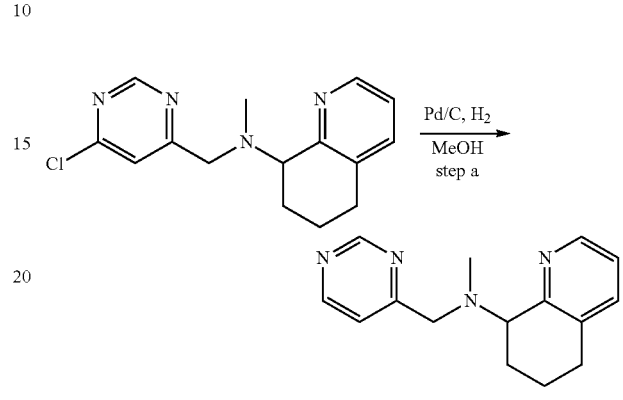

Method AG-Step a. N-methyl-N-(pyrimidin-4-ylmethyl)-5,6,7,8-tetrahydroquinolin-8-amine: A mixture of N4(6-chloropyrimidin-4-yl)methyl)-N-methyl-5,6,7,8-tetrahydroquinolin-8-amine (70 mg, 0.24 mmol) and Pd/C (5%, 15 mg) in 5 mL of methanol was stirred at 50° C. under H$_2$ (1 atm) overnight. The reaction solution was filtered and the filtrate was evaporated. The residue was purified by silica gel column chromatography (dichloromethane/methanol=100/1) to give the desired product (50 mg, 82%) as a colorless oil. $^1$H NMR (400 MHz, CDCl$_3$) δ 9.06 (s, 1H), 8.65 (d, J=4.8 Hz, 1H), 8.50 (s, 1H), 7.80 (d, J=4.4 Hz, 1H), 7.37 (d, J=7.2 Hz, 1H), 7.08-7.05 (m, 1H), 4.04-4.01 (m, 1H), 3.82-3.72 (m, 2H), 2.82-2.78 (m, 1H), 2.73-2.69 (m, 1H), 2.39 (s, 3H), 2.13 (s, 1H), 2.03 (s, 1H), 1.97-1.88 (m, 1H), 1.72 (s, 1H). MS (ESI/APCI) m/z 254.9 [M+H]$^+$.

Example 8

Preparation of (S)-(2-methyl-4-((methyl(1-(pyridin-2-yl)ethyl)amino)methyl)-6-(4-methylpiperazin-1-yl)pyrimidin-5-yl)methanol (A85)

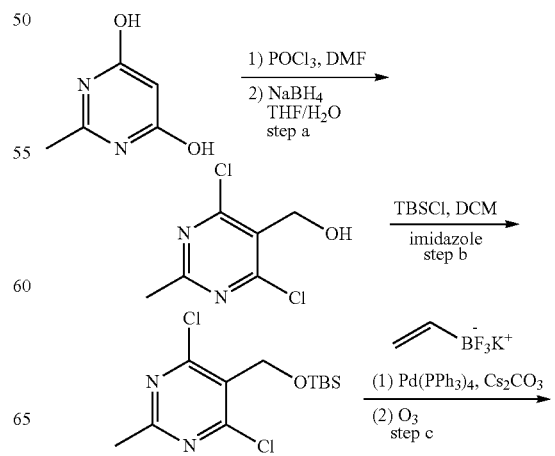

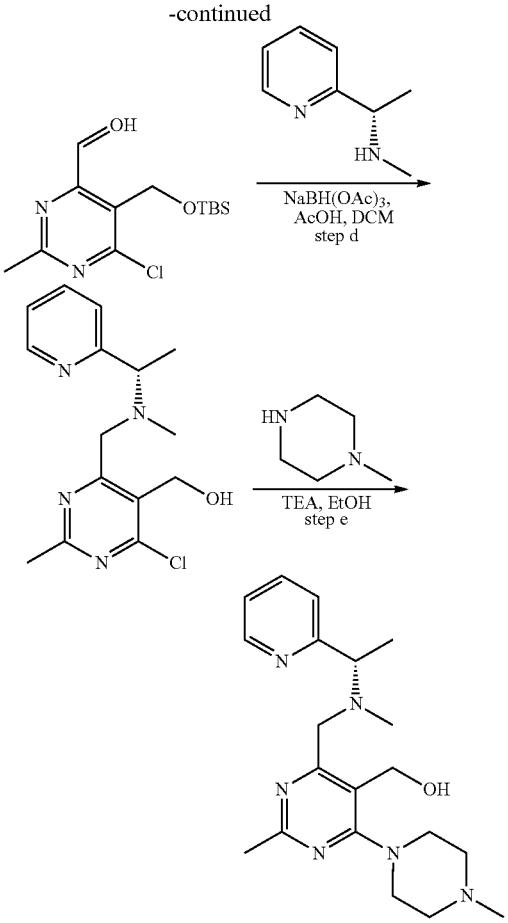

Method AH-Step a. (4,6-dichloro-2-methylpyrimidin-5-yl)methanol: To POCl$_3$ (60.6 g, 396.5 mmol) was added dropwise DMF (9.8 g, 134.8 mmol) at 0° C. The resulting suspension was stirred at the same temperature for 1 h. Then 2-methylpyrimidine-4,6-diol (10 g, 79.3 mmol) was added in portions and stirred at room temperature for 1 h, after that, stirred at 105° C. overnight. The reaction solution was concentrated and diluted with cold ethyl acetate (100 mL). This solution was added dropwise into ice-water, filtered and the filtrate was extracted with ethyl acetate (200 mL). The combined organic layer was dried over Na$_2$SO$_4$, filtered and evaporated to give a yellow oil (10 g). This oil was dissolved in THF (50 mL) and water (10 mL), and NaBH$_4$ (4 g, 104.7 mmol) was added in portions at 0° C. The resulting suspension was stirred at the same temperature for 30 min. Water (50 mL) was added, and extracted with ethyl acetate (50 mL). The organic layer was dried over Na$_2$SO$_4$, filtered and evaporated. The residue was purified by silica gel column chromatography (petroleum ether/ethyl acetate=10/1) to give the desired product (2 g, 20%) as a yellow solid. $^1$H NMR (400 MHz, CDCl$_3$) δ 4.91 (s, 2H), 2.69 (s, 3H).

Method AH-Step b. 5-((tert-butyldimethylsilyloxy)methyl)-4,6-dichloro-2-methylpyrimidine: To the solution of (4,6-dichloro-2-methylpyrimidin-5-yl)methanol (2 g, 10.3 mmol) and imidazole (770 mg, 11.3 mmol) in dichloromethane (20 mL) was added TBSCl (1.7 g, 11.3 mmol) in portions. The resulting suspension was stirred at room temperature overnight. Water (20 mL) was added, and extracted with dichloromethane (20 mL). The combined organic layer was dried over Na$_2$SO$_4$, filtered and evaporated. The residue was purified by silica gel column chromatography (petroleum ether/ethyl acetate=100/1) to give the desired product (2.6 g, 84%) as a colorless oil. $^1$H NMR (400 MHz, CDCl$_3$) δ 4.85 (s, 2H), 2.68 (s, 3H), 0.91 (s, 9H), 0.14 (s, 6H).

Method AH-Step c. 5-((tert-butyldimethylsilyloxy)methyl)-6-chloro-2-methylpyrimidine-4-carbaldehyde: To the solution of 5-((tert-butyldimethylsilyloxy)methyl)-4,6-dichloro-2-methylpyrimidine (1.5 g, 4.8 mmol), potassium vinyltrifluoroborate (655 mg, 4.88 mmol), Cs$_2$CO$_3$ (2.4 g, 7.32 mmol) and Pd(PPh$_3$)$_4$ (566 mg, 0.49 mmol) in 1,4-dioxane (20 mL) and water (4 mL) was stirred at reflux overnight under N$_2$ atmosphere. The reaction mixture was concentrated, and the residue was purified by silica gel column chromatography (petroleum ether/ethyl acetate=100/1) to give a crude oil (900 mg). This resulting oil was added methanol (30 mL) and dichloromethane (7 mL) to dissolve. Then O$_3$ was introduced into this reaction solution at −65° C. and stirred at this temperature for 4 h before dimethyl sulfide was added to quench the reaction. The solvent was concentrated and added water (20 mL), extracted with dichloromethane (50 mL). The combined organic layer was dried over Na$_2$SO$_4$, filtered and evaporated to give the crude desired product (610 mg) as a white solid.

Method AH-Step d. (S)-(4-chloro-2-methyl-6-((methyl(1-(pyridin-2-yl)ethyl)amino)methyl)pyrimidin-5-yl)methanol: A mixture of (S)-N-methyl-1-(pyridin-2-yl)ethanamine (544 mg, 4.0 mmol), 5-((tert-butyldimethylsilyloxy)methyl)-6-chloro-2-methylpyrimidine-4-carbaldehyde (610 mg, 2.0 mmol) and AcOH (360 mg, 6.0 mmol) in dichloromethane (10 mL) was stirred for 1 h. NaBH(OAc)$_3$ (1.3 g, 6.0 mmol) was then added to the reaction solution. The resulting suspension was stirred at room temperature overnight. The reaction mixture was added water (10 mL) and extracted with dichloromethane (10 mL). The combined organic layers was dried over Na$_2$SO$_4$, filtered and evaporated. The residue was purified by silica gel column chromatography (dichloromethane/methanol=100/1 to 50/1) to give the desired product (480 mg, 80%) as a yellow oil. $^1$H NMR (400 MHz, CDCl$_3$) δ 8.66-8.55 (m, 1H), 7.82-7.65 (m, 1H), 7.38-7.30 (m, 1H), 7.25-7.18 (m, 1H), 4.77 (s, 2H), 4.15-3.85 (m,3H), 2.66 (s, 3H), 2.19 (s, 3H), 1.56 (d, J=7.2 Hz, 3H).

Method AH-Step e. (S)-(2-methyl-4-((methyl(1-(pyridin-2-yl)ethyl)amino)methyl)-6-(4-methylpiperazin-1-yl)pyrimidin-5-yl)methanol: The mixture of (S)-(4-chloro-2-methyl-6-((methyl(1-(pyridin-2-yl)ethyl)amino)methyl)pyrimidin-5-yl)methanol (50 mg, 0.16 mmol), TEA (80 mg, 0.8 mmol) and 1-methylpiperazine (48 mg, 0.48 mmol) in ethanol (5 mL) was stirred at reflux overnight. The reaction solution was evaporated. The residue was purified by silica gel column chromatography (dichloromethane/methanol/ammonium hydroxide=100/1/1 to 100/2/1) to give the desired product (26 mg, 80%) as a colorless oil. $^1$H NMR (400 MHz, CDCl$_3$) δ 8.62-8.56 (m, 1H), 7.73-7.63 (m, 1H), 7.31 (d, J=8.0 Hz, 1H), 7.23-7.15 (m, 1H), 4.45-4.35 (m, 2H), 3.92 (q, J=6.8 Hz,1H), 3.87 (d, J=13.2 Hz, 1H), 3.79 (s, 4H), 3.68 (d, J=13.2 Hz, 1H), 2.70 (s, 4H), 2.48 (s, 3H), 2.45 (s, 3H), 2.07 (s, 3H), 1.55 (d, J=6.8 Hz, 3H).

Example 9

Preparation of (3R,5R)-5-(2-methyl-6-(4-methylpiperazin-1-yl)pyrimidin-4-yl)-1-((S)-5,6,7,8-tetrahydroquinolin-8-yl)pyrrolidin-3-ol (C16)

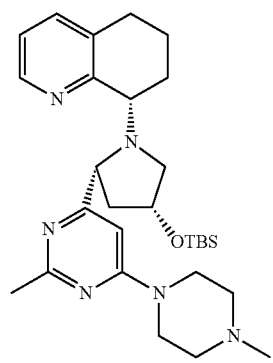

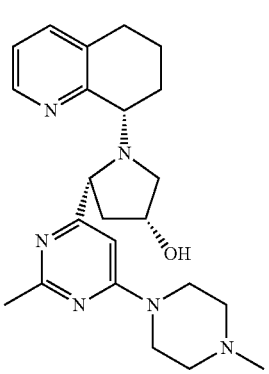

Method AI-Step a. (3R,5R)-5-(2-methyl-6-(4-methylpiperazin-1-yl)pyrimidin-4-yl)-1-((S)-5,6,7,8-tetrahydroquinolin-8-yl)pyrrolidin-3-ol: The solution of (S)-8-((2R,4R)-4-(tert-butyldimethylsilyloxy)-2-(2-methyl-6-(4-methylpiperazin-1-yl)pyrimidin-4-yl)pyrrolidin-1-yl)-5,6,7,8-tetrahydroquinoline (50 mg, 0.1 mmol) in 2M HCl aqueous solution (5 mL) was stirred at room temperature for 2 h. The reaction mixture was added saturated NaHCO₃ aqueous solution (100 mL) and extracted with dichloromethane (100 mL). The organic layer was dried over Na₂SO₄, filtered and evaporated to give the desired product (35 mg, 86%) as a white solid. $^1$H NMR (400 MHz, CDCl₃) δ 8.38 (d, J=4.8 Hz, 1H), 7.12 (d, J=7.2 Hz, 1H), 7.05-6.99 (m, 1H), 5.29 (s, 1H), 4.28 (s, 1H), 4.03 (d, J=10.0 Hz, 1H), 3.89 (s, 1H), 3.55-3.38 (m, 4H), 3.30 (d, J=9.2 Hz, 1H), 2.92-2.83 (m, 1H), 2.63-2.53 (m, 1H), 2.53-2.45 (m, 1H), 2.44-2.37 (m, 7H), 2.33 (s, 3H), 2.14-2.05 (m, 2H), 1.77 (d, J=13.6 Hz, 1H), 1.62-1.51 (m, 3H).

Example 10

Preparation of (8-(methyl((2-methyl-6-(4-methylpiperazin-1-yl)pyrimidin-4-yl)methyl)amino)quinolin-6-yl)methanol (D55)

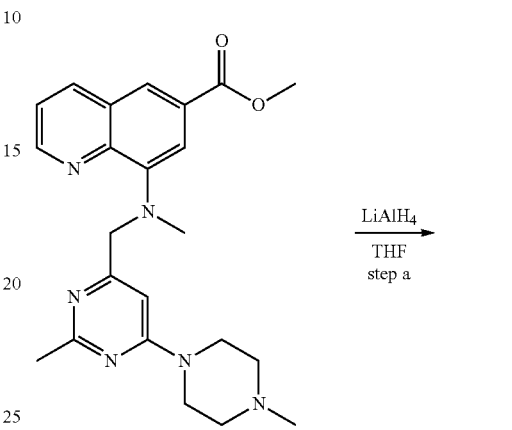

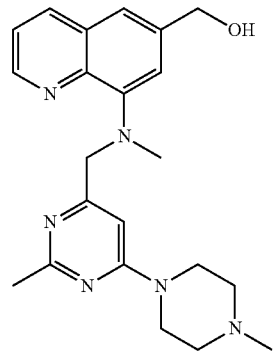

Method AJ-Step a. (8-(methyl((2-methyl-6-(4-methylpiperazin-1-yl)pyrimidin-4-yl)methyl)amino)quinolin-6-yl)methanol: The solution of methyl 8-(methyl((2-methyl-6-(4-methylpiperazin-1-yl)pyrimidin-4-yl)methyl)amino)quinoline-6-carboxylate(105 mg, 0.25 mmol) in THF (3 mL) was added LiAlH₄ (19 mg, 0.5 mmol) at 0° C., and stirred at room temperature for 20 min. Water and NaOH aqueous solution (15 wt percent in water) was added to quench the reaction. The mixture was filtered and the filtrate was evaporated. The residue was purified by silica gel column chromatography (dichloromethane/methanol/ammonium hydroxide=100/1/1) to give the desired product (60 mg, 61%) as a slight yellow oil. $^1$H NMR (400 MHz, CDCl₃) δ 8.76 (s, 1H), 8.07 (d, J=8.0 Hz, 1H), 7.45-7.30 (m, 2H), 7.17 (s, 1H), 6.79 (s, 1H), 4.81 (s, 2H), 4.66 (s, 2H), 3.63 (s, 4H), 3.03 (s, 3H), 2.54 (s, 3H), 2.50-2.43 (m, 4H), 2.32 (s, 3H).

Example 11

Preparation of (S)-5-(4-methylpiperazin-1-yl)-2-((2-(3-methylpyridin-2-yl)pyrrolidin-1-yl)methyl)imidazo11,2-a]pyridine (C38) and (S)-(5-(4-methylpiperazin-1-yl)-2-((2-(3-methylpyridin-2-yl)pyrrolidin-1-yl)methyl)imidazo[1,2-a]pyridin-3-yl)methanol (C39)

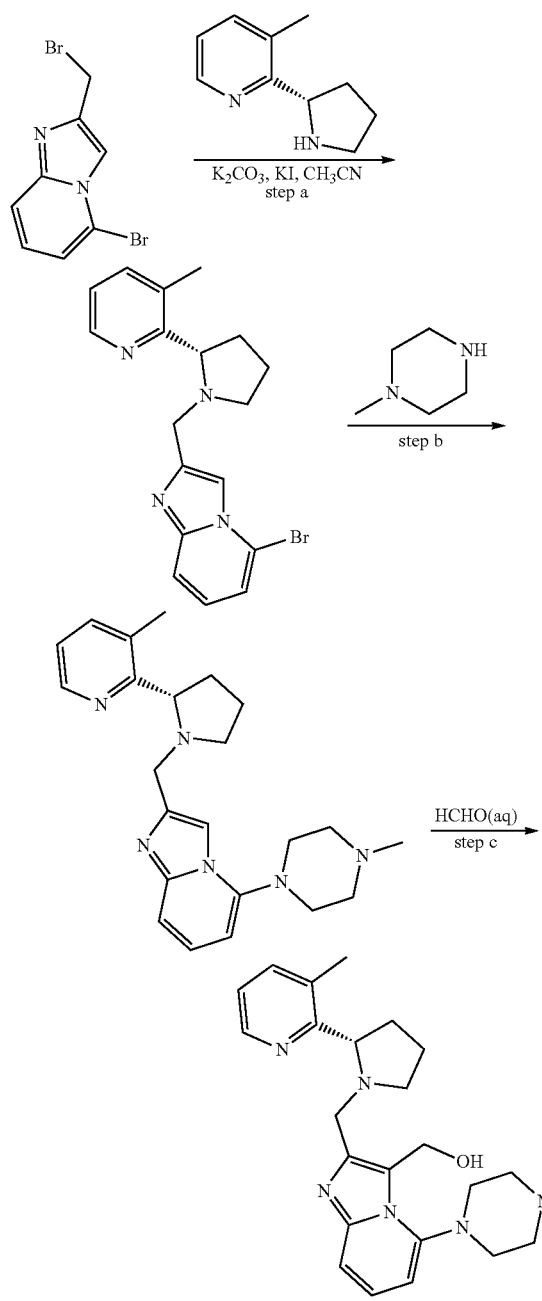

Method AK-Step a. (S)-5-bromo-2-((2-(3-methylpyridin-2-yl)pyrrolidin-1-yl)methyl)imidazo[1,2-a]pyridine: The mixture of 5-bromo-2-(bromomethyl)imidazo[1,2-a]pyridine(48 mg, 0.17 mmol), (S)-3-methyl-2-(pyrrolidin-2-yl) pyridine (30 mg, 0.12 mmol), KI (3 mg, 0.017 mmol) and K₂CO₃ (46 mg, 0.34 mmol) in MeCN (15 mL) was stirred at room temperature overnight. The reaction mixture was filtered and the filtrate was evaporated. The residue was purified by silica gel column chromatography (dichloromethane/methanol=50/1) to give the desired product (40 mg, 78%) as a colorless oil. $^1$H NMR (400 MHz, CDCl$_3$) δ 8.48 (s, 1H),7.61 (s,1H), 7.48 (d, J=8.8 Hz, 1H), 7.31 (d, J=7.6 Hz, 1H), 7.03-6.95 (m, 3H), 3.97-3.94 (m, 2H), 3.74 (s,1H), 3.43 (s, 1H), 2.55 (s, 1H), 2.37 (s, 3H), 2.21-1.95 (m, 4H).

Method AK-Step b. (S)-5-(4-methylpiperazin-1-yl)-2-42-(3-methylpyridin-2-yl)pyrrolidin-1-yl)methyl)imidazo[1,2-a]pyridine: The mixture of (S)-5-bromo-2-((2-(3-methylpyridin-2-yl)pyrrolidin-1-yl)methyl)imidazo[1,2a] pyridine (40 mg, 0.11 mmol) in 1-methylpiperazine (3 mL) was stirred at 170° C. under microwave for 1.5 h. The reaction mixture was concentrated. The residue was purified by silica gel column chromatography (dichloromethane/methanol=60/1) to give the desired product (20 mg, 48%) as a colorless oil. $^1$H NMR (400 MHz, CDCl$_3$) δ 8.49 (d, J=3.6 Hz, 1H), 7.33 (s, 2H), 7.28 (s, 1H), 7.13-7.09 (m, 1H), 7.01-6.98 (m, 1H), 6.24 (d, J=7.2 Hz, 1H), 3.96 (d, J=13.6 Hz, 1H), 3.84 (t, J=8.0 Hz, 1H), 3.67(d, J=13.6 Hz, 1H), 3.39 (t, J=8.0 Hz, 1H), 3.10 (s, 4H), 2.64 (s, 4H), 2.59-2.52 (m, 1H), 2.42 (s, 3H), 2.38 (s, 3H), 2.22-2.17 (m, 2H), 2.05-1.90 (m, 2H).

Method AK-Step c. (S)-(5-(4-methylpiperazin-1-yl)-2-((2-(3-methylpyridin-2-yl)pyrrolidin-1-yl)methyl)imidazo [1,2-a]pyridin-3-yl)methanol: The mixture of (S)-5-(4-methylpiperazin-1-yl)-24(2-(3-methylpyridin-2-yl) pyrrolidin-1-yl)methyl)imidazo[1,2-a]pyridine (46 mg, 0.12 mmol) and formaldehyde (37 wt percent in water, 5 mL) in a sealed tube was stirred at 50° C. for 2 days. The reaction mixture was added saturated NaHCO₃ aqueous solution (10 mL) and extracted with dichloromethane (30 m). The organic layer was dried over Na₂SO₄, filtered and evaporated. The residue was purified by silica gel column chromatography (dichloromethane/methanol=50/1) to give the desired product (35 mg, 71%) as a colorless oil. $^1$H NMR (400 MHz, CDCl$_3$) δ 8.50 (d, J=3.6 Hz, 1H), 7.40 (d, J=7.2 Hz, 1H), 7.29 (d, J=8.8 Hz, 1H), 7.08-7.02 (m, 2H), 6.39 (d, J=6.8 Hz, 1H), 6.19 (brs, 1H), 5.27 (d, J=14.0 Hz, 1H), 5.07 (d, J=14.0 Hz, 1H), 4.05 (d, J=12.8 Hz, 1H), 3.86-3.84 (m, 1H), 3.50-3.47 (m, 2H), 3.26-3.23 (m, 1H), 3.18-3.15 (m, 1H), 3.01-2.91 (m, 3H), 2.85-2.80 (m, 1H), 2.54-2.46 (m, 3H), 2.41(s, 3H), 2.38(s, 3H), 2.28-2.24 (m, 1H), 1.91-1.82 (m, 3H).

Example 12

Preparation of 7-fluoro-N-methyl-N-((2-methyl-6-(4-methylpiperazin-1-yl)pyrimidin-4-yl)methyl)-5,6-dihydroquinolin-8-amine (D1)

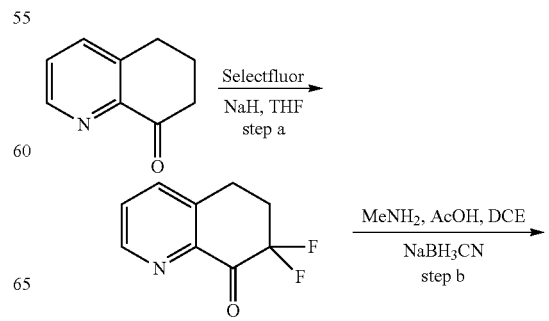

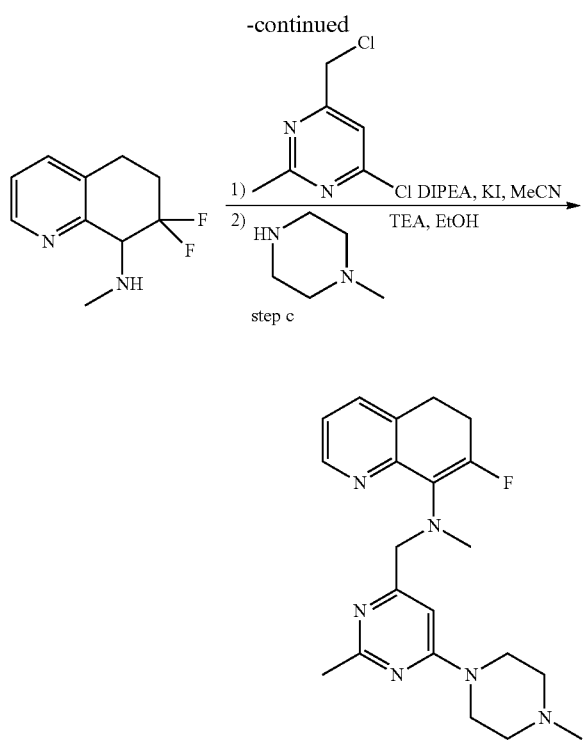

Method AL-Step a. 7,7-difluoro-6,7-dihydroquinolin-8 (5H)-one: To a solution of NaH (60 wt percent moistened with oil, 511 mg, 12.8 mmol) in THF (20 mL) was added dropwise the THF solution (5 mL) containing 6,7-dihydroquinolin-8(5H)-one (588 mg, 4 mmol) at 0° C. The reaction was stirred at 0° C. for 10 min followed by adding selectfluro (3.0 g, 8.4 mmol) in portions. The reaction mixture was stirred at room temperature for 1 h. Water (20 mL) was added to quench the reaction. The water phase was extracted with diethyl ether (20 mL×3). The combined organic layer was dried over Na$_2$SO$_4$, filtered and evaporated. The residue was purified by silica gel column chromatography (petroleum ether/ethyl acetate=10/1) to give the desired product (380 mg, 52%) as a white solid. $^1$H NMR (400 MHz, CDCl$_3$) δ 8.81 (s, 1H), 7.73 (d, J=7.6 Hz, 1H), 7.57-7.45 (m, 1H), 3.26-3.08 (m, 2H), 2.76-2.51 (m, 2H).

Method AL-Step b. 7,7-difluoro-N-methyl-5,6,7,8-tetrahydroquinolin-8-amine: The solution of 7,7-difluoro-6,7-dihydroquinolin-8(5H)-one (18.3 mg, 0.1 mmol), MeNH$_2$ solution (30 wt percent in ethanol, 1 mL) and HOAc (5 mg, 0.083 mmol) in 1,2-dichloroethane (2 mL) was added NaBH$_3$CN (13 mg, 0.2 mmol). The resulting suspension was stirred at room temperature overnight. The reaction mixture was filtered and the filtrate was evaporated. The residue was purified by silica gel column chromatography (dichloromethane/methanol=150/1) to give the desired product (15 mg, 75%) as a yellow oil. $^1$H NMR (400 MHz, CDCl$_3$) δ 8.47 (d, J=4.0 Hz, 1H), 7.46 (d, J=7.6 Hz, 1H), 7.19-7.15 (m, 1H), 3.89 (t, J=10.0 Hz, 1H), 3.01-2.91 (m, 2H), 2.72 (s, 3H), 2.61-2.41 (m, 1H), 2.30-2.17 (m, 1H).

Method AL-Step c. 7-fluoro-N-methyl-N-((2-methyl-6-(4-methylpiperazin-1-yl)pyrimidin-4-yl)methyl)-5,6-dihydroquinolin-8-amine: A mixture of 4-chloro-6-(chloromethyl)-2-methylpyrimidine (54 mg, 0.31 mmol), 7,7-difluoro-N-methyl-5,6,7,8-tetrahydroquinolin-8-amine (55 mg, 0.28 mmol), KI (5 mg, 0.028 mmol) and DIPEA (90 mg, 0.7 mmol) in CH$_3$CN (10 mL) was stirred at room temperature overnight. The reaction solution was evaporated to remove most of CH$_3$CN, diluted with dichloromethane (15 mL) and washed with saturated brine solution (10 mL). The organic layer was dried over Na$_2$SO$_4$, filtered and evaporated. The residue was dissolved in ethanol (10 mL). TEA (252 mg, 2.5 mmol) and N-methylpiperazine (125 mg, 1.25 mmol) were added and stirred at reflux for 3 h. The reaction mixture was cooled to room temperature and concentrated. The residue was purified by silica gel column chromatography (dichloromethane/methanol/ammonium hydroxide=50/1/1) to give the desired product (15 mg, 15%) as a colorless oil. $^1$H NMR (400 MHz, CDCl$_3$) δ 8.44 (d, J=4.0 Hz, 1H), 7.40 (d, J=7.2 Hz, 1H), 7.06-6.98 (m, 1H), 6.93 (s, 1H), 4.26 (s, 2H), 3.60 (s, 4H), 2.93 (s, 3H), 2.93-2.81 (m, 2H), 2.64-2.56 (m, 2H), 2.47 (s, 3H), 2.42 (s, 4H), 2.32 (s, 3H). MS (ESI/APCI) m/z 382.9 [M+H]$^+$.

Example 13

Preparation of N-methyl-N-((2-methyl-6-(4-methylpiperazin-1-yl)pyrimidin-4-yl)methyl)quinolin-8-amine (D2)

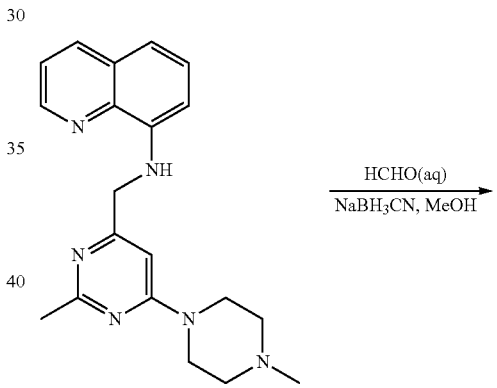

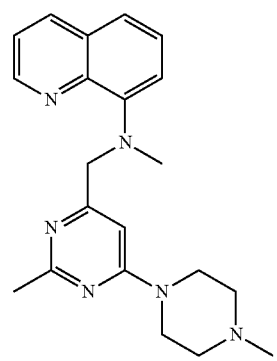

Method AM-Step a. N-methyl-N-((2-methyl-6-(4-methylpiperazin-1-yl)pyrimidin-4-yl)methyl)quinolin-8-amine: A mixture of N-((2-methyl-6-(4-methylpiperazin-1-yl)pyrimidin-4-yl)methyl)quinolin-8-amine (75 mg, 0.26 mmol) and formaldehyde (37 wt percent in water, 42 mg, 0.52 mmol) in methanol (3 mL) was added NaBH$_3$CN (25 mg, 0.4 mmol). The resulting suspension was stirred at room temperature overnight. Water (10 mL) was added to quench the reaction. The water phase was extracted with diethyl ether (10 mL×3). The combined organic layer was dried over Na$_2$SO$_4$, filtered and evaporated. The residue was purified by silica gel column chromatography (dichloromethane/methanol/ammonium hydroxide=100/1/1) to give the desired product (37 mg, 39%) as a yellow oil. $^1$H NMR (400 MHz, CDCl$_3$) δ 8.82 (d, J=2.4 Hz, 1H), 8.11 (d, J=8.4 Hz, 1H), 7.44-7.35 (m, 3H), 7.13 (d, J=7.2 Hz, 1H), 6.68 (s, 1H), 4.69 (s, 2H), 3.57 (s, 4H), 3.06 (s, 3H), 2.51 (s, 3H), 2.39 (t, J=4.8 Hz, 4H), 2.30 (s, 3H).

Example 14

Preparation of N-methyl-N-((2-methyl-6-(4-methylpiperazin-1-yl)pyrimidin-4-yl)methyl)-1,7-naphthyridin-8-amine (D21)

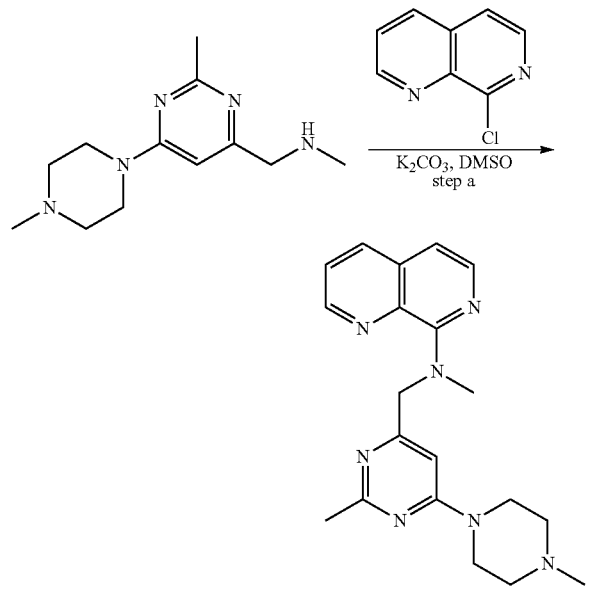

Method AN-step a. N-methyl-N-((2-methyl-6-(4-methylpiperazin-1-yl)pyrimidin-4-yl)methyl)-1,7-naphthyridin-8-amine: To the solution of 8-chloro-1,7-naphthyridine (56 mg, 0.34 mmol) and N-methyl-1-(2-methyl-6-(4-methylpiperazin-1-yl)pyrimidin-4-yl)methanamine (80 mg, 0.34 mmol) in DMSO (3 mL), was added K$_2$CO$_3$ (140 mg, 1.02 mmol). The resulting suspension was stirred at 110° C. overnight. The reaction mixture was concentrated. The residue was purified by silica gel column chromatography (dichloromethane/methanol/ammonium hydroxide=10/1/1) to give the desired product (17 mg, 11%) as a yellow oil. $^1$H NMR (400 MHz, CDCl$_3$) δ 8.66 (s, 1H), 8.10 (d, J=5.2 Hz, 1H), 7.96 (d, J=8.0 Hz, 1H), 7.43 (dd, J=7.6, 4.0 Hz, 1H), 6.96 (d, J=5.6 Hz, 1H), 6.46 (s, 1H), 5.26 (s, 2H), 3.57 (s, 4H), 3.36 (s, 3H), 2.52 (s, 3H), 2.45-2.34 (m, 4H), 2.29 (s, 3H).

Example 15

Preparation of N-methyl-N-((2-methyl-6-(4-methylpiperazin-1-yl)pyrimidin-4-yl)methyl)-1,6-naphthyridin-8-amine (D22)

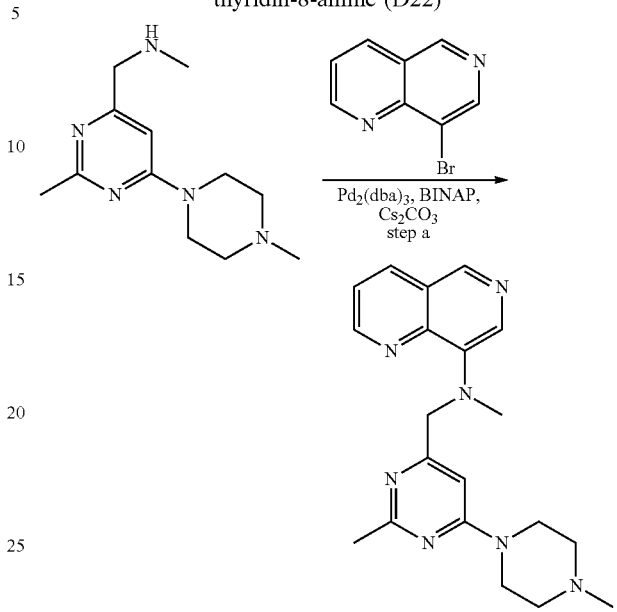

Method AO-step a. N-methyl-N-((2-methyl-6-(4-methylpiperazin-1-yl)pyrimidin-4-yl)methyl)-1,6-naphthyridin-8-amine: The mixture of 8-bromo-1,6-naphthyridine (41 mg, 0.20 mmol), N-methyl-1-(2-methyl-6-(4-methylpiperazin-1-yl)pyrimidin-4-yl)methanamine (99 mg, 0.42 mmol), BINAP (13 mg, 0.02 mmol), Cs$_2$CO$_3$ (152 mg, 0.46 mol) and Pd$_2$(dba)$_3$ (9 mg, 0.01 mmol) in toluene (5 mL) was stirred at 100° C. overnight under N$_2$ atmosphere. The reaction mixture was cooled to room temperature and filtered. The filtrate was concentrated. The residue was purified by silica gel column chromatography (dichloromethane/methanol/ammonium hydroxide=100/1/1) to give the desired product (20 mg, 28%) as a yellow oil. $^1$H NMR (400 MHz, CDCl$_3$) δ 8.96 (s, 1H), 8.81 (s, 1H), 8.37-8.13 (m, 2H), 7.50 (s, 1H), 6.62 (s, 1H), 4.84 (s, 2H), 3.60 (s, 4H), 3.13 (s, 3H), 2.51 (s, 3H), 2.42 (s, 4H), 2.31 (s, 3H).

Example 16

Preparation of 4-(((2-methyl-6-(4-methylpiperazin-1-yl)pyrimidin-4-yl)methyl)(quinolin-8-yl)amino) butanoic acid (D30) and 4-(((2-methyl-6-(4-methylpiperazin-1-yl)pyrimidin-4-yl)methyl)(quinolin-8-yl)amino)butanamide (D31)

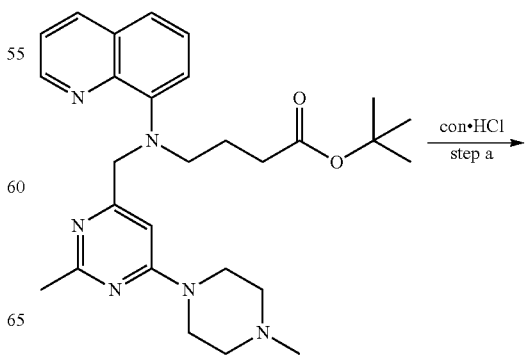

-continued

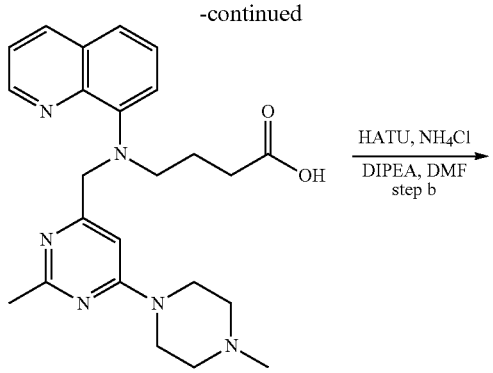

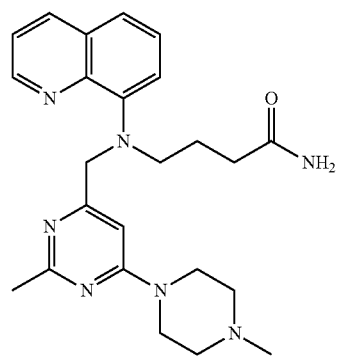

Method AP-Step a. 4-(((2-methyl-6-(4-methylpiperazin-1-yl)pyrimidin-4-yl)methyl)(quinolin-8-yl)amino)butanoic acid: The solution of tert-butyl 4-(((2-methyl-6-(4-methylpiperazin-1-yl)pyrimidin-4-yl)methyl)(quinolin-8-yl)amino)butanoate (55 mg, 0.112 mmol) in concentrated HCl aqueous solution (6 mL) was stirred at 50° C. overnight. The reaction mixture was evaporated to give the desired product hydrochloride (535 mg, 96%) as a yellow oil. $^1$H NMR (400 MHz, D$_2$O) δ 9.14 (d, J=8.4 Hz, 1H), 9.07 (d, J=5.6 Hz, 1H), 8.12 (d, J=8.0 Hz, 1H), 8.09-8.06 (m, 1H), 8.02 (d, J=7.6 Hz, 1H), 7.92-7.88 (m, 1H), 7.00 (s, 1H), 5.25 (s, 1H), 4.44 (s, 2H), 4.33 (s, 1H), 3.68-3.46 (m, 4H), 3.41-3.12 (m, 4H), 2.92 (s, 3H), 2.54 (s, 3H), 2.17 (t, J=6.8 Hz, 2H), 1.61 (s, 2H).

Method AP-Step b. 4-(((2-methyl-6-(4-methylpiperazin-1-yl)pyrimidin-4-yl)methyl)(quinolin-8-yl)amino)butanamide: The mixture of 4-(((2-methyl-6-(4-methylpiperazin-1-yl)pyrimidin-4-yl)methyl)(quinolin-8-yl)amino)butanoic acid (50 mg, 0.098 mmol), NH$_4$Cl (27 mg, 0.51 mmol), HATU (47 mg, 0.122 mmol) and DIPEA (131 mg, 1.02 mmol) in DMF (3 mL) was stirred at 50° C. overnight. The reaction mixture was concentrated. The residue was purified by silica gel column chromatography (dichloromethane/methanol/ammonium hydroxide=20/1/0.1) to give the desired product (25 mg, 58%) as a yellow oil. $^1$H NMR (400 MHz, CDCl$_3$) δ 8.82 (d, J=4.4 Hz, 1H), 8.18 (d, J=8.4 Hz, 1H), 7.45-7.42 (m, 3H), 7.30-7.29 (m, 1H), 6.90 (s, 1H), 6.81 (s, 1H), 5.35 (s, 1H), 4.62 (s, 2H), 3.71 (s, 4H), 3.52 (t, J=7.2 Hz, 2H), 2.58 (s, 3H), 2.50-2.48 (m, 4H), 2.34 (s, 3H), 2.26 (t, J=7.2 Hz, 2H), 2.00-1.97 (m, 2H).

Example 17

Preparation of 8-(methyl((2-methyl-6-(4-methylpiperazin-1-yl)pyrimidin-4-yl)methyl)amino)quinoline-7-carbonitrile (D50)

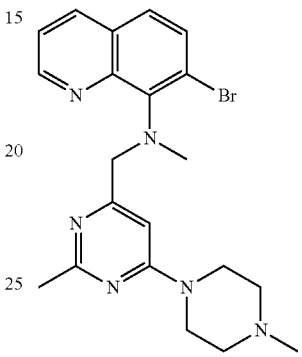

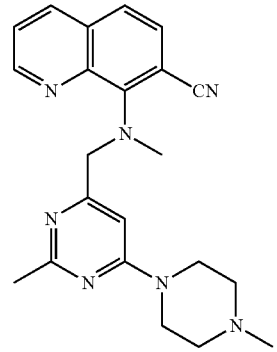

Method AQ-Step a. 8-(methyl((2-methyl-6-(4-methylpiperazin-1-yl)pyrimidin-4-yl)methyl)amino)quinoline-7-carbonitrile: The mixture of 7-bromo-N-methyl-N-((2-methyl-6-(4-methylpiperazin-1-yl)pyrimidin-4-yl)methyl)quinolin-8-amine (210 mg, 0.48 mmol), ZnCN$_2$ (112 mg, 0.95 mmol), dppf (53 mg, 0.1 mmol), Pd(PPh$_3$)$_4$ (110 mg, 0.1 mmol) and Pd$_2$(dba)$_3$ (44 mg, 0.05 mmol) in DMAc (8 mL) was stirred at 150° C. for 2 days under N$_2$ atmosphere. The reaction mixture was concentrated. The residue was purified by silica gel column chromatography (dichloromethane/methanol/ammonium hydroxide=100/1/0.5) to give the a crude product (80 mg). The crude product was further purified by Combi-Flash-C18 (MeCN/water, MeCN gradient 30% to 60% volume percent through 30 min) to give the desired product (13 mg, 7%) as a yellow oil. $^1$H NMR (400 MHz, CDCl$_3$) δ 8.91 (d, J=2.4 Hz, 1H), 8.14 (d, J=8.0 Hz, 1H), 7.58-7.46 (m, 3H), 7.06 (s, 1H), 4.91 (s, 2H), 3.75 (s, 4H), 3.31 (s, 3H), 2.49 (s, 7H), 2.34 (s, 3H).

Example 18

Preparation of N-methyl-N-((2-methyl-6-(4-methylpiperazin-1-yl)pyrimidin-4-yl)methyl)-5-(methylsulfonyl)quinolin-8-amine (D43)

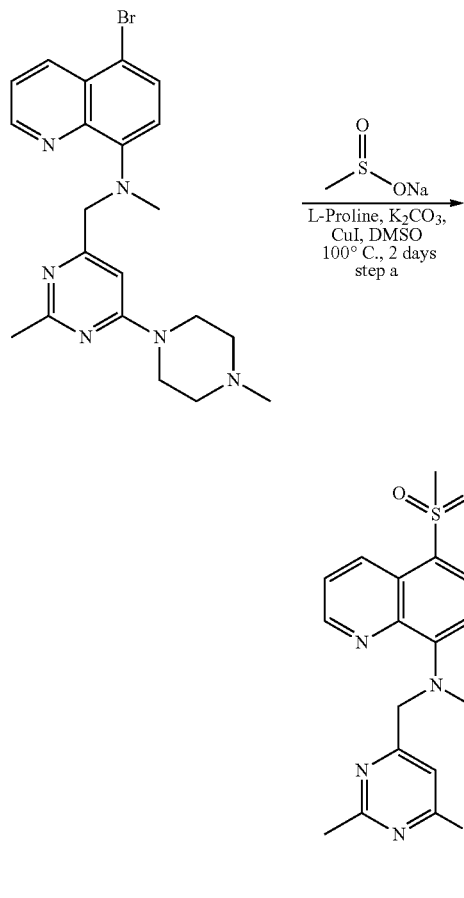

Method AR-Step a. N-methyl-N-((2-methyl-6-(4-methylpiperazin-1-yl)pyrimidin-4-yl)methyl)-5-(methylsulfonyl)quinolin-8-amine: The mixture of 5-bromo-N-methyl-N-((2-methyl-6-(4-methylpiperazin-1-yl)pyrimidin-4-yl)methyl)quinolin-8-amine (150 mg, 0.34 mmol), sodium methanesulfinate (70 mg, 0.68 mmol), L-Proline (47 mg, 0.41 mmol), $K_2CO_3$ (28 mg, 0.2 mmol) and CuI (40 mg, 0.2 mmol) in DMSO (2 mL) was stirred at 100° C. for 2 days under $N_2$ atmosphere. The reaction mixture was cooled to room temperature and diluted with dichloromethane (20 mL). The mixture was filtered and the filtrate was concentrated. The residue was purified by silica gel column chromatography (dichloromethane/methanol/ammonium hydroxide=20/1/0.1) to give the a crude product (50 mg). The crude product was further purified by Combi-Flash-C18 (MeCN/water, MeCN gradient 30% to 70% volume percent through 30 min) to give the desired product (15 mg, 10%) as a yellow oil. $^1$H NMR (400 MHz, CDCl$_3$) δ 9.01 (dd, J=8.8, 2.0 Hz, 1H), 8.75 (dd, J=4.0, 2.0 Hz, 1H, 1H), 8.21 (d, J=8.4 Hz, 1H), 7.52 (dd, J=8.8, 4.0 Hz, 1H), 7.01 (d, J=8.4 Hz, 1H), 6.55 (s, 1H), 4.97 (s, 2H), 3.68-3.55 (m, 4H), 3.20 (s, 3H), 3.14 (s, 3H), 2.52 (s, 3H), 2.46-2.38 (m, 4H), 2.31 (s, 3H). MS (ESI/APCI) m/z 441.2 [M+H]$^+$.

Example 19

Preparation of N-(8-(methyl((2-methyl-6-(4-methylpiperazin-1-yl)pyrimidin-4-yl)methyl)amino)quinolin-5-yl)methanesulfonamide(D57)

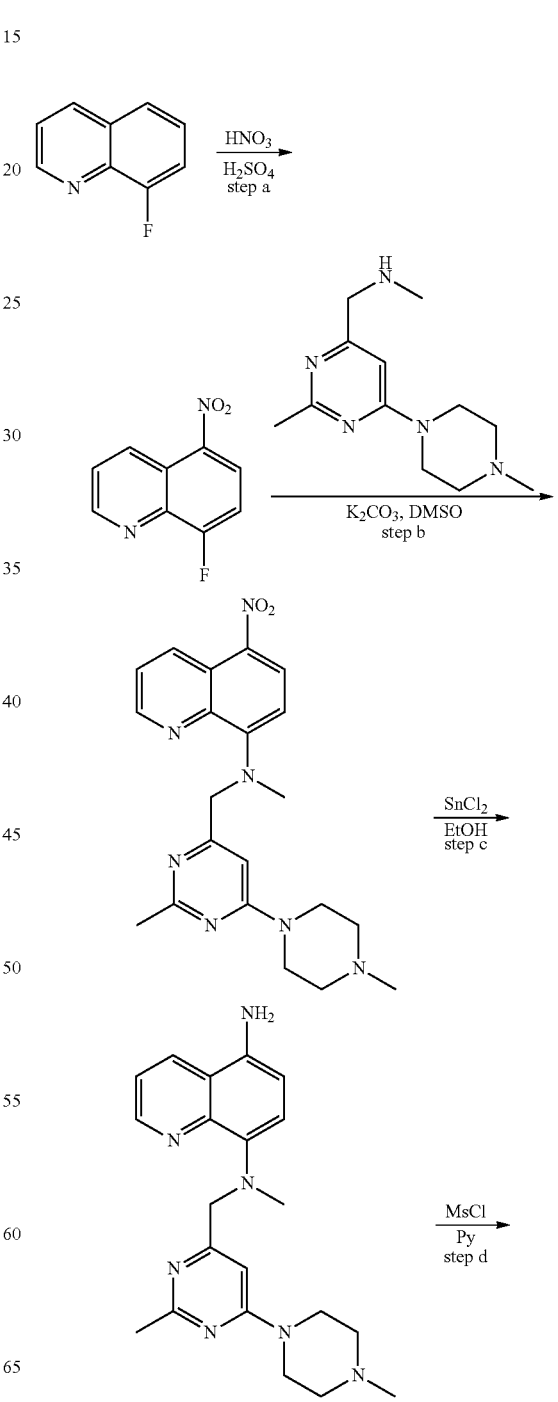

-continued

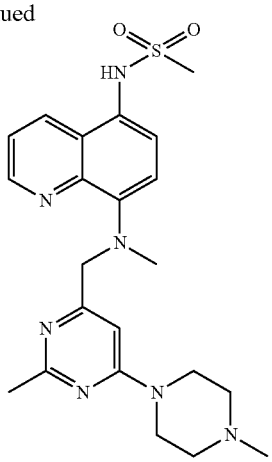

Method AS-Step a. 8-fluoro-5-nitroquinoline: To the solution of concentrated sulfuric acid (2 mL) diluted with concentrated nitric acid (1 mL), was added dropwise 8-fluoroquinoline (3.76 g, 40.0 mmol) at 0° C. The resulting suspension was stirred at 0° C. for 2 h. The reaction mixture was poured into ice-water and filtered. The filter cake was added saturated $Na_2CO_3$ aqueous solution to adjust pH to 7 and extracted with dichloromethane (20 mL×2). The combined organic layer was evaporated. The residue was purified by silica gel column chromatography (petroleum ether/ethyl acetate=30/1) to give the desired product (330 mg, 61%) as a white solid. $^1$H NMR (400 MHz, $CDCl_3$) δ 9.16 (d, J=8.4 Hz, 1H), 9.12 (s, 1H), 8.56-8.42 (m, 1H), 7.78-7.74(m, 1H), 7.53-7.48(m, 1H).

Method AS-step b. N-methyl-N-((2-methyl-6-(4-methylpiperazin-1-yl)pyrimidin-4-yl)methyl)-5-nitroquinolin-8-amine: To the solution of 8-fluoro-5-nitroquinoline (80 mg, 0.42 mmol) and N-methyl-1-(2-methyl-6-(4-methylpiperazin-1-yl)pyrimidin-4-yl)methanamine (100 mg, 0.42 mmol) in DMSO (3 mL), was added $K_2CO_3$ (58 mg, 0.42 mmol). The resulting suspension was stirred at 110° C. overnight. The reaction mixture was cooled to room temperature and filtered. The filtrate was concentrated. The residue was purified by silica gel column chromatography (dichloromethane/methanol/ammonium hydroxide=50/1/0.5) to give the desired product (80 mg, 47%) as a yellow oil. $^1$H NMR (400 MHz, $CDCl_3$) δ 9.32 (d, J=8.4 Hz, 1H), 8.69 (s, 1H), 8.48 (d, J=9.2 Hz, 1H), 7.58-7.50 (m, 1H), 6.92 (d, J=8.8 Hz, 1H), 6.54 (s, 1H), 5.07 (s, 2H), 3.70-3.60 (s, 4H), 3.27 (s, 3H), 2.61 (s, 3H), 2.55 (s, 7H).

Method AS-step c. $N^8$-methyl-$N^8$4(2-methyl-6-(4-methylpiperazin-1-yl)pyrimidin-4-yl)methyl)quinoline-5,8-diamine: To the solution of N-methyl-N-((2-methyl-6-(4-methylpiperazin-1-yl)pyrimidin-4-yl)methyl)-5-nitroquinolin-8-amine (80 mg, 0.2 mmol) in ethanol (4 mL), was added $SnCl_2$ (135 mg, 0.6 mmol). The resulting suspension was stirred at 80° C. for 3 h. The reaction mixture was cooled to room temperature and filtered. The filtrate was concentrated. The residue was purified by silica gel column chromatography (dichloromethane/methanol/ammonium hydroxide=50/1/0.5) to give the desired product (19 mg, 25%) as a yellow solid. MS (ESI/APCI) m/z 377.8 $[M+H]^+$.

Method AS-Step d. N-(8-(methyl((2-methyl-6-(4-methylpiperazin-1-yl)pyrimidin-4-yl)methyl)amino)quinolin-5-yl)methanesulfonamide To the solution of $N^8$-methyl-$N^8$-((2-methyl-6-(4-methylpiperazin-1-yl)pyrimidin-4-yl) methyl)quinoline-5,8-diamine (19 mg, 0.05 mmol) in Pyridine (3 mL) was added dropwise MsCl (10 mg, 0.09 mmol) at 0° C. The reaction mixture was stirred at room temperature for 1 h. The saturated $NaHCO_3$ aqueous solution was added to adjust pH to 7, and extracted with dichloromethane (20 mL×2). The organic layer was evaporated. The residue was purified by preparation TLC (dichloromethane/methanol/ammonium hydroxide=30/1/0.3) to give the desired product (12 mg, 53%) as a yellow solid. $^1$H NMR (400 MHz, $CDCl_3$) δ 8.76 (s, 1H), 8.61 (d, J=8.0 Hz, 1H), 7.51-7.46 (m, 2H), 7.00 (d, J=8.0 Hz, 1H), 6.87 (s, 1H), 4.69 (s, 2H), 3.78 (s, 4H), 3.05 (s, 3H), 3.01 (s, 3H), 2.61 (s, 7H), 2.43 (s, 3H),MS (ESI/APCI) m/z 455.9 $[M+H]^+$.

Example 20

Preparation of N-(8-(methyl((2-methyl-6-(4-methylpiperazin-1-yl)pyrimidin-4-yl)methyl)amino)quinolin-6-yl)methane sulfonamide(D58)

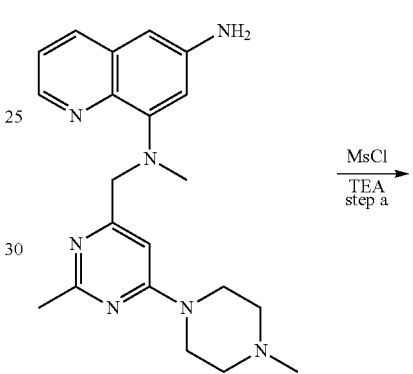

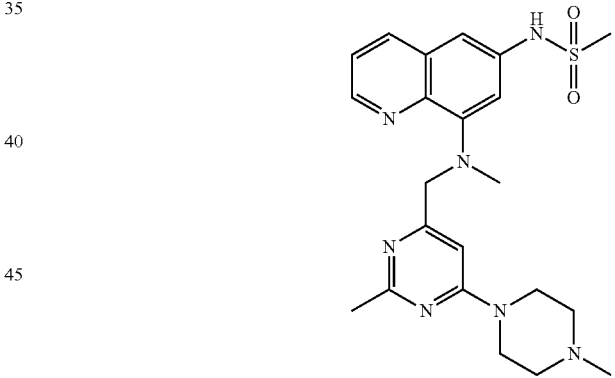

Method AT-Step a. N-(8-(methyl((2-methyl-6-(4-methylpiperazin-1-yl)pyrimidin-4-yl)methyl)amino)quinolin-6-yl)methanesulfonamide: To the solution of $N^8$-methyl-$N^8$-((2-methyl-6-(4-methylpiperazin-1-yl)pyrimidin-4-yl) methyl)quinoline-6,8-diamine (crude 100 mg, 0.1 mmol) and TEA (101 mg, 1 mmol) in dichloromethane (10 mL) was added dropwise MsCl (23 mg, 0.2 mmol) at 0° C. The reaction mixture was stirred at room temperature for 1 h. The 2M NaOH aqueous solution was added to adjust pH to 11 and stirred for 1 h. The mixture was partitioned and the water phase was added 6MHCl aqueous solution to adjust pH to 5. The saturated $NaHCO_3$ aqueous solution was added to adjust pH to 8 and extracted with ethyl acetate (30 mL×3). The combined organic layer was evaporated. The residue was purified by silica gel column chromatography (dichloromethane/methanol/ammonium hydroxide=20/1/0.05) to give the desired product (10 mg, 22%) as a brown oil. $^1$H NMR (400 MHz, CDCl₃) δ 8.70 (d, J=4.0 Hz, 1H), 8.01 (d, J=8.4 Hz, 1H), 7.38-7.30 (m, 1H), 7.27 (s, 1H), 6.91 (s, 1H), 6.67 (s, 1H), 4.68 (s, 2H), 3.77 (t, J=4.4 Hz, 2H), 3.63 (t, J=4.4 Hz, 2H), 3.07 (s, 3H), 3.04 (s, 3H), 2.48 (s, 3H), 2.44-2.34 (m, 4H), 2.29 (s, 3H). MS (ESI/APCI) m/z 455.7 [M+H]⁺.

Example 21

Preparation of (S)-N-methyl-N-((2-methyl-6-(4-methylpiperazin-1-yl)pyrimidin-4-yl)methyl)-1-(pyridin-2-yl)ethan-1-amine (A75)

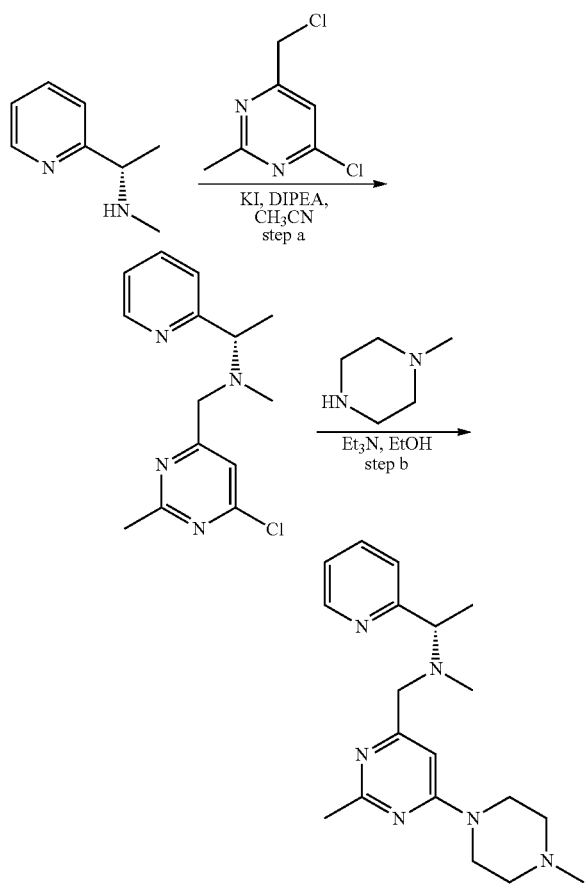

Method AA-Step a. (S)-N-((6-chloro-2-methylpyrimidin-4-yl)methyl)-N-methyl-1-(pyridin-2-yl)ethan-1-amine: A mixture of (S)-N-methyl-1-(pyridin-2-yl)ethan-1-amine (150 mg, 1.1 mmol), 4-chloro-6-(chloromethyl)pyrimidine (195 mg, 1.1 mmol), KI (16 mg, 0.1 mmol) and DIPEA (426 mg, 3.3 mmol) in CH₃CN (20 mL) was stirred at room temperature overnight. The reaction solution was evaporated to remove most of CH₃CN. The residue was added saturated NaHCO₃ aqueous solution (20 mL) and extracted with ethyl acetate (50 mL×3). The combined organic layers was dried over Na₂SO₄, filtered and evaporated. The residue was purified by silica gel column chromatography (dichloromethane/methanol/ammonium hydroxide=200/1/0.5) to give the desired product (280 mg, 92%) as a yellow oil. ¹H NMR (400 MHz, CDCl₃) δ 8.57 (d, J=4.4 Hz, 1H), 7.72-7.63 (m, 1H), 7.46 (s, 1H), 7.42 (d, J=7.6 Hz, 1H), 7.17 (dd, J=7.6, 4.8 Hz, 1H), 3.91 (q, J=6.8 Hz, 1H), 3.72 (d, J=16.4 Hz, 1H), 3.59 (d, J=16.4 Hz, 1H), 2.67(s, 3H), 2.28(s, 3H), 1.49 (d, J=6.8 Hz, 3H).

Method AA-Step b. (S)-N-methyl-N-((2-methyl-6-(4-methylpiperazin-1-yl)pyrimidin-4-yl)methyl)-1-(pyridin-2-yl)ethan-1-amine: A mixture of (S)-N-((6-chloro-2-methylpyrimidin-4-yl)methyl)-N-methyl-1-(pyridin-2-yl)ethan-1-amine (90 mg, 0.33 mmol), TEA (333 mg, 3.3 mmol) and N-methylpiperazine (163 mg, 1.6 mmol) in ethanol (10 mL) was stirred at reflux overnight. The reaction mixture was concentrated. The residue was purified by silica gel column chromatography (dichloromethane/methanol/ammonium hydroxide=100/2/1) to give the desired product (70 mg, 63%) as a colorless oil. ¹H NMR (400 MHz, CDCl₃) δ 8.56 (d, J=4.0 Hz, 1H), 7.69-7.58 (m, 1H), 7.41 (d, J=7.6 Hz, 1H), 7.18-7.11 (m, 1H), 6.64(s, 1H), 3.92-3.80 (m, 1H), 3.68 (s, 4H), 3.57 (d, J=15.6 Hz, 1H), 3.44 (d, J=15.6 Hz, 1H), 2.55-2.40 (m, 7H), 2.34 (s, 3H), 2.27(s, 3H), 1.47(d, J=6.4 Hz, 3H).

Example 22

Preparation of (S)-N-methyl-N-((5-(4-methylpiperazin-1-yl)imidazo[1,2-a]pyridin-2-yl)methyl)-1-(pyridin-2-yl)ethan-1-amine (A95) and (S)-(2-((methyl(1-(pyridin-2-yl)ethyl)amino)methyl)-5-(4-methylpiperazin-1-yl)imidazo[1,2-a]pyridin-3-yl) methanol (A96)

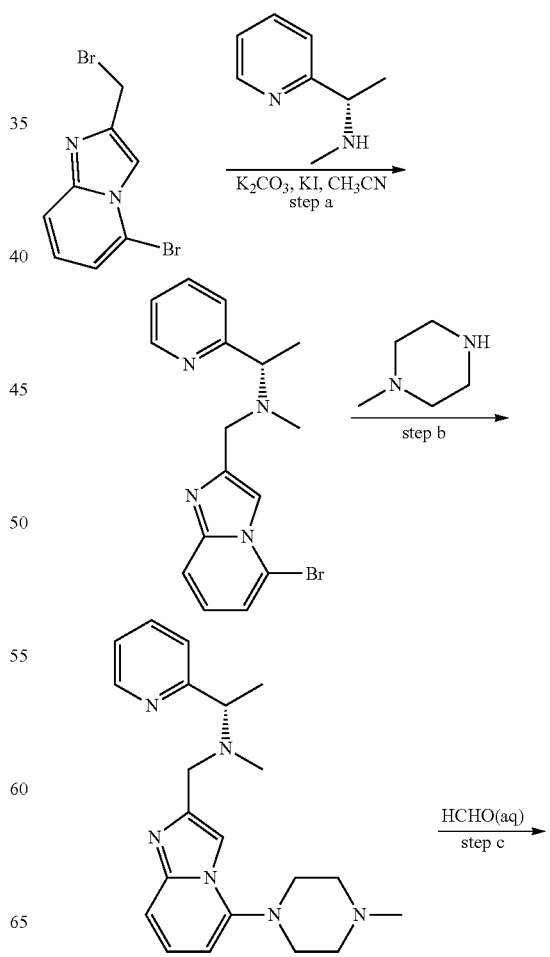

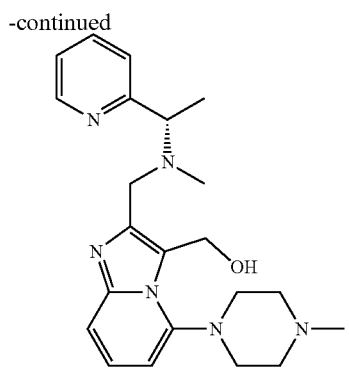

Method AK-Step a. (S)-N-((5-bromoimidazo[1,2-a]pyridin-2-yl)methyl)-N-methyl-1-(pyridin-2-yl)ethan-1-amine: The mixture of 5-bromo-2-(bromomethyl)imidazo[1,2-a]pyridine (127 mg, 0.4 mmol), (S)-N-methyl-1-(pyridin-2-yl)ethanamine (55 mg, 0.4 mmol), KI (7 mg, 0.04 mmol) and DIPEA (130 mg, 1 mmol) in MeCN (10 mL) was stirred at room temperature overnight. The reaction mixture was evaporated. The residue was purified by silica gel column chromatography (dichloromethane/methanol=100/1) to give the desired product (100 mg, 72%) as a yellow oil. $^1$H NMR (400 MHz, CDCl$_3$) δ 8.59 (d, J=4.0 Hz,1H), 7.92 (s, 1H), 7.74-7.67 (m, 1H), 7.62-7.52(m, 2H), 7.24-7.18 (m, 1H), 7.13-7.01 (m, 2H), 4.17-4.05 (m, 1H), 4.04-3.96 (m, 1H), 3.96-3.87 (m, 1H), 2.44 (s, 3H), 1.64-1.59 (m, 3H).

Method AK-Step b. (S)-N-methyl-N-((5-(4-methylpiperazin-1-yl)imidazo[1,2-a]pyridin-2-yl)methyl)-1-(pyridin-2-yl)ethan-1-amine: The mixture of (S)-N-((5-bromoimidazo[1,2-a]pyridin-2-yl)methyl)-N-methyl-1-(pyridin-2-yl)ethan-1-amine (100 mg, 0.29 mmol) in N-methylpiperazine (3 mL) was stirred at 190° C. under microwave for 2 h. The reaction mixture was concentrated. The residue was purified by silica gel column chromatography (dichloromethane/methanol=50/1) to give the desired product (60 mg, 57%) as a yellow oil. $^1$H NMR (400 MHz, CDCl$_3$) δ 8.56 (d, J=4.0 Hz, 1H), 7.72-7.62 (m, 1H), 7.54 (d, J=7.6 Hz, 1H), 7.46 (s, 1H), 7.31 (d, J=8.8 Hz, 1H), 7.20-7.11 (m, 2H), 6.26 (d, J=7.2 Hz, 1H), 3.97-3.81 (m, 2H), 3.72 (d, J=14.0 Hz, 1H), 3.14 (s, 4H), 2.67 (s, 4H), 2.41 (s, 3H), 2.32 (s, 3H), 1.50 (d, J=6.4 Hz, 3H).

Method AK-Step c. (S)-(2-((methyl(1-(pyridin-2-yl)ethyl)amino)methyl)-5-(4-methylpiperazin-1-yl)imidazo[1,2-a]pyridin-3-yl)methanol: The mixture of (S)-N-methyl-N-((5-(4-methylpiperazin-1-yl)imidazo[1,2-a]pyridin-2-yl)methyl)-1-(pyridin-2-yl)ethan-1-amine (43 mg, 0.12 mmol) and formaldehyde (37 wt percent in water, 10 mL) in a sealed tube was stirred at 50° C. for 3 days. The reaction mixture was added saturated NaHCO$_3$ aqueous solution (10 mL) and extracted with dichloromethane (20 mL). The organic layer was dried over Na$_2$SO$_4$, filtered and evaporated. The residue was purified by silica gel column chromatography (dichloromethane/methanol=50/1) to give the desired product (25 mg, 50%) as a colorless oil. $^1$H NMR (400 MHz, CDCl$_3$) δ 8.57 (s, 1H), 7.73-7.58 (m, 1H), 7.40 (d, J=7.6 Hz, 1H), 7.29 (d, J=8.8 Hz, 1H), 7.20-7.12 (m, 1H), 7.12-7.04 (m, 1H), 6.40 (d, J=7.2 Hz, 1H), 5.24-5.11 (m, 2H), 3.95-3.85 (m, 1H), 3.84-3.73 (m, 2H), 3.73-3.62 (m,1H), 3.42-3.29 (m, 2H), 3.00-2.86 (m, 4H), 2.50-2.42 (m, 2H), 2.39 (s, 3H), 2.13 (s, 3H), 1.52 (d, J=6.4 Hz, 3H).

Table 1 shows a selection of the compounds prepared according to the methods discussed above in details and indicated in the third column of the table.

TABLE 1

Selected compounds (A1-A100, B1-B8, C1-C39 and D1-D59) of the present invention

| Compd number | structure | method | $^1$HNMR and MS |
|---|---|---|---|
| A1 | 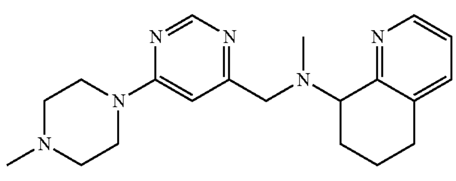 [SMILES: CN1CCN(c2cc(CN(C)C3CCCc4cccnc43)ncn2)CC1] | A, AA | $^1$H NMR (400 MHz, CDCl$_3$) δ 8.45 (s, 2H), 7.33 (d, J = 6.8 Hz, 1H), 7.20 (s, 1H), 7.03 (s, 4.8 Hz, 1H), 3.99 (s, 1H), 3.68 (s, 4H), 3.62 (s, 2H), 2.77 (s, 1H), 2.68-2.64 (m, 1H), 2.44 (s, 4H), 2.35 (s, 3H), 2.30 (s, 3H), 1.97 (s, 1H), 1.91-1.88 (m, 1H), 1.85 (s, 1H), 1.67 (s, 1H).HRMS (ESI): calcd for C$_{20}$H$_{29}$N$_6$ [M + H]$^+$ 353.2448, found 353.2451. |
| A2 | 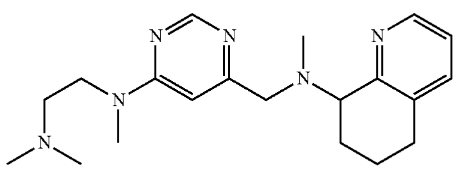 [SMILES: CN(C)CCN(C)c1cc(CN(C)C2CCCc3cccnc32)ncn1] | A, AA | $^1$H NMR (400 MHz, CDCl$_3$) δ 8.49 (d, J= 4.0 Hz, 1H), 8.47 (s, 1H), 7.35 (d, J = 7.6 Hz, 1H), 7.05 (dd, J = 7.6, 4.8 Hz, 1H), 6.98 (s, 1H), 4.04-4.01 (m, 1H), 3.69 (s, 2H), 3.65 (s, 2H), 3.09 (s, 3H), 2.81-2.80 (m, 1H), 2.78-2.71 (m, 1H), 2.47 (t, J = 7.2 Hz, 2H), 2.38 (s, 3H), 2.27 (s, 6H), 2.10-2.09 (m, 1H), 2.03-2.01 (m, 1H), 1.94-1.91 (m, 1H), 1.71-1.67 (m, 1H).MS (ESI/APCI) m/z 354.9 [M + H]$^+$. |
| A3 | 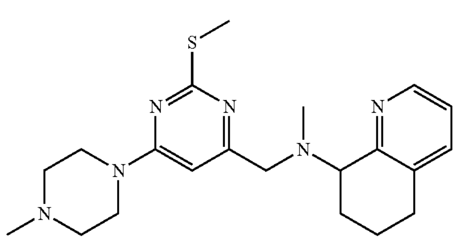 [SMILES: CSc1nc(CN(C)C2CCCc3cccnc32)cc(N2CCN(C)CC2)n1] | B, AA | $^1$H NMR (400 MHz, CDCl$_3$) δ 8.49 (d, J = 3.9 Hz, 1H), 7.36 (d, J = 7.6 Hz, 1H), 7.06 (dd, J = 7.6, 4.8 Hz, 1H), 6.96 (s, 1H), 4.09-3.98 (m, 1H), 3.72 (s, 4H), 3.58 (s, 2H), 2.86-2.75 (m, 1H), 2.74-2.65 (m, 1H), 2.49 (s, 3H), 2.47-2.43 (m, 4H), 2.39 (s, 3H), 2.33 (s, 3H), 2.10 (s, 1H), 2.03-2.00 (m, 1H), 1.91-1.87 (m, 1H), 1.65 (s, 1H). |

TABLE 1-continued

Selected compounds (A1-A100, B1-B8, C1-C39 and D1-D59) of the present invention

| Compd number | structure | method | ¹HNMR and MS |
|---|---|---|---|
| A4 | 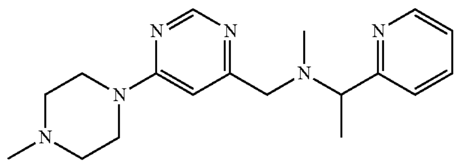 [SMILES: CC(c1ccccn1)N(C)Cc1cc(N2CCN(C)CC2)ncn1] | A, AA | ¹H NMR (400 MHz, CDCl₃) δ 8.57 (d, J = 4.2 Hz, 1H), 8.51 (s, 1H), 7.65 (t, J = 7.2 Hz, 1H), 7.43 (d, J = 8.0 Hz, 1H), 7.19-7.13 (m, 1H), 6.78 (s, 1H), 3.90 (q, J = 6.8 Hz, 1H), 3.69 (s, 4H), 3.61 (d, J = 15.6 Hz, 1H), 3.46 (d, J = 15.6 Hz, 1H), 2.54-2.45 (m, 4H), 2.35 (s, 3H), 2.29 (s, 3H), 1.48 (d, J = 6.8 Hz, 3H). |
| A5 | 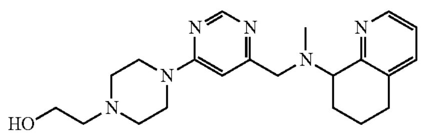 [SMILES: CN(Cc1cc(N2CCN(CCO)CC2)ncn1)C1CCCc2cccnc21] | A, AA | ¹H NMR (400 MHz, CDCl₃) δ 8.48 (s, 2H), 7.37 (d, J = 7.2 Hz, 1H), 7.26 (s, 1H), 7.07 (s, 1H), 4.02 (s, 1H), 3.71-3.65 (m, 8H), 2.81-2.78 (m, 1H), 2.71-2.67 (m, 2H), 2.57 (s, 6H), 2.39 (s, 3H), 2.11 (s, 1H), 2.00 (s, 1H), 1.97-1.88 (m, 1H), 1.70-1.68 (m, 1H). HRMS (ESI): calcd for C₂₁H₃₁N₆O [M + H]⁺ 383.2554, found 383.2555. |
| A6 | 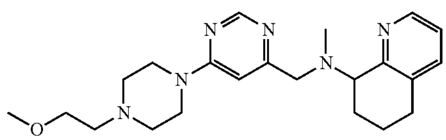 [SMILES: COCCN1CCN(c2cc(CN(C)C3CCCc4cccnc43)ncn2)CC1] | A, AA | ¹H NMR (400 MHz, CDCl₃) δ 8.50-8.47 (m, 2H), 7.37 (d, J = 7.8 Hz, 1H), 7.20 (s, 1H), 7.07 (dd, J = 7.6, 4.8 Hz, 1H), 4.03 (t, J = 7.4 Hz, 1H), 3.73 (s, 4H), 3.64 (s, 2H), 3.55 (t, J = 5.4 Hz, 2H), 3.38 (s, 3H), 2.85-2.77 (m, 1H), 2.72-2.68 (m, 1H), 2.62 (t, J = 5.4 Hz, 2H), 2.56 (t, J = 5.0 Hz, 4H), 2.39 (s, 3H), 2.17-2.07 (m, 1H), 2.07-1.98 (m, 1H), 1.99-1.88 (m, 1H), 1.76-1.67 (m, 1H). |
| A7 | 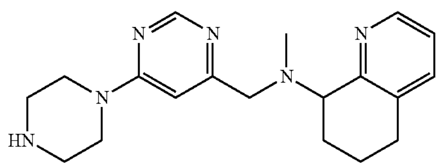 [SMILES: CN(Cc1cc(N2CCNCC2)ncn1)C1CCCc2cccnc21] | A, AB | ¹H NMR (400 MHz, CDCl₃) δ 8.49 (s, 2H), 7.38 (d, J = 7.2 Hz, 1H), 7.21 (s, 1H), 7.08 (s, 1H), 4.05-4.04 (m, 1H), 3.80-3.70 (m, 6H), 3.02-2.98 (m, 4H), 2.81-2.79 (m, 1H), 2.72-2.68 (m, 1H), 2.58 (s, 1H), 2.41 (s, 3H), 2.13 (s, 1H), 2.01 (m, 1H), 1.95-1.89 (m, 1H), 1.71-1.69 (m, 1H). MS (ESI/APCI) m/z 338.9 [M + H]⁺. |
| A8 | 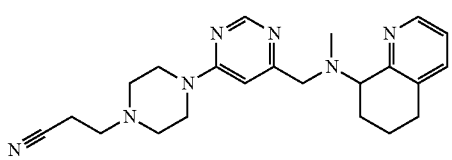 [SMILES: CN(Cc1cc(N2CCN(CCC#N)CC2)ncn1)C1CCCc2cccnc21] | A, AB | ¹H NMR (400 MHz, CDCl₃) δ 8.53-8.47 (m, 2H), 7.38 (d, J = 7.6 Hz, 1H), 7.25 (s, 1H), 7.08 (dd, J = 7.6, 4.8 Hz, 1H), 4.09-3.97 (m, 1H), 3.73 (s, 4H), 3.65 (s, 2H), 2.86-2.78 (m, 1H), 2.75-2.71 (m, 3H), 2.58-2.53 (m, 6H), 2.40 (s, 3H), 2.16-2.08 (s, 1H), 2.05-1.97 (m, 1H), 1.93-1.88 (m, 1H), 1.75-1.69 (m, 1H). |
| A9 | 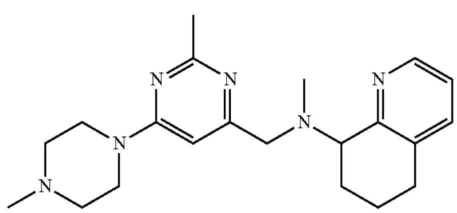 | E, AC | ¹H NMR (400 MHz, CDCl₃) δ 8.49 (d, J = 4.6 Hz, 1H), 7.35 (d, J = 8.0 Hz, 1H), 7.07-7.03 (m, 2H), 4.04 (t, J = 7.4 Hz, 1H), 3.71 (t, J = 5.2 Hz, 4H), 3.60 (s, 2H), 2.86-2.75 (m, 1H), 2.73-2.65 (m, 1H), 2.46-2.43 (m, 7H), 2.39 (s, 3H), 2.33 (s, 3H), 2.15-2.07 (m, 1H), 2.04-1.96 (m, 1H), 1.95-1.87 (m, 1H), 1.74-1.71 (m, 1H). |
| A10 | 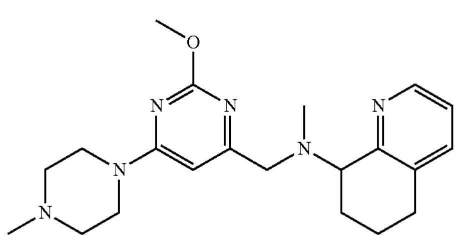 | E, AC | ¹H NMR (400 MHz, CDCl₃) δ 8.48 (d, J = 4.4 Hz, 1H), 7.35 (d, J = 7.6 Hz, 1H), 7.05 (dd, J = 7.6, 4.8 Hz, 1H), 6.87 (s, 1H), 4.03 (t, J = 7.4 Hz, 1H), 3.88 (s, 3H), 3.70 (d, J = 5.0 Hz, 4H), 3.58 (s, 2H), 2.84-2.78 (m, 1H), 2.74-2.65 (m, 1H), 2.44 (t, J = 5.6 Hz, 4H), 2.37 (s, 3H), 2.32 (s, 3H), 2.15-2.06 (m, 1H), 2.05-1.96 (m, 1H), 1.97-1.87 (m, 1H), 1.72-1.66 (m, 1H). |
| A11 | 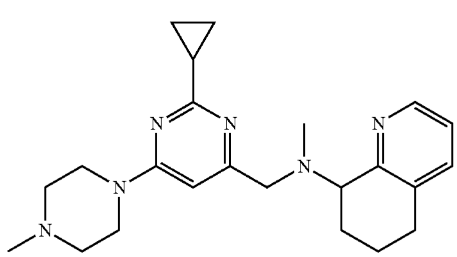 [SMILES: CN1CCN(c2cc(CN(C)C3CCCc4cccnc43)nc(C3CC3)n2)CC1] | E, AC | ¹H NMR (400 MHz, CDCl₃) δ 8.49 (d, J = 4.6 Hz, 1H), 7.35 (d, J = 7.6 Hz, 1H), 7.05 (dd, J = 7.6, 4.8 Hz, 1H), 7.02 (s, 1H), 4.04 (s, 1H), 3.67 (t, J = 5.0 Hz, 4H), 3.61 (s, 2H), 2.85-2.75 (m, 1H), 2.73-2.65 (m, 1H), 2.44 (t, J = 5.0 Hz, 4H), 2.40 (s, 3H), 2.32 (s, 3H), 2.15-1.94 (m, 4H),. 1.74-1.64 (m, 1H), 1.04-1.00 (m, 2H), 0.91-0.86 (m, 2H). |

TABLE 1-continued

Selected compounds (A1-A100, B1-B8, C1-C39 and D1-D59) of the present invention

| Compd number | structure | method | ¹HNMR and MS |
|---|---|---|---|
| A12 | 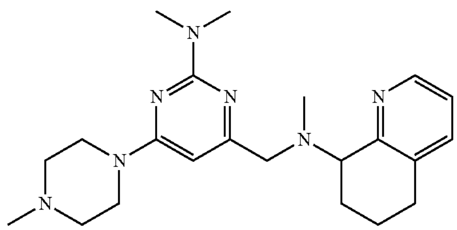 [SMILES: CN1CCN(c2cc(CN(C)C3CCCc4cccnc43)nc(N(C)C)n2)CC1] | F, AC | ¹H NMR (400 MHz, CDCl₃) δ 8.49 (d, J = 4.6 Hz, 1H), 7.34 (d, J = 7.2 Hz, 1H), 7.04 (dd, J = 7.6, 4.8 Hz, 1H), 6.49 (s, 1H), 4.06 (s, 1H), 3.65 (s, 4H), 3.55-.49 (m, 2H), 3.11 (s, 6H), 2.83-2.76 (m, 1H), 2.74-2.64 (m, 1H), 2.46-2.40 (m, 4H), 2.38 (s, 3H), 2.32 (s, 3H), 2.12-2.07 (m, 1H), 2.03-1.97 (m, 1H), 1.95-1.91 (m, 1H), 1.72-1.64 (m, 1H). |
| A13 | 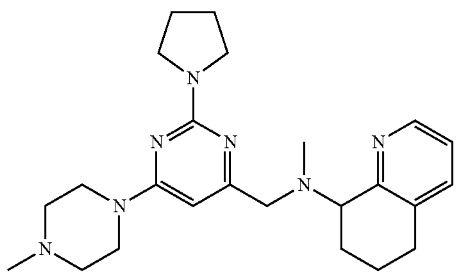 [SMILES: CN1CCN(c2cc(CN(C)C3CCCc4cccnc43)nc(N3CCCC3)n2)CC1] | F, AC | ¹H NMR (400 MHz, CDCl₃) δ 8.48 (d, J = 4.6 Hz, 1H), 7.34 (d, J = 7.6 Hz, 1H), 7.04 (dd, J = 7.6, 4.8 Hz, 1H), 6.48 (s, 1H), 4.07 (t, J = 7.4 Hz, 1H), 3.65 (t, J = 5.2 Hz, 4H), 3.58-3.48 (m, 6H), 2.84-2.76 (m, 1H), 2.71-2.68 (m, 1H), 2.43 (t, J = 5.2 Hz, 4H), 2.35 (s, 3H), 2.31 (s, 3H), 2.13-2.08 (m, 1H), 2.03-1.98 (m, 1H), 1.96-1.87 (m, 5H), 1.70-1.64 (m, 1H). |
| A14 | 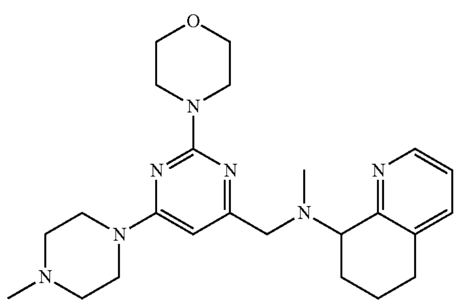 [SMILES: CN1CCN(c2cc(CN(C)C3CCCc4cccnc43)nc(N3CCOCC3)n2)CC1] | F, AC | ¹H NMR (400 MHz, CDCl₃) δ 8.49 (d, J = 4.6 Hz, 1H), 7.35 (d, J = 7.6 Hz, 1H), 7.05 (dd, J = 7.6, 4.8 Hz, 1H), 6.57 (s, 1H), 4.05 (t, J = 7.2 Hz, 1H), 3.72 (s, 8H), 3.64 (d, J = 5.0 Hz, 4H), 3.52 (d, J = 4.8 Hz, 2H), 2.84-2.76 (m, 1H), 2.72-2.64 (m, 1H), 2.44 (t, J = 5.0 Hz, 4H), 2.38 (s, 3H), 2.32 (s, 3H), 2.14-2.06 (m, 1H), 2.04-1.98 (m, 1H), 1.98-1.88 (m, 1H), 1.73-1.63 (m, 1H). |
| A15 | 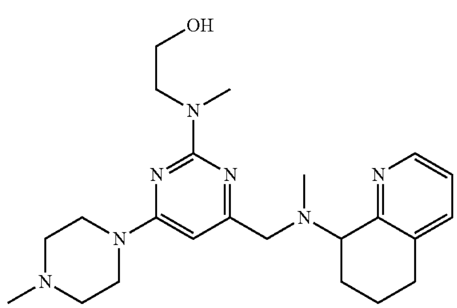 [SMILES: CN1CCN(c2cc(CN(C)C3CCCc4cccnc43)nc(N(C)CCO)n2)CC1] | F, AC | ¹H NMR (400 MHz, CDCl₃) δ 8.49 (d, J = 4.6 Hz, 1H), 7.34 (s, 1H), 7.05 (s, 1H), 6.52 (s, 1H), 4.04 (s, 1H), 3.83 (t, J = 4.6 Hz, 2H), 3.69-3.63 (m, 6H), 3.50 (d, J = 8.0 Hz, 2H), 3.15 (s, 3H), 2.85-2.75 (m, 1H), 2.72-2.64 (s, 1H), 2.45-2.41 (m, 4H), 2.36 (s, 3H), 2.32 (s, 3H), 2.12-2.05 (m, 1H), 2.04-1.97 (m, 1H), 1.94-1.86 (m, 2H), 1.73-1.63 (m, 1H). |
| A16 | 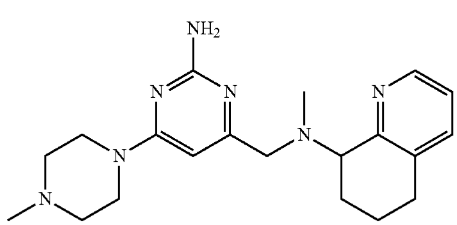 [SMILES: CN1CCN(c2cc(CN(C)C3CCCc4cccnc43)nc(N)n2)CC1] | F, AC | ¹H NMR (400 MHz, CDCl₃) δ 8.49 (s, 1H), 7.35 (d, J = 7.6 Hz, 1H), 7.05 (s, 1H), 6.59 (s, 1H), 4.65 (s, 2H), 4.04 (s, 1H), 3.65 (s, 4H), 3.50 (s, 2H), 2.84-2.75 (m, 1H), 2.75-2.64 (m, 1H), 2.45-2.40 (m, 4H), 2.37 (s, 3H), 2.32 (s, 3H), 2.13-2.06 (m, 1H), 2.04-1.98 (m, 1H), 1.96-1.87 (m, 1H), 1.72-1.64 (m, 1H). |

TABLE 1-continued

Selected compounds (A1-A100, B1-B8, C1-C39 and D1-D59) of the present invention

| Compd number | structure | method | ¹HNMR and MS |
|---|---|---|---|
| A17 | 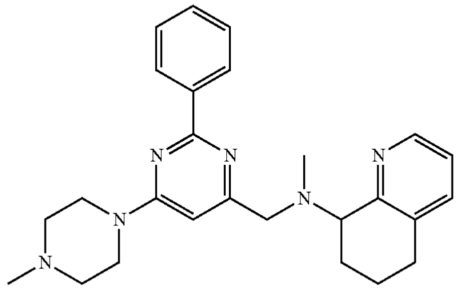 [SMILES: CN1CCN(c2cc(CN(C)C3CCCc4cccnc43)nc(-c3ccccc3)n2)CC1] | H, AC | ¹H NMR (400 MHz, CDCl₃) δ 8.52 (s, 1H), 8.37-8.32 (m, 2H), 742 -7.40 (m, 3H), 7.37 (d, J = 7.2 Hz, 1H), 7.19 (s, 1H), 7.07 (s, 1H), 4.17-4.02 (m, 1H), 3.84-3.82 (m, 4H), 3.74 (s, 2H), 2.90-2.77 (m, 1H), 2.75-2.65 (m, 1H), 2.52-2.50 (m, 4H), 2.45 (s, 3H), 2.36 (s, 3H), 2.16-2.14 (m, 1H), 2.02-1.87 (m, 2H), 1.73-1.71 (m, 1H). |
| A18 | 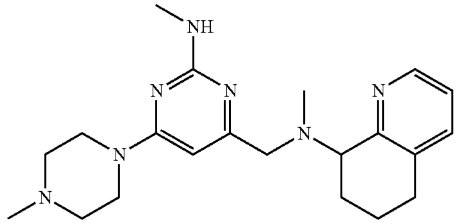 [SMILES: CNc1nc(CN(C)C2CCCc3cccnc32)cc(N2CCN(C)CC2)n1] | F, AC | ¹H NMR (400 MHz, CDCl₃) δ 8.49 (d, J = 4.8 Hz, 1H), 7.35 (d, J = 7.6 Hz, 1H), 7.05 (dd, J = 7.6, 4.8 Hz, 1H), 6.51 (s, 1H), 4.79 (s, 1H), 4.12-.02 (m, 1H), 3.67 (t, J = 5.0 Hz, 4H), 3.50 (d, J = 5.2 Hz, 2H), 2.92 (d, J = 4.8 Hz, 3H), 2.84-2.75 (m, 1H), 2.75-2.64 (m, 1H), 2.44 (t, J = 5.0 Hz, 4H), 2.36 (s, 3H), 2.32 (s, 3H), 2.13-1.04 (m, 1H), 2.03-1.97 (m, 1H), 1.93-1.87 (m, 1H), 1.74-1.63 (m, 1H). |
| A19 | 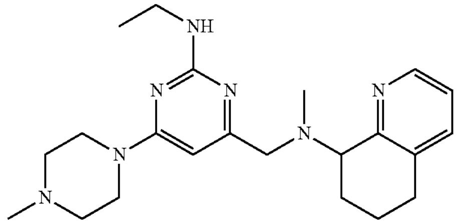 [SMILES: CCNc1nc(CN(C)C2CCCc3cccnc32)cc(N2CCN(C)CC2)n1] | F, AC | ¹H NMR (400 MHz, CDCl₃) δ 8.49 (d, J = 4.6 Hz, 1H), 7.35 (d, J = 7.8 Hz, 1H), 7.05 (t, J = 6.0 Hz, 1H), 6.49 (s, 1H), 4.77 (s, 1H), 4.05 (t, J = 7.6 Hz, 1H), 3.66 (d, J = 5.0 Hz, 4H), 3.49 (d, J = 4.4 Hz, 2H), 3.38 (t, J = 7.0 Hz, 2H), 2.83-2.75 (m, 1H), 2.72-2.64 (m, 1H), 2.43 (d, J = 5.2 Hz, 4H), 2.35 (s, 3H), 2.32 (s, 3H), 2.13-2.05 (m, 1H), 2.03-1.98 (m, 1H), 1.96-1.85 (m, 1H), 1.72-1.64 (s, 1H), 1.18 (t, J = 7.2 Hz, 3H). |
| A20 | 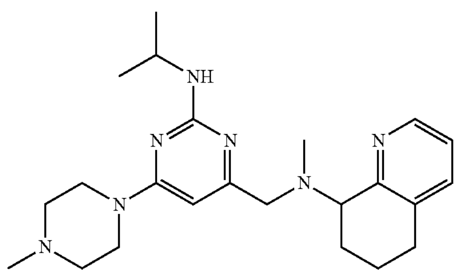 [SMILES: CC(C)Nc1nc(CN(C)C2CCCc3cccnc32)cc(N2CCN(C)CC2)n1] | F, AC | ¹H NMR (400 MHz, CDCl₃) δ 8.49 (d, J = 4.6 Hz, 1H), 7.34 (d, J =7.6 Hz, 1H), 7.08-7.02 (m, 1H), 6.48 (s, 1H), 4.60 (s, 1H), 4.09-4.02 (m, 2H), 3.65 (d, J = 5.2 Hz, 4H), 3.47 (d, J = 7.8 Hz, 2H), 2.84-2.75 (m, 1H), 2.71-2.63 (m, 1H), 2.43 (t, J = 5.0 Hz, 4H), 2.36 (s, 3H), 2.32 (s, 3H), 2.13-2.05 (s, 1H), 2.03-1.95 (m, 1H), 1.92-1.86 (m, 1H), 1.68-1.62 (m, 1H), 1.18 (d, J = 6.4 Hz, 6H). |
| A21 | 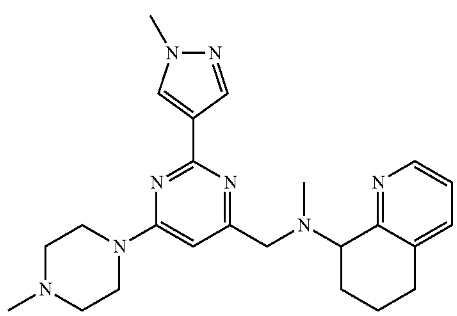 [SMILES: CN1CCN(c2cc(CN(C)C3CCCc4cccnc43)nc(-c3cnn(C)c3)n2)CC1] | H, AC | ¹H NMR (400 MHz, CDCl₃) δ 8.50 (d, J = 2.8 Hz, 1H), 8.07 (s, 1H), 8.00 (s, 1H), 7.36 (d, J = 7.2 Hz, 1H), 7.06 (s, 2H), 4.10-4.09 (m, 1H), 3.92 (s, 3H), 3.77-3.75 (m, 4H), 3.66 (s, 2H), 2.84-2.76 (m, 1H), 2.72-2.66 (m, 1H), 2.49-2.47 (m, 4H), 2.41 (s, 3H), 2.34 (s, 3H), 2.13-2.10 (m, 1H), 2.01-1.93 (m, 2H), 1.92-1.90 (m, 1H). |
| A22 | 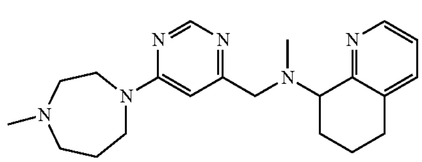 [SMILES: CN1CCCN(c2cc(CN(C)C3CCCc4cccnc43)ncn2)CC1] | A, AA | ¹H NMR (400 MHz, CDCl₃) δ¹H NMR (400 MHz, CDCl₃) δ 8.47 (s, 2H), 7.35 (d, J = 7.2 Hz, 1H), 7.05 (s, 2H), 4.04-4.01 (m, 1H), 3.84 (s, 1H), 3.69 (s, 1H), 3.64 (s, 3H), 2.81-2.77 (m, 1H), 2.71-2.67 (m, 3H), 2.55 (s, 2H), 2.39 (s, 3H), 2.35 (s, 3H), 2.09 (s, 1H), 1.99 (s, 1H), 1.94-1.89 (m, 4H), 1.72 (s, 1H).MS (ESI/APCI) m/z 366.9 [M + H]⁺. |

TABLE 1-continued

Selected compounds (A1-A100, B1-B8, C1-C39 and D1-D59) of the present invention

| Compd number | structure | method | ¹HNMR and MS |
|---|---|---|---|
| A23 | 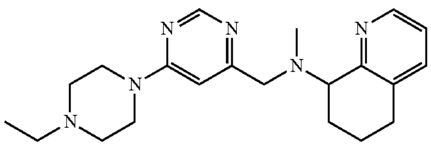 [SMILES: CCN1CCN(c2cc(CN(C)C3CCCc4cccnc43)ncn2)CC1] | A, AA | ¹H NMR (400 MHz, CDCl$_3$) δ 8.48 (s, 2H), 7.36 (d, J = 7.2 Hz, 1H), 7.22 (s, 1H), 7.06 (s, 1H), 4.02 (t, J = 6.8 Hz, 1H), 3.72 (s, 4H), 3.64 (s, 2H), 2.81-2.78 (m, 1H), 2.71-2.67 (m, 1H), 2.50 (s, 4H), 2.46-2.42 (m, 2H), 2.40 (s, 3H), 2.10 (s, 1H), 2.00 (s, 1H), 1.94-1.88 (m, 1H), 1.71 (s, 1H), 1.12 (t, J = 6.8 Hz, 3H). MS (ESI/APCI) m/z 366.9 [M + H]⁺. |
| A24 | 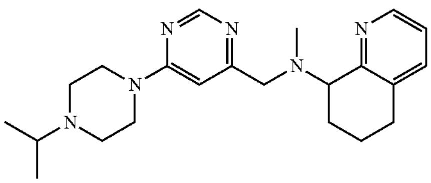 [SMILES: CC(C)N1CCN(c2cc(CN(C)C3CCCc4cccnc43)ncn2)CC1] | A, AA | ¹H NMR (400 MHz, CDCl$_3$) δ 8.49-8.47 (m, 2H), 7.36 (d, J = 7.2 Hz, 1H), 7.19 (s, 1H), 7.06 (s, 1H), 4.02 (s, 1H), 3.70 (s, 4H), 3.64 (s, 2H), 2.81-2.78 (m, 1H), 2.72 (s, 2H), 2.57 (s, 4H), 2.39 (s, 3H), 2.10 (s, 1H), 2.00 (s, 1H), 1.94-1.89 (m, 1H), 1.67 (s, 1H), 1.07 (d, J = 6.0 Hz, 6H). MS (ESI/APCI) m/z 380.9 [M + H]⁺. |
| A25 | 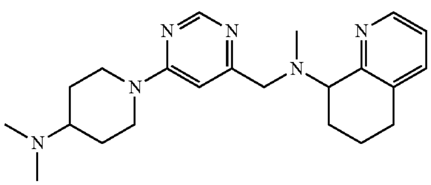 | A, AA | ¹H NMR (400 MHz, CDCl$_3$) δ 8.50-8.47 (m, 2H), 7.36 (d, J = 6.8 Hz, 1H), 7.23 (s, 1H), 7.06 (s, 1H), 4.53 (s, 2H), 4.02 (s, 1H), 3.72-3.71 (m, 1H), 3.63 (s, 2H), 2.90-2.84 (m, 3H), 2.71-2.67 (m, 1H), 2.38 (s, 4H), 2.29 (s, 6H), 2.10 (s, 1H), 2.01 (s, 1H), 1.91 (s, 3H), 1.43 (t, J = 11.0 Hz, 2H). MS (ESI/APCI) m/z 380.9 [M + H]⁺ |
| A26 | 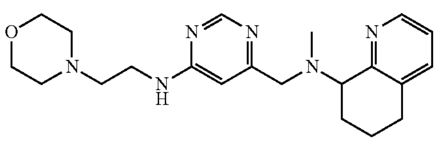 [SMILES: CN(Cc1cc(NCCN2CCOCC2)ncn1)C1CCCc2cccnc21] | A, AA | ¹H NMR (400 MHz, CDCl$_3$) δ 8.50 (s, 1H), 8.42 (s, 1H), 7.35 (s, 1H), 7.05 (s, 1H), 6.90 (s, 1H), 4.03 (s, 1H), 3.71 (s, 4H), 3.57 (s, 2H), 3.41 (s, 2H), 2.78 (s, 1H), 2.71-2.68 (m, 1H), 2.58 (s, 2H), 2.46 (s, 4H), 2.38 (s, 3H), 2.11 (s, 1H), 2.00 (m, 1H), 1.95-1.89 (m, 1H), 1.68 (s, 1H). HRMS (ESI): calcd for C$_{21}$H$_{31}$N$_6$ [M + H]⁺ 383.2554, found 383.2553. |
| A27 | 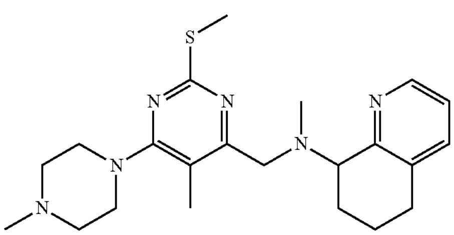 | E, AC | ¹H NMR (400 MHz, CDCl$_3$) δ 8.46 (d, J = 4.0 Hz, 1H), 7.35 (d, J = 7.6 Hz, 1H), 7.09-7.02 (m, 1H), 3.99-3.94 (m, 1H), 3.76-3.66 (m, 2H), 3.45-3.30 (m, 4H), 2.88-2.77 (m, 1H), 2.72-2.65 (m, 1H), 2.53-2.47 (m, 7H), 2.33 (s, 3H), 2.28 (s, 3H), 2.09 (s, 3H), 2.06-2.00 (m, 2H), 1.96-1.88 (s, 1H), 1.75-1.64 (m, 1H). |
| A28 | 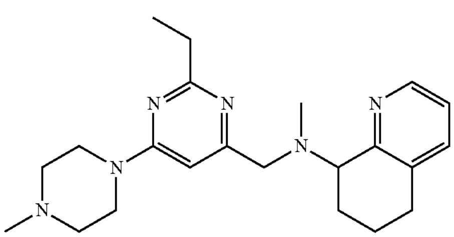 [SMILES: CCc1nc(CN(C)C2CCCc3cccnc32)cc(N2CCN(C)CC2)n1] | E, AC | ¹H NMR (400 MHz, CDCl$_3$) δ 8.49 (d, J = 4.6 Hz, 1H), 7.35 (d, J = 7.6 Hz, 1H), 7.05 (d, J = 6.9 Hz, 2H), 4.04 (t, J = 7.4 Hz, 1H), 3.72 (d, J = 5.2 Hz, 4H), 3.61 (s, 2H), 2.85-2.76 (m, 1H), 2.71 (dd, J = 7.8, 4.0 Hz, 3H), 2.46 (t, J = 4.6 Hz, 4H), 2.41 (s, 3H), 2.34 (s, 3H), 2.10 (s, 1H), 1.99 (d, J = 4.8 Hz, 1H), 1.97-1.90 (m, 1H), 1.75-1.63 (m, 1H), 1.28 (t, J = 7.6 Hz, 3H). |
| A29 | 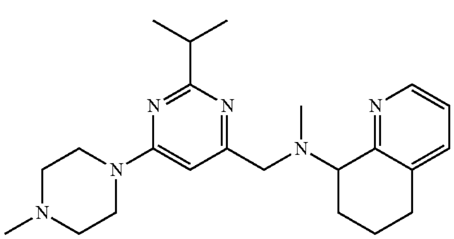 | E, AC | ¹H NMR (400 MHz, CDCl$_3$) δ 8.49 (d, J = 4.6 Hz, 1H), 7.35 (d, J = 7.6 Hz, 1H), 7.07-7.00 (m, 2H), 4.04 (t, J = 7.6 Hz, 1H), 3.72 (d, J = 5.2 Hz, 4H), 3.61 (s, 2H), 2.94 (p, J = 6.8 Hz, 1H), 2.82 (dd, J = 15.8, 4.6 Hz, 1H), 2.69 (d, J = 16.4 Hz, 1H), 2.47 (t, J = 4.6 Hz, 4H), 2.40 (s, 3H), 2.34 (s, 3H), 2.14 (dd, J = 14.2, 7.8 Hz, 1H), 2.01 (d, J = 7.2 Hz, 1H), 1.93 (q, J = 12.0 Hz, 1H), 1.72-1.65 (m, 1H), 1.25 (dd, J = 6.4, 3.2 Hz, 6H). |

TABLE 1-continued

Selected compounds (A1-A100, B1-B8, C1-C39 and D1-D59) of the present invention

| Compd number | structure | method | ¹HNMR and MS |
|---|---|---|---|
| A30 | 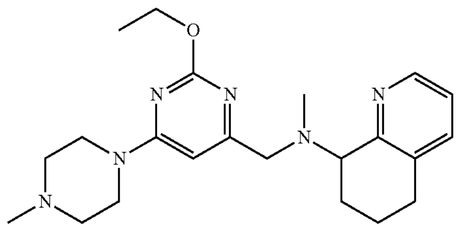 [SMILES: CCOc1nc(CN(C)C2CCCc3cccnc32)cc(N2CCN(C)CC2)n1] | G, AC | ¹H NMR (400 MHz, CDCl₃) δ 8.49 (d, J = 4.0 Hz, 1H), 7.36 (d, J = 7.6 Hz, 1H), 7.13-7.00 (m, 1H), 6.87 (s, 1H), 4.31 (q, J = 7.2 Hz, 2H), 4.08-3.96 (m, 1H), 3.69 (s, 4H), 3.57 (s, 2H), 2.88-2.76 (m, 1H), 2.74-2.65 (m, 1H), 2.49-2.42 (m, 4H), 2.39 (s, 3H), 2.32 (s, 3H), 2.14-2.06 (m, 1H), 2.05-1.98 (m, 1H), 1.98-1.87 (m, 1H), 1.37 (t, J = 7.2 Hz, 3H). |
| A31 | 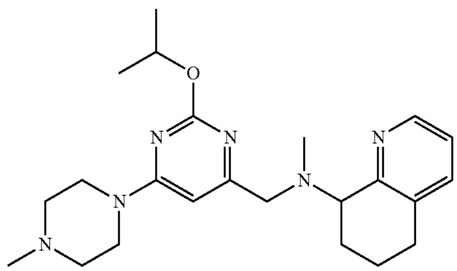 [SMILES: CC(C)Oc1nc(CN(C)C2CCCc3cccnc32)cc(N2CCN(C)CC2)n1] | G, AC | ¹H NMR (400 MHz, CDCl₃) δ 8.48 (d, J = 4.8 Hz, 1H), 7.35 (d, J = 7.6 Hz, 1H), 7.08-7.02 (m, 1H), 6.86 (s, 1H), 5.25-5.12 (m, 1H), 4.10-3.99 (m, 1H), 3.75-3.64 (m, 4H), 3.56 (s, 2H), 2.85-2.76 (m, 1H), 2.74-2.65 (m, 1H), 2.44 (t, J = 5.0 Hz, 4H), 2.38 (s, 3H), 2.32 (s, 3H), 2.13-2.06 (m, 1H), 2.05-1.98 (m, 1H), 1.98-1.87 (m, 1H), 1.69-1.64 (m, 1H), 1.33 (d, J = 6.0 Hz, 6H). |
| A32 | 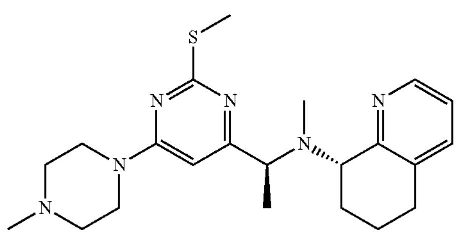 [SMILES: CSc1nc([C@H](C)N(C)[C@H]2CCCc3cccnc32)cc(N2CCN(C)CC2)n1] | J, BC | ¹H NMR (400 MHz, CDCl₃) δ 8.46 (d, J = 3.6 Hz, 1H), 7.33 (d, J = 7.2 Hz, 1H), 7.10-6.98 (m, 1H), 6.85 (s, 1H), 4.18-4.03 (m, 2H), 3.74-3.63 (m, 4H), 2.86-2.74 (m, 1H), 2.72-2.61 (m, 1H), 2.50 (s, 3H), 2.46 (t, J = 4.6 Hz, 4H), 2.33 (s,3H), 2.15 (s, 3H), 1.98 (m, 4H), 1.68-1.60 (m, 1H), 1.42 (d, J = 6.4 Hz, 3H). |
| A33 | 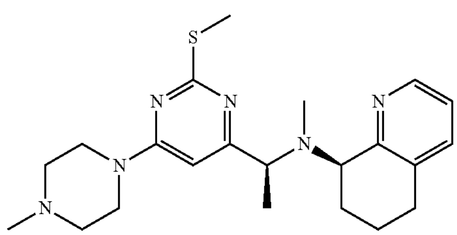 [SMILES: CSc1nc([C@H](C)N(C)[C@@H]2CCCc3cccnc32)cc(N2CCN(C)CC2)n1] | J, BC | ¹H NMR (400 MHz, CDCl₃) δ 8.53-8.46 (m, 1H), 7.33 (d, J = 8.0 Hz, 1H), 7.28-7.26 (m, 1H), 7.06-7.00 (m, 1H), 4.02-3.91 (m, 1H), 3.88-3.78 (m, 1H), 3.71 (s, 4H), 2.83-2.72 (m, 1H), 2.70-2.58 (m, 1H), 2.49 (s, 3H), 2.44-2.36 (m, 4H), 2.30 (s,3H), 2.21 (s, 3H), 2.08-1.98 (m, 1H), 1.90-1.78 (m, 2H), 1.66-1.54 (m, 1H), 1.41 (d, J = 6.4 Hz, 3H). |
| A34 | 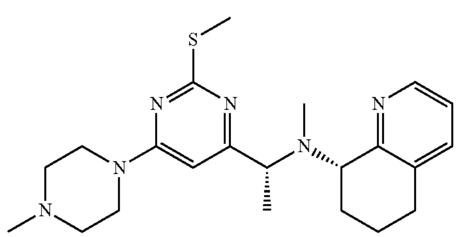 [SMILES: CSc1nc([C@@H](C)N(C)[C@H]2CCCc3cccnc32)cc(N2CCN(C)CC2)n1] | J, BC | ¹H NMR (400 MHz, CDCl₃) δ 8.46 (d, J = 4.0 Hz, 1H), 7.34 (d, J = 7.6 Hz, 1H), 7.09-7.00 (m, 1H), 6.83 (s, 1H), 4.16-4.00 (m, 2H), 3.74-3.63 (m, 4H), 2.87-2.75 (m, 1H), 2.72-2.63 (m, 1H), 2.50 (s, 3H), 2.46 (t, J = 4.8 Hz, 4H), 2.34 (s, 3H), 2.14 (s, 3H), 2.05-1.90 (m, 4H), 1.43 (d, J = 6.8 Hz, 3H). |
| A35 | 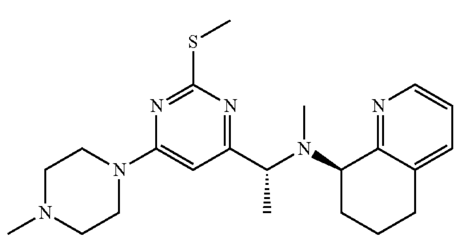 [SMILES: CSc1nc([C@@H](C)N(C)[C@@H]2CCCc3cccnc32)cc(N2CCN(C)CC2)n1] | J, BC | ¹H NMR (400 MHz, CDCl₃) δ 8.52 (d, J = 3.6 Hz, 1H), 7.33 (d, J = 7.6 Hz, 1H), 7.30 (s, 1H), 7.08-7.01 (m, 1H), 4.02-3.92 (m, 1H), 3.90-3.80 (m, 1H), 3.72 (s, 4H), 2.83-2.73 (m, 1H), 2.72-2.63 (m, 1H), 2.50 (s, 3H), 2.47-2.37 (m, 4H), 2.31 (s, 3H), 2.22 (s, 3H), 2.15-1.85 (m, 4H), 1.42 (d, J = 6.8 Hz, 3H). |

TABLE 1-continued

Selected compounds (A1-A100, B1-B8, C1-C39 and D1-D59) of the present invention

| Compd number | structure | method | ¹HNMR and MS |
|---|---|---|---|
| A36 | 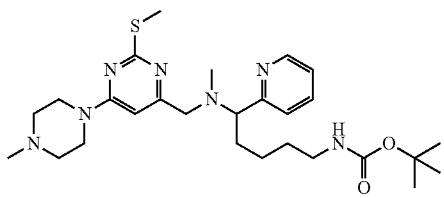 [SMILES: CSc1nc(CN(C)C(CCCCNC(=O)OC(C)(C)C)c2ccccn2)cc(N2CCN(C)CC2)n1] | K, BA, B, AA | ¹H NMR (400 MHz, CDCl$_3$) δ 8.58 (d, J = 4.8 Hz, 1H), 7.70-7.61 (m, 1H), 7.26-7.21 (m, 1H), 7.20-7.13 (m, 1H), 6.46 (s, 1H), 4.59 (s, 1H), 3.75-3.65 (m, 5H), 3.58 (d, J = 15.6 Hz, 1H), 3.33 (d, J = 15.6 Hz, 1H), 3.13-3.00 (m, 2H), 2.54-2.43 (m, 7H), 2.34 (s, 3H), 2.23 (s, 3H), 2.04-1.90 (m, 2H), 1.53-1.45 (m, 2H), 1.42 (s, 9H), 1.33-1.27 (m, 1H), 1.22-1.12 (m, 1H). |
| A37 | 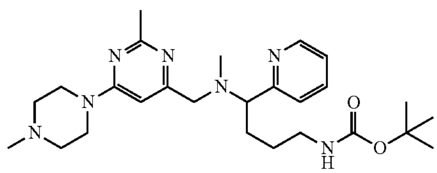 [SMILES: Cc1nc(CN(C)C(CCCNC(=O)OC(C)(C)C)c2ccccn2)cc(N2CCN(C)CC2)n1] | K, BA, C, AA | ¹H NMR (400 MHz, CDCl$_3$) δ8.58 (d, J = 4.8 Hz, 1H), 7.64 (t, J = 7.6 Hz, 1H), 7.22 (d, J = 8.0 Hz, 1H),7.20-7.13 (m, 1H), 6.59 (s, 1H), 4.80 (s, 1H), 3.74 (t, J = 7.2 Hz, 1H), 3.71-3.61 (m, 5H), 3.34 (d, J = 15.6 Hz, 1H), 3.18-3.08 (m, 2H), 2.52-2.44 (m, 7H), 2.34 (s, 3H), 2.22 (s, 3H), 2.07-1.96 (m, 2H), 1.59-1.51 (m, 1H), 1.42 (s, 10H). |
| A38 | 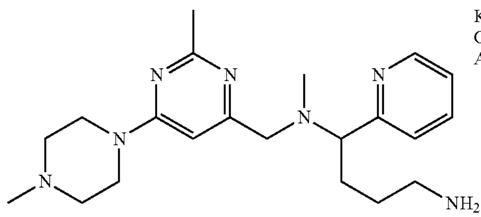 | K, BA, C, AA, AD | ¹H NMR (400 MHz, DMSO-d$_6$) δ 11.99 (s, 1H), 8.82 (d, J = 4.8 Hz, 1H), 8.29 (t, J = 7.8 Hz, 1H), 8.19 (s, 3H), 7.99 (d, J = 7.6 Hz, 1H), 7.78 (t, J = 6.4 Hz, 1H), 7.64 (s, 1H), 5.06-4.50 (m, 3H), 4.25 (d, J = 14.8 Hz, 1H), 4.11 (d, J = 14.4 Hz, 1H), 3.81-3.45 (m, 4H), 3.25-3.11 (m, 2H), 2.79 (s, 5H), 2.61 (s, 3H), 2.46 (s, 3H), 2.38-2.21 (m, 2H), 1.58-1.44 (m, 1H), 1.41-1.29 (m, 1H). |
| A39 | 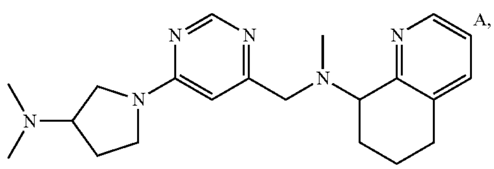 | A, AA | ¹H NMR (400 MHz, CDCl$_3$) δ 8.48 (s, 2H), 7.35 (d, J = 7.2 Hz, 1H), 7.05 (s, 1H), 6.90 (s, 1H), 4.03 (s, 1H), 3.92-3.84 (m, 1H), 3.66 (s, 3H), 3.44 (s, 1H), 3.26 (s, 1H), 2.83-2.78 (m, 2H), 2.71-2.67 (m, 1H), 2.40 (s, 3H), 2.31 (s, 6H), 2.23 (s, 1H), 2.10 (s, 1H), 2.01 (s, 1H), 1.93-1.88 (m, 2H), 1.69 (s, 1H). MS (ESI/APCI) m/z 366.9 [M + H]⁺. |
| A40 | 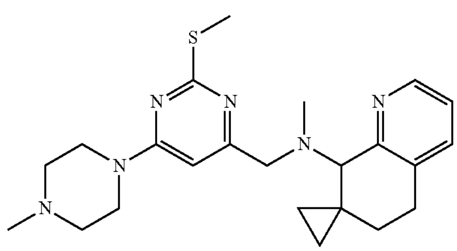 [SMILES: CSc1nc(CN(C)C2c3ncccc3CCC23CC3)cc(N2CCN(C)CC2)n1] | BD, BA, E, AC | ¹H NMR (400 MHz, CDCl$_3$) δ 8.35(d, J = 4.0 Hz, 1H), 7.41(d, J = 8.0 Hz, 1H), 7.11-7.08(m, 1H), 6.46(s, 1H), 3.79-3.46(m, 6H), 2.99(s, 2H), 2.61-2.60(m, 1H), 2.47-2.33(m, 14H), 1.11-1.09(m, 1H), 0.92-0.89(m, 1H), 0.64-0.62(m, 1H), 0.23-0.21(m, 2H). |
| A41 | 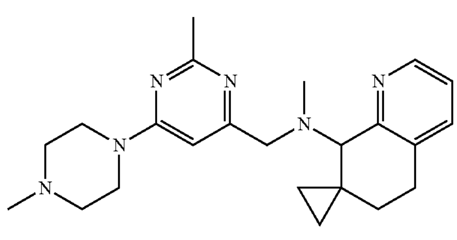 [SMILES: Cc1nc(CN(C)C2c3ncccc3CCC23CC3)cc(N2CCN(C)CC2)n1] | BD, BA, C, AA | ¹H NMR (400 MHz, CDCl$_3$) δ 8.36(d, J = 4.4 Hz, 1H), 7.43(d, J = 4.0 Hz, 1H), 7.15-7.04 (m, 1H), 6.63(s, 1H), 3.88-3.58(m, 6H), 3.01(s, 1H), 2.95-2.80(m, 1H), 2.48-2.35(m, 14H), 1.15-1.10(t, J = 4.0, 1 Hz), 0.94-0.88(t, J = 4.0, 1 Hz), 0.66(t, J = 4.0 Hz, 1H), 0.23(t, J = 4.8 Hz, 2H). |
| A42 | 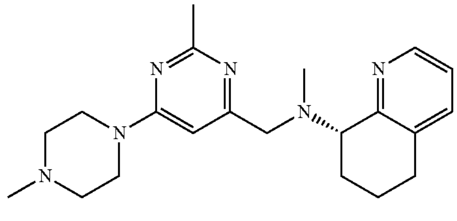 [SMILES: Cc1nc(CN(C)[C@H]2CCCc3cccnc32)cc(N2CCN(C)CC2)n1] | BB, C, AA | ¹H NMR (400 MHz, CDCl$_3$) δ 8.49 (d, J = 4.4 Hz, 1H), 7.35 (d, J = 7.6 Hz, 1H), 7.09-7.01 (m, 2H), 4.04 (t, J = 7.6 Hz, 1H), 3.71 (s, 4H), 3.60 (s, 2H), 2.88-2.75 (m, 1H), 2.74-2.65 (m, 1H), 2.48-2.44 (m, 7H), 2.39 (s, 3H), 2.33 (s, 3H), 2.16-2.06 (m, 1H), 2.04-1.98(m, 1H), 1.95-1.84 (m, 1H), 1.77-1.68 (m, 1H). |

TABLE 1-continued

Selected compounds (A1-A100, B1-B8, C1-C39 and D1-D59) of the present invention

| Compd number | structure | method | $^1$HNMR and MS |
|---|---|---|---|
| A43 | 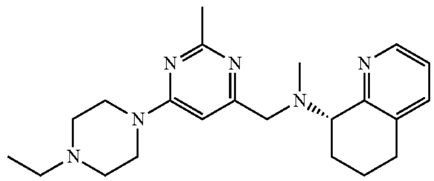 [SMILES: CCN1CCN(c2cc(CN(C)[C@H]3CCCc4cccnc43)nc(C)n2)CC1] | BB, C, AA | $^1$H NMR (400 MHz, CDCl$_3$) δ 8.54-8.46 (m, 1H), 7.35 (d, J = 8.0 Hz, 1H), 7.10-7.02 (m, 2H), 4.10-4.00 (m, 1H), 3.72 (s, 4H), 3.60 (s, 2H), 2.87-2.76 (m, 1H), 2.75-2.64 (m, 1H), 2.53-2.42 (m, 9H), 2.40 (s, 3H), 2.16-2.07 (m, 1H), 2.05-1.98 (m, 1H), 1.96-1.89 (m, 1H), 1.76-1.66 (m, 1H), 1.12 (t, J = 7.4 Hz, 3H). |
| A44 | 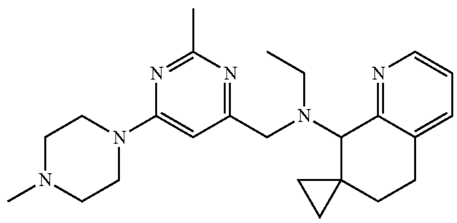 [SMILES: CCN(Cc1cc(N2CCN(C)CC2)nc(C)n1)C1c2ncccc2CCC12CC2] | BD, BA, C, AA | $^1$H NMR (400 MHz, CDCl$_3$) δ 8.36(s, 1H), 7.36(d, J = 6.8 Hz), 7.05(s, 1H), 6.75(s, 1H), 3.66(s, 4H), 3.60(s, 2H), 3.47(s, 1H), 3.15-3.07(m, 1H), 2.90-2.86(m, 1H), 2.8-2.70(m, 2H), 2.48(s, 4H), 2.42(s, 3H), 2.35(s, 3H), 2.10-2.04(m, 1H), 1.28-1.20(m, 1H), 1.01(t, J = 6.8 Hz, 3H), 0.89-0.82(m, 1H), 0.51-0.46(m, 1H), 0.42-0.38(m, 1H), 0.27-0.23(m, 1H). |
| A45 | 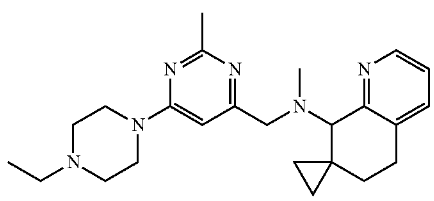 [SMILES: CCN1CCN(c2cc(CN(C)C3c4ncccc4CCC34CC4)nc(C)n2)CC1] | BD, BA, C, AA | $^1$H NMR (400 MHz, CDCl$_3$) δ 8.36(s, 1H), 7.42(d, J = 8.0 Hz, 1H), 7.11(d, J = 4.8 Hz, 1H), 6.61(s, 1H), 3.86-3.56(m, 6H), 3.00(s, 2H), 2.86-2.83(m, 1H), 2.50-2.36(m, 12H), 1.15-1.11 (m, 4H), 0.93-0.88(m, 1H), 0.68-0.60(m, 1H), 0.28-0.19(m, 1H). |
| A46 | 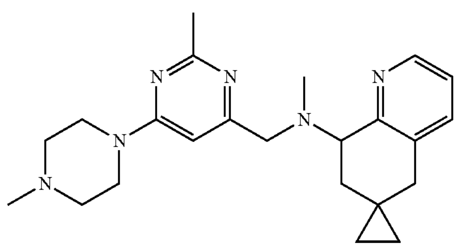 [SMILES: Cc1nc(CN(C)C2CC3(CC3)Cc3cccnc32)cc(N2CCN(C)CC2)n1] | BE, BC, C, AA | $^1$H NMR (400 MHz, CDCl$_3$) δ 8.51(s, 1H), 7.30(d, J = 7.2 Hz, 1H), 7.07-7.01(m, 2H), 4.17-4.13(m, 1H), 3.71(s, 4H), 3.60(d, J = 5.2 Hz, 2H), 3.23(d, J = 16.8 Hz, 1H), 2.47(s, 7H), 2.42 (s, 3H), 2.34(s, 3H), 2.26-2.17(m, 1H), 2.01(d, J = 16.0 Hz, 1H), 1.52-1.45(m, 1H), 0.57-0.48(m, 2H), 0.37-0.30(m, 2H). |
| A47 | 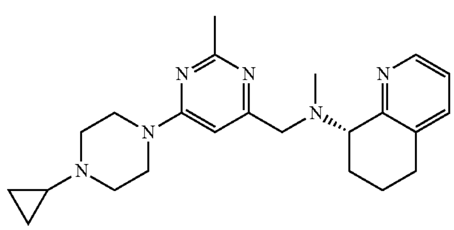 [SMILES: Cc1nc(CN(C)[C@H]2CCCc3cccnc32)cc(N2CCN(C3CC3)CC2)n1] | BB, C, AA | $^1$H NMR (400 MHz, CDCl$_3$) δ 8.49 (d, J = 3.6 Hz, 1H), 7.35 (d, J = 8.4 Hz, 1H), 7.07-7.03 (m, 2H), 4.08-4.01 (m, 1H), 3.70-3.63 (m, 4H), 3.61 (s, 2H), 2.83-2.74 (m, 1H), 2.73-2.69 (m, 1H), 2.68-2.63 (m, 4H), 2.47 (s, 3H), 2.40 (s, 3H), 2.16-2.07 (m, 1H), 2.05-1.96 (m, 1H), 1.95-1.86 (m, 1H), 1.69-1.66 (m, 1H), 1.65-1.59 (m, 1H), 0.51-0.43 (m, 4H). |
| A48 | 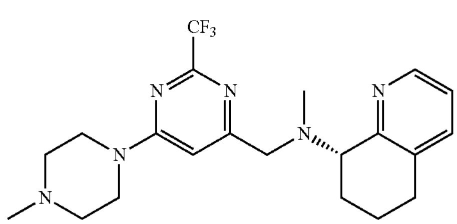 [SMILES: CN1CCN(c2cc(CN(C)[C@H]3CCCc4cccnc43)nc(C(F)(F)F)n2)CC1] | E, BB, AC | $^1$H NMR (400 MHz, CDCl$_3$) δ 8.47 (d, J = 3.6 Hz, 1H), 7.46 (s, 1H), 7.36 (d, J = 7.6 Hz, 1H), 7.08-7.04 (m, 1H), 4.06-3.96 (m, 1H), 3.84-3.72 (m, 4H), 3.72-3.60 (m, 2H), 2.87-2.75 (m, 1H), 2.74-2.61 (m, 1H), 2.53-2.42 (m, 4H), 2.42 (s, 3H), 2.34 (s, 3H), 2.16-2.08 (m, 1H), 2.07-1.96 (m, 1H), 1.96-1.86 (m, 1H), 1.76-1.64 (m, 1H). |

TABLE 1-continued

Selected compounds (A1-A100, B1-B8, C1-C39 and D1-D59) of the present invention

| Compd number | structure | method | ¹HNMR and MS |
|---|---|---|---|
| A49 | 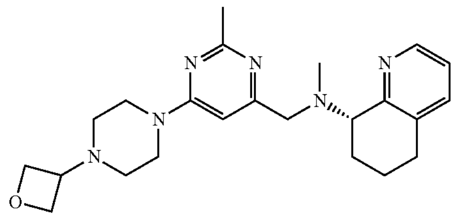 [SMILES: Cc1nc(CN(C)[C@H]2CCCc3cccnc32)cc(N2CCN(C3COC3)CC2)n1] | BB, C, AA | 1H NMR (400 MHz, CDCl$_3$) δ 8.49 (d, J = 4.0 Hz, 1H), 7.36 (d, J = 7.2 Hz, 1H), 7.10-7.01 (m, 2H), 4.713-4.60 (m, 4H), 4.10-3.95 (m, 1H), 3.74 (s, 4H), 3.61 (s, 2H), 3.55-3.46 (m, 1H), 2.86-2.75 (m, 1H), 2.713-2.673 (m, 1H), 2.47 (s, 3H), 2.38 (s, 7H), 2.20-2.07 (m, 1H), 2.06-1.96 (m, 1H), 1.93-1.88 (m, 1H), 1.78-1.65 (m, 1H). |
| A50 | 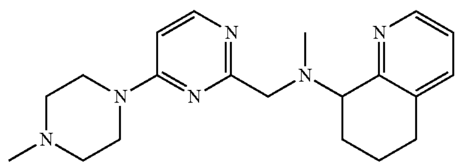 [SMILES: CN1CCN(c2ccnc(CN(C)C3CCCc4cccnc43)n2)CC1] | L, AE | ¹H NMR (400 MHz, CDCl$_3$) δ 8.46 (s, 1H), 8.18 (d, J = 6.0 Hz, 1H), 7.34 (d, J = 8.0 Hz, 1H), 7.05-7.02 (m, 1H), 6.32 (d, J = 6.4 Hz, 1H), 4.15-4.12 (m, 1H), 3.81 (s, 2H), 3.65 (s, 4H), 2.87-2.77 (m, 1H), 2.72-2.69 (m, 1H), 2.65-2.44 (m, 7H), 2.32 (s, 3H), 2.11-1.98 (m, 3H), 1.73-1.64 (m, 1H). |
| A51 | 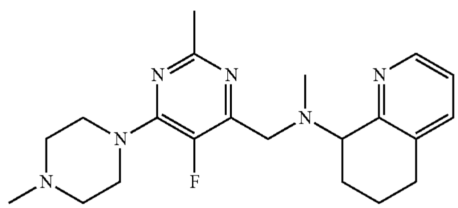 | I, BC | ¹H NMR (400 MHz, CDCl$_3$) δ 8.48 (d, J = 4.0 Hz, 1H), 7.34 (d, J = 7.6 Hz, 1H), 7.06-7.02 (m, 1H), 4.11-4.00 (m, 1H), 3.81-3.73 (m, 4H), 3.73-3.69 (m, 2H), 3.68-3.60 (m, 1H), 2.89-2.75 (m, 1H), 2.75-2.62 (m, 1H), 2.50-2.45 (m, 4H), 2.46-2.42 (m, 3H), 2.40 (s, 3H), 2.32 (s, 3H), 2.07-2.01 (m, 2H), 1.76-1.680 (m, 1H). |
| A52 | 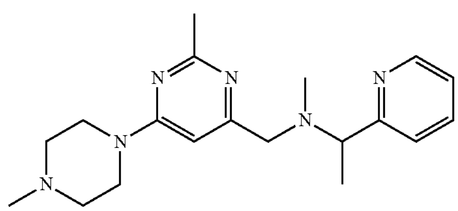 [SMILES: Cc1nc(CN(C)C(C)c2ccccn2)cc(N2CCN(C)CC2)n1] | C, AA | ¹H NMR (400 MHz, CDCl$_3$) δ 8.57 (d, J = 4.8 Hz, 1H), 7.70-7.60 (m, 1H), 7.42 (d, J = 7.8 Hz, 1H), 7.15 (dd, J = 7.6, 4.8 Hz, 1H), 6.65 (s, 1H), 3.90 (q, J = 6.6 Hz, 1H), 3.69 (t, J = 5.0 Hz, 4H), 3.57 (d, J = 15.6 Hz, 1H), 3.44 (d, J = 15.6 Hz, 1H), 2.48 (d, J = 5.0 Hz, 7H), 2.35 (s, 3H), 2.28 (s, 3H), 1.47 (d, J = 6.8 Hz, 3H). |
| A53 | 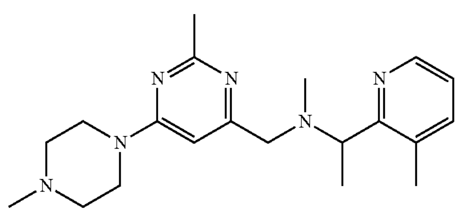 | BA, C, AA | ¹H NMR (400 MHz, CDCl$_3$) δ 8.40 (d, J = 4.8 Hz, 1H), 7.41 (d, J = 7.6 Hz, 1H), 7.05 (dd, J = 7.6, 4.8 Hz, 1H), 6.44 (s, 1H), 4.12 (q, J = 6.8 Hz, 1H), 3.62 (t, J = 5.0 Hz, 4H), 3.53 (s, 2H), 2.48-2.40 (m, 10H), 2.33 (s, 3H), 2.26 (s, 3H), 1.45 (d, J = 6.6 Hz, 3H). |
| A54 | 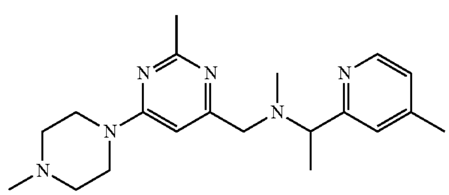 | BA, C, AA | ¹H NMR (400 MHz, CDCl$_3$) δ 8.41 (d, J = 4.8 Hz, 1H), 7.24 (s, 1H), 6.97 (d, J = 4.8 Hz, 1H), 6.65 (s, 1H), 3.90-3.83 (m, 1H), 3.75-3.64 (m, 4H), 3.57 (d, J = 15.6 Hz, 1H), 3.43 (d, J = 15.6 Hz, 1H), 2.50-2.45 (m, 7H), 2.36-2.32 (m, 6H), 2.29 (s, 3H), 1.46 (d, J = 6.8 Hz, 3H). |
| A55 | 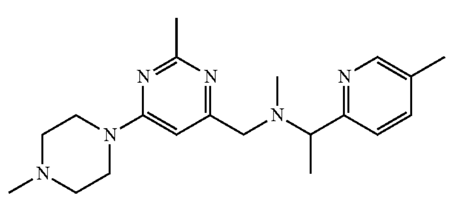 | BA, C, AA | ¹H NMR (400 MHz, CDCl$_3$) δ 8.38 (s, 1H), 7.45 (d, J = 8.0 Hz, 1H), 7.30 (d, J = 8.0 Hz, 1H), 6.65 (s, 1H), 3.87 (d, J = 6.9 Hz, 1H), 3.69-3.67 (m, 4H), 3.56 (d, J = 15.6 Hz, 1H), 3.42 (d, J = 15.6 Hz, 1H), 2.50-2.46 (m, 7H), 2.35 (s, 3H), 2.31 (s, 3H), 2.27 (s, 3H), 1.45 (d, J = 6.8 Hz, 3H). |

TABLE 1-continued

Selected compounds (A1-A100, B1-B8, Cl-C39 and D1-D59) of the present invention

| Compd number | structure | method | ¹HNMR and MS |
|---|---|---|---|
| A56 | 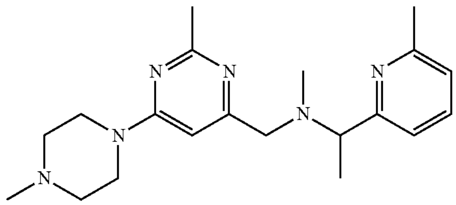 [SMILES: Cc1cccc(C(C)N(C)Cc2cc(N3CCN(C)CC3)nc(C)n2)n1] | BA, C, AA | ¹H NMR (400 MHz, CDCl₃) δ 7.56-7.48 (m, 1H), 7.21 (d, J = 7.8 Hz, 1H), 6.99 (d, J = 7.6 Hz, 1H), 6.67 (s, 1H), 3.83 (q, J = 6.6 Hz, 1H), 3.69 (s, 4H), 3.57 (d, J = 15.6 Hz, 1H), 3.42 (d, J = 15.6 Hz, 1H), 2.53 (s, 3H), 2.47 (d, J = 6.4 Hz, 7H), 2.34 (s, 3H), 2.28 (s, 3H), 1.44 (d, J = 6.8 Hz, 3H). |
| A57 | 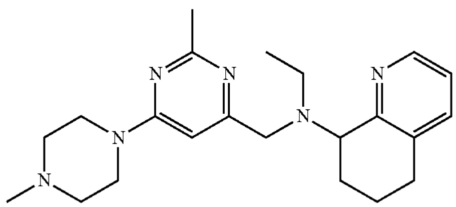 [SMILES: CCN(Cc1cc(N2CCN(C)CC2)nc(C)n1)C1CCCc2cccnc21] | C, BC, AA | ¹H NMR (400 MHz, CDCl₃) δ 8.43 (s, 1H), 7.38-7.29 (m, , 1H), 7.21 (s, 1H), 7.03 (s, 1H), 4.13 (s, 1H), 3.73 (s, 4H), 3.64-3.45 (m, 2H), 2.90-2.60(m, 4H), 2.55-2.40 (m, 7H), 2.34 (s, 3H), 2.20-2.06 (m, 1H), 2.06-1.90 (m, 1H), 1.90-1.78 (m, 1H), 1.78-1.70 (m, 1H), 1.10-0.98 (m, 3H). |
| A58 | 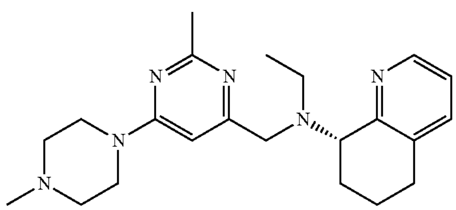 [SMILES: CCN(Cc1cc(N2CCN(C)CC2)nc(C)n1)[C@H]1CCCc2cccnc21] | BB, C, AA | ¹H NMR (400 MHz, CDCl₃) δ 8.42 (s, 1H), 7.31 (d, J = 7.2 Hz, 1H), 7.22 (s, 1H), 7.04-6.99 (m, 1H), 4.18-4.05 (m, 1H), 3.72 (s, 4H) 3.64-3.48 (m, 2H), 2.90-2.65 (m, 4H), 2.53-2.39(m, 7H), 2.34 (s, 3H), 2.20-2.03 (s, 1H), 2.05-1.90 (m, 1H), 1.90-1.73 (m, 1H), 1.75-1.68 (m, 1H), 1.10-0.94 (m, 3H). |
| A59 | 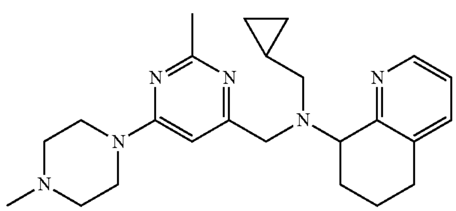 [SMILES: Cc1nc(CN(CC2CC2)C2CCCc3cccnc32)cc(N2CCN(C)CC2)n1] | C, BC, AA | ¹H NMR (400 MHz, CDCl₃) δ 8.42 (s, 1H), 7.32 (d, J = 7.2 Hz, 2H), 7.02 (s, 1H), 4.30-4.18 (m, 1H), 3.80-3.55 (m, 6H), 2.85-2.52 (m, 4H), 2.52-2.40 (m, 7H), 2.35 (s, 3H), 2.20-2.10 (m, 1H), 2.02-1.90 (m, 1H), 1.88-1.76 (m, 2H), 0.90-0.78 (m, 1H), 0.45-0.30 (m, 2H), 0.12-0.03 (m, 2H). |
| A60 | 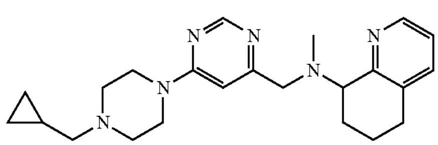 [SMILES: CN(Cc1cc(N2CCN(CC3CC3)CC2)ncn1)C1CCCc2cccnc21] | A, E, AC | ¹H NMR (400 MHz, CDCl₃) δ 8.54-8.46 (m, 2H), 7.37 (d, J = 7.6 Hz, 1H), 7.21 (s, 1H), 7.12-7.03 (m, 1H), 4.03 (t, J = 7.2 Hz, 1H), 3.74 (s, 4H), 3.65 (s, 2H), 2.88-2.76 (m, 1H), 2.74-2.66 (m, 1H), 2.59 (s, 4H), 2.39 (s, 3H), 2.30 (d, J = 6.4 Hz, 2H), 2.17-2.08 (m, 1H), 2.06-1.98 (m, 1H), 1.98-1.87 (m, 1H), 1.76-1.741 (m, 1H), 0.94-0.84 (m, 1H), 0.60-0.50 (m, 2H), 0.17-0.06 (m, 2H). MS (ESI/APCI) m/z 392.9 [M + H]⁺. |
| A61 | 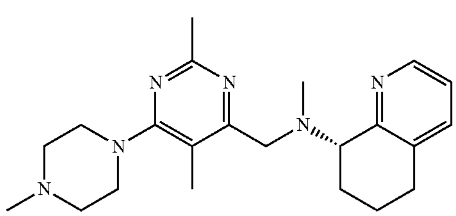 [SMILES: Cc1nc(CN(C)[C@H]2CCCc3cccnc32)c(C)c(N2CCN(C)CC2)n1] | E, BB, AC | ¹H NMR (400 MHz, CDCl₃) δ 8.46 (d, J = 4.8 Hz, 1H), 7.35 (d, J = 7.6 Hz, 1H), 7.07-7.01 (m, 1H), 4.02-3.92 (m, 1H), 3.80-3.69 (m, 2H), 3.39-3.25 (m, 4H), 2.88-2.76 (m, 1H), 2.73-2.65 (m, 1H), 2.51 (s, 7H), 2.33 (s, 3H), 2.23 (s, 3H), 2.08-1.98 (m, 3H), 1.74-1.63 (m, 1H). |
| A62 | 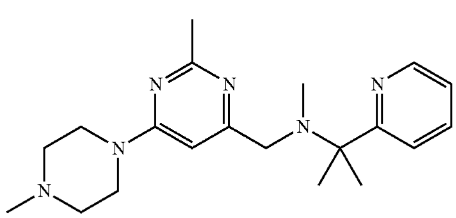 [SMILES: Cc1nc(CN(C)C(C)(C)c2ccccn2)cc(N2CCN(C)CC2)n1] | C, BS, AA | ¹H NMR (400 MHz, CDCl₃) δ 8.53 (d, J = 4.8 Hz, 1H), 7.73 (d, J = 8.4 Hz, 1H), 7.65-7.55 (m, 1H), 7.13-7.08 (m, 1H), 6.70 (s, 1H), 3.71 (t, J = 5.0 Hz, 4H), 3.40 (s, 2H), 2.51 (t, J = 5.0 Hz, 4H), 2.45 (s, 3H), 2.36 (s, 3H), 2.27 (s, 3H), 1.48 (s, 6H). |

TABLE 1-continued

Selected compounds (A1-A100, B1-B8, C1-C39 and D1-D59) of the present invention

| Compd number | structure | method | $^1$HNMR and MS |
|---|---|---|---|
| A63 | 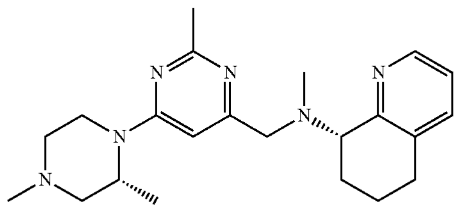 [SMILES: Cc1nc(CN(C)[C@H]2CCCc3cccnc32)cc(N2CCN(C)C[C@H]2C)n1] | BB, C, AA, AD | $^1$H NMR (400 MHz, CDCl$_3$) δ 8.48 (s, 1H), 7.35 (d, J = 7.6 Hz, 1H), 7.09-6.92 (m, 2H), 4.62 (s, 1H), 4.35-4.28 (m, 1H), 4.09-3.98 (m, 1H), 3.74-3.49 (m, 2H), 3.23-3.08 (m, 1H), 2.91-2.83 (m, 1H), 2.82-2.75 (m, 1H), 2.74-2.65 (m, 2H), 2.46 (s, 3H), 2.42-2.36 (m, 3H), 2.28 (s, 3H), 2.22-2.17 (m, 1H), 2.14-2.07 (m, 1H), 2.05-1.91 (m, 3H), 1.74-1.63 (m, 1H), 1.29-1.23 (m, 3H). |
| A64 | 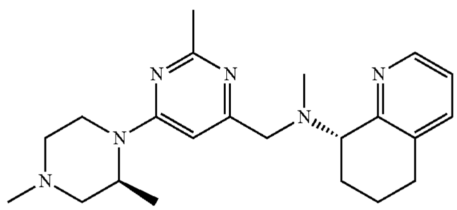 [SMILES: Cc1nc(CN(C)[C@H]2CCCc3cccnc32)cc(N2CCN(C)C[C@@H]2C)n1] | BB, C, AA, AD | $^1$H NMR (400 MHz, CDCl$_3$) δ 8.51-8.44 (m, 1H), 7.35 (d, J = 7.6 Hz, 1H), 7.09-7.02 (m, 1H), 7.02-6.89 (m, 1H), 4.61 (s, 1H), 4.31 (d, J = 13.2 Hz, 1H), 4.05 (q, J = 7.8 Hz, 1H), 3.63 (d J = 8.0 Hz, 1H), 3.56 (s, 1H) 3.21-3.10 (m, 1H), 2.89-2.83 (m, 1H), 2.81-2.74 (m, 1H), 2.74-2.67 (m, 2H), 2.46 (s, 3H), 2.37 (d, J = 6.0 Hz, 3H), 2.23 (s, 3H), 2.21-2.15 (m, 1H), 2.15-2.05 (m, 1H), 2.04-1.95 (m, 2H), 1.95-1.92 (m, 1H), 1.74-1.63 (m, 1H), 1.30-1.25 (m, 2H), 1.18 (d, J = 6.8 Hz, 1H). |
| A65 | 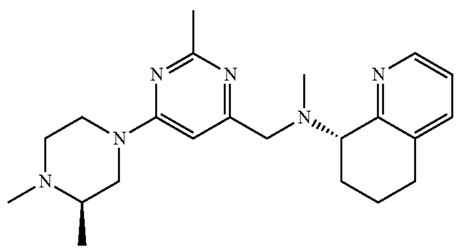 [SMILES: Cc1nc(CN(C)[C@H]2CCCc3cccnc32)cc(N2CCN(C)[C@H](C)C2)n1] | BB, C, AA | $^1$H NMR (400 MHz, CDCl$_3$) δ 8.52-8.47 (m, 1H), 7.36 (d, J = 7.6 Hz, 1H), 7.09-7.00 (m, 2H), 4.35 (s, 1H), 4.25 (s, 1H), 4.04 (t, J = 7.6 Hz, 1H), 3.68-3.55 (m, 2H), 3.14-3.03 (m, 1H), 2.88-2.82 (m, 1H), 2.82-2.76 (m, 1H), 2.74-2.63 (m, 2H), 2.46 (s, 3H), 2.37 (s, 3H), 2.31 (s, 3H), 2.29-2.18 (m, 1H), 2.14-2.06 (m, 2H), 2.04-1.97 (m, 1H), 1.93-1.87 (m, 1H), 1.73-1.64 (m, 1H), 1.17-1.09 (m, 3H). |
| A66 | 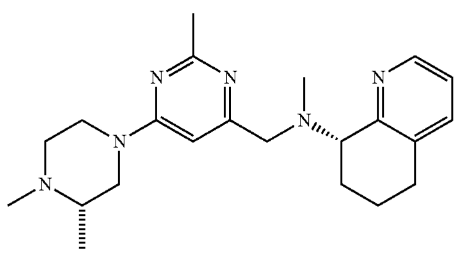 [SMILES: Cc1nc(CN(C)[C@H]2CCCc3cccnc32)cc(N2CCN(C)[C@@H](C)C2)n1] | BB, C, AA | $^1$H NMR (400 MHz, CDCl$_3$) δ 8.50 (d, J = 4.4 Hz, 1H), 7.36 (d, J = 7.6 Hz, 1H), 7.09-7.01 (m, 2H), 4.35 (s, 1H), 4.25 (s, 1H), 4.05 (t, J = 7.6 Hz, 1H), 3.68-3.55 (m, 2H), 3.14-3.02 (m, 1H), 2.89-2.82 (m, 1H), 2.80-2.74 (m, 1H), 2.74-2.63 (m, 2H), 2.46 (s, 3H), 2.37 (s, 3H), 2.31 (s, 3H), 2.28-2.19 (m, 1H), 2.14-2.06 (m, 2H), 2.04-1.98 (m, 1H), 1.97-1.87 (m, 1H), 1.73-1.64 (m, 1H), 1.16-1.10 (m, 3H). |
| A67 | 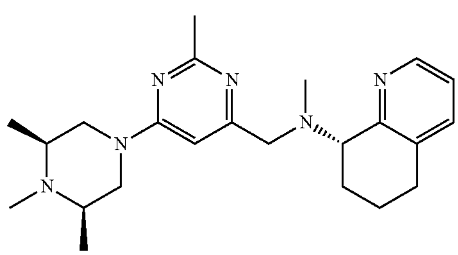 [SMILES: Cc1nc(CN(C)[C@H]2CCCc3cccnc32)cc(N2C[C@@H](C)N(C)[C@@H](C)C2)n1] | BB, C, AA, AD | $^1$H NMR (400 MHz, CDCl$_3$) δ 8.52 (s, 1H), 7.36 (d, J = 7.2 Hz, 1H), 7.06 (s, 2H), 4.32 (s, 2H), 4.05 (t, J = 7.6 Hz, 1H), 3.63 (s, 2H), 2.85-2.76 (m, 1H), 2.75-2.62 (m, 3H), 2.47 (s, 3H), 2.39 (s, 3H), 2.29 (s, 3H), 2.24-2.16 (m, 2H), 2.13-2.07 (m, 1H), 2.05-1.96 (m, 1H), 1.95-1.87 (m, 1H), 1.71-1.65 (m, 1H), 1.18 (t, J = 6.0 Hz, 6H). |
| A68 | 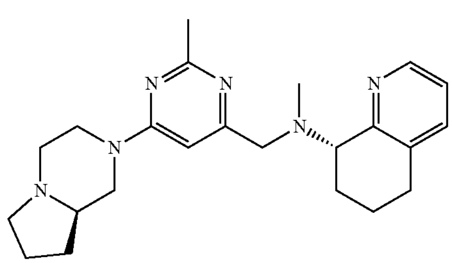 [SMILES: Cc1nc(CN(C)[C@H]2CCCc3cccnc32)cc(N2CCN3CCC[C@@H]3C2)n1] | BB, C, AA | $^1$H NMR (400 MHz, CDCl$_3$) δ 8.55-8.48 (m, 1H), 7.35 (d, J = 7.6 Hz, 1H), 7.14-7.02 (m, 2H), 4.75-4.35 (m, 2H), 4.11-3.97 (m, 1H), 3.61 (s, 2H), 3.15-3.08 (m, 2H), 3.05-2.96 (m, 1H), 2.86-2.76 (m, 1H), 2.74-2.57 (m, 2H), 2.46 (s, 3H), 2.38 (s, 3H), 2.23-1.83 (m, 9H), 1.74-1.63 (m, 2H), 1.55-1.42 (m, 1H). |

TABLE 1-continued

Selected compounds (A1-A100, B1-B8, C1-C39 and D1-D59) of the present invention

| Compd number | structure | method | ¹HNMR and MS |
|---|---|---|---|
| A69 | 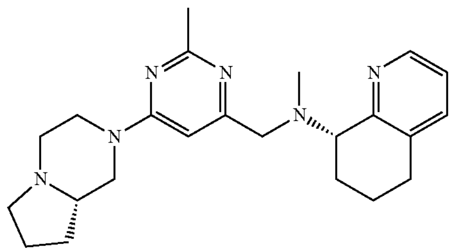 [SMILES: Cc1nc(CN(C)[C@H]2CCCc3cccnc32)cc(N2CCN3CCC[C@H]3C2)n1] | BB, C, AA | ¹H NMR (400 MHz, CDCl₃) δ 8.49 (s, 1H), 7.36 (d, J = 7.6 Hz, 1H), 7.11-7.03 (m, 2H), 4.68-4.37 (m, 2H), 4.09-3.99 (m, 1H), 3.68-3.55 (m, 2H), 3.17-3.07 (m, 2H), 3.06-2.97 (m, 1H), 2.84-2.74 (m, 1H), 2.71-2.60 (m, 2H), 2.47 (s, 3H), 2.38 (s, 3H), 2.28-2.06 (m, 3H), 2.04-1.82 (m, 6H), 1.71-1.59 (m, 1H), 1.54-1.43 (m, 1H). |
| A70 | 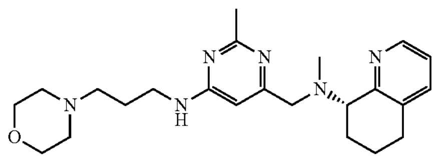 [SMILES: Cc1nc(CN(C)[C@H]2CCCc3cccnc32)cc(NCCCN2CCOCC2)n1] | BB, C, AA | ¹H NMR (400 MHz, CDCl₃) δ 8.50 (s, 1H), 7.37 (d, J = 6.8 Hz, 1H), 7.12-7.02 (m, 1H), 6.73 (s, 1H), 5.50 (s, 1H), 4.13-3.95 (m, 1H), 3.72 (s, 4H), 3.59 (s, 2H), 3.44 (s, 2H), 2.88-2.76 (m, 1H), 2.75-2.63 (m, 1H), 2.50-2.40 (m, 9H), 2.38 (s, 3H), 2.18-2.08 (m, 1H), 2.06-1.96 (m, 1H), 1.96-1.88 (m, 2H), 1.76-1.73 (m, 2H). |
| A71 | 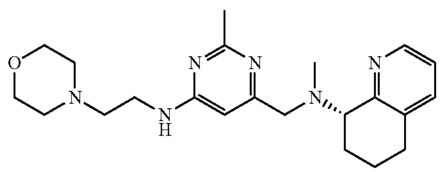 [SMILES: Cc1nc(CN(C)[C@H]2CCCc3cccnc32)cc(NCCN2CCOCC2)n1] | BB, C, AA | ¹H NMR (400 MHz, CDCl₃) δ 8.53-8.48 (m, 1H), 7.36 (d, J = 7.6 Hz, 1H), 7.10-7.02 (m, 2H), 6.75 (s, 1H), 5.52 (s, 1H), 4.08-4.02 (m, 1H), 3.72 (s, 4H), 3.56 (s, 2H), 3.42 (s, 2H), 2.84-2.77 (m, 1H), 2.74-2.65 (m, 1H), 2.62-2.56 (m, 2H), 2.46 (s, 7H), 2.38 (s, 3H), 2.15-2.08 (m, 1H), 2.06-1.98 (m, 1H), 1.96-1.85 (m, 1H), 1.80-1.75 (m, 1H). |
| A72 | 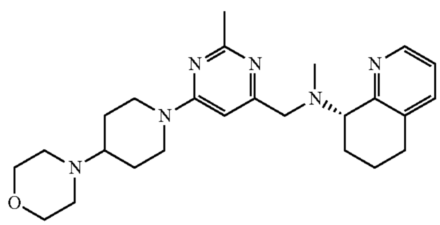 [SMILES: Cc1nc(CN(C)[C@H]2CCCc3cccnc32)cc(N2CCC(N3CCOCC3)CC2)n1] | BB, C, AA | ¹H NMR (400 MHz, CDCl₃) δ 8.51-8.47 (m, 1H), 7.36 (d, J = 7.6 Hz, 1H), 7.11-7.02 (m, 2H), 4.58 (d, J = 12.0 Hz, 2H), 4.03 (t, J = 7.2 Hz, 1H), 3.72 (s, 4H), 3.61 (s, 2H), 2.88-2.76 (m, 3H), 2.74-2.65 (m, 1H), 2.56 (s, 4H), 2.46 (s, 4H), 2.38 (s, 3H), 2.15-1.96 (m, 2H), 1.95-1.85 (m, 3H), 1.76-1.65 (m, 1H), 1.55-1.42 (m, 2H). |
| A73 | 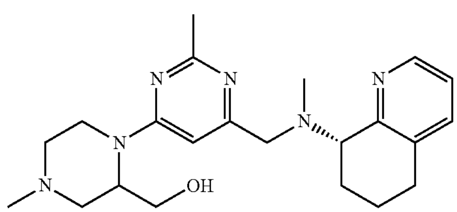 [SMILES: Cc1nc(CN(C)[C@H]2CCCc3cccnc32)cc(N2CCN(C)CC2CO)n1] | C, BB, AA, AD | ¹H NMR (400 MHz, CDCl₃) δ 8.52-8.45 (m, 1H), 7.37 (d, J = 7.6 Hz, 1H), 7.115-7.04 (m, 2H), 4.63 (s, 1H), 4.29 (s, 1H), 4.08-3.83 (m, 3H), 3.62-3.58 (m, 2H), 3.48-3.36 (m, 1H), 3.06 (d, J = 11.6 Hz, 1H), 2.90 (d, J = 10.8 Hz, 1H), 2.85-2.75 (m, 1H), 2.74-2.63 (m, 1H), 2.45 (d, J = 5.2 Hz, 3H), 2.38 (d, J = 14.0 Hz, 3H), 2.30 (s, 3H), 2.17-2.07 (m, 2H), 2.06-1.97 (m, 2H), 1.96-1.88 (m, 1H), 1.75-1.63 (m, 1H). |
| A74 | 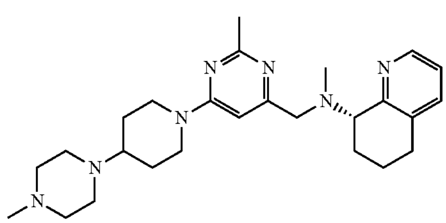 [SMILES: Cc1nc(CN(C)[C@H]2CCCc3cccnc32)cc(N2CCC(N3CCN(C)CC3)CC2)n1] | BB, C, AA | ¹H NMR (400 MHz, CDCl₃) δ 8.49 (d, J = 4.4 Hz, 1H), 7.35 (d, J = 7.6 Hz, 1H), 7.10-7.02 (m, 2H), 4.59 (d, J = 13.2 Hz, 2H), 4.04 (t, J = 7.2 Hz, 1H), 3.60 (s, 2H), 2.90-2.75 (m, 3H), 2.71-2.55 (m, 5H), 2.54-2.43 (m, 7H), 2.39 (s, 3H), 2.29 (s,3H), 2.17-1.84 (m, 7H), 1.56-1.40 (m, 2H). |
| A75 | 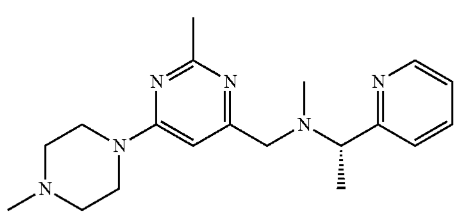 | BB, C, AA | ¹H NMR (400 MHz, CDCl₃) δ 8.56 (d, J = 4.0 Hz, 1H), 7.64 (t, J = 7.2 Hz, 1H), 7.41 (d, J =7.6 Hz, 1H), 7.15 (t, J = 6.4 Hz, 1H), 6.64(s, 1H), 3.92-3.80 (m, 1H), 3.68 (s, 4H), 3.59-3.42 (m, 2H), 2.55-2.40 (m, 7H), 2.34 (s, 3H), 2.27(s, 3H), 1.47(d, J = 6.4 Hz, 3H). |

TABLE 1-continued

Selected compounds (A1-A100, B1-B8, C1-C39 and D1-D59) of the present invention

| Compd number | structure | method | ¹HNMR and MS |
|---|---|---|---|
| A76 | 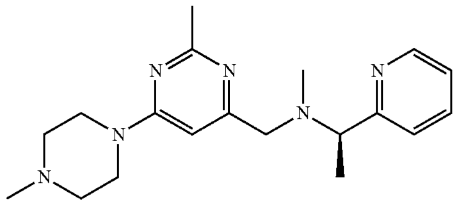 [SMILES: Cc1nc(CN(C)[C@H](C)c2ccccn2)cc(N2CCN(C)CC2)n1] | BB, C, AA | ¹H NMR (400 MHz, CDCl₃) δ 8.56 (d, J = 4.0 Hz, 1H), 7.70-7.56 (m, 1H), 7.41 (d, J = 7.6 Hz, 1H), 7.21-7.11 (m, 1H), 6.64(s, 1H), 3.92-3.80 (m, 1H), 3.68 (s, 4H), 3.59-3.42 (m, 2H), 2.55-2.40 (m, 7H), 2.34 (s, 3H), 2.27(s, 3H), 1.47(d, J = 6.4 Hz, 3H). |
| A77 | 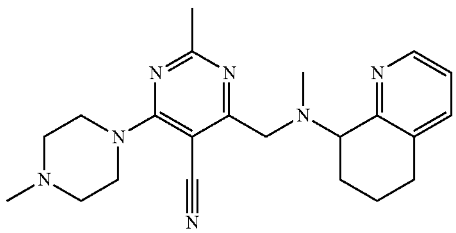 [SMILES: Cc1nc(CN(C)C2CCCc3cccnc32)c(C#N)c(N2CCN(C)CC2)n1] | M, AD | ¹H NMR (400 MHz, CDCl₃) δ 8.44 (d, J = 4.0 Hz, 1H), 7.35 (d, J = 7.2 Hz, 1H), 7.04 (dd, J = 8.0, 4.8 Hz, 1H), 4.15-4.08 (m, 1H), 4.08-3.93 (m, 6H), 2.87-2.75 (m, 1H), 2.75-2.62 (m, 1H), 2.55-2.45 (m, 7H), 2.33 (s, 3H), 2.23 (s, 3H), 2.08-1.90 (m, 3H), 1.77-1.64 (m, 1H). |
| A78 | 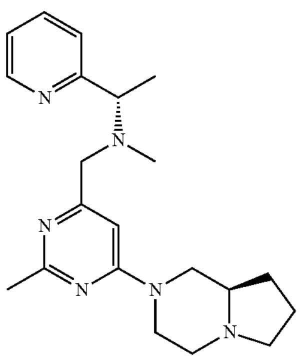 [SMILES: Cc1nc(CN(C)[C@@H](C)c2ccccn2)cc(N2CCN3CCC[C@@H]3C2)n1] | BB, C, AA | ¹H NMR (400 MHz, CDCl₃) δ 8.54 (d, J = 4.8 Hz, 1H), 7.67-7.57 (m, 1H), 7.40 (d, J = 8.0 Hz, 1H), 7.18-7.08 (m, 1H), 6.65 (s, 1H), 4.63-4.50 (m, 1H), 4.46-4.30 (m, 1H), 3.89 (q, J = 6.8 Hz, 1H), 3.56 (d, J = 15.6 Hz, 1H), 3.43 (d, J = 15.6 Hz, 1H), 3.17-3.07 (m, 2H), 3.07-2.95 (m, 1H), 2.69-2.58 (m, 1H), 2.45 (s, 3H), 2.26 (s, 3H), 2.23-2.11 (m, 2H), 2.00-1.71 (m, 4H), 1.54-1.39 (m, 4H). |
| A79 | 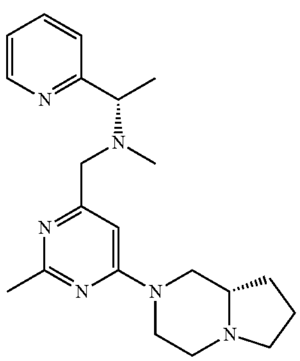 [SMILES: Cc1nc(CN(C)[C@@H](C)c2ccccn2)cc(N2CCN3CCC[C@H]3C2)n1] | BB, C, AA | ¹H NMR (400 MHz, CDCl₃) δ 8.57 (d, J = 4.8 Hz, 1H), 7.67-7.57 (m, 1H), 7.42 (d, J = 8.0 Hz, 1H), 7.18-7.10 (m, 1H), 6.70 (s, 1H), 4.63-4.50 (m, 1H), 4.46-4.30 (m, 1H), 3.91 (q, J = 6.8 Hz, 1H), 3.58 (d, J = 15.6 Hz, 1H), 3.45 (d, J = 15.6 Hz, 1H), 3.19-3.10 (m, 2H), 3.09-2.98 (m, 1H), 2.73-2.61 (m, 1H), 2.47 (s, 3H), 2.28 (s, 3H), 2.26-2.13 (m, 2H), 2.03-1.76 (m, 4H), 1.57-1.42 (m, 4H). |
| A80 | 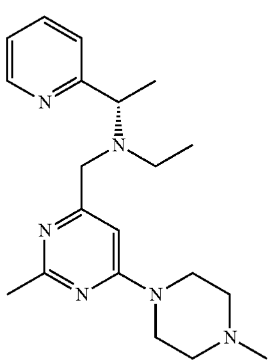 | BB, C, AA | ¹H NMR (400 MHz, CDCl₃) δ 8.53 (d, J = 4.8 Hz, 1H), 7.68-7.54 (m, 1H), 7.42 (d, J = 7.6 Hz, 1H), 7.16-7.06 (m, 1H), 6.72 (s, 1H), 4.08 (q, J = 6.8 Hz, 1H), 3.73-3.60 (m, 5H), 3.54 (d, J = 16.8 Hz, 1H), 2.75-2.63 (m, 1H), 2.60-2.51 (m, 1H), 2.49-2.40 (m, 7H), 2.33 (s, 3H), 1.44 (d, J = 6.8 Hz, 3H), 1.03 (t, J = 6.8 Hz, 3H). |

TABLE 1-continued

Selected compounds (A1-A100, B1-B8, C1-C39 and D1-D59) of the present invention

| Compd number | structure | method | ¹HNMR and MS |
| --- | --- | --- | --- |
| A81 | 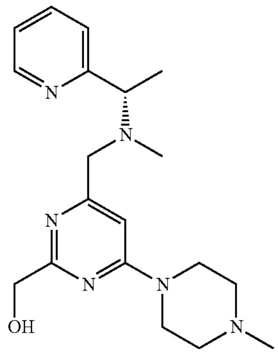 [SMILES: C[C@@H](c1ccccn1)N(C)Cc1cc(N2CCN(C)CC2)nc(CO)n1] | E, BB, AC | ¹H NMR (400 MHz, CDCl$_3$) δ 8.56 (s, 1H), 7.68-7.62 (m, 1H), 7.41 (d, J = 7.6 Hz, 1H), 7.18-7.14 (m, 1H), 6.69 (s, 1H), 4.55 (s, 2H), 3.95-3.83 (m, 2H), 3.77-3.65 (m, 4H), 3.60 (d, J = 16.0 Hz, 1H), 3.47 (d, J = 16.0 Hz, 1H), 2.55-2.42 (m, 4H), 2.35 (s, 3H), 2.29 (s, 3H), 1.47 (d, J = 6.8 Hz, 3H). MS (ESI/APCI) m/z 356.9 [M + H]⁺. |
| A82 | 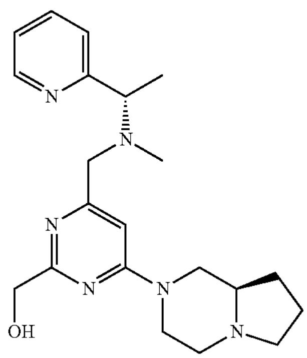 [SMILES: C[C@@H](c1ccccn1)N(C)Cc1cc(N2CCN3CCC[C@@H]3C2)nc(CO)n1] | E, BB, AC | ¹H NMR (400 MHz, CDCl$_3$) δ 8.51 (s, 1H), 7.61-7.57 (m, 1H), 7.35 (d, J = 7.6 Hz, 1H), 7.11-7.06 (m, 1H), 6.64 (s, 1H), 4.58-4.42 (m, 3H), 4.41-4.26 (m, 1H), 3.98-3.72 (m, 2H), 3.55 (d, J = 15.6 Hz, 1H), 3.41 (d, J = 15.6 Hz, 1H), 3.08-2.95 (m, 3H), 2.71-2.56 (m, 1H), 2.24 (s, 3H), 2.21-2.09 (m, 2H), 1.98-1.72 (m, 4H), 1.51-1.47 (m, 1H), 1.42 (d, J = 6.4 Hz, 3H). MS (ESI/APCI) m/z 382.9 [M + H]⁺. |
| A83 | 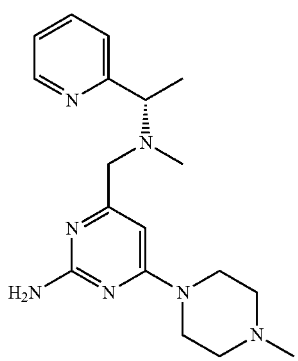 [SMILES: C[C@@H](c1ccccn1)N(C)Cc1cc(N2CCN(C)CC2)nc(N)n1] | F, BB, AC | ¹H NMR (400 MHz, CDCl$_3$) δ 8.55 (s, 1H), 7.68-7.58 (m, 1H), 7.47-7.37 (m, 1H), 7.18-7.09 (m, 1H), 6.22 (s, 1H), 4.66 (s, 2H), 3.95-3.76 (m, 1H), 3.61 (s, 4H), 3.44 (d, J = 15.2 Hz, 1H), 3.29 (d, J = 15.2 Hz, 1H), 2.45 (s, 4H), 2.33 (s, 3H), 2.26 (s, 3H), 1.46 (d, J = 6.8 Hz, 1H). |
| A84 | 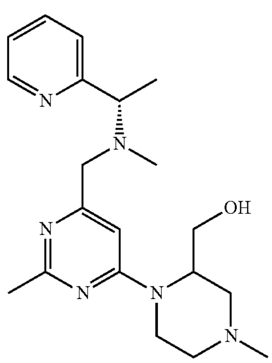 | C, BB, AA, AD | ¹H NMR (400 MHz, CDCl$_3$) δ 8.58 (s, 1H), 7.80-7.60 (m, 1H), 7.44 (d, J = 7.6 Hz, 1H), 7.25-7.05 (m, 2H), 4.66-4.27 (m, 2H), 4.10-3.88 (m, 3H), 3.87-3.60 (m, 3H), 3.41 (s, 1H), 3.15-3.00 (m, 1H), 2.94 (d, J = 10.8 Hz, 1H), 2.49 (d, J = 6.0 Hz, 3H), 2.40 (s, 3H), 2.35-2.30 (m, 4H), 2.20-2.10 (m, 1H), 1.60-1.50 (m, 3H). |

TABLE 1-continued

Selected compounds (A1-A100, B1-B8, C1-C39 and D1-D59) of the present invention

| Compd number | structure | method | ¹HNMR and MS |
|---|---|---|---|
| A85 | 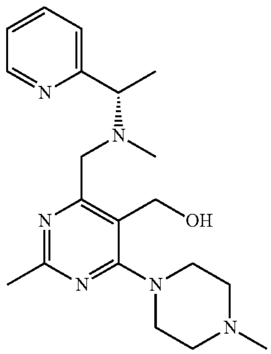 | BB, AH | ¹H NMR (400 MHz, CDCl₃) δ 8.62-8.56 (m, 1H), 7.73-7.63 (m, 1H), 7.31 (d, J = 8.0 Hz, 1H), 7.23-7.15 (m, 1H), 4.45-4.35 (m, 2H), 3.92 (q, J = 6.8 Hz,1H), 3.87 (d, J = 13.2 Hz, 1H), 3.79 (s, 4H), 3.68 (d, J = 13.2 Hz, 1H), 2.70 (s, 4H), 2.48 (s, 3H), 2.45 (s, 3H), 2.07 (s, 3H), 1.55 (d, J = 6.8 Hz, 3H). |
| A86 | 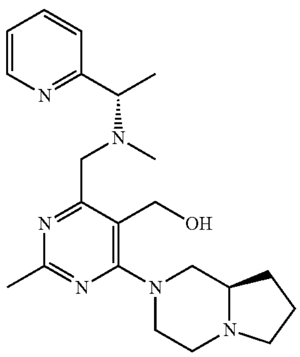 [SMILES: Cc1nc(CN(C)[C@@H](C)c2ccccn2)c(CO)c(N2CCN3CCC[C@@H]3C2)n1] | BB, AH | ¹H NMR (400 MHz, CDCl₃) δ 8.59 (d, J = 4.8 Hz, 1H), 7.73-7.63 (m, 1H), 7.31 (d, J = 8.0 Hz, 1H), 7.22-7.15 (m, 1H), 6.81 (br s, 1H), 4.48-4.32 (m, 3H), 4.28 (d, J = 12.0 Hz, 1H), 4.00-3.83 (m, 2H), 3.61 (d, J = 13.2 Hz, 1H), 3.20-3.05 (m, 3H), 2.79 (t, J = 11.4 Hz, 1H), 2.47 (s, 3H), 2.40-2.30 (m, 1H), 2.24-2.16 (m, 1 H), 2.15-2.10 (m, 1H), 2.08 (s, 3H), 1.92-1.83 (m, 2H), 1.80-1.74 (m, 2H), 1.55 (d, J = 6.8 Hz, 3H). |
| A87 | 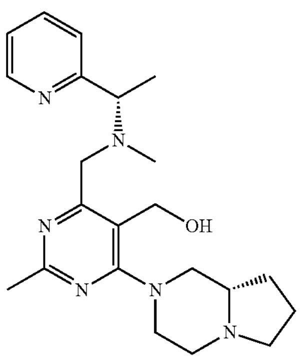 [SMILES: Cc1nc(CN(C)[C@@H](C)c2ccccn2)c(CO)c(N2CCN3CCC[C@H]3C2)n1] | BB, AH | ¹H NMR (400 MHz, CDCl₃) δ 8.60 (d, J = 4.8 Hz, 1H), 7.71-7.65 (m, 1H), 7.33 (d, J = 8.0 Hz, 1H), 7.22-7.15 (m, 1H), 6.80 (br s, 1H), 4.43-4.35 (m, 3H), 4.28 (d, J = 12.8 Hz, 1H), 3.93 (q, J = 6.8 Hz, 1H), 3.78 (d, J = 13.2 Hz, 1H), 3.70 (d, J = 13.2 Hz, 1H), 3.25-3.05 (m, 3H), 2.79 (t, J = 11.4 Hz, 1H), 2.47 (s, 3H), 2.40-2.30 (m, 1H), 2.24-2.16 (m, 1 H), 2.15-2.10 (m, 1H), 2.08 (s, 3H), 1.93-1.83 (m, 2H), 1.80-1.72 (m, 2H), 1.55 (d, J = 6.8 Hz, 3H). |
| A88 | 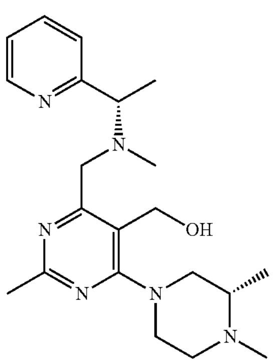 | BB, AH | ¹H NMR (400 MHz, CDCl₃) δ 8.60 (d, J = 5.2 Hz, 1H), 7.72-7.63 (m, 1H), 7.32 (d, J = 8.0 Hz, 1H), 7.22-7.16 (m, 1H), 4.48-4.35 (m, 2H), 4.21-4.13 (m, 1H), 4.12-4.04 (m, 1H), 3.93 (q, J = 6.8 Hz, 1H), 3.86 (d, J = 12.8 Hz, 1H), 3.63 (d, J = 13.2 Hz, 1H), 3.28-3.16 (m, 1H), 2.91-2.84 (m, 1H), 2.84-2.77 (m, 1H), 2.48 (s, 3H), 2.41-2.35 (m, 1 H), 2.33 (s, 3H), 2.27-2.21 (m, 1H), 2.08 (s, 3H), 1.55 (d, J = 6.8 Hz, 3H), 1.13 (d, J = 6.4 Hz, 3H). |

TABLE 1-continued

Selected compounds (A1-A100, B1-B8, C1-C39 and D1-D59) of the present invention

| Compd number | structure | method | $^1$HNMR and MS |
|---|---|---|---|
| A89 | 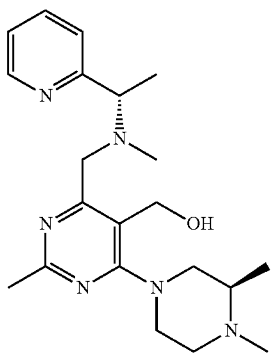 | BB, AH | $^1$H NMR (400 MHz, CDCl$_3$) δ 8.60 (s, 1H), 7.74-7.64 (m, 1H), 7.38-7.30 (m, 1H), 7.22-7.14 (m, 1H), 6.75 (br s, 1H), 4.40 (s, 2H), 4.16 (d, J = 13.2 Hz, 1H), 4.08 (d, J = 13.2 Hz, 1H), 3.97-3.85 (m, 1H), 3.80 (d, J = 13.2 Hz, 1H), 3.68 (d, J = 13.2 Hz, 1H), 3.20 (t, J = 12.8 Hz, 1H), 2.92-2.83 (m, 1H), 2.82-2.75 (m, 1H), 2.48 (s, 3H), 2.42-2.36 (m, 1 H), 2.33 (s, 3H), 2.23 (s, 1H), 2.08 (s, 3H), 1.55 (d, J = 6.8 Hz, 3H), 1.13 (d, J = 5.6 Hz, 3H). |
| A90 | 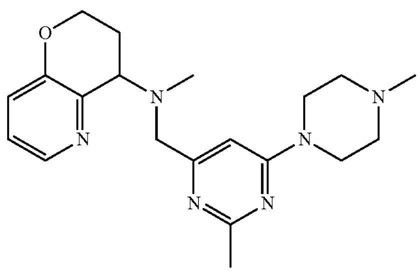 [SMILES: Cc1nc(CN(C)C2CCOc3cccnc32)cc(N2CCN(C)CC2)n1] | D, BC | $^1$H NMR (400 MHz, CDCl$_3$) δ 8.21 (s, 1H), 7.08 (s, 2H), 6.88 (s, 1H), 4.39 (s, 1H), 4.17 (s, 1H), 4.06 (s, 1H), 3.81-3.60 (m, 6H), 2.55-2.40 (m, 7H), 2.38 (s, 3H), 2.33(s, 3H), 2.26 (s, 1H), 2.13 (s, 1H). |
| A91 | 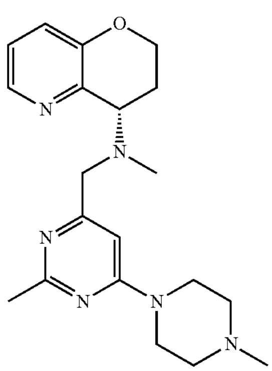 | C, BB, AA | $^1$H NMR (400 MHz, CDCl$_3$) δ 8.22 (s, 1H), 7.09 (s, 2H), 6.89 (s, 1H), 4.44-4.37 (m, 1H), 4.17 (t, J = 8.4 Hz, 1H), 4.06 (t, J = 6.4 Hz, 1H), 3.75-3.63 (m, 6H), 2.47 (s, 7H), 2.39 (s, 3H), 2.33 (s, 3H), 2.30-2.21 (m, 1H), 2.18-2.10 (m, 1H). |
| A92 | 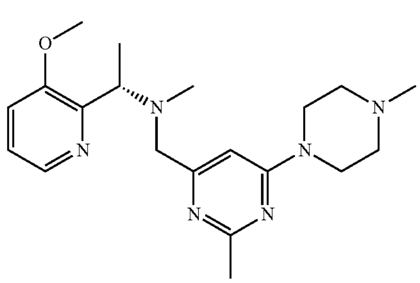 [SMILES: COc1cccnc1[C@H](C)N(C)Cc1cc(N2CCN(C)CC2)nc(C)n1] | C, BB, AA | $^1$H NMR (400 MHz, CDCl$_3$) δ 8.19 (d, J = 2.4 Hz, 1H), 7.12 (s, 2H), 6.59 (s, 1H), 4.50--4.46 (m, 1H), 3.79 (s, 3H), 3.66 (s, 4H), 3.58-3.47 (m, 2H), 2.46 (s, 7H), 2.32 (s, 3H), 2.26 (s, 3H), 1.47-1.45 (m, 3H). |

TABLE 1-continued

Selected compounds (A1-A100, B1-B8, C1-C39 and D1-D59) of the present invention

| Compd number | structure | method | ¹HNMR and MS |
|---|---|---|---|
| A93 | 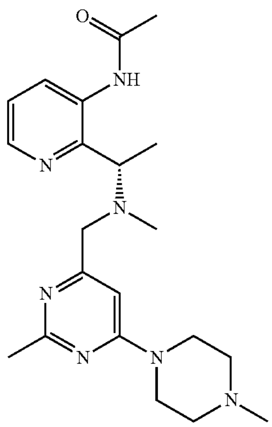 | C, BF, BB, AA | ¹H NMR (400 MHz, CDCl₃) δ 11.18 (s, 1H), 8.49 (d, J = 8.0 Hz, 1H), 8.23 (d, J = 4.8 Hz, 1H), 7.24-7.12 (m, 1H), 6.19 (s, 1H), 4.13-4.00 (m, 1H), 3.82-3.72 (m, 1H), 3.73-3.60 (m, 5H), 2.54-2.42 (m, 7H), 2.38-2.26 (m, 6H), 2.13 (s, 3H), 1.48 (d, J = 6.8 Hz, 3H). MS (ESI/APCI) m/z 398.1 [M + H]⁺· |
| A94 | 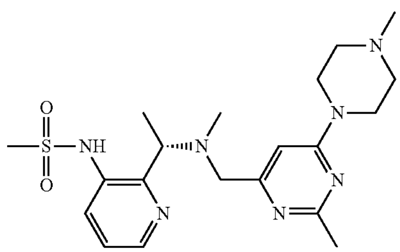 | C, BG, BB, AA | ¹H NMR (400 MHz, CDCl₃) δ 8.21 (d, J = 4.8 Hz, 1H), 7.82 (d, J = 8.0 Hz, 1H), 7.18-7.13 (m, 1H), 6.39 (s, 1H), 4.12-3.98 (m, 1H), 3.74-3.61 (m, 4H), 3.52(s, 2H), 2.98(s, 3H), 2.50-2.37 (m, 7H), 2.28(s, 3H), 2.16(s, 3H), 1.48 (d, J = 6.4 Hz, 3H). |
| A95 | 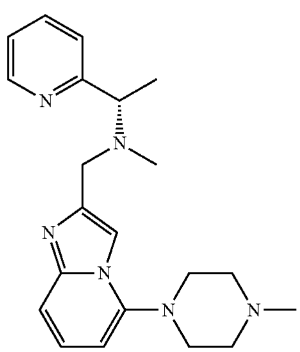 [SMILES: C[C@@H](c1ccccn1)N(C)Cc1cn2c(N3CCN(C)CC3)cccc2n1] | N, BB, AK | ¹H NMR (400 MHz, CDCl₃) δ 8.56 (d, J = 4.0 Hz, 1H), 7.72-7.62 (m, 1H), 7.54 (d, J = 7.6 Hz, 1H), 7.46 (s, 1H), 7.31 (d, J = 8.8 Hz, 1H), 7.20-7.11 (m, 2H), 6.26 (d, J = 7.2 Hz, 1H), 3.97-3.81 (m, 2H), 3.72 (d, J = 14.0 Hz, 1H), 3.14 (s, 4H), 2.67 (s, 4H), 2.41 (s, 3H), 2.32 (s, 3H), 1.50 (d, J = 6.4 Hz, 3H). |
| A96 | 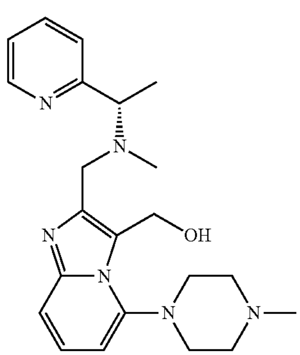 [SMILES: C[C@@H](c1ccccn1)N(C)Cc1nc2cccc(N3CCN(C)CC3)n2c1CO] | N, BB, AK | ¹H NMR (400 MHz, CDCl₃) δ 8.57 (s, 1H), 7.73-7.58 (m, 1H), 7.40 (d, J = 7.6 Hz, 1H), 7.29 (d, J = 8.8 Hz, 1H), 7.20-7.12 (m, 1H), 7.12-7.04 m, 1H), 6.40 (d, J = 7.2 Hz, 1H), 5.24-5.11 (m, 2H), 3.95-3.85 (m, 1H), 3.84-3.73 (m, 2H), 3.73-3.62 (m, 1H), 3.42-3.29 (m, 2H), 3.00-2.86 (m, 4H), 2.50-2.42 (m, 2H), 2.39 (s, 3H), 2.13 (s, 3H), 1.52 (d, J = 6.4 Hz, 3H). |

TABLE 1-continued

Selected compounds (A1-A100, B1-B8, Cl-C39 and D1-D59) of the present invention

| Compd number | structure | method | ¹HNMR and MS |
|---|---|---|---|
| A97 | 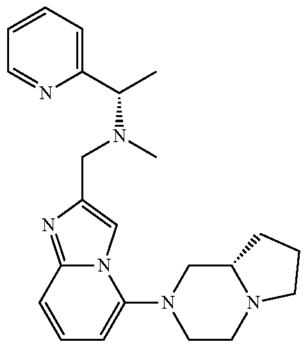 [SMILES: C[C@@H](c1ccccn1)N(C)Cc1cn2c(N3CCN4CCC[C@H]4C3)cccc2n1] | N, BB, AK | ¹H NMR (400 MHz, CDCl₃) δ 8.56 (d, J = 2.8Hz, 1H), 7.68-7.63 (m, 1H), 7.54 (d, J = 8.0 Hz, 1H), 7.48 (s, 1H), 7.31 (d, J = 8.8 Hz, 1H), 7.21-7.08 (m, 2H), 6.29 (d, J = 6.8 Hz, 1H), 4.00-3.82 (m, 2H), 3.80-3.68 (m, 1H), 3.59-3.49 (m, 1H), 3.45-3.37(m, 1H), 3.22-3.11 (m, 2H), 3.00-2.89 (m, 1H), 2.70-2.48 (m, 2H), 2.40-2.25 (m, 5H), 1.93-1.75 (m, 3H), 1.58-1.40 (m, 4H). |
| A98 | 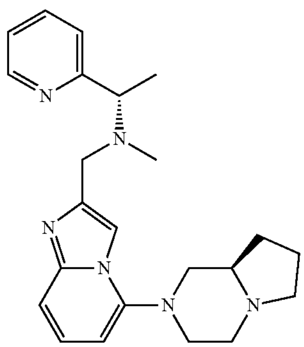 [SMILES: C[C@@H](c1ccccn1)N(C)Cc1cn2c(N3CCN4CCC[C@@H]4C3)cccc2n1] | N, BB, AK | ¹H NMR (400 MHz, CDCl₃) δ 8.56 (d, J = 4.0 Hz, 1H), 7.73-7.61 (m, 1H), 7.54 (d, J = 7.6 Hz, 1H), 7.46 (s, 1H), 7.31 (d, J = 8.8 Hz, 1H), 7.18-7.06 (m, 2H), 6.28 (d, J = 6.8 Hz, 1H) 3.93-3.81 (m, 3H), 3.72 (d, J = 14.0 Hz, 1H), 3.58-3.48 (m, 1H), 3.47-3.38 (m, 1H), 3.22-3.11 (m, 2H), 3.00-2.87 (m, 1H), 2.66-2.59 (m, 1H), 2.56-2.51 (m, 1H), 2.36-2.26 (m, 5H), 1.93-1.76 (m, 3H), 1.57-1.44 (m, 4H). |
| A99 | 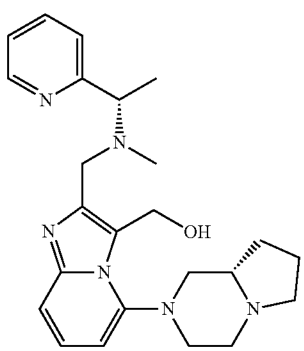 [SMILES: C[C@@H](c1ccccn1)N(C)Cc1nc2cccc(N3CCN4CCC[C@H]4C3)n2c1CO] | N, BB, AK | ¹H NMR (400 MHz, CDCl₃) δ 8.57 (s, 1H), 7.80-7.60 (m, 1H), 7.48-7.36 (m, 1H), 7.35-7.28 (m, 1H), 7.20-7.16 (m, 1H), 7.15-7.06 (m, 1H), 6.45-6.30(m, 1H), 6.00 (brs, 1H), 5.36-5.00 (m, 2H), 4.00-3.70 (m, 3H), 3.55-3.35 (m, 2H), 3.20-3.07 (m, 2H), 2.97-2.80 (m, 1H), 2.70-2.50 (m, 2H), 2.34-2.21 (m, 2H), 2.15 (d, J = 3.6 Hz, 3H), 1.95-1.70 (m, 3H), 1.56-1.40 (m, 4H). |
| A100 | 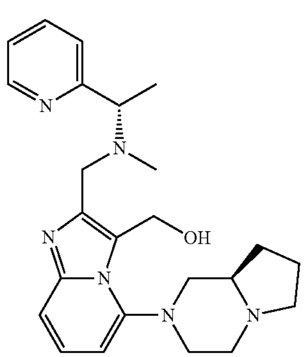 [SMILES: C[C@@H](c1ccccn1)N(C)Cc1nc2cccc(N3CCN4CCC[C@@H]4C3)n2c1CO] | N, BB, AK | ¹H NMR (400 MHz, CDCl₃) δ 8.59 (s, 1H), 7.69 (d, J = 6.4 Hz, 1H), 7.42 (d, J =6.0 Hz, 1H), 7.33 (d, J = 8.8 Hz, 1H), 7.21-7.14 (m, 1H), 7.14-7.06 (m, 1H), 6.46 (d, J = 6.4 Hz, 1H), 5.30-5.07 (m, 2H), 3.99-3.72 (m, 3H), 3.53 (d, J = 9.6 Hz, 1H), 3.44 (d, J = 10.8 Hz, 1H), 3.25-3.09 (s, 2H), 3.00-2.83 (m, 1H), 2.71-2.53 (m, 2H), 2.47-2.26 (m, 2H), 2.17 (s, 3H), 2.03-1.84 (m, 3H), 1.60-1.45 (m, 4H). |

TABLE 1-continued

Selected compounds (A1-A100, B1-B8, C1-C39 and D1-D59) of the present invention

| Compd number | structure | method | ¹HNMR and MS |
|---|---|---|---|
| B1 | 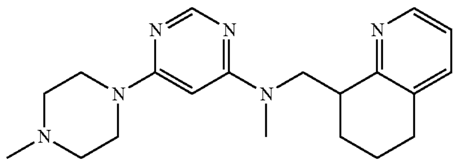 [SMILES: CN1CCN(c2cc(N(C)CC3CCCc4cccnc43)ncn2)CC1] | A, AA | ¹H NMR (400 MHz, CDCl₃) δ 8.39 (d, J = 4.6 Hz, 1H), 8.22 (s, 1H), 7.37 (d, J = 7.8 Hz, 1H), 7.04 (dd, J = 7.6, 4.8 Hz, 1H), 5.80 (s, 1H), 4.00-3.82 (m, 1H), 3.66-3.56 (m, 4H), 3.31-3.23 (m, 1H), 3.11 (s, 3H), 2.83-2.70 (m, 2H), 2.48 (t, J = 5.2 Hz, 4H), 2.33 (s, 3H), 2.03-1.91 (m, 1H), 1.91-1.85 (m, 2H), 1.76-1.70 (m, 2H). |
| B2 | 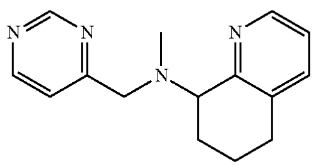 [SMILES: CN(Cc1ccncn1)C1CCCc2cccnc21] | A, AA, AG | ¹H NMR (400 MHz, CDCl₃) δ 9.06 (s, 1H), 8.65 (d, J = 4.8 Hz, 1H), 8.50 (s, 1H), 7.80 (d, J = 4.4 Hz, 1H), 7.37 (d, J = 7.2 Hz, 1H), 7.08-7.05 (m, 1H), 4.04-4.01 (m, 1H), 3.82-3.72 (m, 2H), 2.82-2.78 (m, 1H), 2.73-2.69 (m, 1H), 2.39 (s, 3H), 2.13 (s, 1H), 2.03 (s, 1H), 1.97-1.88 (m, 1H), 1.72 (s, 1H). MS (ESI/APCI) m/z 254.9 [M + H]⁺. |
| B3 | 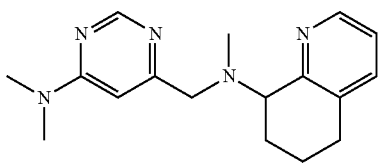 [SMILES: CN(C)c1cc(CN(C)C2CCCc3cccnc32)ncn1] | A, AA | ¹H NMR (400 MHz, CDCl₃) δ 8.49 (s, 2H), 7.36 (s, 1H), 7.06 (s, 2H), 4.04 (s, 1H), 3.67 (s, 2H), 3.12 (s, 6H), 2.81 (s, 1H), 2.71-2.67 (m, 1H), 2.40 (s, 3H), 2.16-2.12 (m, 1H), 2.04-2.01 (m, 1H), 1.94-1.92 (m, 1H), 1.69 (s, 1H). |
| B4 | 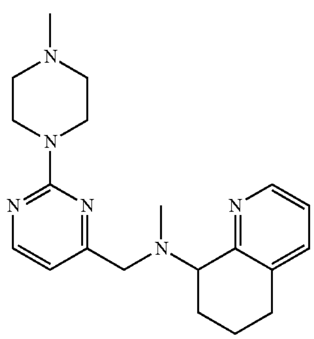 [SMILES: CN1CCN(c2nccc(CN(C)C3CCCc4cccnc43)n2)CC1] | L, AE | ¹H NMR (400 MHz, CDCl₃) δ 8.50 (d, J = 4.4 Hz, 1H), 8.24 (d, J = 5.2 Hz, 1H), 7.36 (d, J = 8.0 Hz, 1H), 7.06 (dd, J = 7.6, 4.8 Hz, 1H), 6.93 (d, J = 4.8 Hz, 1H), 4.06-3.98 (m, 1H), 3.82 (t, J = 5.0 Hz, 4H), 3.59 (q, J = 13.8 Hz, 2H), 2.87-2.77 (m, 1H), 2.74-2.66 (m, 1H), 2.45 (t, J = 5.2 Hz, 4H), 2.38 (s, 3H), 2.33 (s, 3H), 2.14-1.99 (m, 2H), 1.98-1.89 (m, 1H), 1.73-1.66 (m, 1H). |
| B5 | 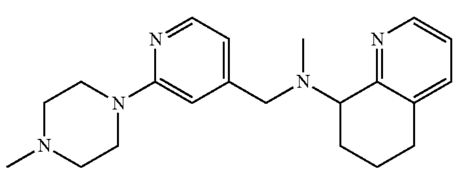 | AF | ¹H NMR (400 MHz, CDCl₃) δ 8.51 (d, J = 4.0 Hz, 1H), 8.07 (d, J = 5.2 Hz, 1H), 7.35 (d, J = 7.2 Hz, 1H), 7.06 (dd, J = 7.2, 4.8 Hz, 1H), 6.86 (s, 1H), 6.67 (d, J = 4.8 Hz, 1H), 3.99-3.96 (m, 1H), 3.67-3.64 (m, 1H), 3.56 (s, 4H), 3.52-3.48 (m, 1H), 2.84-2.78 (m, 1H), 2.71-2.67 (m, 1H), 2.51 (t, J = 4.6 Hz, 4H), 2.34 (s, 3H), 2.31 (s, 3H), 2.04-2.02 (m, 2H), 1.96-1.90 (m, 1H), 1.73-1.69 (m, 1H). |
| B6 | 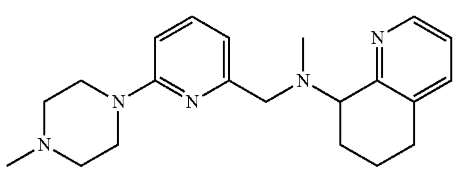 | AF | ¹H NMR (400 MHz, CDCl₃) δ 8.51 (d, J = 4.4 Hz, 1H), 7.43 (t, J = 7.8 Hz, 1H), 7.34 (d, J = 7.6 Hz, 1H), 7.05 (d, J = 4.8 Hz, 1H), 7.00 (d, J = 7.2 Hz, 1H), 6.46 (d, J = 8.4 Hz, 1H), 4.03 (s, 1H), 3.64 (q, J= 15.0 Hz, 2H), 3.53 (s, 4H), 2.82-2.78 (m, 1H), 2.71-2.66 (m, 1H), 2.50 (t, J = 4.4 Hz, 5H), 2.37 (s, 3H), 2.33 (s, 3H), 2.07 (s, 1H), 2.02-2.98 (m, 1H), 1.95-1.92 (m, 1H), 1.65 (s, 1H). |
| B7 | 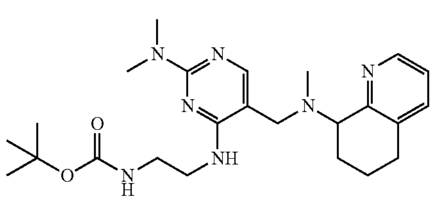 [SMILES: CN(C)c1ncc(CN(C)C2CCCc3cccnc32)c(NCCNC(=O)OC(C)(C)C)n1] | WO2009121063 | ¹H NMR (400 MHz, CDCl₃) δ 8.63 (s, 1H), 8.47 (d, J = 4.8 Hz, 1H), 7.61 (s, 1H), 7.40 (d, J = 7.6 Hz, 1H), 7.14-7.04 (m, 1H), 6.30 (s, 1H), 4.08-3.96 (m, 1H), 3.75-3.59 (m, 2H), 3.49-3.32 (m, 3H), 3.24 (d, J = 12.8 Hz, 1H), 3.13 (s, 6H), 2.86-2.68 (m, 2H), 2.19 (s, 3H), 2.14-2.08 (m, 1H), 2.06-1.99 (m, 1H), 1.90-1.79 (m, 1H), 1.77-1.66 (m, 1H), 1.37 (s, 9H). |

TABLE 1-continued

Selected compounds (A1-A100, B1-B8, C1-C39 and D1-D59) of the present invention

| Compd number | structure | method | ¹HNMR and MS |
|---|---|---|---|
| B8 | 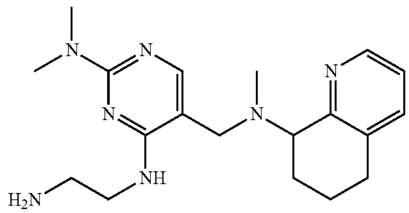 [SMILES: CN(C)c1ncc(CN(C)C2CCCc3cccnc32)c(NCCN)n1] | WO20091 21063 | ¹H NMR (400 MHz, CDCl₃) δ 13.27 (s, 1H), 9.35 (s, 1H), 8.59 (s, 1H), 8.40 (s, 3H), 8.12 (s, 1H), 7.76 (d, J = 7.2 Hz, 1H), 7.44 (s, 1H), 4.91 (s, 1H), 4.61 (d, J = 14.0 Hz, 1H), 4.31 (d, J = 13.2 Hz, 2H), 3.86-3.72 (m, 3H), 3.21 (s, 6H), 3.10 (s, 2H), 2.86-2.77 (m, 2H), 2.69 (s, 3H), 2.42 (s, 1H), 2.09-1.99 (m, 2H). |
| C1 | 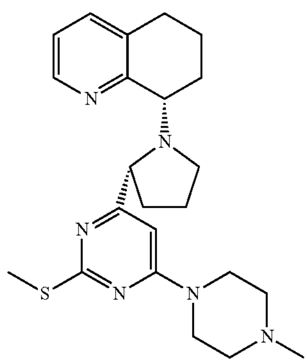 | J, BC | ¹H NMR (400 MHz, CDCl₃) δ 8.39 (d, J = 4.4 Hz, 1H), 7.30-7.26 (m, 1H), 7.07-6.95 (m, 2H), 4.05-3.93 (m, 2H), 3.74-3.61 (m, 4H), 3.01-2.90 (m, 1H), 2.82-2.72 (m, 2H), 2.72-2.64 (m, 1H), 2.48 (s, 3H), 2.44 (t, J = 5.0 Hz, 4H), 2.32 (s, 3H), 2.30-2.24 (m, 1H), 2.12-2.01 (m, 1H), 2.00-1.90 (m, 2H), 1.83-1.69 (m, 4H). |
| C2 | 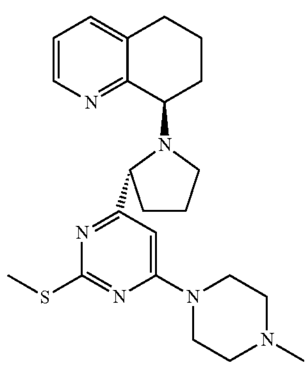 | J, BC | ¹H NMR (400 MHz, CDCl₃) δ 8.37 (d, J = 4.4 Hz, 1H), 7.30 (d, J = 7.6 Hz, 1H), 7.04-6.96 (m, 1H), 6.57 (s, 1H), 4.65-4.53 (m, 1H), 4.06-3.98 (m, 1H), 3.72-3.58 (m, 4H), 2.98-2.89 (m, 1H), 2.84-2.73 (m, 1H), 2.69-2.58 (m, 2H), 2.51-2.44 (m, 7H), 2.34 (s, 3H), 2.33-2.26 (m, 1H), 2.00-1.90 (m, 3H), 1.66-1.55 (m, 1H). |
| C3 | 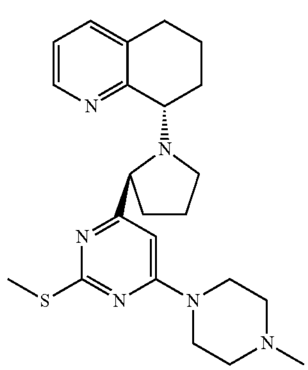 | J, BC | ¹H NMR (400 MHz, CDCl₃) δ 8.38 (d, J = 4.4 Hz, 1H), 7.30 (d, J = 7.6 Hz, 1H), 7.04-6.97 (m, 1H), 6.57 (s, 1H), 4.57 (s, 1H), 4.01 (s, 1H), 3.67 (s, 4H), 2.98-2.90 (m, 1H), 2.85-2.74 (m, 1H), 2.69-2.58 (m, 2H), 2.51-2.45 (m, 7H), 2.35 (s, 3H), 2.33-2.23 (m, 2H), 1.95 (s, 3H), 1.72 (s, 3H). |

TABLE 1-continued

Selected compounds (A1-A100, B1-B8, C1-C39 and D1-D59) of the present invention

| Compd number | structure | method | ¹HNMR and MS |
|---|---|---|---|
| C4 | 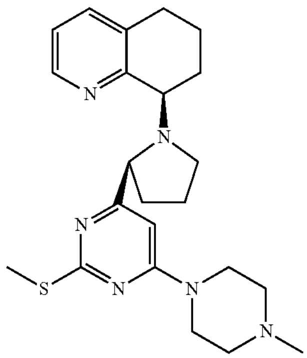 | J, BC | ¹H NMR (400 MHz, CDCl₃) δ 8.39 (d, J = 4.4 Hz, 1H), 7.31-7.27 (m, 1H), 7.06-6.96 (m, 2H), 3.98 (s, 2H), 3.68 (s, 4H), 2.96 (s, 1H), 2.83-2.73 (m, 2H), 2.72-2.63 (m, 1H), 2.49 (s, 3H), 2.47-2.42 (m, 4H), 2.32 (s, 5H), 2.11-2.01 (s, 1H), 2.01-1.90 (m, 2H), 1.82-1.74 (m, 3H). |
| C5 | 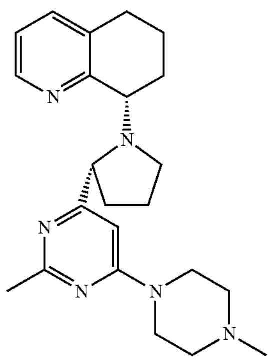 | J, BA | ¹H NMR (400 MHz, CDCl₃) δ 8.39 (d, J = 4.4 Hz, 1H), 7.30-7.26 (m, 1H), 7.11 (s, 1H), 7.02-6.92 (m, 1H), 4.06-3.92 (m, 2H), 3.67 (s, 4H), 3.03-2.89 (m, 1H), 2.81-2.62 (m, 3H), 2.45 (s, 7H), 2.32 (s, 3H), 2.30-2.23 (m, 1H), 2.10-2.01 (m, 3H), 2.00-1.87 (m, 3H), 1.71-1.60 (m, 1H). |
| C6 | 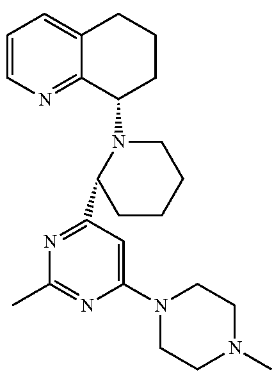 [SMILES: Cc1nc([C@H]2CCCCN2[C@H]2CCCc3cccnc32)cc(N2CCN(C)CC2)n1] | J, BC | ¹H NMR (400 MHz, CDCl₃) δ 8.53-8.47 (m, 1H), 7.30 (d, J = 7.2 Hz, 1H), 7.05-6.95 (m, 2H), 4.08-3.97 (m, 1H), 3.69 (s, 4H), 3.58 (d, J = 10.4 Hz, 1H), 2.77-2.65 (m, 1H), 2.64-2.56 (m, 1H), 2.49 (s, 3H), 2.43 (s, 4H), 2.38-2.34 (m, 1H), 2.30 (s, 3H), 1.97-1.85 (m, 4H), 1.83-1.56 (m, 4H), 1.55-1.45 (m, 2H), 1.40-1.28 (m, 1H). |
| C7 | 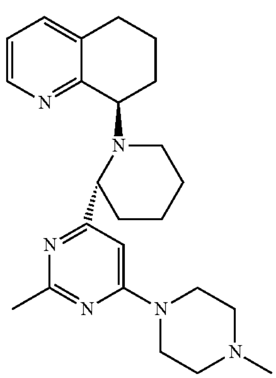 [SMILES: Cc1nc([C@H]2CCCCN2[C@@H]2CCCc3cccnc32)cc(N2CCN(C)CC2)n1] | J, BC | ¹H NMR (400 MHz, CDCl₃) δ 8.45 (d, J = 4.4 Hz, 1H), 7.22 (d, J = 7.6 Hz, 1H), 7.01-6.91 (m, 1H), 6.55 (s, 1H), 4.54 (d, J = 10.8 Hz, 1H), 3.91 (t, J = 8.6 Hz, 1H), 3.63 (s, 4H), 2.75-2.60 (m, 2H), 2.57-2.53 (m, 1H), 2.51 (s, 3H), 2.48-2.44 (m, 4H), 2.34 (s, 3H), 2.20-2.02 (m, 2H), 1.93-1.84 (m, 2H), 1.82-1.67 (m, 2H), 1.67-1.44 (m, 4H), 1.38-1.28 (m, 1H). |

TABLE 1-continued

Selected compounds (A1-A100, B1-B8, C1-C39 and D1-D59) of the present invention

| Compd number | structure | method | ¹HNMR and MS |
|---|---|---|---|
| C8 | 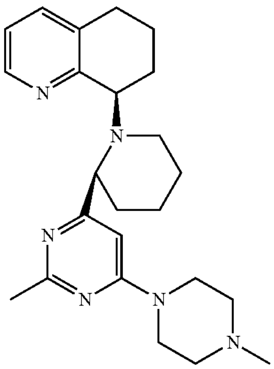 [SMILES: Cc1nc([C@@H]2CCCCN2[C@@H]2CCCc3cccnc32)cc(N2CCN(C)CC2)n1] | J, BC | ¹H NMR (400 MHz, CDCl₃) δ 8.53 (d, J = 4.8 Hz, 1H), 7.38 (d, J = 7.6 Hz, 1H), 7.22 (s, 1H), 7.14-7.08 (m, 1H), 4.08-4.00 (m, 1H), 3.88-3.61 (m, 5H), 2.76-2.70 (m, 1H), 2.68-2.62 (m, 1H), 2.57-2.53 (m, 1H), 2.52-2.47 (m, 7H), 2.35 (s, 3H), 2.08-1.92 (m, 4H), 1.84-1.75 (m, 2H), 1.70-1.62 (m, 2H), 1.62-1.50 (m, 2H), 1.33-1.26 (m, 1H). |
| C9 | 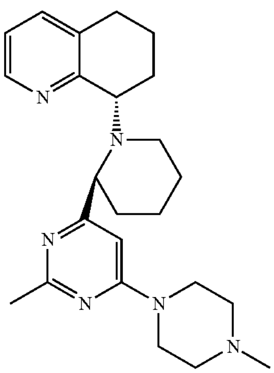 [SMILES: Cc1nc([C@@H]2CCCCN2[C@H]2CCCc3cccnc32)cc(N2CCN(C)CC2)n1] | J, BC | ¹H NMR (400 MHz, CDCl₃) δ 8.45 (d, J = 4.8 Hz, 1H), 7.22 (d, J = 7.6 Hz, 1H), 6.98-6.91 (m, 1H), 6.55 (s, 1H), 4.53 (d, J = 10.8 Hz, 1H), 3.91 (t, J = 8.4 Hz, 1H), 3.63 (s, 4H), 2.75-2.67 (m, 1H), 2.67-2.59 (m, 1H), 2.55 (s, 1H), 2.51 (s, 3H), 2.46 (d, J = 4.6 Hz, 4H), 2.34 (s, 3H), 2.13-2.05 (m, 1H), 1.95-1.85 (m, 4H), 1.80-1.68 (m, 2H), 1.68-1.59 (m, 1H), 1.60-1.50 (m, 2H), 1.53-1.40 (m, 1H). |
| C10 | 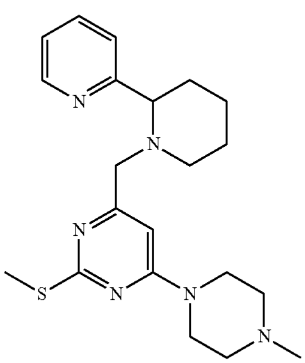 | E, AC | ¹H NMR (400 MHz, CDCl₃) δ 8.50 (d, J = 4.4 Hz, 1H), 7.67-7.55 (m, 1H), 7.44 (d, J = 8.0 Hz, 1H), 7.16-7.07 (m, 1H), 6.45 (s, 1H), 3.70 (s, 4H), 3.50-3.42 (m, 2H), 3.09-3.02 (m, 2H), 2.50-2.45 (m, 7H), 2.45 (s, 3H), 2.36 (s, 2H), 1.90-1.25 (m, 5H). |
| C11 | 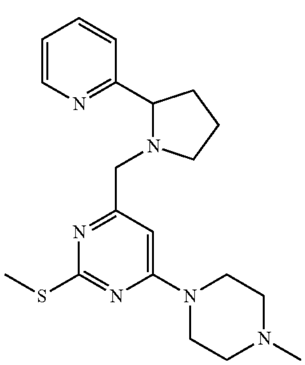 | E, AC | ¹H NMR (400 MHz, CDCl₃) δ 8.53 (d, J = 4.0 Hz, 1H), 7.67-7.57 (m, 1H), 7.46 (d, J = 8.0 Hz, 1H), 7.17-7.06 (m, 1H), 6.32 (s, 1H), 3.73-3.64 (m, 6H), 3.36-3.31 (m, 2H), 2.47-1.95 (m, 15H). |

TABLE 1-continued

Selected compounds (A1-A100, B1-B8, C1-C39 and D1-D59) of the present invention

| Compd number | structure | method | ¹HNMR and MS |
|---|---|---|---|
| C12 | 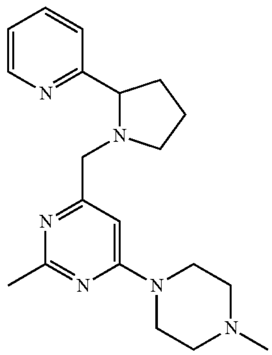 | C, AA | ¹H NMR (400 MHz, CDCl₃) δ 8.52 (d, J = 4.0 Hz, 1H), 7.65-7.54 (m, 1H), 7.45 (d, J = 8.0 Hz, 1H), 7.16-7.05 (m, 1H), 6.45 (s, 1H), 3.72-3.68 (m, 2H), 3.63(s, 4H), 3.40-3.31 (m, 2H), 2.46-2.40 (m, 8H), 2.34-2.29 (m, 4H), 2.05-1.95 (m, 1H), 1.93-1.90 (m, 2H). |
| C13 | 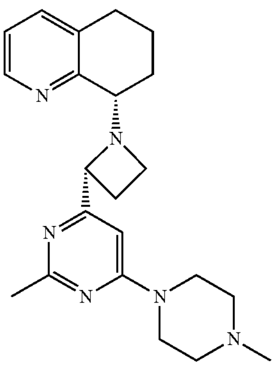 [SMILES: Cc1nc([C@H]2CCN2[C@H]2CCCc3cccnc32)cc(N2CCN(C)CC2)n1] | J, BA | ¹H NMR (400 MHz, CDCl₃) δ 7.94 (d, J = 4.8 Hz, 1H), 7.26 (s, 1H), 6.90-6.81 (m, 1H), 5.84 (s, 1H), 4.66 (t, J = 8.6 Hz, 1H), 3.58 (s, 1H), 3.48-3.42 (m, 1H), 3.41-3.28 (m, 4H), 3.13 (q, J = 8.2 Hz, 1H), 2.89-2.72 (m, 2H), 2.52-2.43 (m, 1H), 2.40 (s, 3H), 2.39-2.33 (m, 4H), 2.34-2.30 (m, 4H), 2.13-2.05 (m, 1H), 1.92-1.83 (m, 1H), 1.75-1.65 (m, 2H). |
| C14 | 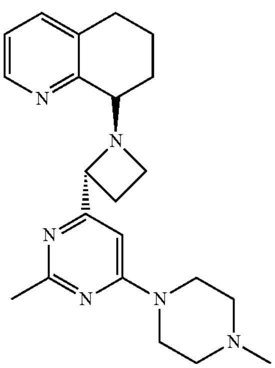 | J, BA | ¹H NMR (400 MHz, CDCl₃) δ 8.39 (d, J = 4.4 Hz, 1H), 7.39 (d, J = 7.6 Hz, 1H), 7.13-7.07 (m, 1H), 6.81 (s, 1H), 4.25 (t, J = 8.2 Hz, 1H), 3.69 (s, 4H), 3.66-3.58 (m, 2H), 3.27 (t, J = 8.0 Hz, 1H), 2.88-2.75 (m, 1H), 2.75-2.62 (m, 1H), 2.50 (s, 3H), 2.49-2.43 (m, 4H), 2.42-2.36 (m, 1H), 2.34 (s, 3H), 2.04-1.89 (m, 2H), 1.78-1.71 (m, 1H), 1.66-1.56 (m, 1H), 1.53-1.42 (m, 1H). |
| C15 | 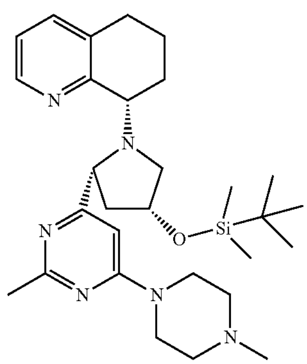 [SMILES: Cc1nc([C@H]2C[C@@H](O[Si](C)(C)C(C)(C)C)CN2[C@H]2CCCc3cccnc32)cc(N2CCN(C)CC2)n1] | J, BA | ¹H NMR (400 MHz, CDCl₃) δ 8.30 (d, J = 4.8 Hz, 1H), 7.23 (s, 1H), 7.19 (s, 1H), 7.00-6.93 (m, 1H), 4.36 (s, 1H), 4.05 (s, 1H), 3.94-3.88 (m, 1H), 3.66 (s, 4H), 3.07-3.01 (m, 1H), 2.99-2.93 (m, 1H), 2.79-2.63 (m, 2H), 2.61-2.51 (m, 1H), 2.45-2.42 (m, 7H), 2.32 (s, 3H), 2.12-2.06 (m, 1H), 1.93-1.88 (m, 2H), 1.81-1.75 (m, 1H), 1.71-1.62 (m, 1H), 0.79 (s, 9H), 0.01 (s, 6H). |

TABLE 1-continued

Selected compounds (A1-A100, B1-B8, C1-C39 and D1-D59) of the present invention

| Compd number | structure | method | ¹HNMR and MS |
|---|---|---|---|
| C16 | 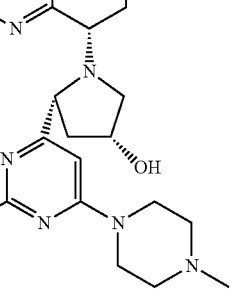 | J, BA, AI | ¹H NMR (400 MHz, CDCl₃) δ 8.38 (d, J = 4.8 Hz, 1H), 7.12 (d, J = 7.2 Hz, 1H), 7.05-6.99 (m, 1H), 5.29 (s, 1H), 4.28 (s, 1H), 4.03 (d, J = 10.0 Hz, 1H), 3.89 (s, 1H), 3.55-3.38 (m, 4H), 3.30 (d, J = 9.2 Hz, 1H), 2.92-2.83 (m, 1H), 2.63-2.53 (m, 1H), 2.53-2.45 (m, 1H), 2.44-2.37 (m, 7H), 2.33 (s, 3H), 2.14-2.05 (m, 2H), 1.77 (d, J = 13.6 Hz, 1H), 1.62-1.51 (m, 3H). |
| C17 | 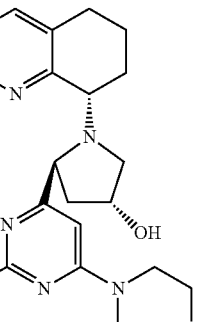 | J, AI, BA | ¹H NMR (400 MHz, CDCl₃) δ 8.33 (d, J = 4.8 Hz, 1H), 7.39 (d, J = 8.0 Hz, 1H), 7.11 (dd, J = 7.6, 4.8 Hz, 1H), 6.74 (s, 1H), 4.31 (s, 1H), 4.22 (dd, J = 11.6, 5.2 Hz, 1H), 4.04 (t, J = 8.4 Hz, 1H), 3.86 (dd, J = 11.2, 4.0 Hz, 1H), 3.68 (s, 4H), 3.43 (d, J = 11.2 Hz, 1H), 2.71-2.63 (m, 2H), 2.48 (t, J = 5.2 Hz, 4H), 2.44 (s, 3H), 2.35 (s, 3H), 2.02-1.98 (m, 1H), 1.89-1.83 (m, 2H), 1.72-1.63 (m, 2H), 1.54-1.45 (m, 1H). |
| C18 | 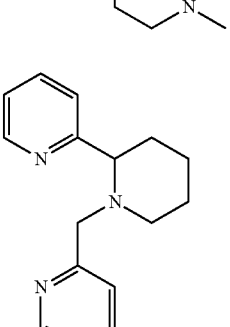 | C, AA | ¹H NMR (400 MHz, CDCl₃) δ 8.50 (s, 1H), 7.63-7.59 (m, 1H), 7.45 (d, J =7.2 Hz, 1H), 7.13 (t, J =6.4 Hz, 1H), 6.64 (s, 1H), 3.70 (s, 4H), 3.56-3.48 (m, 2H), 3.14-3.07 (m, 2H), 2.51 (s, 4H), 2.45 (s, 3H), 2.36 (s, 3H), (s, 1H), 2.06 (s, 4H), 1.86 (t, J = 16.0 Hz, 2H) |
| C19 | 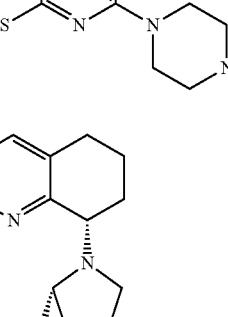 | J, BA | ¹H NMR (400 MHz, CDCl₃) δ 8.40 (s, 1H), 7.30 (d, J = 8.0 Hz, 1H), 7.18 (s, 1H), 7.07-6.99 (m, 1H), 4.26 (t, J = 8.4 Hz, 1H), 4.05-3.95 (m, 1H), 3.70 (s, 4H), 3.41-3.23 (m, 1H), 3.23-3.06 (m, 1H), 2.83-2.62 (m, 4H), 2.49-2.43 (m, 7H), 2.33 (s, 3H), 2.30-2.18 (m, 1H), 1.91-1.78 (m, 2H), 1.75-1.58 (m, 1H). |

TABLE 1-continued

Selected compounds (A1-A100, B1-B8, C1-C39 and D1-D59) of the present invention

| Compd number | structure | method | ¹HNMR and MS |
|---|---|---|---|
| C20 | 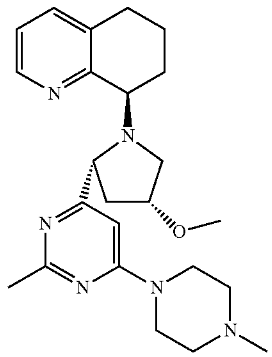 | J, BA | ¹H NMR (400 MHz, CDCl$_3$) δ 8.43 (d, J = 4.8 Hz, 1H), 7.30 (d, J = 7.6 Hz, 1H), 7.22 (s, 1H), 7.06-6.99 (m, 1H), 4.17 (t, J = 8.0 Hz, 1H), 4.03-3.96 (m, 1H), 3.95-3.87 (m, 1H), 3.70 (s, 4H), 3.27 (s, 3H), 3.25-3.16 (m, 1H), 2.85-2.71 (m, 1H), 2.71-2.61 (m, 2H), 2.48 (s, 3H), 2.46-2.41 (m, 4H), 2.41-2.34 (m, 1H), 2.32 (s, 3H), 2.20-2.06 (m, 1H), 1.97-1.90 (m, 2H), 1.86-1.77 (m, 1H), 1.72-1.59 (m, 1H). |
| C21 | 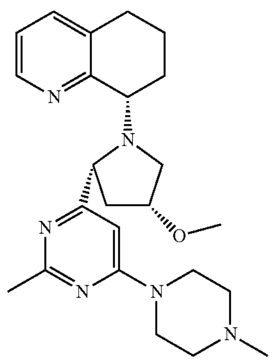 | J, BA | ¹H NMR (400 MHz, CDCl$_3$) δ 8.34 (d, J = 4.8 Hz, 1H), 7.32-7.27 (m, 1H), 7.17 (s, 1H), 7.03-6.97 (m, 1H), 4.07-3.96 (m, 1H), 3.97-3.85 (m, 2H), 3.73-3.65 (m, 4H), 3.21 (s, 3H), 3.09-2.96 (m, 1H), 2.938-2.82 (m, 1H), 2.80-2.57 (m, 4H), 2.46-2.43 (m, 7H), 2.35-2.28 (m, 4H), 2.14-2.02 (m, 1H), 1.87-1.78 (m, 1H), 1.70-1.60 (m, 1H). |
| C22 | 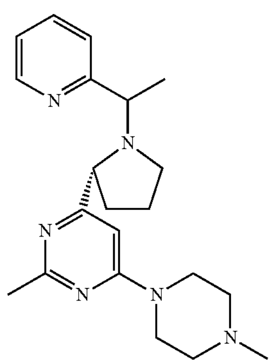 | J, BA | ¹H NMR (400 MHz, CDCl$_3$) δ 8.58-8.42 (m, 1H), 7.68-7.40 (m, 1H), 7.36-7.25 (m, 1H), 7.18-6.98 (m, 1H), 6.82-6.45 (m, 1H), 3.95-3.85 (m, 1H), 3.83-3.74 (m, 1H), 3.70 (s, 2H), 3.60 (s, 2H), 3.15-3.03 (m, 1H), 2.78-2.2 (m, 1H), 2.51-2.48 (m, 4H), 2.44 (s, 3H), 2.38-2.30 (m, 3H), 2.28-2.15 (m, 1H), 1.87-1.73 (m, 2H), 1.68-1.57 (m, 1H), 1.45-1.30 (m, 3H). |
| C23 | 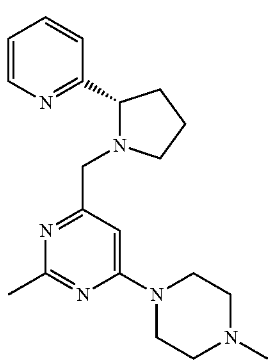 | C, BH, AA | ¹H NMR (400 MHz, CDCl$_3$) δ 8.51 (s, 1H), 7.61-7.57 (m, 1H), 7.45 (d, J = 7.6 Hz, 1H), 7.17-7.05 (m, 1H), 6.45 (s, 1H), 3.71-3.67 (m, 2H), 3.63 (s, 4H), 3.39-3.32 (m, 2H), 2.46-2.43 (m, 8H), 2.40-2.31 (m, 4H), 2.01-1.95 (m, 1H), 1.97-1.86 (m, 2H). |

TABLE 1-continued

Selected compounds (A1-A100, B1-B8, C1-C39 and D1-D59) of the present invention

| Compd number | structure | method | ¹HNMR and MS |
|---|---|---|---|
| C24 | 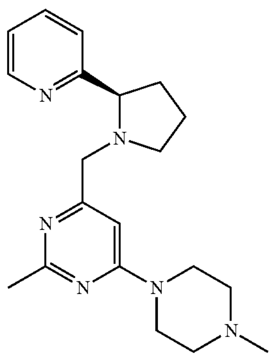 | C, BI, AA | ¹H NMR (400 MHz, CDCl₃) δ 8.52 (d, J = 4.0 Hz, 1H), 7.65-7.54 (m, 1H), 7.45 (d, J = 8.0 Hz, 1H), 7.15-7.08 (m, 1H), 6.45 (s, 1H), 3.72-3.68 (m, 2H), 3.63 (s, 4H), 3.40-3.31 (m, 2H), 2.46-2.40 (m, 8H), 2.40-2.31 (m, 4H), 2.05-1.95 (m, 1H), 1.91-1.83 (m, 2H). |
| C25 | 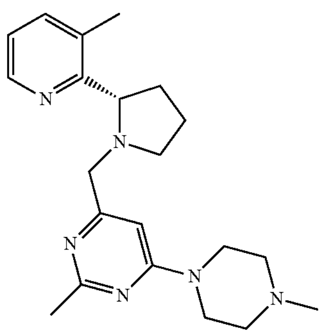 [SMILES: Cc1nc(CN2CCC[C@H]2c2ncccc2C)cc(N2CCN(C)CC2)n1] | C, BH, AA | ¹H NMR (400 MHz, CDCl₃) δ 8.46 (s, 1H), 7.34 (d, J = 6.8 Hz, 1H), 7.01 (s, 1H), 6.39 (s, 1H), 3.92-3.78 (m, 1H), 3.71-3.48 (m, 5H), 3.41-3.29 (m, 2H), 2.43(s, 8H), 2.33(d, J = 7.6 Hz, 6H), 2.25-1.83 (m, 4H). |
| C26 | 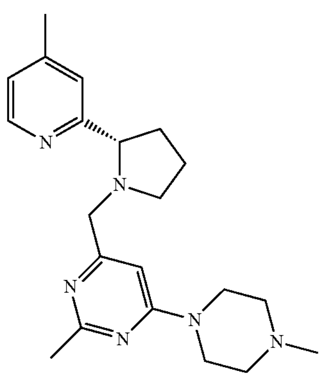 [SMILES: Cc1ccnc([C@@H]2CCCN2Cc2cc(N3CCN(C)CC3)nc(C)n2)c1] | C, BH, AA | ¹H NMR (400 MHz, CDCl₃) δ 8.36 (s, 1H), 7.26 (s, 1H), 6.93 (s, 1H), 6.42 (s, 1H), 3.74-3.54 (m, 6H), 3.41-3.27 (m, 2H), 2.57-2.38 (m, 8H), 2.38-2.32 (s, 3H), 2.31-2.25 (m, 4H), 2.00-1.90 (m, 1H), 1.90-1.86 (m, 2H). |
| C27 | 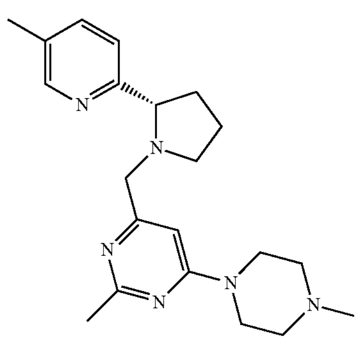 | C, BH, AA | ¹H NMR (400 MHz, CDCl₃) δ 8.35 (s, 1H), 7.41 (d, J = 7.6 Hz, 1H), 7.33 (d, J = 7.6 Hz, 1H), 6.46 (s, 1H), 3.71-3.54 (m, 6H), 3.37-3.25 (m, 2H), 2.54-2.38 (m, 8H), 2.34 (s, 3H), 2.29 (s, 4H), 2.07-1.94 (m, 1H), 1.89-1.78 (m, 2H). |

TABLE 1-continued

Selected compounds (A1-A100, B1-B8, C1-C39 and D1-D59) of the present invention

| Compd number | structure | method | ¹HNMR and MS |
|---|---|---|---|
| C28 | 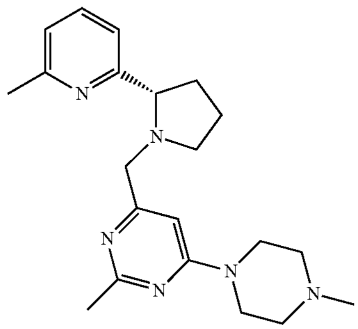 | C, BH, AA | ¹H NMR (400 MHz, CDCl$_3$) δ 7.56-7.44 (m, 1H), 7.31 (d, J = 7.6 Hz, 1H), 6.97 (d, J = 7.6 Hz, 1 H), 6.48 (s, 1H), 3.74-3.55 (m, 6 H), 3.38-3.15 (m, 2H), 2.52 (s, 3H), 2.49-2.30 (m, 8H), 2.30-2.26 (m, 4H), 1.99-1.75 (m, 3H). |
| C29 | 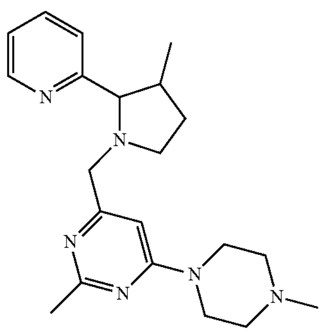 [SMILES: Cc1nc(CN2CCC(C)C2c2ccccn2)cc(N2CCN(C)CC2)n1] | C, BJ, AA | ¹H NMR (400 MHz, CDCl$_3$) δ 8.54 (d, J = 3.6 Hz, 1H), 7.62-7.58 (m, 1H), 7.44(d, J = 8.0 Hz, 1H), 7.14-7.11 (m, 1H), 6.44 (s, 1H), 3.65-3.61 (m, 5H), 3.35-3.31 (m, 2H), 3.22 (d, J = 7.6 Hz, 1H), 2.47-2.43 (m, 8H), 2.35 (s, 3H), 2.27-2.21 (m, 2H), 1.52 (s, 1H), 1.05 (d, J = 8.0 Hz, 3H). |
| C30 | racemate | C, BK, AA | ¹H NMR (400 MHz, CDCl$_3$) δ 8.53 (d, J = 4.4 Hz, 1H), 7.62-7.58 (m, 1H), 7.45 (d, J = 7.6 Hz, 1H), 7.15-7.12 (m, 1H), 6.51 (s, 1H), 4.18 (d, J = 9.6 Hz, 1H), 3.75-3.66 (m, 5H), 3.56-3.38 (m, 4H), 2.54-2.48 (m, 5H), 2.45 (s, 3H), 2.37 (s, 3H), 2.11-2.07 (m, 1H), 0.81 (t, J = 7.2 Hz, 3H). MS (ESI/APCI) m/z 424.8 [M + H]⁺. |
| C31 | racemate | C, BK, AA, AJ | ¹H NMR (400 MHz, CD$_3$OD) δ 8.43 (d, J = 4.8 Hz, 1H), 7.75-7.71 (m, 1H), 7.57-7.55 (m, 1H), 7.26-7.23 (m, 1H), 6.58 (s, 1H), 3.94-3.92 (m, 1H), 3.71-3.58 (m, 6H), 3.44-3.41 (m, 1H), 3.35-3.33 (m, 1H), 3.04 (d, J = 7.2 Hz, 1H), 2.71-2.65 (m, 1H), 2.50-2.48 (m, 6H), 2.35 (s, 3H), 2.33 (s, 3H), 2.13-2.06 (m, 1H), 1.88-1.78 (m, 1H).MS (ESI/APCI) m/z 382.9 [M + H]⁺. |

TABLE 1-continued

Selected compounds (A1-A100, B1-B8, C1-C39 and D1-D59) of the present invention

| Compd number | structure | method | ¹HNMR and MS |
|---|---|---|---|
| C32 | 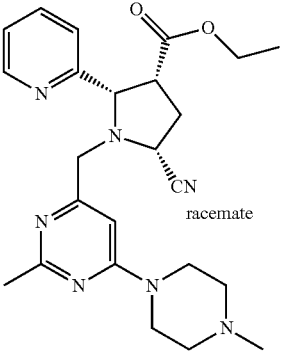 [SMILES: CCOC(=O)[C@@H]1C[C@H](C#N)N(Cc2cc(N3CCN(C)CC3)nc(C)n2)[C@@H]1c1ccccn1] racemate | C, BK, AA | ¹H NMR (400 MHz, CDCl$_3$) δ 8.53 (d, J = 4.8 Hz, 1H), 7.65-7.58 (m, 1H), 7.46-7.31 (m, 1H), 7.19-7.14 (m, 1H), 6.33-6.22 (m, 1H), 4.59-4.29 (m, 2H), 3.92-3.40 (m, 9H), 3.04-2.84 (m, 1H), 2.49-2.30 (m, 11H), 0.91-0.80 (m, 3H). MS (ESI/APCI) m/z 450.1 [M + H]⁺. |
| C33 | 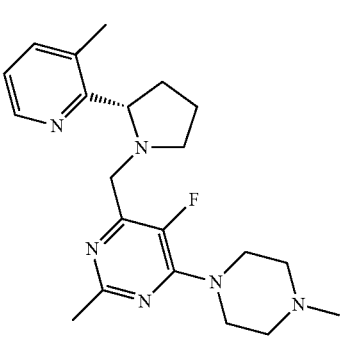 [SMILES: Cc1nc(CN2CCC[C@H]2c2ncccc2C)c(F)c(N2CCN(C)CC2)n1] | BH, I | ¹H NMR (400 MHz, CDCl$_3$) δ 8.45 (s, 1H), 7.35 (s, 1H), 7.00 (s, 1H), 4.03-3.65 (m, 6H), 3.62-3.43 (m, 1H), 3.41-3.24 (m, 1H), 2.67-2.45 (m, 5H), 2.39 (s, 6H), 2.33(s, 3H), 2.26-2.12 (m, 1H), 2.09-1.96 (m, 1H), 1.95-1.77 (m, 2H). |
| C34 | 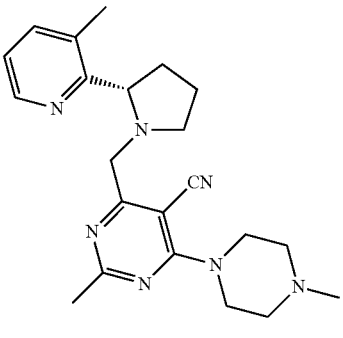 [SMILES: Cc1nc(CN2CCC[C@H]2c2ncccc2C)c(C#N)c(N2CCN(C)CC2)n1] | M, BH, AD | ¹H NMR (400 MHz, CDCl$_3$) δ 8.43 (s, 1H), 7.35 (d, J = 6.4 Hz, 1H), 7.01 (s, 1H), 4.11-3.93 (m, 1H), 3.92 (s, 4H), 3.87-3.78 (m, 1H), 3.71-3.58 (m, 1H), 3.48-3.34 (m, 1H), 2.64-2.55 (m, 1H), 2.49 (s, 4H), 2.45 (s, 3H), 2.41(s, 3H), 2.33 (s, 3H), 2.26-2.14 (m, 1H), 2.14-2.01 (m, 1H), 2.01-1.93 (m, 1H), 1.91-1.81 (m, 1H). |
| C35 | 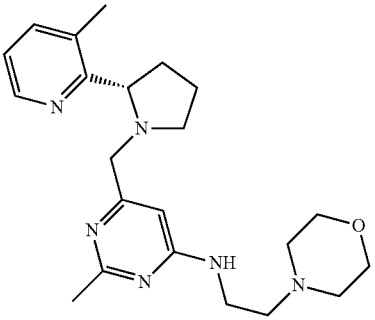 [SMILES: Cc1nc(CN2CCC[C@H]2c2ncccc2C)cc(NCCN2CCOCC2)n1] | C, BH, AA | ¹H NMR (400 MHz, CDCl$_3$) δ 8.47 (d, J = 4.0 Hz, 1H), 7.36 (d, J = 7.2 Hz, 1H), 7.03-6.98 (m, 1H), 6.33 (s, 1H), 5.42 (s, 1H), 3.86 (s, 1H), 3.73 (s, 4H), 3.66-3.57 (m, 1H), 3.44-3.19 (m, 4H), 2.56 (t, J = 6.0 Hz, 2H), 2.47 (s, 4H), 2.43 (s, 3H), 2.40-2.30 (m, 4H), 2.25-2.12 (m, 1H), 2.12-1.95 (m, 2H), 1.95-1.83 (m, 1H). |

TABLE 1-continued

Selected compounds (A1-A100, B1-B8, C1-C39 and D1-D59) of the present invention

| Compd number | structure | method | ¹HNMR and MS |
|---|---|---|---|
| C36 | 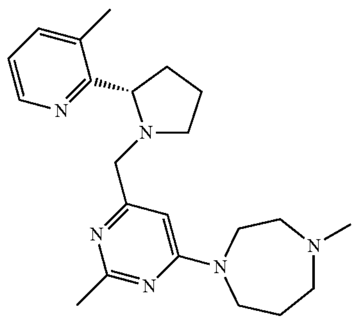 [SMILES: Cc1nc(CN2CCC[C@H]2c2ncccc2C)cc(N2CCCN(C)CC2)n1] | C, BH, AA | ¹H NMR (400 MHz, CDCl₃) δ 8.45 (d, J = 3.2 Hz, 1H), 7.35 (d, J =7.2 Hz,1H), 7.01 (t, J = 6.0 Hz, 1H), 6.30 (s, 1H), 3.83-3.87 (m, 3H), 3.63-3.66 (m, 3H), 3.35 (d, J = 14.2 Hz, 2H), 2.62 (s, 2H), 2.53 (s 2H), 2.41 (s, 3H), 2.36 (d, J = 2.8 Hz, 6H), 2.17-2.19 (m, 1H),1.96-2.06 (m, 6H). |
| C37 | 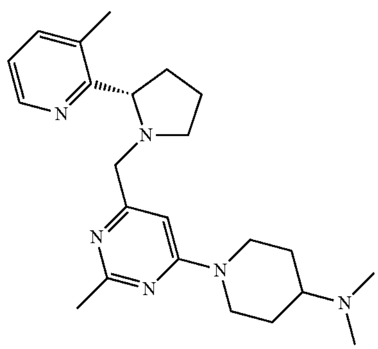 [SMILES: Cc1nc(CN2CCC[C@H]2c2ncccc2C)cc(N2CCC(N(C)C)CC2)n1] | C, BH, AA | ¹H NMR (400 MHz, CDCl₃) δ 8.46 (s, 1H), 7.45-7.30 (m, 1H), 7.09-6.95 (m, 1H), 6.39 (s, 1H), 4.40 (s, 2H), 3.84 (s, 1H), 3.72-3.58 (m, 1H), 3.47-3.28 (m, 2H), 2.77 (s, 2H), 2.55-2.40 (m, 5H), 2.40-2.33 (s, 3H), 2.29 (s, 6H), 2.08-1.95 (m, 2H), 1.95-1.80 (m, 4H), 1.40 (s, 2H). |
| C38 | 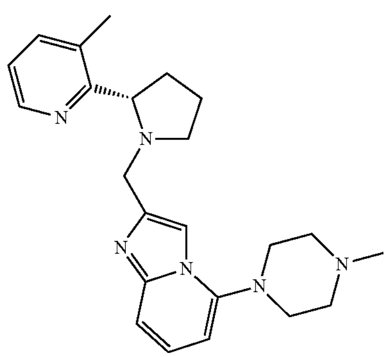 [SMILES: Cc1cccnc1[C@@H]1CCCN1Cc1cn2c(N3CCN(C)CC3)cccc2n1] | N, BH, AK | ¹H NMR (400 MHz, CDCl₃) δ 8.49 (d, J = 3.6 Hz, 1H), 7.33 (s, 2H), 7.28 (s, 1H), 7.13-7.09 (m, 1H), 7.01-6.98 (m, 1H), 6.24 (d, J = 7.2 Hz, 1H), 3.96 (d, J = 13.6 Hz, 1H), 3.84 (t, J = 8.0 Hz, 1H), 3.67(d, J = 13.6 Hz, 1H), 3.39 (t, J = 8.0 Hz, 1H), 3.10 (s, 4H), 2.64 (s, 4H), 2.59-2.52 (m, 1H), 2.42 (s, 3H), 2.38 (s, 3H), 2.22-2.17 (m, 2H), 2.05-1.90 (m, 2H). |
| C39 | 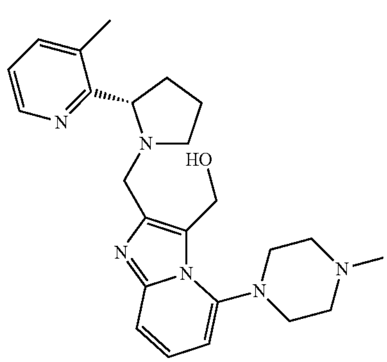 [SMILES: Cc1cccnc1[C@@H]1CCCN1Cc1nc2cccc(N3CCN(C)CC3)n2c1CO] | N, BH, AK | ¹H NMR (400 MHz, CDCl₃) δ 8.50 (d, J = 3.6 Hz, 1H), 7.40 (d, J = 7.2 Hz,1H), 7.29(d, J = 8.8 Hz, 1H), 7.02-7.08 (m, 2H), 6.39 (d, J = 6.8 Hz, 1H), 6.19 (d, J = 14.4 Hz, 1H), 5.27 (d, J = 14.0 Hz ,1H), 5.07 (d, J = 14.0 Hz, 1H), 4.05 (d, J = 12.8 Hz, 1H), 3.85 (d, J = 8.0 Hz, 1H), 3.49 (d, J = 12.8 Hz, 2H), 3.24 (d, J = 10.8 Hz, 1H), 3.16 (t, J = 7.8 Hz, 1H), 2.91-3.01 (m, 3H), 2.83 (t, J = 11.0 Hz, 1H), 2.46-2.51 (m, 3H), 2.41(s, 3H), 2.38(s, 3H), 2.24(s, 1H), 1.84-1.91 (m, 3H). |

TABLE 1-continued

Selected compounds (A1-A100, B1-B8, C1-C39 and D1-D59) of the present invention

| Compd number | structure | method | ¹HNMR and MS |
|---|---|---|---|
| D1 | 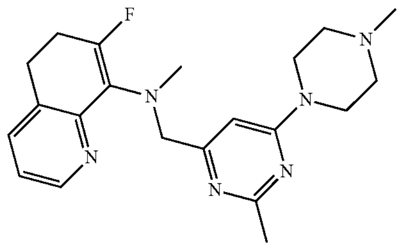 [SMILES: Cc1nc(CN(C)C2=C(F)CCc3cccnc32)cc(N2CCN(C)CC2)n1] | C, AL | ¹H NMR (400 MHz, CDCl$_3$) δ 8.44 (d, J = 4.0 Hz, 1H), 7.40 (d, J = 7.2 Hz, 1H), 7.06-6.98 (m, 1H), 6.93 (s, 1H), 4.26 (s, 2H), 3.60 (s, 4H), 2.93 (s, 3H), 2.93-2.81 (m, 2H), 2.64-2.56 (m, 2H), 2.47 (s, 3H), 2.42 (s, 4H), 2.32 (s, 3H). MS (ESI/APCI) m/z 382.9 [M + H]$^+$. |
| D2 | 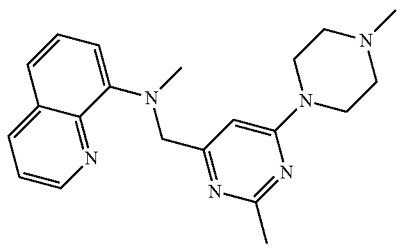 [SMILES: Cc1nc(CN(C)c2cccc3cccnc23)cc(N2CCN(C)CC2)n1] | C, AA, AM | ¹H NMR (400 MHz, CDCl$_3$) δ 8.82 (d, J = 2.4 Hz, 1H), 8.11 (d, J = 8.4 Hz, 1H), 7.44-7.35 (m, 3H), 7.13 (d, J = 7.2 Hz, 1H), 6.68 (s, 1H), 4.69 (s, 2H), 3.57 (s, 4H), 3.06 (s, 3H), 2.51 (s, 3H), 2.39 (t, J = 4.8 Hz, 4H), 2.30 (s, 3H). |
| D3 | 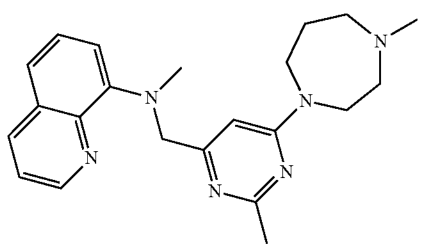 [SMILES: Cc1nc(CN(C)c2cccc3cccnc23)cc(N2CCCN(C)CC2)n1] | C, BM, AA | ¹H NMR (400 MHz, CDCl$_3$) δ 8.82 (d, J = 2.4 Hz, 1H), 8.10 (d, J = 8.0 Hz, 1H), 7.42-7.32 (m, 3H), 7.11 (d, J = 7.2 Hz, 1H), 6.44 (s, 1H), 4.72 (s, 2H), 4.10 -3.22 (m, 4H), 3.08 (s, 3H), 2.50-2.42(m, 7H), 2.30 (s, 3H), 1.82 (s, 2H). |
| D4 | 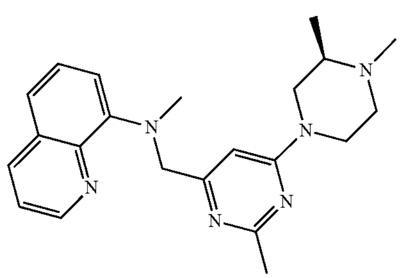 [SMILES: Cc1nc(CN(C)c2cccc3cccnc23)cc(N2CCN(C)[C@H](C)C2)n1] | C, BM, AA | ¹H NMR (400 MHz, CDCl$_3$) δ 8.82 (s, 1H), 8.12 (d, J = 7.6 Hz, 1H), 7.42-7.36 (m, 3H), 7.14 (d, J = 6.0 Hz, 1H), 6.67 (s, 1H), 4.71 (s, 2H), 4.14-4.03 (m, 2H), 3.06 (s, 4H), 2.82-2.78 (m, 1H), 2.65-2.62 (m, 1H), 2.52 (s, 3H), 2.03-2.17(m, 1H), 1.08 (d, J = 4.4 Hz, 3H). |
| D5 | 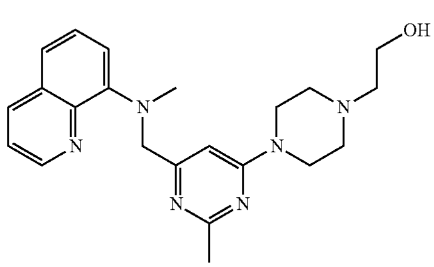 [SMILES: Cc1nc(CN(C)c2cccc3cccnc23)cc(N2CCN(CCO)CC2)n1] | C, BM, AA | ¹H NMR (400 MHz, CDCl$_3$) δ 8.82 (d, J = 2.8 Hz, 1H), 8.12 (d, J = 7.2 Hz, 1H), 7.42-7.36 (m, 3H), 7.13 (d, J = 6.8 Hz, 1H), 6.68 (s, 1H), 4.69 (s, 2H), 3.63 (t, J = 5.2 Hz, 2H), 3.56 (s, 4H), 3.06 (s, 3H), 2.75-2.45 (m, 10H). |

TABLE 1-continued

Selected compounds (A1-A100, B1-B8, C1-C39 and D1-D59) of the present invention

| Compd number | structure | method | ¹HNMR and MS |
|---|---|---|---|
| D6 | 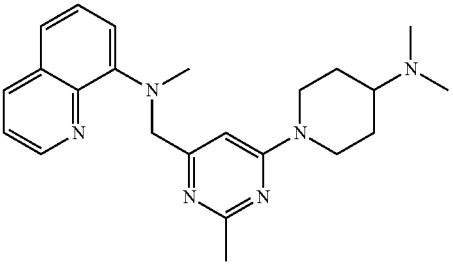 [SMILES: Cc1nc(CN(C)c2cccc3cccnc23)cc(N2CCC(N(C)C)CC2)n1] | C, BM, AA | ¹H NMR (400 MHz, CDCl₃) δ 8.82 (s, 1H), 8.11 (d, J = 6.8 Hz, 1H), 7.50-7.30 (m, 3H), 7.13-7.11 (m, 1H), 6.68 (s, 1H), 4.71 (s, 2H), 4.37( s, 2H), 3.07 (s, 3H), 2.76 ( s, 2H), 2.52 (s, 4H), 2.34 (s, 6H), 1.86 (s, 2H), 1.49-1.30 (m, 2H). |
| D7 | 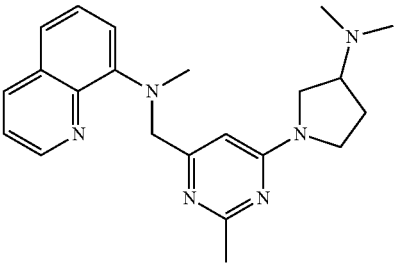 [SMILES: Cc1nc(CN(C)c2cccc3cccnc23)cc(N2CCC(N(C)C)C2)n1] | C, BM, AA | ¹H NMR (400 MHz, CDCl₃) δ 8.82 (s, 1H), 8.11 (d, J = 7.6 Hz,1H), 7.44-7.29 (m, 3H), 7.12 (d, J = 6.8 Hz, 1H), 6.32 (s, 1H), 4.74 (s, 2H), 4.20-3.10 (m, 4H), 3.08 (s, 3H), 2.69 (s, 1H), 2.52 (s, 3H), 2.26 (s, 6H), 2.20-2.12 (m, 1H), 1.80 (s, 1H). |
| D8 | 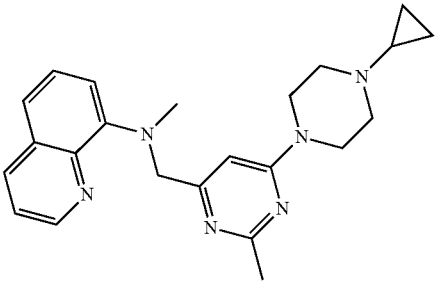 [SMILES: Cc1nc(CN(C)c2cccc3cccnc23)cc(N2CCN(C3CC3)CC2)n1] | C, BM, AA | ¹H NMR (400 MHz, CDCl₃) δ 8.82 (s, 1H), 8.12 (d, J = 8 Hz, 1H), 7.41-7.32 (m, 3H), 7.12 (d, J = 6.8 Hz, 1H), 6.65 (s, 1H), 4.69 (s, 2H), 3.50 (m, 4H), 3.06 (s, 3H), 2.59 (s, 4H), 2.51 (s, 3H), 1.59 (s, 1H), 0.46-0.43 (m, 4H). |
| D9 | 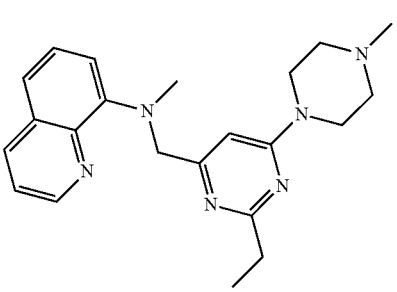 [SMILES: CCc1nc(CN(C)c2cccc3cccnc23)cc(N2CCN(C)CC2)n1] | C, BM, AA | ¹H NMR (400 MHz, CDCl₃) δ 8.82 (s, 1H), 8.10 (d, J = 8.0 Hz, 1H), 7.41-7.35 (m, 3H), 7.12 (d, J = 7.2 Hz, 1H), 6.65 (s, 1H), 4.71 (s, 2H), 3.57 (s, 4H), 3.07 (s, 3H), 2.76 (d, J = 7.6 Hz, 2H), 2.39 (s, 4H), 2.29 (s, 3H), 1.30(t, J = 7.6 Hz, 3H). |
| D10 | 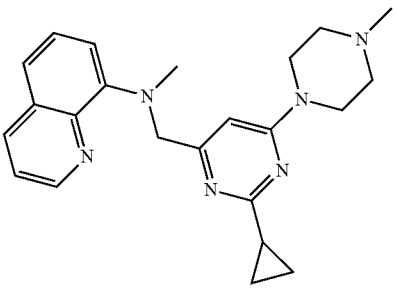 [SMILES: CN1CCN(c2cc(CN(C)c3cccc4cccnc34)nc(C3CC3)n2)CC1] | C, BM, AA | ¹H NMR (400 MHz, CDCl₃) δ 8.83 (s, 1H), 8.16 (s, 1H), 7.42 (s, 3H), 7.18 (s, 1H), 6.72 (s, 1H), 4.65 (s, 2H), 3.61 (s, 4H), 3.07 (s, 3H), 2.42 (s, 4H), 2.31 (s, 3H), 2.04 (s, 1H), 1.10 (s, 2H), 1.00 (s, 2H). |

TABLE 1-continued

Selected compounds (A1-A100, B1-B8, C1-C39 and D1-D59) of the present invention

| Compd number | structure | method | ¹HNMR and MS |
|---|---|---|---|
| D11 | 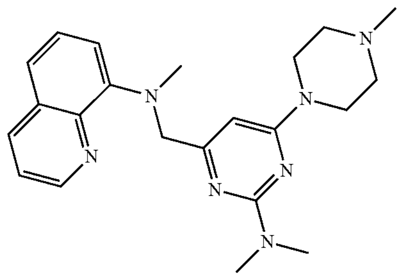 [SMILES: CN1CCN(c2cc(CN(C)c3cccc4cccnc34)nc(N(C)C)n2)CC1] | F, AC, AM | ¹H NMR (400 MHz, CDCl$_3$) δ 8.85 (s, 1H), 8.11 (s, 1H), 7.38 (s, 3H), 7.13 (s, 1H), 5.92 (s, 1H), 4.69 (s, 2H), 3.75-3.27 (m, 4H), 3.08 (s, 9H), 2.44 (s, 4H), 2.33 (s, 3H). |
| D12 | 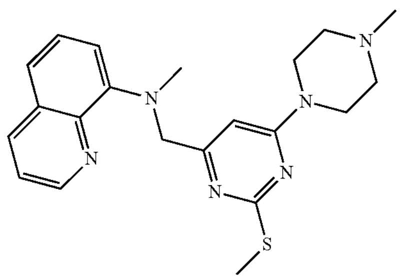 | B, BM, AA | ¹H NMR (400 MHz, CDCl$_3$) δ 8.83 (s, 1H), 8.11 (d, J = 8.0 Hz, 1H), 7.43-7.33 (m, 3H), 7.11 (d, J = 7.2 Hz, 1H), 6.47 (s, 1H), 4.71 (s, 2H), 3.56 (s, 4H), 3.06 (s, 3H), 2.44 (s, 3H), 2.42-2.35 (m, 4H), 2.30 (s, 3H). |
| D13 | 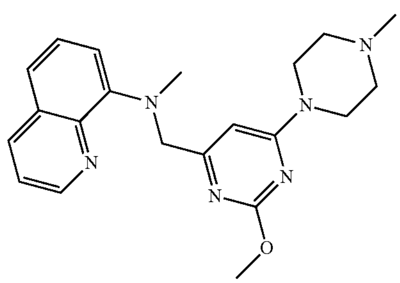 [SMILES: COc1nc(CN(C)c2cccc3cccnc23)cc(N2CCN(C)CC2)n1] | G, AC, AM | ¹H NMR (400 MHz, CDCl$_3$) δ 8.84 (s, 1H), 8.11 (d, J = 7.6 Hz, 1H), 7.40-7.37 (m, 3H), 7.12 (d, J = 5.6 Hz, 1H), 6.39(s, 1H), 4.71 (s, 2H), 3.85 (s, 3H), 3.55 (s, 4H), 3.08 (s, 3H), 2.37 (s, 4H), 2.29 (s, 3H). |
| D14 | 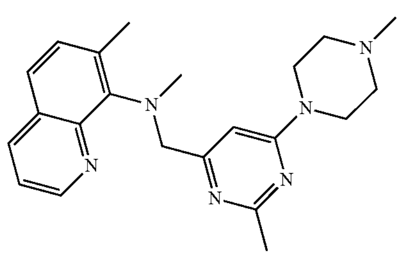 [SMILES: Cc1nc(CN(C)c2c(C)ccc3cccnc23)cc(N2CCN(C)CC2)n1] | C, BL, BM, AA | ¹H NMR (400 MHz, CDCl$_3$) δ 8.92-8.90 (m, 1H), 8.13 (d, J = 8.0 Hz, 1H), 7.58-7.55 (m, 1H), 7.44-7.41 (m, 1H), 7.38-7.34 (m, 1H), 7.22 (s, 1H), 4.62 (s, 2H), 3.76-3.73 (m, 4H), 3.10 (s, 3H), 2.65 (s, 3H), 2.56-2.51 (m, 7H), 2.39 (s, 3H). |
| D15 | 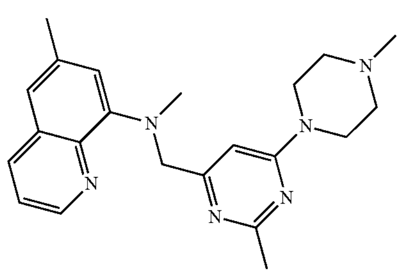 [SMILES: Cc1cc(N(C)Cc2cc(N3CCN(C)CC3)nc(C)n2)c2ncccc2c1] | C, BL, BM, AA | ¹H NMR (400 MHz, CDCl$_3$) δ 8.75 (d, J = 4.4 Hz, 1H), 8.01 (d, J = 8.0 Hz, 1H), 7.33-7.30 (m, 1H), 7.15 (s, 1H), 6.96 (s, 1H), 6.69 (s, 1H), 4.68 (s, 2H), 3.58-3.55 (m, 4H), 3.04 (s, 3H), 2.52 (s, 3H), 2.47 (s, 3H), 2.41-2.38 (m, 4H), 2.30 (s, 3H). MS (ESI/APCI) m/z 377.0 [M + H]⁺. |

TABLE 1-continued

Selected compounds (A1-A100, B1-B8, C1-C39 and D1-D59) of the present invention

| Compd number | structure | method | ¹HNMR and MS |
|---|---|---|---|
| D16 | 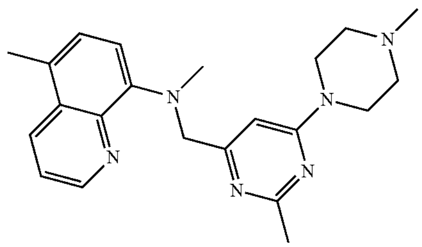 | C, BN, AA | ¹H NMR (400 MHz, CDCl$_3$) δ 8.83 (d, J = 4.8 Hz, 1H), 8.29-8.25 (m, 1H), 7.41-7.38 (m, 1H), 7.25-7.21 (m, 1H), 7.075-7.03 (m, 1H), 6.75 (s, 1H), 4.60 (s, 2H), 3.59-3.58 (m, 4H), 3.01 (s, 3H), 2.57 (s, 3H), 2.51 (s, 3H), 2.41-2.39 (m, 4H), 2.30 (s, 3H). |
| D17 | 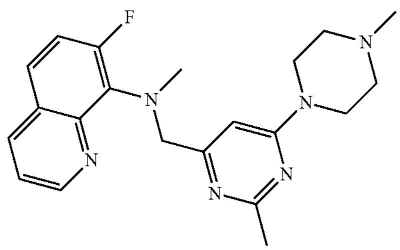 | C, BN, BO, AA, AM | ¹H NMR (400 MHz, CDCl$_3$) δ 8.80 (d, J = 4.4 Hz, 1H), 8.09 (d, J = 8.4 Hz, 1H), 7.42-7.39 (m, 1H), 7.23-7.13 (m, 2H), 6.69 (s, 1H), 4.70 (s, 2H), 3.96-3.94 (m, 4H), 3.73-3.69 (m, 4H), 3.63-3.61 (m, 6H), 2.53 (s, 3H). |
| D18 | 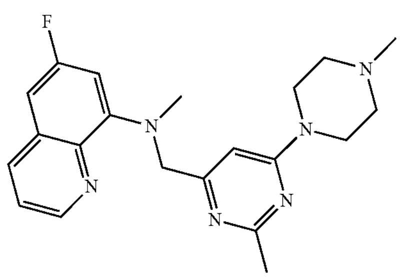 [SMILES: Cc1nc(CN(C)c2cc(F)cc3cccnc23)cc(N2CCN(C)CC2)n1] | C, BN, AA | ¹H NMR (400 MHz, CDCl$_3$) δ 8.71 (s, 1H), 8.02 (d, J = 8.4 Hz, 1H), 7.37-7.34 (m, 1H), 6.95-6.92 (m, 1H), 6.85-6.82 (m, 1H), 6.64 (s, 1H), 4.80 (s, 2H), 3.59 (s, 4H), 3.05 (s, 3H), 2.51 (s, 3H), 2.41 (s, 4H), 2.31 (s, 3H). |
| D19 | 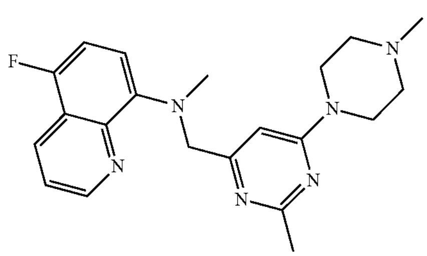 [SMILES: Cc1nc(CN(C)c2ccc(F)c3cccnc23)cc(N2CCN(C)CC2)n1] | C, BN, AA | ¹H NMR (400 MHz, CDCl$_3$) δ 8.90 (s, 1H), 8.40 (d, J = 9.2 Hz, 1H), 7.47-7.44 (m, 1H), 7.10-7.05 (m, 2H), 6.72 (s, 1H), 4.58 (s, 2H), 3.60 (s, 4H), 3.02 (s, 3H), 2.51 (s, 3H), 2.42-2.40 (m, 4H), 2.31 (s, 3H). MS (ESI/APCI) m/z 381.0 [M + H]⁺. |
| D20 | 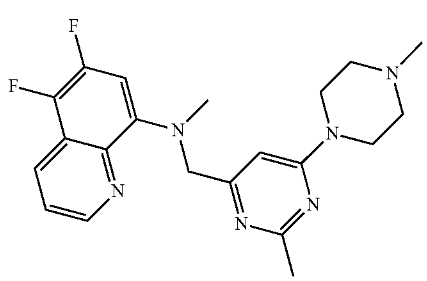 [SMILES: Cc1nc(CN(C)c2cc(F)c(F)c3cccnc23)cc(N2CCN(C)CC2)n1] | C, BN, AA | ¹H NMR (400 MHz, CDCl$_3$) δ 8.77 (s, 1H), 8.39-8.35 (m, 1H), 7.44 (s, 1H), 6.92 (s, 1H), 6.70 (s, 1H), 4.67 (s, 2H), 3.63 (s, 4H), 3.01 (s, 3H), 2.53-2.45 (m, 7H), 2.30 (s, 3H). MS (ESI/APCI) m/z 399.2 [M + H]⁺. |

TABLE 1-continued

Selected compounds (A1-A100, B1-B8, C1-C39 and D1-D59) of the present invention

| Compd number | structure | method | ¹HNMR and MS |
|---|---|---|---|
| D21 | 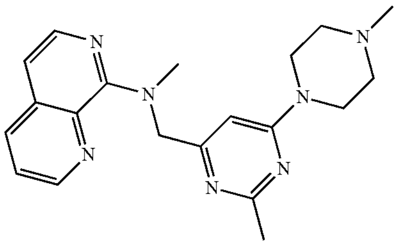 | D, BP, AN | ¹H NMR (400 MHz, CDCl₃) δ 8.66 (s, 1H), 8.10 (d, J = 5.2 Hz, 1H), 7.96 (d, J = 8.0 Hz, 1H), 7.43 (dd, J = 7.6, 4.0 Hz, 1H), 6.96 (d, J = 5.6 Hz, 1H), 6.46 (s, 1H), 5.26 (s, 2H), 3.57 (s, 4H), 3.36 (s, 3H), 2.52 (s, 3H), 2.45-2.34 (m, 4H), 2.29 (s, 3H). |
| D22 | 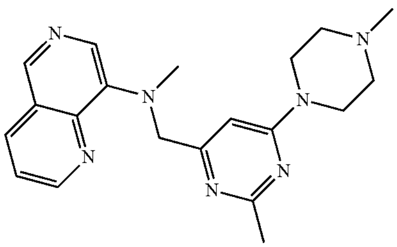 [SMILES: Cc1nc(CN(C)c2cncc3cccnc23)cc(N2CCN(C)CC2)n1] | D, BQ, AO | ¹H NMR (400 MHz, CDCl₃) δ 8.96 (s, 1H), 8.81 (s, 1H), 8.37-8.13 (m, 2H), 7.50 (s, 1H), 6.62 (s, 1H), 4.84 (s, 2H), 3.60 (s, 4H), 3.13 (s, 3H), 2.51 (s, 3H), 2.42 (s, 4H), 2.31 (s, 3H). |
| D23 | 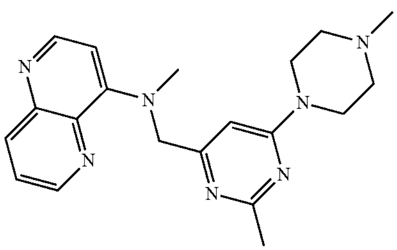 | D, BR, AN | ¹H NMR (400 MHz, CDCl₃) δ 8.67 (s, 1H), 8.59 (d, J = 5.2 Hz, 1H), 8.28 (d, J = 8.8 Hz, 1H), 7.54-7.52 (m, 1H), 6.75 (d, J = 5.6 Hz, 1H), 6.40 (s, 1H), 5.24 (s, 2H), 3.58 (s, 4H), 3.26 (s, 3H), 2.53 (s, 3H), 2.41 (s, 4H), 2.31 (s, 3H). MS (ESI/APCI) m/z 364.2 [M + H]⁺. |
| D24 | 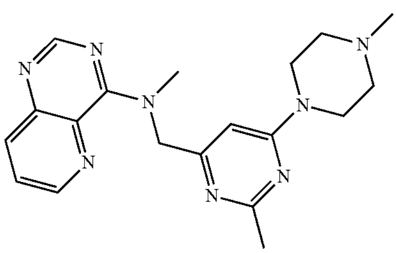 [SMILES: Cc1nc(CN(C)c2ncnc3cccnc23)cc(N2CCN(C)CC2)n1] | D, AN | ¹H NMR (400 MHz, CDCl₃) δ 8.64 (s, 2H), 8.09 (d, J = 7.6 Hz, 1H), 7.58 (s, 1H), 6.20 (s, 1H), 5.49 (s, 2H), 3.55 (s, 7H), 2.51 (s, 3H), 2.39 (s, 4H), 2.28 (s, 3H). |
| D25 | 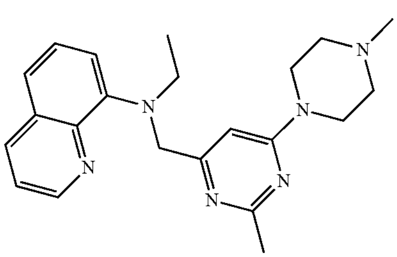 [SMILES: CCN(Cc1cc(N2CCN(C)CC2)nc(C)n1)c1cccc2cccnc12] | C, AA, AM | ¹H NMR (400 MHz, CDCl₃) δ 8.86 (d, J = 2.0 Hz, 1H), 8.11 (d, J = 7.6 Hz, 1H), 7.38 (s, 3H), 7.14 (s, 1H), 6.58 (s, 1H), 4.62 (s, 2H), 3.65 (q, J = 6.8 Hz, 2H), 3.46 (s, 4H), 2.50 (s, 3H), 2.31 (s, 4H), 2.26 (s, 3H), 1.12 (t, J = 6.8 Hz, 3H). |
| D26 | 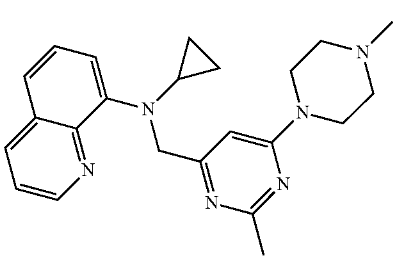 [SMILES: Cc1nc(CN(c2cccc3cccnc23)C2CC2)cc(N2CCN(C)CC2)n1] | C, AO, AA | ¹H NMR (400 MHz, CDCl₃) δ 8.80 (s, 1H), 8.09 (d, J = 8.4 Hz, 1H), 7.47-7.44k (m, 2H), 7.41-7.36 (m, 2H), 6.21 (s, 1H), 5.16 (s, 2H), 3.44 (s, 4H), 2.81 (s, 1H), 2.46 (s, 3H), 2.35 (s, 4H), 2.29 (s, 3H), 0.80 (d, J = 5.6 Hz, 2H), 0.68 (s, 2H). |

TABLE 1-continued

Selected compounds (A1-A100, B1-B8, C1-C39 and D1-D59) of the present invention

| Compd number | structure | method | ¹HNMR and MS |
|---|---|---|---|
| D27 | 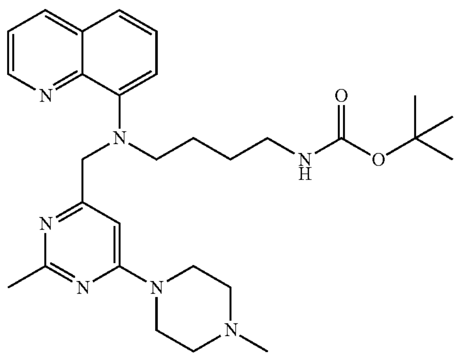 [SMILES: Cc1nc(CN(CCCCNC(=O)OC(C)(C)C)c2cccc3cccnc23)cc(N2CCN(C)CC2)n1] | C, AO, AA | ¹H NMR (400 MHz, CDCl₃) δ 8.86 (s, 1H), 8.11 (s, 1H), 7.37 (s, 3H), 7.11 (s, 1H), 6.57 (s, 1H), 4.62 (s, 3H), 3.57 (s, 2H), 3.47 (s, 4H), 3.05 (s, 2H), 2.49 (s, 3H), 2.33 (s, 3H), 2.29 (s, 4H), 1.63 (s, 2H), 1.40 (s, 11H). |
| D28 | 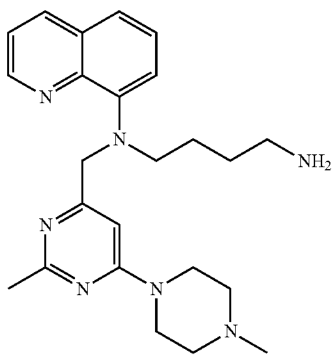 [SMILES: Cc1nc(CN(CCCCN)c2cccc3cccnc23)cc(N2CCN(C)CC2)n1] | C, AO, AA, AD | ¹H NMR (400 MHz, CDCl₃) δ 8.86 (s, 1H), 8.11 (d, J = 8.0 Hz, 2H), 7.37 (s, 3H), 7.12 (s, 1H), 6.58 (s, 1H), 4.62 (s, 2H), 3.57 (t, J = 7.2 Hz, 2H), 3.47 (s, 4H), 2.63 (t, J = 6.4 Hz, 2H), 2.49 (s, 3H), 2.33 (s, 4H), 2.26 (s, 3H), 1.68-1.60 (m, 4H), , 1.42-1.40 (m, 2H). |
| D29 | 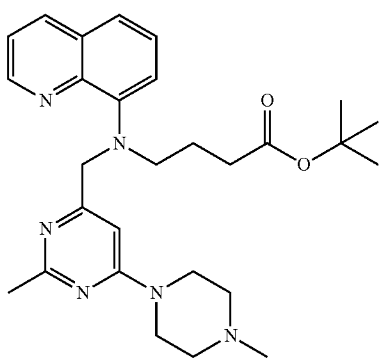 [SMILES: Cc1nc(CN(CCCC(=O)OC(C)(C)C)c2cccc3cccnc23)cc(N2CCN(C)CC2)n1] | C, AO, AA | ¹H NMR (400 MHz, CDCl₃) δ 8.84-8.82 (m, 1H), 8.11-8.09 (m, 1H), 7.38-7.35 (m, 3H), 7.19-7.17 (m, 1H), 6.75 (s, 1H), 4.64 (s, 2H), 3.58-3.53 (m, 6H), 2.50 (s, 3H), 2.38-2.35 (m, 4H), 2.29 (s, 3H), 2.18 (t, J = 7.6 Hz, 2H), 1.90-1.83 (m, 2H), 1.34 (s, 9H). |
| D30 | 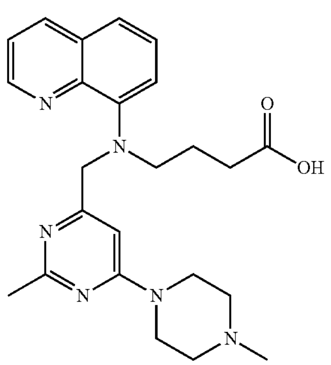 [SMILES: Cc1nc(CN(CCCC(=O)O)c2cccc3cccnc23)cc(N2CCN(C)CC2)n1] | C, AO, AA, AP | ¹H NMR (400 MHz, D₂O) δ 9.14 (d, J = 8.4 Hz, 1H), 9.07 (d, J =5.6 Hz, 1H), 8.12 (d, J = 8.0 Hz, 1H), 8.09-8.06 (m, 1H), 8.02 (d, J = 7.6 Hz, 1H), 7.92-7.88 (m, 1H), 7.00 (s, 1H), 5.25 (s, 1H), 4.44 (s, 2H), 4.33 (s, 1H), 3.68-3.46 (m, 4H), 3.41-3.12 (m, 4H), 2.92 (s, 3H), 2.54 (s, 3H), 2.17 (t, J = 6.8 Hz, 2H), 1.61 (s, 2H). |

TABLE 1-continued

Selected compounds (A1-A100, B1-B8, C1-C39 and D1-D59) of the present invention

| Compd number | structure | method | ¹HNMR and MS |
|---|---|---|---|
| D31 | 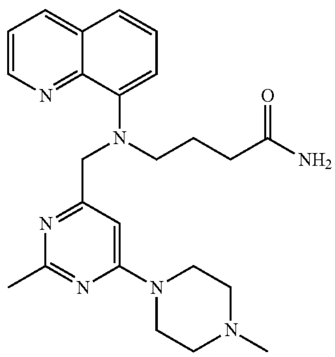 [SMILES: Cc1nc(CN(CCCC(N)=O)c2cccc3cccnc23)cc(N2CCN(C)CC2)n1] | C, AO, AA, AP | ¹H NMR (400 MHz, CDCl$_3$) δ 8.82 (d, J = 4.4 Hz, 1H), 8.18 (d, J = 8.4 Hz, 1H), 7.45-7.42 (m, 3H), 7.30-7.29 (m, 1H), 6.90 (s, 1H), 6.81 (s, 1H), 5.35 (s, 1H), 4.62 (s, 2H), 3.71 (s, 4H), 3.52 (t, J = 7.2 Hz, 2H), 2.58 (s, 3H), 2.50-2.48 (m, 4H), 2.34 (s, 3H), 2.26 (t, J = 7.2 Hz, 2H), 2.00-1.97 (m, 2H). |
| D32 | 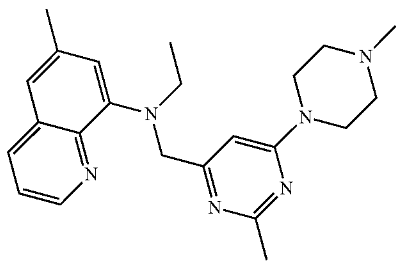 [SMILES: CCN(Cc1cc(N2CCN(C)CC2)nc(C)n1)c1cc(C)cc2cccnc12] | C, BL, AA, AM | ¹H NMR (400 MHz, CDCl$_3$) δ 8.76 (d, J = 4.0 Hz, 1H), 8.04 (d, J = 8.4 Hz, 1H), 7.36-7.33 (m, 1H), 7.20 (s, 1H), 7.07 (s, 1H), 6.91 (s, 1H), 4.64 (s, 2H), 3.74-3.55 (m, 6H), 2.57 (s, 3H), 2.53-2.45 (m, 7H), 2.34 (s, 3H), 1.11 (t, J = 7.2 Hz, 3H). |
| D33 | 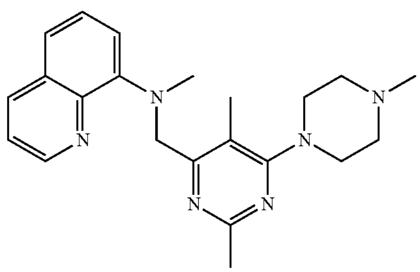 [SMILES: Cc1nc(CN(C)c2cccc3cccnc23)c(C)c(N2CCN(C)CC2)n1] | E, AC, AM | ¹H NMR (400 MHz, CDCl$_3$) δ 8.87 (s, 1H), 8.11 (d, J = 8.0 Hz, 1H), 7.43-7.30 (m, 3H), 7.11 (d, J = 4.4 Hz, 1H), 4.85 (s, 2H), 3.24 (s, 4H), 3.05 (s, 3H), 2.53 (s, 3H), 2.47 (s, 4H), 2.31 (s, 3H), 1.86 (s, 3H). |
| D34 | 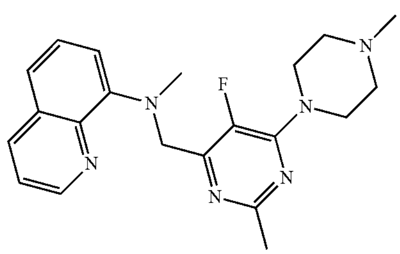 | I, BM | ¹H NMR (400 MHz, CDCl$_3$) δ 8.90 (s, 1H), 8.11 (d, J = 7.6 Hz, 1H), 7.38 (s, 3H), 7.03 (s, 1H), 4.95 (s, 2H), 3.60 (s, 4H), 3.07 (s, 3H), 2.40 (s, 7H), 2.29 (s, 3H). |
| D35 | 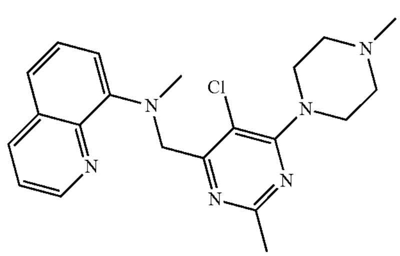 [SMILES: Cc1nc(CN(C)c2cccc3cccnc23)c(F)c(N2CCN(C)CC2)n1] | B, BM, AA | ¹H NMR (400 MHz, CDCl$_3$) δ 8.83 (d, J = 2.4 Hz, 1H), 8.09 (d, J = 8.0 Hz, 1H), 7.41-7.33 (m, 3H), 7.11 (d, J = 6.8 Hz, 1H), 5.10 (s, 2H), 3.53 (s, 4H), 3.16 (s, 3H), 2.49 (s, 4H), 2.45 (s, 3H), 2.32 (s, 3H). |

TABLE 1-continued

Selected compounds (A1-A100, B1-B8, Cl-C39 and D1-D59) of the present invention

| Compd number | structure | method | $^1$HNMR and MS |
|---|---|---|---|
| D36 | 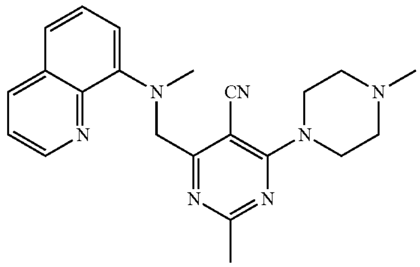 [SMILES: Cc1nc(CN(C)c2cccc3cccnc23)c(C#N)c(N2CCN(C)CC2)n1] | M, BM, AD | $^1$H NMR (400 MHz, CDCl$_3$) δ 8.83 (s, 1H), 8.09 (d, J = 8.0 Hz, 1H), 7.46-7.30 (m, 3H), 7.09 (s, 1H), 5.10 (s, 2H), 3.87 (s, 4H), 3.17 (s, 3H), 2.46 (s, 7H), 2.31 (s, 3H). |
| D37 | 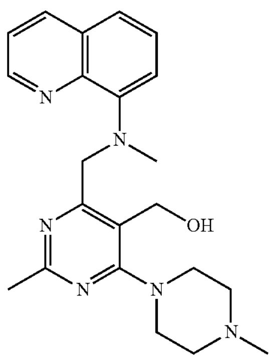 [SMILES: Cc1nc(CN(C)c2cccc3cccnc23)c(CO)c(N2CCN(C)CC2)n1] | AH, AM | $^1$H NMR (400 MHz, CDCl$_3$) δ 8.87 (d, J = 4.0 Hz, 1H), 8.19 (d, J = 8.4 Hz, 1H), 7.62-7.31 (m, 4H), 4.51 (s, 2H), 4.46 (s, 2H), 4.38-3.96 (m, 4H), 3.36-3.11 (m, 4H), 2.83 (s, 3H), 2.79 (s, 3H), 2.59 (s, 3H). MS (ESI/APCI) m/z 392.8 [M + H]$^+$. |
| D38 | 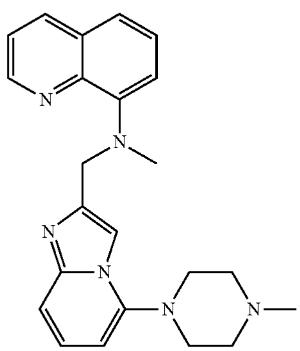 [SMILES: CN1CCN(c2cccc3nc(CN(C)c4cccc5cccnc45)cn23)CC1] | N, BM, AK | $^1$H NMR (400 MHz, CDCl$_3$) δ 8.99 (s, 1H), 8.19 (d, J = 8.0 Hz, 1H), 7.48-7.44 (m, 3H), 7.36 (d, J = 8.8 Hz, 1H), 7.20-7.15 (m, 2H), 7.09 (s, 1H), 6.28 (d, J = 7.2 Hz, 1H), 5.07 (s, 2H), 3.14(s, 3H), 3.03 (s, 4H), 2.56 (s, 4H), 2.42 (s, 3H). |
| D39 | 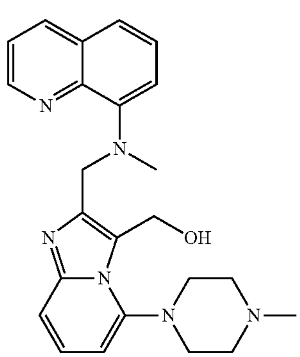 [SMILES: CN1CCN(c2cccc3nc(CN(C)c4cccc5cccnc45)c(CO)n23)CC1] | N, BM, AK | $^1$H NMR (400 MHz, CDCl$_3$) δ 8.93 (s, 1H), 8.18 (d, J = 8.0 Hz, 1H), 7.50 (s, 2H), 7.44-7.38 (m, 2H), 7.32 (s, 1H), 7.15-7.12 (m, 1H), 6.45 (d, J = 7.2 Hz, 1H), 5.81 (s, 1H), 5.21 (s, 2H), 4.75 (s, 2H), 3.44 (d, J = 11.2 Hz, 2H), 2.99-2.91 (m, 7H), 2.53-2.49 (m, 2H), 2.41 (s, 3H). |

TABLE 1-continued

Selected compounds (A1-A100, B1-B8, C1-C39 and D1-D59) of the present invention

| Compd number | structure | method | ¹HNMR and MS |
|---|---|---|---|
| D40 | 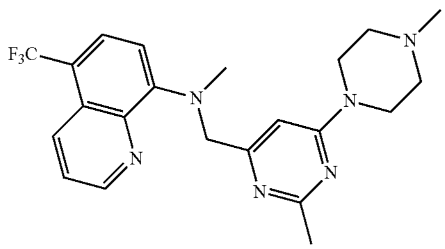 [SMILES: Cc1nc(CN(C)c2ccc(C(F)(F)F)c3cccnc23)cc(N2CCN(C)CC2)n1] | D, BN | ¹H NMR (400 MHz, CDCl₃) δ 8.79 (d, J = 2.8 Hz, 1H), 8.44 (d, J = 8.4 Hz, 1H), 7.77 (d, J = 8.4 Hz, 1H), 7.47 (dd, J = 8.8, 4.0 Hz, 1H), 7.00 (d, J = 8.4 Hz, 1H), 6.61 (s, 1H), 4.84 (s, 2H), 3.59 (s, 4H), 3.13 (s, 3H), 2.52 (s, 3H), 2.46-2.37 (m, 4H), 2.30 (s, 3H). |
| D41 | 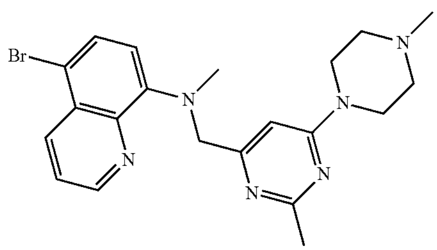 [SMILES: Cc1nc(CN(C)c2ccc(Br)c3cccnc23)cc(N2CCN(C)CC2)n1] | C, BN, AA | ¹H NMR (400 MHz, CDCl₃) δ 8.81-8.79 (m, 1H), 8.48 (d, J = 8.4 Hz, 1H), 7.66 (d, J = 8.4 Hz, 1H), 7.48-7.45 (m, 1H), 6.96 (d, J = 8.4 Hz, 1H), 6.63 (s, 1H), 4.66 (s, 2H), 3.58-3.55 (s, 4H), 3.05 (s, 3H), 2.50 (s, 3H), 2.40-2.38 (s, 4H), 2.29 (s, 3H). |
| D42 | 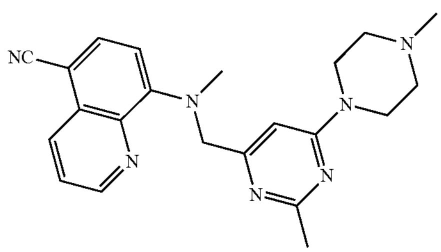 [SMILES: Cc1nc(CN(C)c2ccc(C#N)c3cccnc23)cc(N2CCN(C)CC2)n1] | C, BN, AA, AQ | ¹H NMR (400 MHz, CDCl₃) δ 8.74 (d, J = 3.2 Hz, 1H), 8.43 (d, J = 8.4 Hz, 1H), 7.79 (d, J = 8.4 Hz, 1H), 7.50 (dd, J = 8.4, 4.0 Hz, 1H), 6.94 (d, J = 8.4 Hz, 1H), 6.51 (s, 1H), 4.99 (s, 2H), 3.61-3.52 (m, 4H), 3.19 (s, 3H), 2.50 (s, 3H), 2.43-2.37 (m, 4H), 2.29 (s, 3H). MS (ESI/APCI) m/z 388.2 [M + H]⁺. |
| D43 | 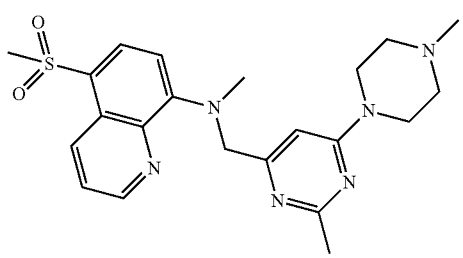 | C, BN, AA, AR | ¹H NMR (400 MHz, CDCl₃) δ 9.01 (dd, J = 8.8, 2.0 Hz, 1H), 8.75 (dd, J = 4.0, 2.0 Hz, 1, 1H), 8.21 (d, J = 8.4 Hz, 1H), 7.52 (dd, J = 8.8, 4.0 Hz, 1H), 7.01 (d, J = 8.4 Hz, 1H), 6.55 (s, 1H), 4.97 (s, 2H), 3.68-3.55 (m, 4H), 3.20 (s, 3H), 3.14 (s, 3H), 2.52 (s, 3H), 2.46-2.38 (m, 4H), 2.31 (s, 3H). MS (ESI/APCI) m/z 441.2 [M + H]⁺. |
| D44 | 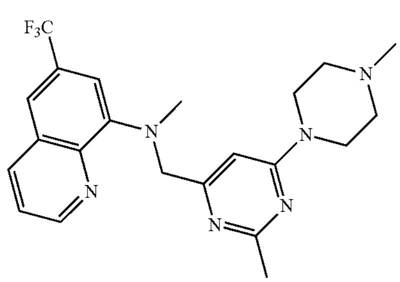 | D, BN | ¹H NMR (400 MHz, CDCl₃) δ 8.85 (s, 1H), 8.17 (d, J = 8.0 Hz, 1H), 7.63 (s, 1H), 7.44 (dd, J = 7.6 Hz, J = 3.6 Hz, 1H), 7.20 (s, 1H), 6.60 (s, 1H), 4.84 (s, 2H), 3.58 (s, 4H), 3.09 (s, 3H), 2.50 (s, 3H), 2.44-2.38 (m, 4H), 2.30 (s, 3H). |

TABLE 1-continued

Selected compounds (A1-A100, B1-B8, C1-C39 and D1-D59) of the present invention

| Compd number | structure | method | ¹HNMR and MS |
|---|---|---|---|
| D45 | 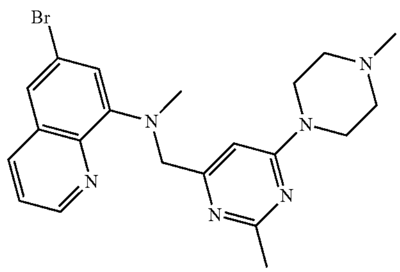 [SMILES: Cc1nc(CN(C)c2cc(Br)cc3cccnc23)cc(N2CCN(C)CC2)n1] | C, BN, AA | ¹H NMR (400 MHz, CDCl$_3$) δ 8.74 (s, 1H), 8.00 (d, J = 8.4 Hz, 1H), 7.51 (s, 1H), 7.39-7.36 (m, 1H), 7.16 (s, 1H), 6.72 (s, 1H), 4.78 (s, 2H), 3.66 (s, 4H), 3.03 (s, 3H), 2.54 (s, 3H), 2.49 (s, 4H), 2.35 (s, 3H). |
| D46 | 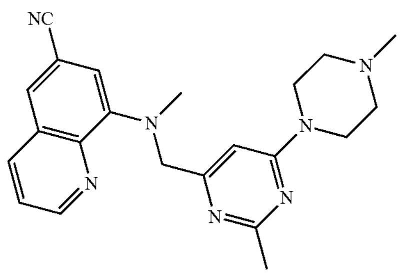 [SMILES: Cc1nc(CN(C)c2cc(C#N)cc3cccnc23)cc(N2CCN(C)CC2)n1] | C, BN, AA, AQ | ¹H NMR (400 MHz, CDCl$_3$) δ 8.85 (dd, J = 4.4, 2.0 Hz, 1H), 8.13 (dd, J = 8.4, 2.0 Hz, 1H), 7.70 (s, 1H), 7.46 (dd, J = 8.4, 4.4 Hz, 1H), 7.14 (s, 1H), 6.63 (s, 1H), 4.80 (s, 2H), 3.67-3.54 (m, 4H), 3.08 (s, 3H), 2.51 (s, 3H), 2.46-2.40 (m, 4H), 2.31 (s, 3H). |
| D47 | 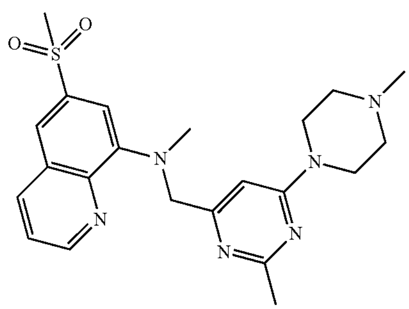 [SMILES: Cc1nc(CN(C)c2cc(S(C)(=O)=O)cc3cccnc23)cc(N2CCN(C)CC2)n1] | C, BN, AA, AR | ¹H NMR (400 MHz, CDCl$_3$) δ 8.87 (d, J = 4.0 Hz, 1H), 8.23 (d, J = 8.4 Hz, 1H), 7.97 (s, 1H), 7.52-7.43 (m, 2H), 6.65 (s, 1H), 4.86 (s, 2H), 3.67-3.58 (m, 4H), 3.12 (s, 6H), 2.51 (s, 3H), 2.47-2.42 (m, 4H), 2.32 (s, 3H). MS (ESI/APCI) m/z 441.1 [M + H]⁺. |
| D48 | 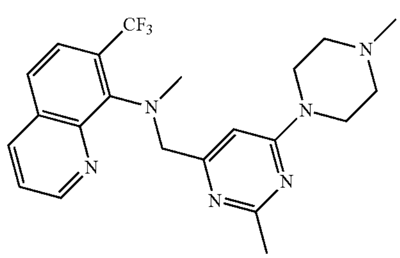 [SMILES: Cc1nc(CN(C)c2c(C(F)(F)F)ccc3cccnc23)cc(N2CCN(C)CC2)n1] | D, BN | ¹H NMR (400 MHz, CDCl$_3$) δ 8.98 (s, 1H), 8.20 (d, J = 8.0 Hz, 1H), 7.76 (s, 2H), 7.49 (dd, J = 8.4, 4.0 Hz, 1H), 7.15 (s, 1H), 4.64 (s, 2H), 3.81 (s, 4H), 3.03 (s, 3H), 2.61-2.58 (m, 4H), 2.52 (s, 3H), 2.40 (s, 3H). |
| D49 | 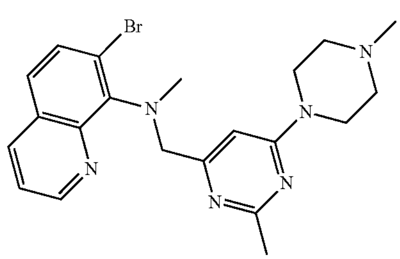 [SMILES: Cc1nc(CN(C)c2c(Br)ccc3cccnc23)cc(N2CCN(C)CC2)n1] | C, BN, AA | ¹H NMR (400 MHz, CDCl$_3$): δ 8.89 (s, 1H), 8.12 (d, J = 8.0 Hz, 1H), 7.72 (d, J = 8.8 Hz, 1H), 7.47 (d, J = 8.8 Hz, 1H), 7.41(s, 2H), 4.68 (s, 2H), 3.74(s, 4H), 3.05 (s, 3H), 2.49 (s, 7H), 2.35 (s, 3H). MS (ESI/APCI) m/z 441.1 [M + H]⁺. |

TABLE 1-continued

Selected compounds (A1-A100, B1-B8, C1-C39 and D1-D59) of the present invention

| Compd number | structure | method | ¹HNMR and MS |
|---|---|---|---|
| D50 | 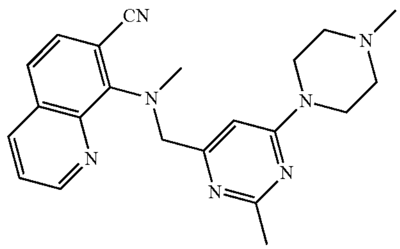 | C, BN, AA, AQ | ¹H NMR (400 MHz, CDCl₃) δ 8.91 (d, J = 2.4 Hz, 1H), 8.14 (d, J = 8.0 Hz, 1H), 7.58-7.46 (m, 3H), 7.06 (s, 1H), 4.91 (s, 2H), 3.75 (s, 4H), 3.31 (s, 3H), 2.49 (s, 7H), 2.34 (s, 3H). |
| D51 | 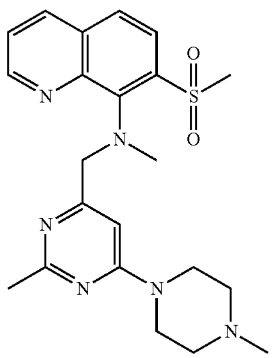 [SMILES: Cc1nc(CN(C)c2c(S(C)(=O)=O)ccc3cccnc23)cc(N2CCN(C)CC2)n1] | C, BN, AA, AR | ¹H NMR (400 MHz, CDCl₃) δ 9.00 (d, J = 3.2 Hz, 1H), 8.23 (dd, J = 8.4, 1.6 Hz, 1H), 8.18 (d, J = 8.8 Hz, 1H), 7.84 (d, J = 8.8 Hz, 1H), 7.52 (dd, J = 8.8, 4.4 Hz, 1H), 7.16 (s, 1H), 5.15 (brs, 1H), 4.21 (brs, 1H), 3.86-3.70 (m, 4H), 3.36 (s, 3H), 3.07 (s, 3H), 2.57-2.42 (m, 7H), 2.35 (s, 3H). MS (ESI/APCI) m/z 441.2 [M + H]⁺. |
| D52 | 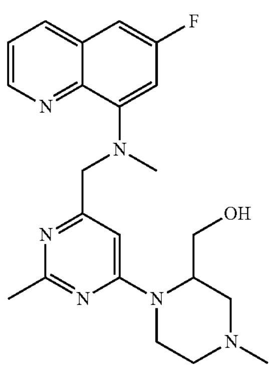 [SMILES: Cc1nc(CN(C)c2cc(F)cc3cccnc23)cc(N2CCN(C)CC2CO)n1] | C, BN, AA | ¹H NMR (400 MHz, CDCl₃) δ 8.70 (s, 1H), 8.03 (d, J = 7.6 Hz, 1H), 7.40-8.32 (m, 1H), 6.94 (d, J = 7.6 Hz, 1H), 6.84 (d, J = 11.2 Hz, 1H), 6.65 (s, 1H), 4.79 (s, 2H), 4.10-3.95 (m, 2H), 3.80-3.76 (m, 1H), 3.52 (d, J = 10.8 Hz, 1H), 3.32 (t, J = 10.8 Hz, 1H), 3.13-2.95 (m, 4H), 2.81 (d, J = 10.4 Hz, 1H), 2.51 (s, 3H), 2.38-2.20 (m, 5H). |
| D53 | 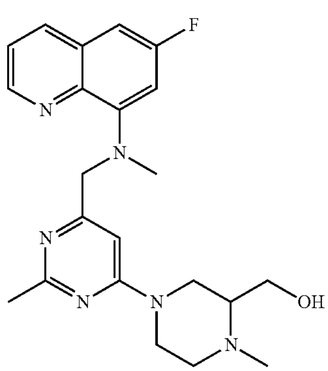 [SMILES: Cc1nc(CN(C)c2cc(F)cc3cccnc23)cc(N2CCN(C)C(CO)C2)n1] | C, BN, AA, AD | ¹H NMR (400 MHz, CDCl₃) δ 8.70 (s, 1H), 8.03 (d, J = 8.0 Hz, 1H), 7.36 (dd, J = 7.2, 3.6 Hz, 1H), 6.95 (d, J = 8.0 Hz, 1H), 6.96-6.70 (m, 2H), 4.78 (s, 2H), 4.56 (s, 1H), 4.10-3.88 (m, 3H), 3.42 (t, J = 10.4 Hz, 1H), 3.10-3.00 (m, 4H), 2.86 (d, J = 10.4 Hz, 1H), 2.51 (s, 3H), 2.35-2.24 (m, 4H), 2.09 (t, J = 9.2 Hz, 1H). |

TABLE 1-continued

Selected compounds (A1-A100, B1-B8, C1-C39 and D1-D59) of the present invention

| Compd number | structure | method | ¹HNMR and MS |
|---|---|---|---|
| D54 | 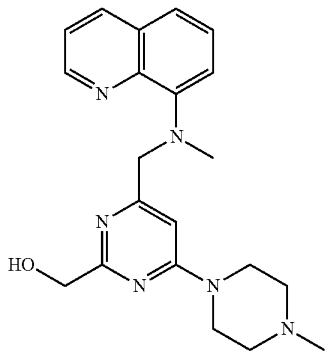 [SMILES: CN1CCN(c2cc(CN(C)c3cccc4cccnc34)nc(CO)n2)CC1] | E, AC, AM | ¹H NMR (400 MHz, CDCl$_3$) δ 8.82 (s, 1H), 8.12 (d, J = 8.0 Hz, 1H), 7.45-7.36 (m, 3H), 7.12 (d, J =7.2 Hz, 1H), 6.70 (s, 1H), 4.75 (s, 2H), 4.56 (s, 2H), 3.86 (br s, 1H), 3.68-3.51 (m, 4H), 3.05 (s, 3H), 2.47-2.35 (m, 4H), 2.30 (s, 3H). MS (ESI/APCI) m/z 378.9 [M + H]$^+$. |
| D55 | 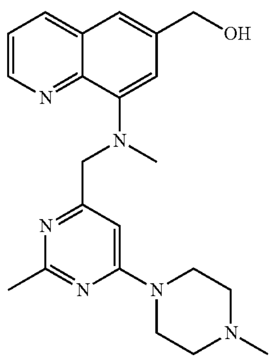 [SMILES: Cc1nc(CN(C)c2cc(CO)cc3cccnc23)cc(N2CCN(C)CC2)n1] | D, BN, AO, AJ | ¹H NMR (400 MHz, CDCl$_3$) δ 8.76 (s, 1H), 8.07 (d, J = 8.0 Hz, 1H), 7.45-7.30 (m, 2H), 7.17 (s, 1H), 6.79 (s, 1H), 4.81 (s, 2H), 4.66 (s, 2H), 3.63 (s, 4H), 3.03 (s, 3H), 2.54 (s, 3H), 2.50-2.43 (m, 4H), 2.32 (s, 3H). |
| D56 | 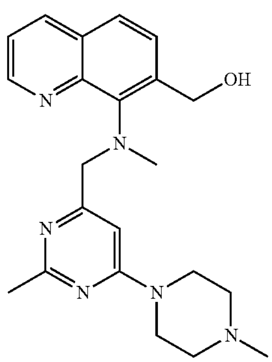 [SMILES: Cc1nc(CN(C)c2c(CO)ccc3cccnc23)cc(N2CCN(C)CC2)n1] | D, BN, AN, AJ | ¹H NMR (400 MHz, CDCl$_3$) δ 8.90 (s, 1H), 8.14 (d, J = 8.0 Hz, 1H), 7.63 (d, J = 8.0 Hz, 1H), 7.50 (d, J = 8.0 Hz, 1H), 7.37-7.30 (m, 1H), 6.36 (s, 1H), 5.30 (s, 1H), 4.70-4.20 (m, 3H), 3.69 (s, 4H), 2.96 (s, 3H), 2.53 (s, 3H), 2.48 (s, 4H), 2.34 (s, 3H). |
| D57 | 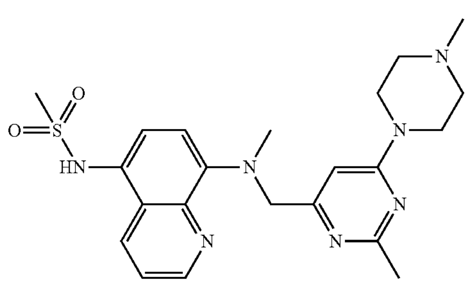 [SMILES: Cc1nc(CN(C)c2ccc(NS(C)(=O)=O)c3cccnc23)cc(N2CCN(C)CC2)n1] | D, AS | ¹H NMR (400 MHz, CDCl$_3$) δ 8.76 (s, 1H), 8.61 (d, J = 8.0 Hz, 1H), 7.51-7.46 (m, 2H), 7.00 (d, J = 8.0 Hz, 1H), 6.87 (s, 1H), 4.69 (s, 2H), 3.78 (s, 4H), 3.05 (s, 3H), 3.01 (s, 3H), 2.61 (s, 7H), 2.43 (s, 3H). MS (ESI/APCI) m/z 455.9 [M + H]$^+$. |

TABLE 1-continued

Selected compounds (A1-A100, B1-B8, C1-C39 and D1-D59) of the present invention

| Compd number | structure | method | ¹HNMR and MS |
|---|---|---|---|
| D58 | 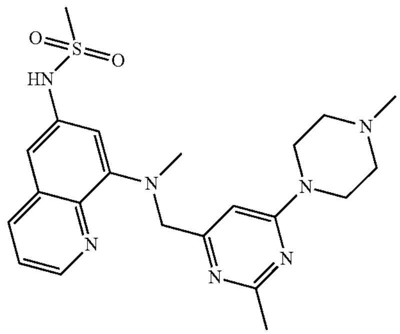 [SMILES: Cc1nc(CN(C)c2cc(NS(C)(=O)=O)cc3cccnc23)cc(N2CCN(C)CC2)n1] | C, BN, AA, AO, BO, AT | ¹H NMR (400 MHz, CDCl₃) δ 8.70 (d, J = 4.0 Hz, 1H), 8.01 (d, J = 8.4 Hz, 1H), 7.38-7.30 (m, 1H), 7.27 (s, 1H), 6.91 (s, 1H) 6.67 (s, 1H), 4.68 (s, 2H), 3.77 (t, J = 4.4 Hz, 2H), 3.63 (t, J = 4.4 Hz, 2H), 3.07 (s, 3H), 3.04 (s, 3H), 2.48 (s, 3H), 2.44-2.34 (m, 4H), 2.29 (s, 3H). MS (ESI/APCI) m/z 455.7 [M + H]⁺. |
| D59 | 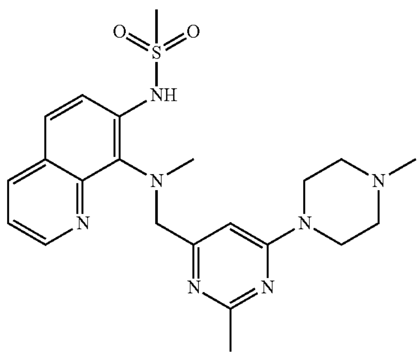 [SMILES: Cc1nc(CN(C)c2c(NS(C)(=O)=O)ccc3cccnc23)cc(N2CCN(C)CC2)n1] | C, BN, AA, AO, BO, AT | ¹H NMR (400 MHz, CDCl₃) δ 8.89 (d, J = 5.2 Hz, 1H), 8.11 (d, J = 8.4 Hz, 1H), 7.96 (d, J = 8.8 Hz, 1H), 7.67 (d, J = 9.2 Hz, 1H), 7.34-7.31 (m, 1H), 6.25 (s, 1H), 4.61-4.34 (m, 1H), 4.24-3.98 (m, 1H), 3.77 (t, J = 4.4 Hz, 2H), 3.62 (t, J = 4.4 Hz, 2H), 3.03 (s, 3H), 2.98 (s, 3H), 2.64 (s, 3H), 2.56-2.49 (m, 4H), 2.37 (s, 3H). MS (ESI/APCI) m/z 455.7 [M + H]⁺. |

Biological Activities

Example 22

HPB-ALL CXCR4 Competitive Binding Assay

Figure 2:
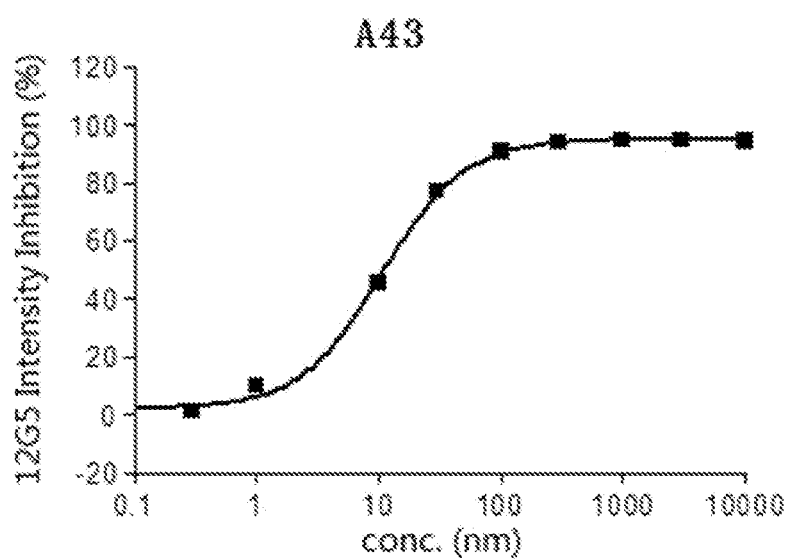
FIG. 2 depicts the 12G5 assay by compound A43.

HPB-ALL cells were maintained in RPMI-1640 (Gibico) supplemented with 10% FBS (Hyclone). APC-conjugated anti-human CXCR4 was from Sungene. $EC_{80}$ was first determined for 12G5 binding to CXCR4. Then the compounds for testing were added into 96-well plates serially diluted at a ratio of 1:3. Cells were washed once with ice-cold assay buffer (DPBS+2% HI-FBS) and then re-suspended in the same buffer at a final concentration of $1\times10^6$/mL. Cell suspension was then added into the wells and with the addition of APC-conjugated anti-human CXCR4 clone 12G5 at its $EC_{80}$ determined. The mix of cell, compounds and APC-conjugated anti-human CXCR4 were incubated at 4° C. for 3 h before addition of 100 μL of 4% PFA. Cells were then washed once and resuspended in assay buffer and examined by FACS. The percent (%) effect at each concentration of compound was calculated and relative to the amount of calcium produced in the positive and negative control wells contained within each assay plate. The concentrations and % effect values for tested compounds were plotted and the concentration of compound required for 50% effect ($IC_{50}$) was determined. Tables 2 summarize results of the CXCR4 competitive binding assay for selected compounds disclosed in the present disclosure. Table 3 summarizes results of the CXCR4 competitive binding assay for control compounds. FIGS. 1-2 depict the $IC_{50}$ curves of compounds A42 and A43.

TABLE 2

Results of selected compounds of the present invention tested by the 12G5 binding assay

| Compound number | IC₅₀ (nM) | Compound number | IC₅₀ (nM) | Compound number | IC₅₀ (nM) |
|---|---|---|---|---|---|
| A1 | 45 | A2 | 228 | A3 | 19 |
| A4 | 229 | A5 | 113 | A6 | 1138 |
| A7 | 393 | A8 | 242 | A9 | 14 |
| A10 | 23 | A11 | 26 | A12 | 8000 |
| A13 | 8000 | A14 | 2253 | A15 | 606 |
| A16 | 17 | A17 | 2689 | A18 | 43 |
| A19 | 67 | A20 | 210 | A21 | 790 |
| A22 | 32 | A23 | 34 | A24 | 42 |
| A25 | 100 | A26 | 41 | A27 | 7.9 |
| A28 | 21 | A29 | 78 | A30 | 65 |
| A31 | 77 | A32 | 22 | A33 | 268 |
| A34 | 47 | A35 | 106 | A36 | 5735 |
| A37 | 4432 | A38 | 6940 | A39 | 94 |
| A40 | 110 | A41 | 97 | A42 | 9.8 |
| A43 | 11 | A44 | 296 | A45 | 886 |
| A46 | 161 | A47 | 58 | A48 | 240 |
| A49 | 123 | A50 | 211 | A51 | 16 |
| A52 | 27 | A53 | 33 | A54 | 356 |
| A55 | 44 | A56 | 131 | A57 | 21 |
| A58 | 19 | A59 | 63 | A60 | 464 |
| A61 | 8.8 | A62 | 2288 | A63 | 29 |
| A64 | 21 | A65 | 13 | A66 | 20 |
| A67 | 12 | A68 | 46 | A69 | 27 |
| A70 | 54 | A71 | 90 | A72 | 146 |
| A73 | 32 | A74 | 100 | A75 | 15 |
| A76 | 220 | A77 | 9 | C1 | 93 |
| C2 | 9000 | C3 | 9000 | C4 | 2324 |
| C5 | 20 | C6 | 3235 | C7 | 9000 |
| C8 | 6957 | C9 | 9000 | C10 | 248 |

TABLE 2-continued

Results of selected compounds of the present
invention tested by the 12G5 binding assay

| Compound number | $IC_{50}$ (nM) | Compound number | $IC_{50}$ (nM) | Compound number | $IC_{50}$ (nM) |
|---|---|---|---|---|---|
| C11 | 142 | C12 | 165 | C13 | 62 |
| C14 | 8105 | C15 | 500 | C16 | 7.74 |
| C17 | 9000 | C18 | 429 | C19 | 1709 |
| C20 | 9000 | C21 | 82 | C22 | 9000 |
| C23 | 144 | C24 | 9000 | C25 | 68 |
| C26 | 206 | C27 | 279 | C28 | 2283 |
| C29 | 1200 | C30 | 9000 | C31 | 9000 |
| C32 | 9000 | D1 | 18 | D2 | 65 |
| D4 | 55 | D14 | 57 | D20 | 675 |
| D25 | 151 | D28 | 338 | D30 | 3822 |
| D36 | 1171 | | | | |

TABLE 3

Results of selected control compounds
tested by the 12G5 binding assay

| Compound number | $IC_{50}$ (nM) | Compound number | $IC_{50}$ (nM) | Compound number | $IC_{50}$ (nM) |
|---|---|---|---|---|---|
| B1 | >10000 | B2 | >10000 | B3 | >10000 |
| B4 | >10000 | B5 | >10000 | B6 | >10000 |
| B7 | >10000 | B8 | >10000 | | |

Example 23

FLIPR Tetra Calcium Mobilization Assay

Figure 3:
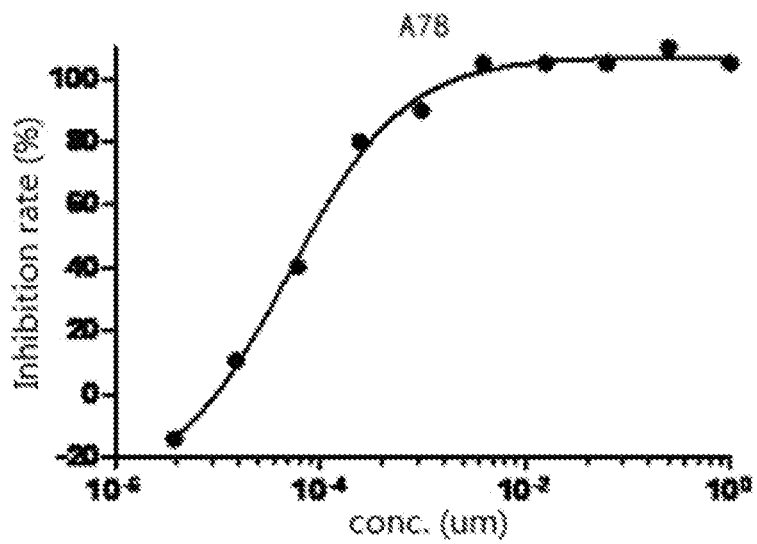
FIG. 3 depicts the 12G5 assay by compound A78.
Figure 4:
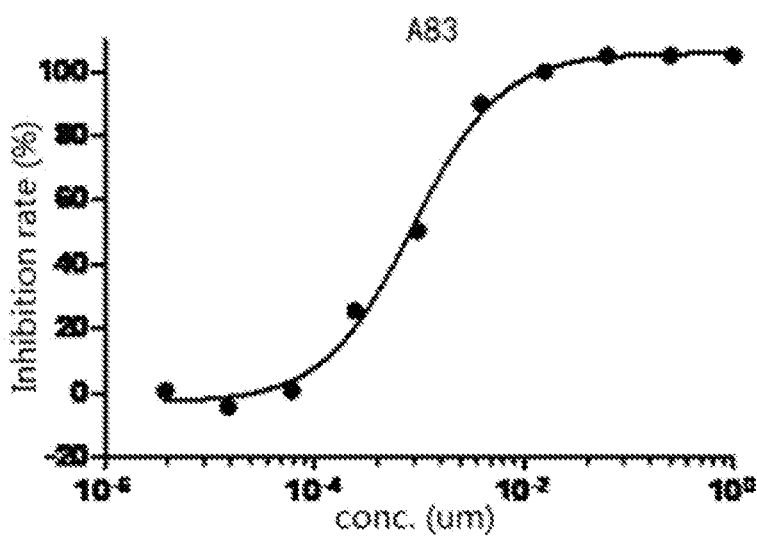
FIG. 4 depicts the 12G5 assay by compound A83.

The FLIPR Tetra calcium mobilization assay was performed by HD Bioscience. Briefly, The Molecular Devices, Fluorescent Imaging Plate Reader (FLIPR) Tetra was used in this assay. Excitation was achieved through unique placement of LED's within the instrument and emission captured by a CCD camera (EMCCD camera for FI and ICCD camera for luminescence). The homogeneous FLIPR Calcium 4 assay kit from Molecular Devices was used as the fluorescence reagent. Compounds were solubilized in 100% dimethyl sulfoxide (DMSO) to a concentration of 30 mM. A 10-point, 4-fold, intermediate dilution series was created in 100% DMSO with a top concentration of 4 mM and a bottom concentration of 0.01 µM. A near assay ready, direct dilution plate (ddNARP) was prepared from this compound dilution plate by transferring 1 µL of each dilution of compound in 100% DMSO to a Greiner #781201 plate. In addition, each ddNARP plate also contained positive and negative control wells to define the upper and lower limits for the assay signal. The final assay concentration range of compound was 10 µM to 0.035 nM in 0.5% DMSO. Human $CD^{4+}$ T-Cells were isolated from human whole blood and subsequently activated and expanded using a CD3/CD28 expansion kit (Life Technologies). The cells were frozen in ThermoFisher-formulated Recovery Cell Culture Freezing Medium containing 10% Dimethyl sulfoxide (DMSO) and 10% Fetal Bovine Serum (FBS) (ThermoFisher Catalog No. 10100147). When used, cells were resuspended using room temperature 1× HBSS/20 mM HEPES/0.005% P-104 assay buffer, adjusted the volume of the suspension to achieve a cell concentration of $2.5 \times 10^6$ cells/mL. 2× Calcium 4 dye (20 µL/well) were added and the mixture were centrifuged briefly (~10 s) and stopped when it reached 1000 rpm. The plates were allowed to equilibrate before compounds and CXCL12 were added to the plates. The raw data were analyzed using Abase. The percent (%) effect at each concentration of compound was calculated by Abase and was based on and relative to the amount of calcium produced in the positive and negative control wells contained within each assay plate. The concentrations and % effect values for tested compounds were plotted by Abase and the concentration of compound required for 50% effect ($IC_{50}$) was determined with a four-parameter logistic dose response equation. Table 4 summarizes the results of selected compounds in the calcium mobilization assay. FIGS. 3 and 4 summarize the results of Compounds A78 and A83 in the calcium mobilization assay.

TABLE 4

Results of selected compounds of the present invention
tested by the calcium mobilization assay

| Compound number | $IC_{50}$ (nM) | Compound number | $IC_{50}$ (nM) | Compound number | $IC_{50}$ (nM) |
|---|---|---|---|---|---|
| A1 | 4.5 | A22 | 3.4 | A42 | 0.021 |
| A61 | 0.024 | A75 | 0.090 | A78 | 0.062 |
| A79 | 0.22 | A80 | 0.18 | A81 | 4.5 |
| A82 | 2.5 | A83 | 0.93 | A84 | 3.0 |
| A85 | 0.99 | A86 | 0.13 | A87 | 0.18 |
| A88 | 0.30 | A89 | 0.13 | A90 | 0.046 |
| A91 | 0.032 | A92 | 118 | A93 | 20000 |
| A94 | 20000 | A95 | 0.13 | A96 | 0.086 |
| A97 | 0.25 | A98 | 0.15 | A99 | 0.39 |
| A100 | 0.29 | C33 | 1.1 | C34 | 1.8 |
| C35 | 2.7 | C36 | 0.5 | C37 | 12 |
| C38 | 0.2 | C39 | 0.1 | D1 | 1.2 |
| D2 | 0.24 | D3 | 0.63 | D4 | 0.14 |
| D5 | 2.1 | D6 | 2.4 | D7 | 0.75 |
| D8 | 1.4 | D9 | 0.59 | D10 | 2.9 |
| D11 | 1700 | D12 | 0.61 | D13 | 2.9 |
| D14 | 0.3 | D15 | 0.4 | D16 | 2.7 |
| D17 | 74 | D18 | 0.79 | D19 | 0.4 |
| D20 | 3.1 | D21 | 1581 | D22 | 965 |
| D23 | 20000 | D24 | 12400 | D25 | 016 |
| D26 | 2.3 | D27 | 1.7 | D28 | 0.21 |
| D29 | 12.7 | D30 | 9.3 | D31 | 1.25 |
| D32 | 0.53 | D33 | 0.51 | D34 | 0.83 |
| D35 | 1.2 | D36 | 3.6 | D37 | 0.95 |
| D38 | 0.18 | D39 | 0.088 | D40 | 2850 |
| D41 | 6.3 | D42 | 96 | D43 | 3380 |
| D44 | 104 | D45 | 3.0 | D46 | 53 |
| D47 | 13 | D48 | 928 | D49 | 4.5 |
| D50 | 14 | D51 | 2087 | D52 | 4.5 |
| D53 | 6.7 | D54 | 7.2 | D55 | 39 |
| D56 | 5.5 | D57 | 2880 | D58 | 55 |
| D59 | 450 | | | | |

What is claimed is:
1. A compound according to Formula III:

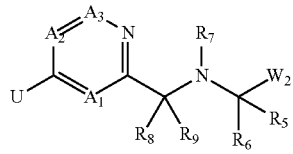

III or a pharmaceutically acceptable salt, hydrate, solvate, stereoisomer or tautomer thereof, wherein
each of $A_1$, $A_2$, and $A_3$ is independently selected from the group consisting of N and $CR_{44}$,
wherein at least one of $A_1$, $A_2$, and $A_3$ is N;

$W_2$ is

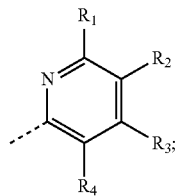

U is

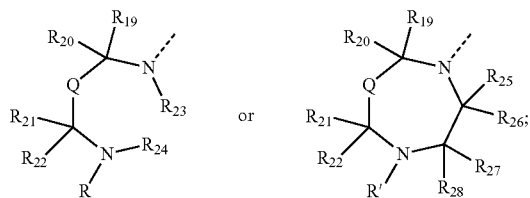

Q is a bond or $CR_{29}R_{30}$;

each of $R_1$, $R_2$, $R_3$, and $R_4$ is independently selected from the group consisting of H, deuterium, —CN, halide, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), —NHS(=O)$_2$($C_{1-6}$ alkyl), $C_{1-6}$ alkyl, $C_{3-6}$ cycloalkyl, $C_{1-8}$ alkoxy, $C_{2-6}$ alkenyl, and $C_{2-6}$ alkynyl, wherein each of $C_{1-6}$ alkyl, $C_{3-6}$ cycloalkyl, and $C_{1-8}$ alkoxy is unsubstituted or substituted with 1-3 groups independently selected from the group consisting of halide and deuterium;

each of $R_5$ and $R_6$ is independently selected from the group consisting of H, deuterium, —CN, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), and $C_{1-3}$ alkoxy; or $R_5$ is O or $CR_{45}R_{46}$, and $R_4$ and $R_5$, together with atoms they attached to, form a ring;

$R_7$ is selected from the group consisting of H, $C_{1-6}$ alkyl, $C_{3-6}$ cycloalkyl, and $C_{3-6}$ heterocycloalkyl comprising an O, wherein each of $C_{1-6}$ alkyl, $C_{3-6}$ cycloalkyl, and $C_{3-6}$ heterocycloalkyl is unsubstituted or substituted with 1-3 groups independently selected from the group consisting of halide, deuterium, $C_{3-6}$ cycloalkyl, and $C_{3-6}$ heterocycloalkyl comprising an O;

each of $R_8$ and $R_9$ is independently selected from the group consisting of H, deuterium, —CN, $C_{1-6}$ alkyl, and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, and $C_{1-3}$ alkoxy; or $R_7$ and $R_8$, and atoms attached thereto, form a ring;

or $R_8$ and $R_9$, together with atoms they attached to, form a ring;

$R_{44}$ is H, deuterium, halide, —CN, —OH, amino, $C_{1-6}$ alkyl, $C_{3-6}$ cycloalkyl, $C_{1-8}$ alkoxy, —NH($C_{1-6}$ alkyl), —N($C_{1-6}$ alkyl)$_2$, —C(=O)NH($C_{1-6}$ alkyl), —C(=O)N($C_{1-6}$ alkyl)$_2$, —S($C_{1-6}$ alkyl), $C_{2-6}$ alkenyl, $C_{2-6}$ alkynyl, 4-7 membered heterocycle comprising 1-3 heteroatoms independently selected from the groups consisting of O, N and S, aryl, and 5-6 membered heteroaryl, wherein each of $C_{1-6}$ alkyl, $C_{3-6}$ cycloalkyl, $C_{1-8}$ alkoxy, heterocycle, aryl and heteroaryl is unsubstituted or substituted with 1-3 groups independently selected from the group consisting of halide, deuterium, —OH and $C_{1-3}$ alkoxy;

$R_{23}$ is selected from the group consisting of H, $C_{1-6}$ alkyl and $C_{3-6}$ cycloalkyl, wherein each of $C_{1-6}$ alkyl and $C_{3-6}$ cycloalkyl is unsubstituted or substituted with 1-3 groups independently selected from the group consisting of halide, deuterium, —OH, amino, —NH($C_{1-6}$ alkyl), —N($C_{1-6}$ alkyl)$_2$, and $C_{1-3}$ alkoxy;

each of $R_{19}$, $R_{20}$, $R_{21}$, $R_{22}$, $R_{25}$, $R_{26}$, $R_{27}$, $R_{28}$, $R_{29}$, and $R_{30}$ is independently selected from the group consisting of H, deuterium, —CN, —OH, $C_{1-6}$ alkyl, $C_{3-6}$ cycloalkyl, and $C_{1-3}$ alkoxy, wherein each of $C_{1-6}$ alkyl, $C_{3-6}$ cycloalkyl, and $C_{1-3}$ alkoxy is unsubstituted or substituted with 1-3 groups independently selected from the group consisting of halide, deuterium, —OH, amino, —NH($C_{1-6}$ alkyl), —N($C_{1-6}$ alkyl)$_2$, —NHC(=O)($C_{1-6}$ alkyl), —NHC(=O)O($C_{1-6}$ alkyl), and $C_{1-3}$ alkoxy; or $R_{22}$ and $R_{23}$, together with atoms they attached to, form a ring; or $R_{19}$ and $R_{26}$, together with atoms they attached to, form a ring;

or $R_{21}$ and $R_{26}$, together with atoms they attached to, form a ring;

each of R and $R_{24}$ is independently selected from the group consisting of H, $C_{1-6}$ alkyl, $C_{3-6}$ cycloalkyl, $C_{3-6}$ heterocycloalkyl comprising N or O, —C(=O)($C_{1-6}$ alkyl), —C(=O)O($C_{1-6}$ alkyl), and —C(=O)NH($C_{1-6}$ alkyl), wherein each of $C_{1-6}$ alkyl, $C_{3-6}$ cycloalkyl, and $C_{3-6}$ heterocycloalkyl is unsubstituted or substituted with 1-3 groups independently selected from the group consisting of halide, deuterium, —OH, —CN, $C_{3-6}$ cycloalkyl, $C_{1-3}$ alkoxy, and $C_{3-6}$ heterocycloalkyl comprising N or O; or R and $R_{24}$, together with N atom they attached to, form a 5-7 membered heterocycle; or R and $R_{21}$, together with N atom they attached to, form a 5-7 membered heterocycle;

R' is selected from the group consisting of H, $C_{1-6}$ alkyl, $C_{3-6}$ cycloalkyl, and $C_{3-8}$ heterocycloalkyl comprising N or O, wherein each of $C_{1-6}$ alkyl, $C_{3-6}$ cycloalkyl, and $C_{3-8}$ heterocycloalkyl is unsubstituted or substituted with 1-3 groups independently selected from the group consisting of halide, deuterium, —OH, —CN, $C_{3-6}$ cycloalkyl, $C_{1-3}$ alkoxy, —S(=O)$_2$($C_{1-6}$ alkyl), —C(=O)($C_{1-6}$ alkyl), and $C_{3-6}$ heterocycloalkyl comprising N or O; or R' and $R_{21}$, together with N atom they attached to, form a 5-7 membered heterocycle; and each of $R_{45}$ and $R_{46}$ is independently selected from the group consisting of H, deuterium, halide, $C_{1-3}$ alkyl; or $R_{45}$ and $R_{46}$, together with the atoms they attached to, form a ring.

2. The compound of claim 1, or a pharmaceutically acceptable salt, hydrate, solvate, stereoisomer or tautomer thereof, wherein $A_3$ is $CR_{44}$;

each of $A_1$ and $A_2$ is independently selected from the group consisting of N and $CR_{44}$, wherein at least one of $A_1$ and $A_2$ is N;

$W_2$ is
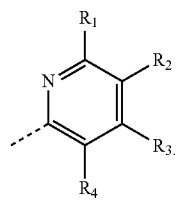
3. The compound of claim 1, or a pharmaceutically acceptable salt, hydrate, solvate, stereoisomer or tautomer thereof, wherein $-C(R_5R_6)W_2$ is selected from the group consisting of:
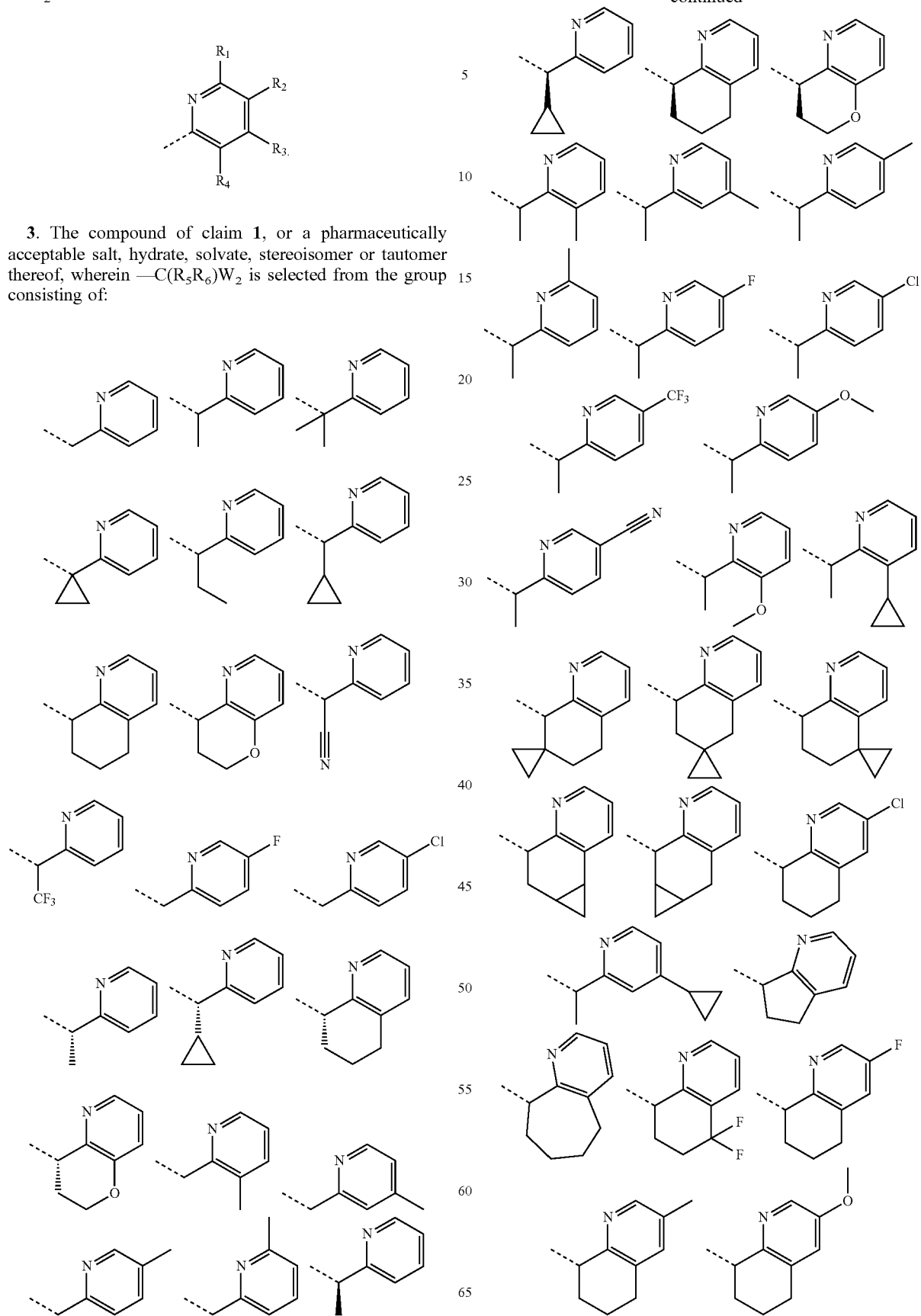

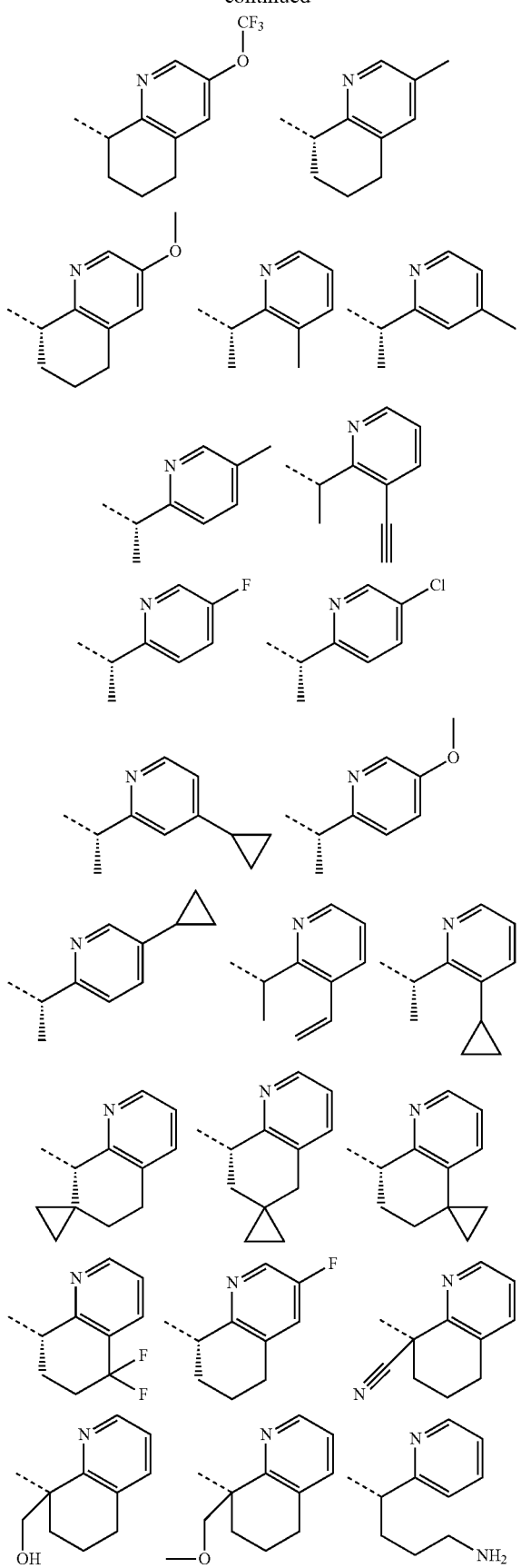
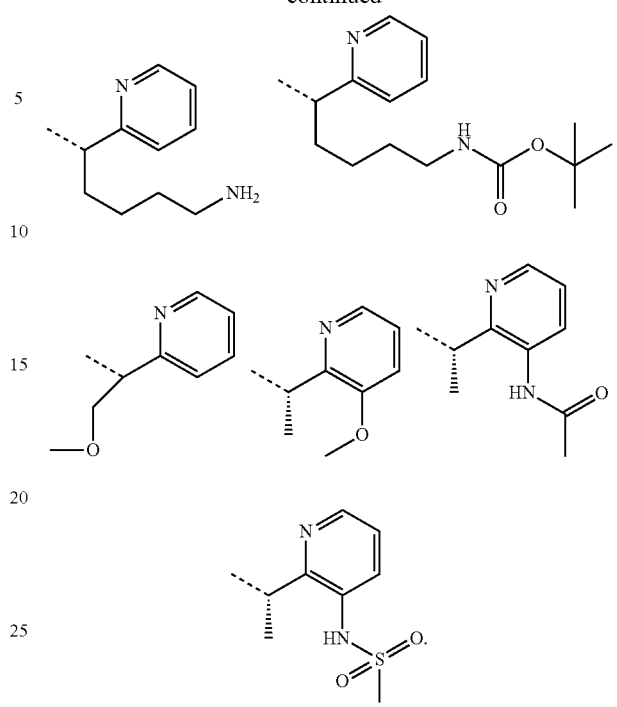
4. The compound of claim 1, or a pharmaceutically acceptable salt, hydrate, solvate, stereoisomer or tautomer thereof, wherein the compound is selected from the group consisting of:
A1
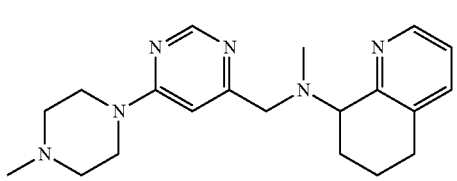
A2
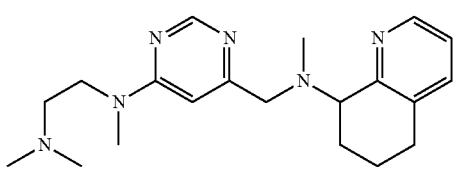
A3
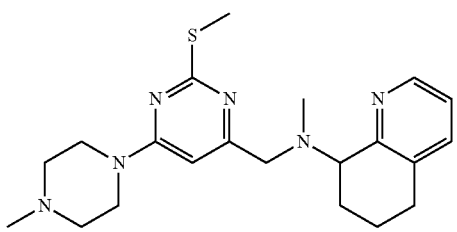
A4
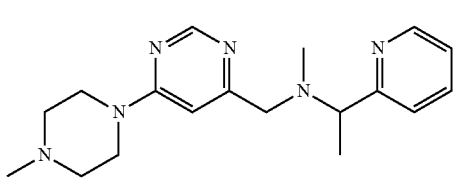

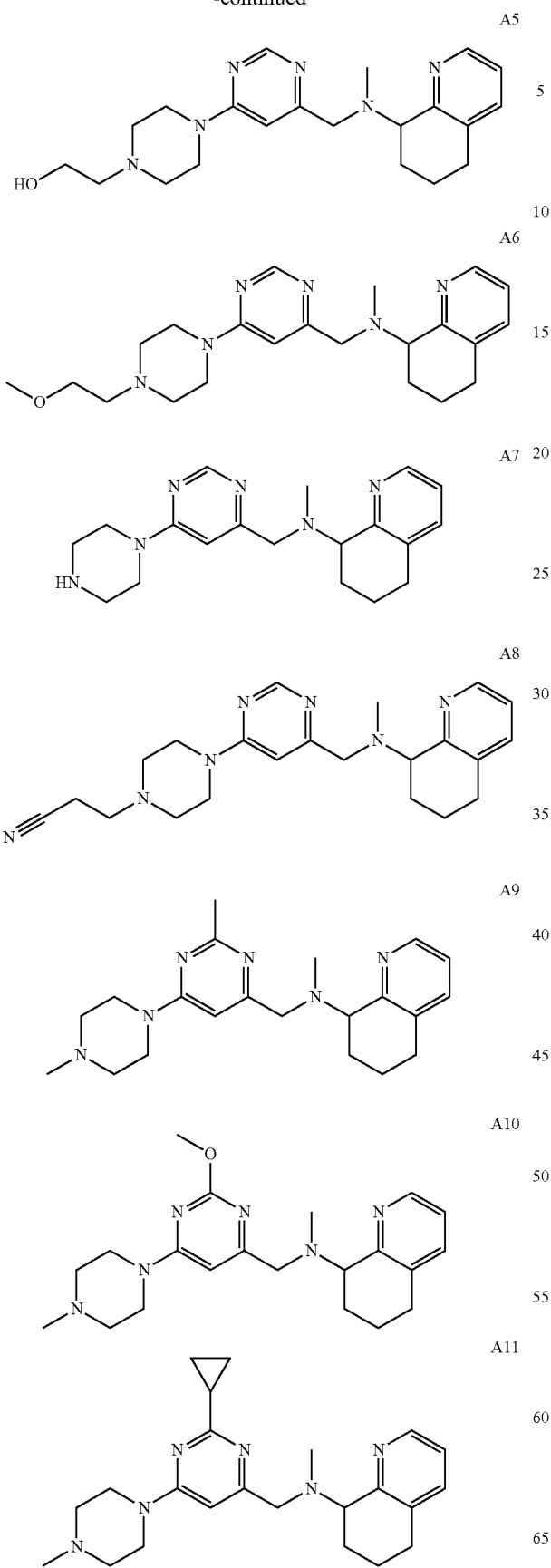

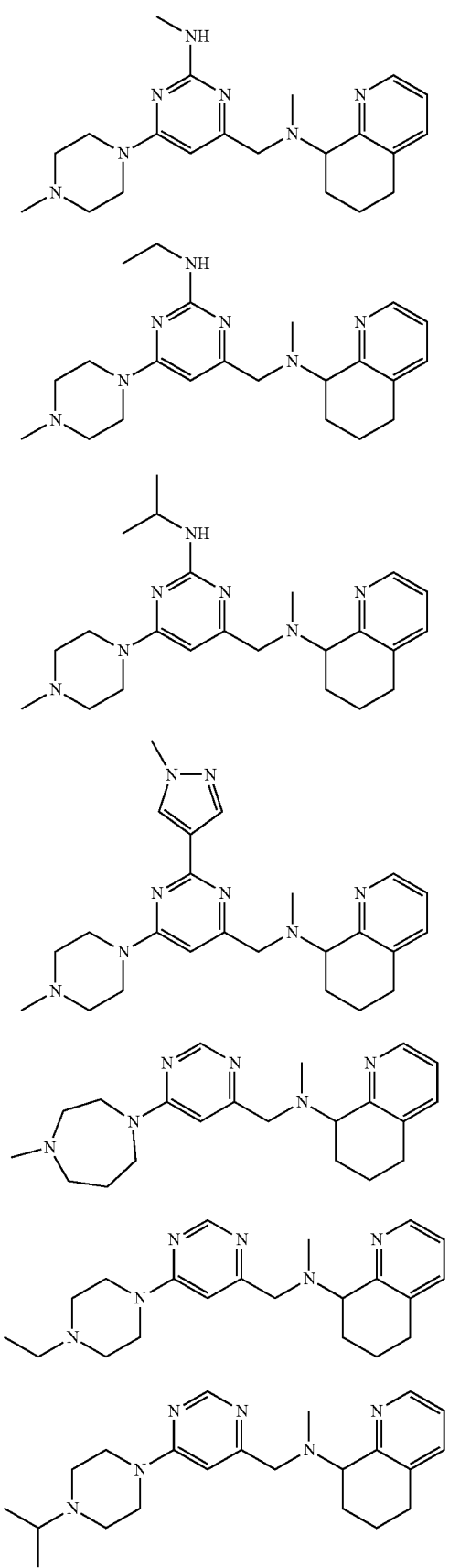
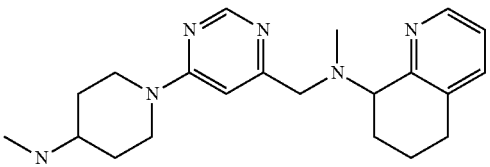
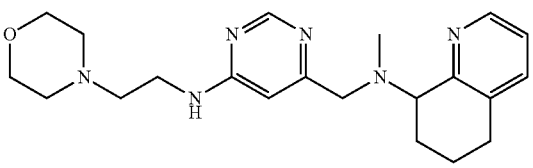
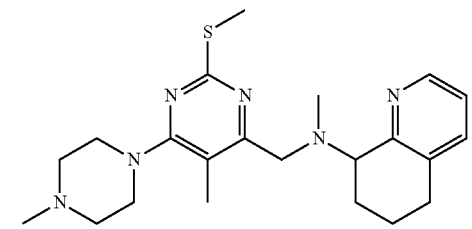
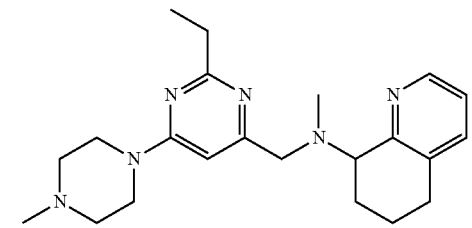
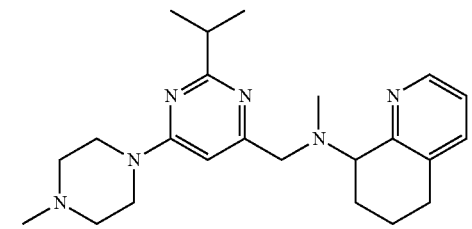
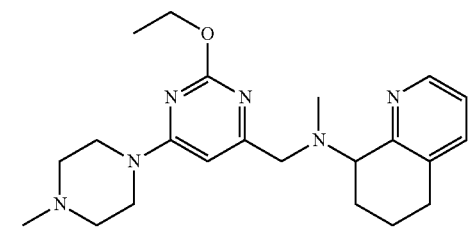
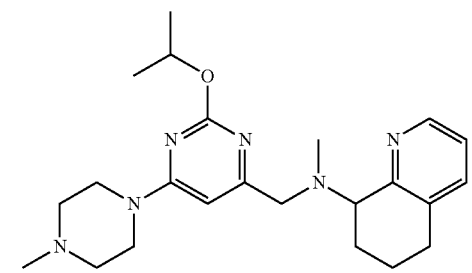

A32
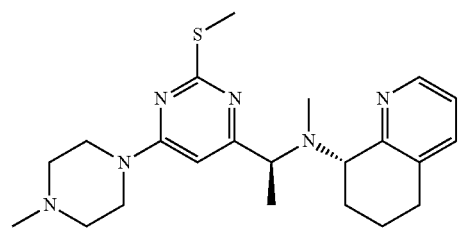
A33
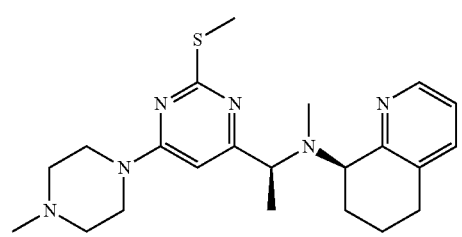
A34
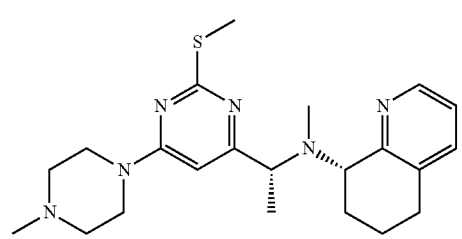
A35
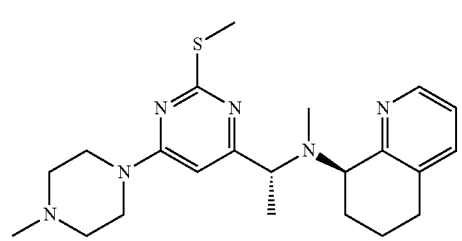
A36
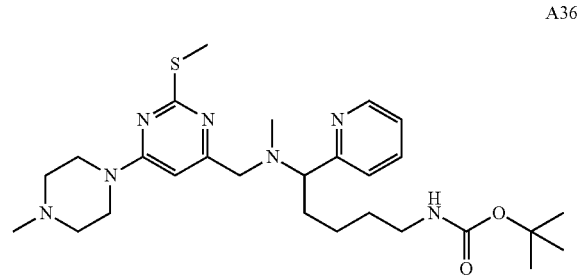
A37
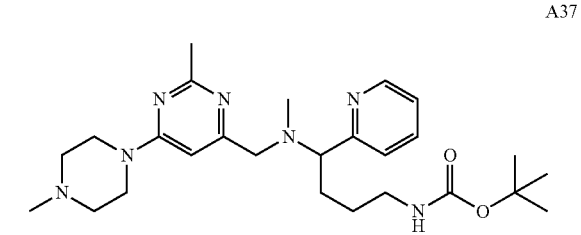
A38
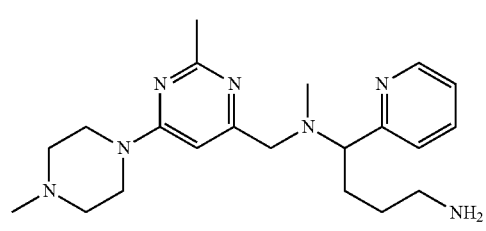
A39
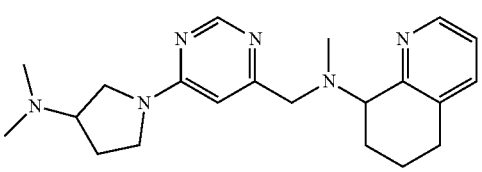
A40
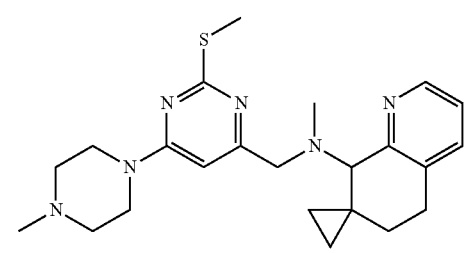
A41
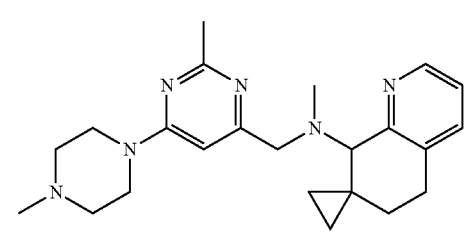
A42
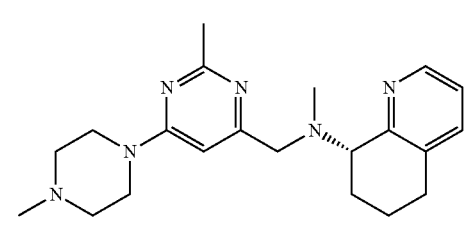
A43
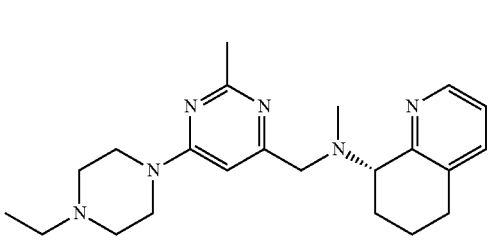
A44
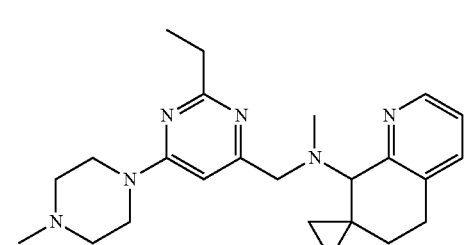
A45
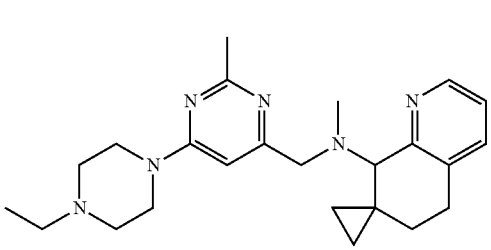

-continued

A46
A47
A48
A49
A50
A51
A52
A53
A54
A55
A56
A57
A58
A59

253
-continued
A60
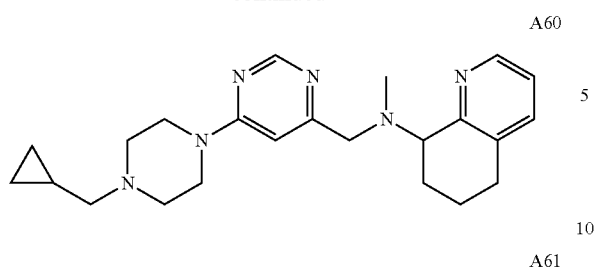
A61
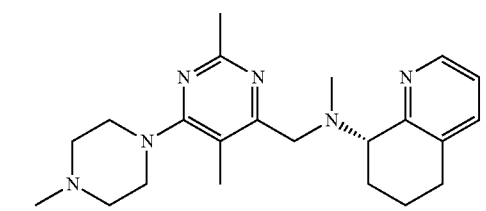
A62
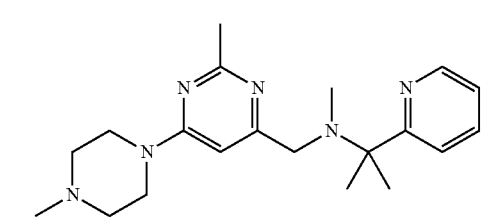
A63
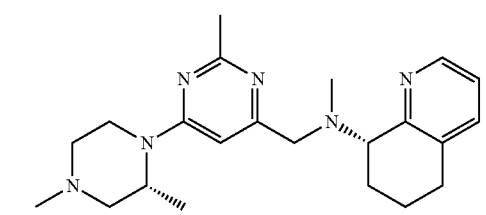
A64
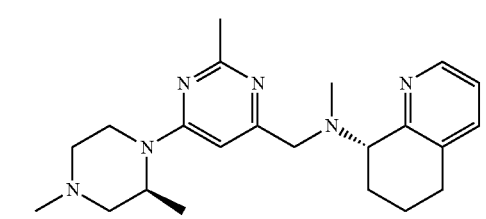
A65
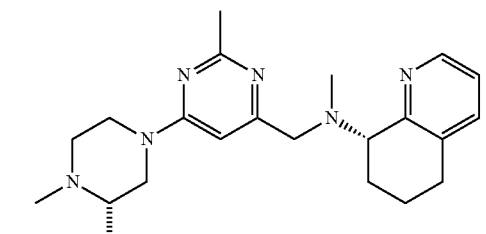
A66
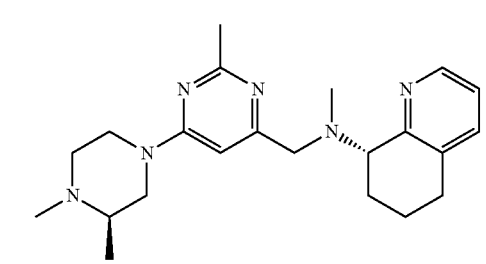
254
-continued
A67
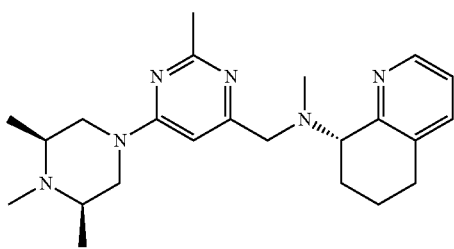
A68
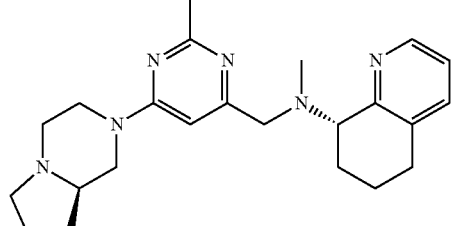
A69
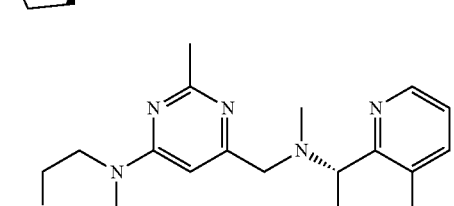
A70
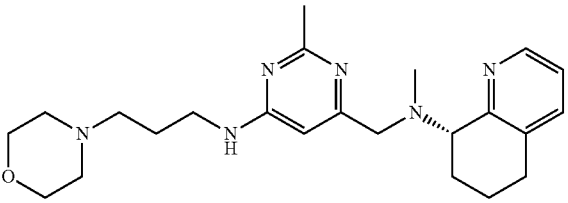
A71
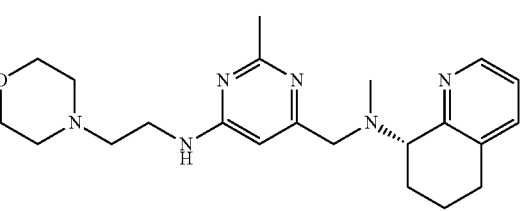
A72
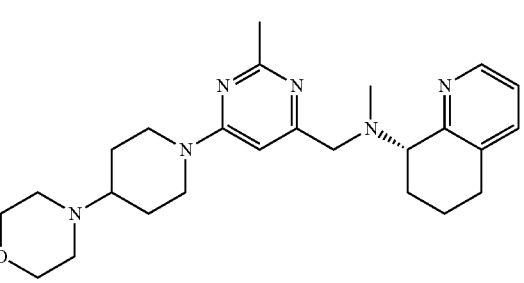

-continued
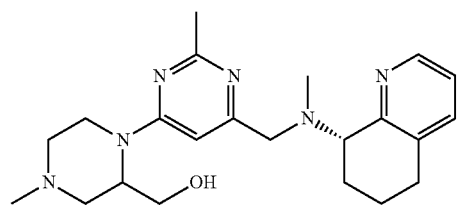
A73
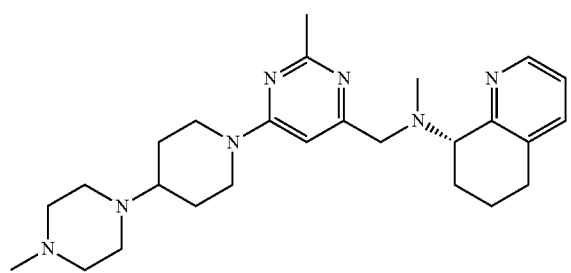
A74
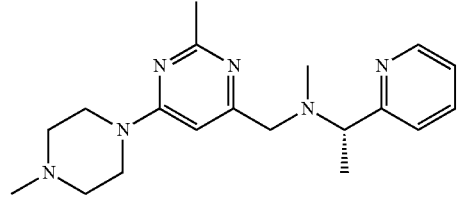
A75
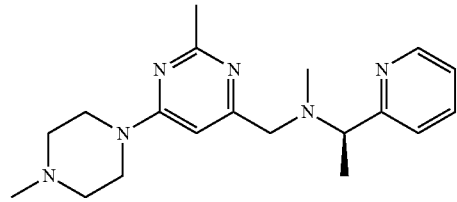
A76
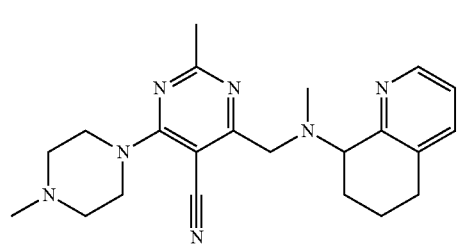
A77
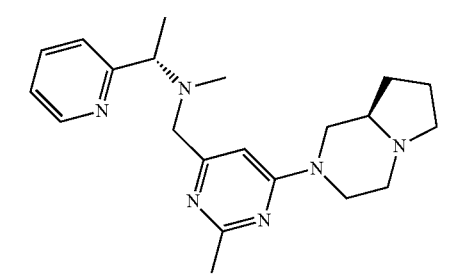
A78
-continued
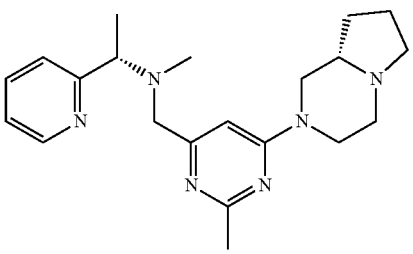
A79
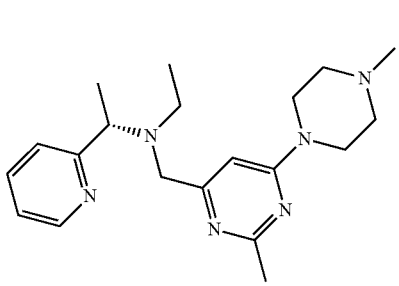
A80
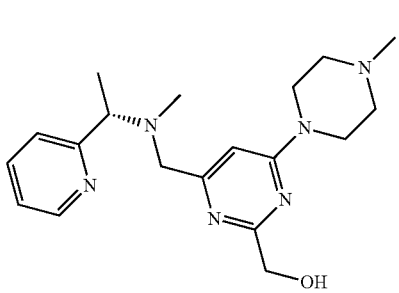
A81
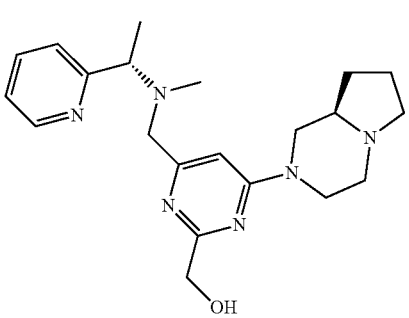
A82
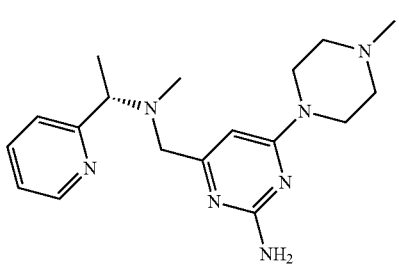
A83

A84
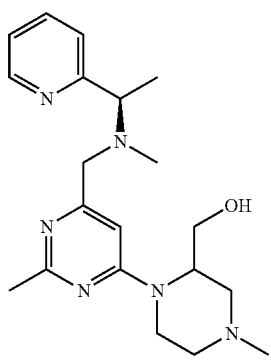
A85
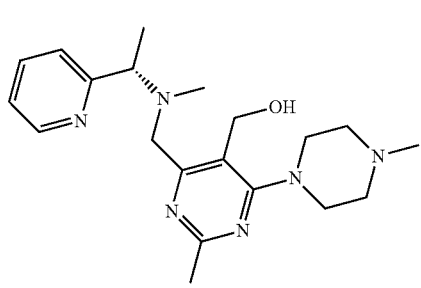
A86
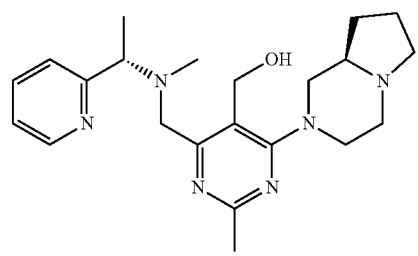
A87
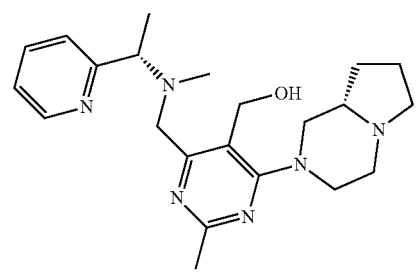
A88
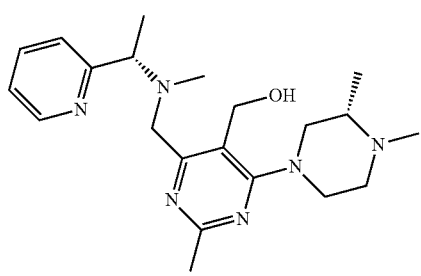
A89
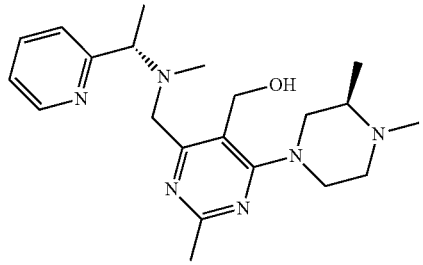
A90
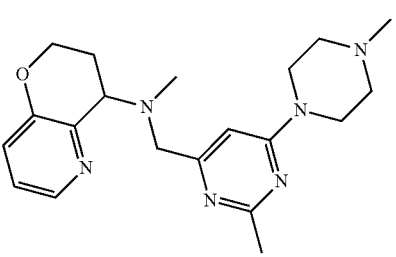
A91
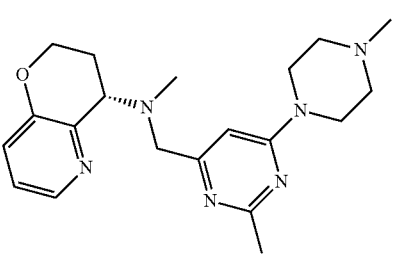
A92
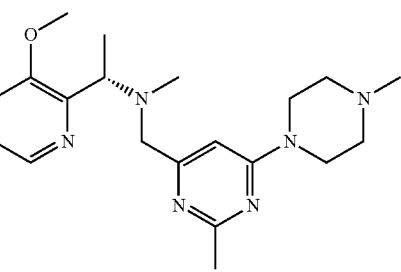
A93
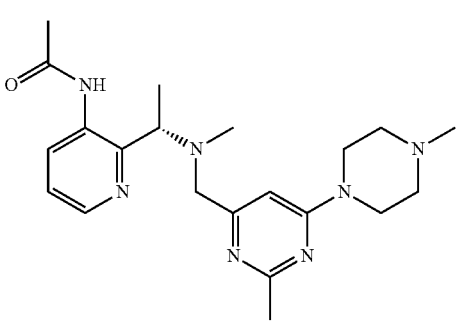

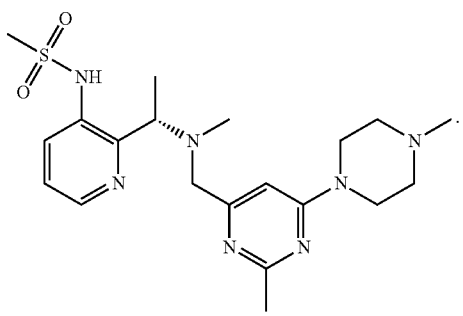
A94
5. The compound of claim 1, or a pharmaceutically acceptable salt, hydrate, solvate, stereoisomer or tautomer thereof, wherein U is unsubstituted or substituted with 1-3 groups selected from the group consisting of deuterium, halide, —OH, $C_{1-3}$ alkyl, and $C_{1-3}$ alkoxy, and U is selected from the group consisting of:
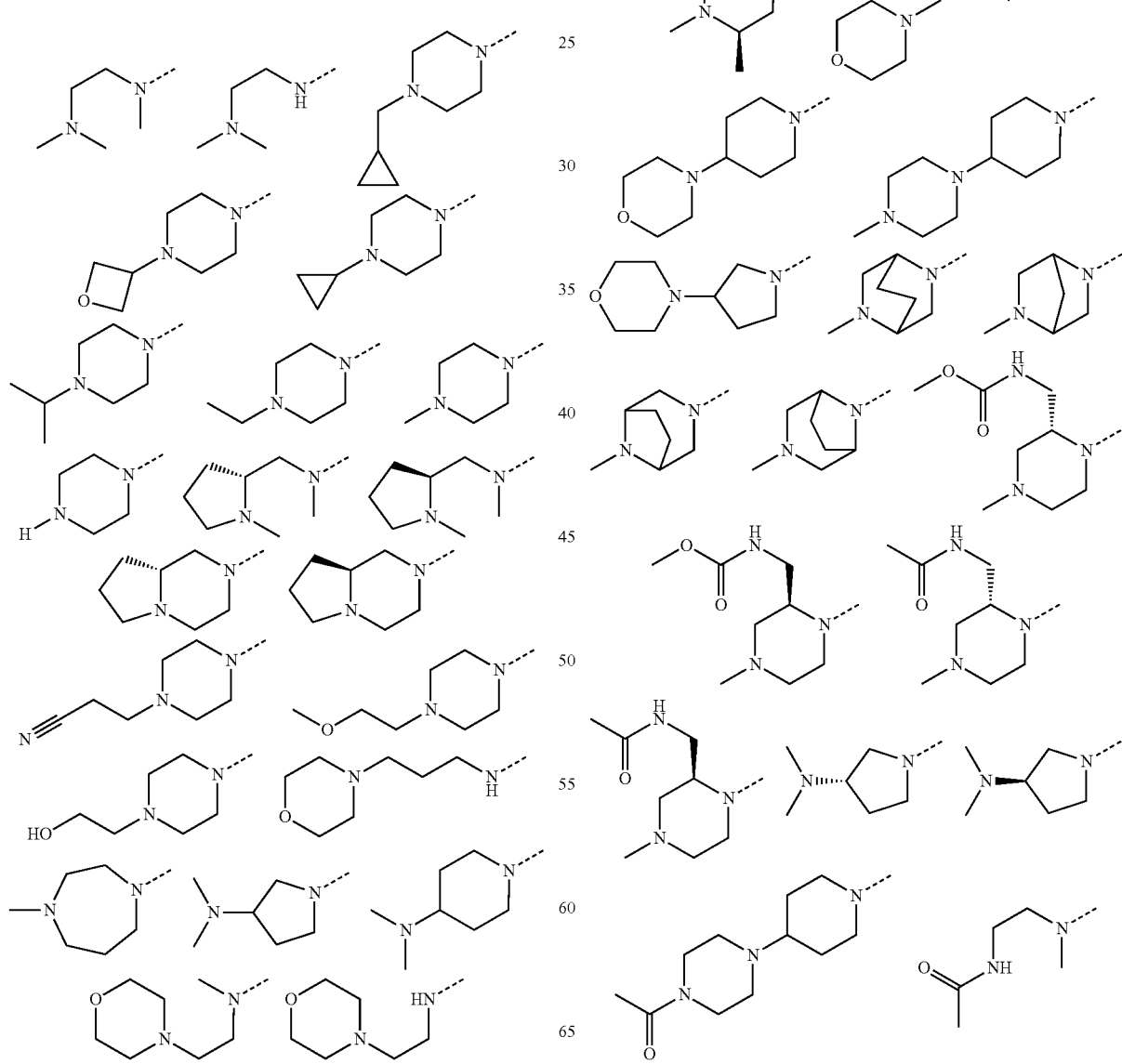
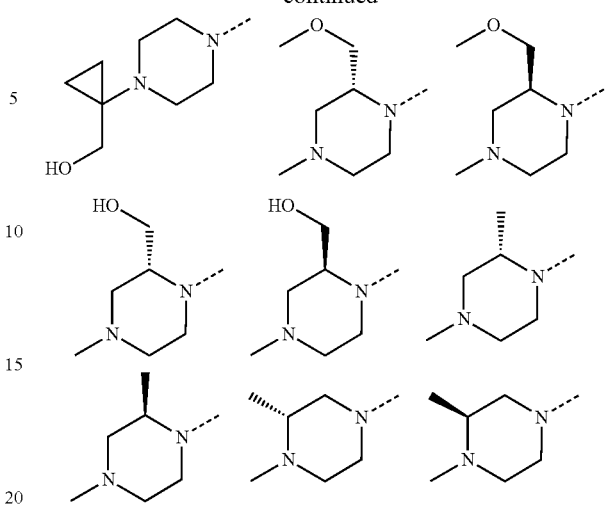

261
-continued
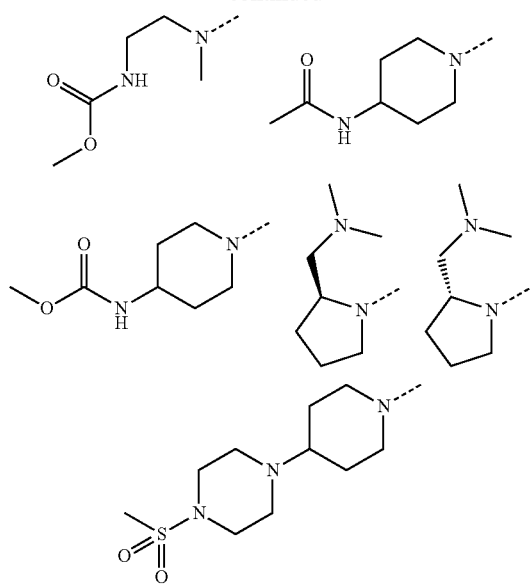
262
-continued
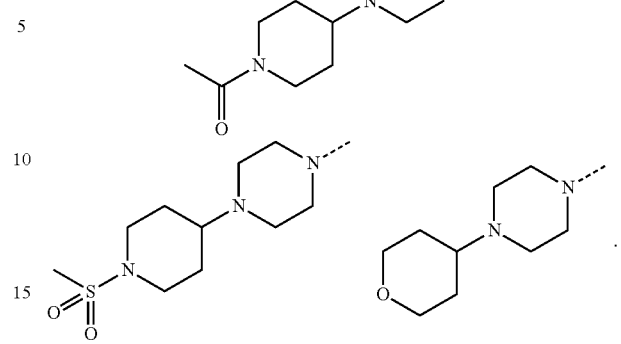
6. A pharmaceutical composition comprising a therapeutically effective amount of a compound of claim 1, or a pharmaceutically acceptable salt, hydrate, solvate, stereoisomer or tautomer thereof, and a pharmaceutically acceptable carrier, diluent, adjuvant or excipient.
* * * * *